(12) United States Patent
Nazare et al.

US007910606B2

(10) Patent No.: US 7,910,606 B2
(45) Date of Patent: Mar. 22, 2011

(54) PYRAZOLE-DERIVATIVES AS FACTOR XA INHIBITORS

(75) Inventors: Marc Nazare, Wiesbaden (DE);
Volkmar Wehner, Sandberg (DE);
David William Will, Kriftel (DE); Hans Matter, Langenselbold (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 5 days.

(21) Appl. No.: 12/562,276

(22) Filed: Sep. 18, 2009

(65) Prior Publication Data

US 2010/0010045 A1    Jan. 14, 2010

Related U.S. Application Data

(63) Continuation of application No. 12/185,388, filed on Aug. 4, 2008, now abandoned, which is a continuation of application No. 10/744,744, filed on Dec. 23, 2003, now Pat. No. 7,429,581.

(60) Provisional application No. 60/468,905, filed on May 8, 2003, provisional application No. 60/507,142, filed on Sep. 30, 2003.

(30) Foreign Application Priority Data

Dec. 23, 2002  (EP) ...................................... 02028915
May 19, 2003  (EP) ...................................... 03011308

(51) Int. Cl.
*A61K 31/454*  (2006.01)
*A61K 31/415*  (2006.01)
*A61K 31/4245*  (2006.01)
*C07D 413/02*  (2006.01)
*C07D 419/02*  (2006.01)
*C07D 401/04*  (2006.01)

(52) U.S. Cl. ........ 514/326; 514/360; 514/361; 514/364; 514/406; 546/208; 548/122; 548/132; 548/374.1

(58) Field of Classification Search ........................ None
See application file for complete search history.

(56) References Cited

U.S. PATENT DOCUMENTS

| | | | |
|---|---|---|---|
| 5,420,141 | A | 5/1995 | Boigegrain et al. |
| 5,998,424 | A | 12/1999 | Galemmo et al. |
| 6,020,357 | A | 2/2000 | Pinto et al. |
| 6,339,099 | B1 | 1/2002 | Lam et al. |
| 6,906,084 | B2 | 6/2005 | Nazare et al. |
| 6,953,857 | B2 | 10/2005 | Nazare et al. |
| 7,067,665 | B2 | 6/2006 | Nazare et al. |
| 7,317,027 | B2 | 1/2008 | Nazare et al. |
| 2004/0171604 | A1 | 9/2004 | Nazare et al. |
| 2004/0235824 | A1 | 11/2004 | Nazare et al. |
| 2005/0009827 | A1 | 1/2005 | Nazare et al. |
| 2005/0009829 | A1 | 1/2005 | Nazare et al. |
| 2005/0033049 | A1 | 2/2005 | Nazare et al. |
| 2005/0043302 | A1 | 2/2005 | Nazare et al. |
| 2007/0049573 | A1 | 3/2007 | Bauer et al. |
| 2007/0179122 | A1 | 8/2007 | Urmann et al. |

FOREIGN PATENT DOCUMENTS

| | | |
|---|---|---|
| EP | 0987274 | 3/2000 |
| WO | WO 92/06711 | 4/1992 |
| WO | WO 95/29189 | 11/1995 |
| WO | WO 96/12800 | 5/1996 |
| WO | WO 97/47651 | 12/1997 |
| WO | WO 98/28269 | 7/1998 |
| WO | WO 99/32454 | 7/1999 |
| WO | WO 99/37304 | 7/1999 |
| WO | WO 00/39131 | 7/2000 |
| WO | WO 00/69849 | 11/2000 |
| WO | WO 01/05784 | 1/2001 |
| WO | WO 01/07436 | 2/2001 |
| WO | WO 01/19798 | 3/2001 |
| WO | WO 01/29006 | 4/2001 |
| WO | WO 01/32628 | 5/2001 |

(Continued)

OTHER PUBLICATIONS

U.S. Appl. No. 09/794,214, filed Feb. 28, 2001, Zhu, et al.
Adang Anton E P et al., A New Generation Of Orally Active Antithrombotics: Comparing Strategies in The GPIIb/IIIa, Thrombin And Factor Xa Acreas, Drugs Of The Future, (2000), vol. 25, No. 4, pp. 369-383.
Articio, et al., Aromatic Hydrazides As Specific Inhibitors Of Bovine Serum Amine Oxidase, Eur. J. Med. (1992), 27, 219-228.
Ashton Wallace T. et al., A Regioselective Route To 3-Alkyl-l-aryl-1H-Pyrazole-5-carboxylates: Synthetic Studies And Structural Assignments, J. Heterocyclic Chem., (1993), vol. 30, pp. 307-311.
Auzzi, et al., Alogenazione DI Alcuni Derivati Pirazolo [1,5-a] Pirimidinici, Ed Sci (1979), 34, 743-750.

(Continued)

*Primary Examiner* — Kamal A Saeed
(74) *Attorney, Agent, or Firm* — Ronald G. Ort; Scully, Scott, Murphy and Presser, P.C.

(57) ABSTRACT

The present invention is directed to a compound of formula I,

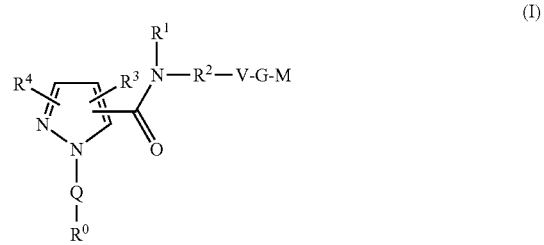

(I)

in which $R^0$; $R^1$; $R^2$; $R^3$; $R^4$; Q; V, G and M have the meanings indicated below. The compound of formula I is a pharmacologically active compound. It exhibits a strong anti-thrombotic effect and is suitable, for example, for the therapy and prophylaxis of a cardio-vascular disorder like a thromboembolic disease or restenosis. It is a reversible inhibitor of the blood clotting enzymes factor Xa (FXa) and/or factor VIIa (FVIIa), and can in general be applied in conditions in which an undesired activity of factor Xa and/or factor VIIa is present or for the cure or prevention of which an inhibition of factor Xa and/or factor VIIa is intended. The invention furthermore is directed to a process for the preparation of the compound of formula I, and pharmaceutical preparation comprising it.

14 Claims, No Drawings

FOREIGN PATENT DOCUMENTS

| | | |
|---|---|---|
| WO | WO 02/00647 | 1/2002 |
| WO | WO 02/00651 | 1/2002 |
| WO | WO 02/085356 | 10/2002 |

OTHER PUBLICATIONS

Booker-Milburn Kevin I., A Convenient Method For The Synthesis Of C-5 Substituted 1-Tosylpryazoles, SynLett; Apr. 1992; pp. 327-328.

Bravo Plerirancesco et al., An Efficient Entry To Perfluoroalkyl Substituted Azoles Starting From Beta-Perfluoroalkyl-Beta-Dicarbonyl Compounds, Tetrahedron, (1994), vol. 50, No. 29, pp. 8827-8836.

Bundgaard Hans, Novel Chemical Approaches In Prodrug Design, Drugs Of The Future, (1991), vol. 16, No. 5, pp. 443-456.

Butler, et al., New General Methods for the Substitution of 5-Chloropyrazoles. The Synthesis of 1,3-Dialkyl-5-chloropyrazol-4-yl Aryl Ketones and New 1,3-Dialkyl-2-pyrazolin-5-ones, J. Org. Chem. (1971) 36(17), 2542-2547.

Cerrada, et al., Synthesis Of p-Nitrophenylazoles By Phase Transfer Catalysis Without Solvent, Synth. Commun (1993). 23(14) 1947-1952.

Chan, et al., New N-and O-Arylations with Phenylboronic Acids and Cupric Acetate, Tetrahedron Letters 39 (1998) 2933-2936.

Cheng, et al, Relationship Between The Inhibition Constant (KI) And The Concentration Of Inhibitor Which Causes 50 Per Cent Inhibition (I50) Of An Enzymatic Reaction, Biochem. Pharmacol. (1973), 22, 3099-3106.

Collot, et al., First Combined Selective N- And C-Arylations With Boronic Acids: Application To The Synthesis Of 1,3-Diarylindazoles. Tetrahedron Letters (2000), 41, 9053-9057.

Cooper, et al., 1,4 Dihidropyridines As Antagonists Of Platelet Activating Factor. 1. Synthesis And Structure-Activity Relationships of 2-(4-Heterocyclyl) Phenyl Derivatives, J. Med. Chem. (1992), 35, 3115-3129.

Cozzi, et al., Ethyl 2- ([5,6-Dihydro-7-(1H-Imidazol-1-YL)-2-Naphthalenyl] Oxy]-2-Methylpropanonate As A New Potent Oxyisobutyrate Hypolipidaemic With Unusual Features, Farmaco (1987) 42, 205-218.

Dewar M. J. S. et al., Sulphaniliamides Of Some Aminopyrazoles And A Note On The Application Of p-phtalimidobenzenesulphonyl Chloride To The Synthesis Of Sulphanilamides, J. Chem. Soc. (1945), pp. 114-116.

Elnagdi Mohamed Hilmy et al., Recent Developments In The Synthesis Of Pyrazole Derivatives, Heterocycles, (1985), vol. 23, No. 12, pp. 3121-3153.

Erian Ayman W. et al., Phosphonium Ylides In Organic Synthesis III 1,2 A Novel Synthesis Of Alpha-Substituted Ylides And Pyrazole Systems, Synthetic Communications, (1999), vol. 29, No. 9, pp. 1527-1537.

Farina, et al., 1,3-Dipolar Cycloadditions With Methyl 4-OXO-And 4-Hydroxy-2-Butynoates. Synthesis Of Functionalized Pyrazoles And Triazoles, Heterocycles (1989) 29, 967.

Fleisher David et al., Improved Oral Drug Delivery: Solubility Limitations Overcome By The Use Of Prodrugs, Advances Drug Delivery Reviews, (1996), vol. 19, pp. 115-130.

Foti, et al., First Synthesis Of A Bromonitrilimine. Direct Formation of 3-Bromopyrazole Derivatives., Tetrahedron Letters (1999) 40, 2605-2606.

Gardner, et al., A Versatile Approach to Analogues of the Cannabinoid-like Anti-emetic Nonabine. J. Heterocyclic Chem. 21, (1984) 121-127.

Grimmett, et al., Synthesis And Reactions Of Lithiated Monocyclic Azoles Containing Two Or More Hetero-Atoms. Part III: Pyrazoles, Heterocycles, 37(3), (1994) 2087-2147.

Haque Tasir S. et al., Parallel Synthesis Of Potent, Pyrazole-Based Inhibitors Of Helicobacter pylori Dihydroorotate Dehydrogenase, J. Med. Chem., (2002), vol. 45, pp. 4669-4678.

Hartwig, J., Recent Advances in Palladium-and Nickel-catalyzed Chemistry Provide New Ways to Constryct C-N and C-O bonds, Angew. Chem. Int. Ed. (1996) 37, pp. 2046-2067.

Hartwig, et al., Room-Temperature Palladium-Catalyzed Amination of Aryl Bromides And Chlorides And Extended Scope Of Aromatic C-N Bond Formation With a Commercial Ligand, J. Org. Chem. (1999) 64, 5575-5580.

Heinisch Gottfried et al., Pyrazole Chemistry. Part 4 Directed Lithiation Of 4-Bromo-1-phenyl-sulphonylpyrazole. A Convenient Approach To Vicinally Disubstituted Pyrazoles. J. Chem. Soc. Perkin Trans., (1990), pp. 1829-1834.

Holzer, et al., N1-Substituted 3,5-Dimethoxy-4-Halogeno-1H-Pyrazoles: Synthesis and NMR Study, J. Heterocyclic Chem. 32, 1351 (1995).

Huang, et al., Regioselective Synthesis of 1,3,5-Triaryl-4-alkylpyrazoles: Novel Ligands For The Estrogen Receptor, Organic Letters, (2000) 2, (18), 2833-2836.

Huisgen, et al., Diazocarbonyl Compounds And 1-Diethylaminopropyne, American Chemical Society, (1979), vol. 101, No. 13, pp. 3647-3648.

Jeon, et al., Synthesis Of New 4-Benzoyl-5-Hydroxy-3-Trifluoromethylpyrazole Derivatives VIA [1,3] Rearrangements Of Benzoyl Group Using tert-Butyllithium, Synth. Commun. (1998), 28(12), 2159-2166.

Jones R. G. et al., vic-Dicarboxylic Acid Derivatives Of Pyrazole, Isoxazole, And Pyrimidine, J. Org. Chem. (1955), 12, 1491.

Kang, et al., Copper-Catalyzed N-Arylation Of Aryl Iodides With Benzamides Or Nitrogen Heterocycles in the Presence Of Ethylenediamine, Synlett. (2002), 3, 427-430.

Klapars, et al., A General And Efficient Copper Catalyst For the Amidation Of Aryl Halides and The N-Arylation Of Nitrogen Heterocycles, J. Am. Chem. Soc. (2001), 123, 7727-7729.

Kudo Noriaki et al., Synthesis And Herbicidal Activity Of 1,5-Diarylpyrazole Derivatives, Chem. Pharm. Bull., (1999), vol. 47, No. 6, pp. 857-868.

Kwong, et al., Copper-Catalyzed Coupling Of Alkylamines and Aryl Iodides: An Efficient System Even In An Air Atmosphere, Organic Letters, (2002), 4 581-584.

Lam, et al., Copper-Catalyzed General C-N and C-O Bond Cross-Coupling With Arylboronic Acid, Tetrahedron Letters (2001) 42, 3415-3418.

Lam, et al., New Aryl/Heteroaryl C-N Bond Cross-coupling Reactions via Arylboronic Acid/Cupric Acetate Arylation, Tetrahedron Letters 39 (1998) 2941-2944.

Makino Kenzi et al., Synthesis Of Pyrazoles And Condensed Pyrazoles, J. Heterocyclic Chem., (1999), vol. 36, pp. 321-332.

Makino Kenzi et al., Synthesis Of Pyrazoles, J. Heterocyclic Chem., (1998), vol. 35, pp. 489-497.

Makino, et al., Selective Fluorination of Ethyl 1-Methylpyrazole-4-carboxylates with Poly (Hydrogen Fluoride)-Amine Complex Under Electrolytic Anodic Oxidation, Journal of Fluorine Chemistry, 39 (1988) 435-440.

Mann, et al., Paliadium-Catalyzed C-N(sp2) Bond Formation: N-Arylation Of Aromatic And Unsaturated Nitrogen And The Reductive Elimination Chemistry Of Palladium Azolyl And Methyleneamido Complexes, J. Am. Chem. Soc. (1998), 120, 827-828.

Markowa, et al., Reaction of 1-Dialkiamino(Alkoxy)-1-Buten-Ones With Some 1,3-Diploar Systems. Zn. Org. Khim. (1983) 19:11, pp. 2281-2285.

Martins Marcos A. P. et al., Haloacetylated Enol Ethers, 11 [16], Synthesis Of 1-Methyl- And 1-Phenyl Pyrazole-3(5)-Ethyl Esters. A One-Pot Procedure, J. Heterocyclic Chem., (1999), vol. 36, pp. 217-220.

Martins Marcos A. P. et al., One-Pot Synthesis Of 3(5)-Ethoxycarbonylpyrazoles, Synthesis, (1995), pp. 1491-1492.

Morimoto, et al., Synthesis Of Halosuffuron-Methyl Via Selective Chlorination At 3- And/Or 5-Position Of Pyrazole-4-Carboxylates, J. Heterocycl. Chem. (1997) 34, 537.

Nagai Toshikazu et al., Recent Progress In The Preparation And Synthetic Uses Of The Reactions Of 3H-Pyrazoles A Review, Organic Preparations And Procedures Int, (1993), vol. 25, No. 4, pp. 403-435.

Nichols, et al., 1-(2,5-Dimethoxy-4-(trifluoromethyl)Phenyl)-2-Aminopropane: A Potant Serotonin 5-HT2A/2C Agonist, J. Med. Chem. (1994). 37, 4346-4351.

Old, et al., Efficient Palladium-Catalyzed N-Arylation Of Indoles, Organic Letters (2000), 2(10), 1403-1406.

Ostrem, et al., Discovery Of A Novel, Potent, And Specific Family Of Factor Xa Inhibitors VIA Combinatorial Chemistry, Biochemistry (1998), 37, 1053-1059.

Padwa Albert et al., Reaction Of Hydrozonyl Chlorides And Carboalkoxymethylene Triphenylphosphoranes To Give 5-Alkoxy Substituted Pyrazoles, J. Heterocyclic. (1987), Vo. 24, pp. 1225-1227.

Patel Himatkumar V. et al., Concise And Efficient Synthesis Of 1h-Pyrazoles: Reaction Of [Hydroxy(Tosyloxy)Iodo]Benzene With Ethyl 2,3-Dioxobutanoate-2-Arylhydrazones, Synthetic Communications, (1991), vol. 21, No. 15 & 16, pp. 1583-1588.

Pawlas, et al., Synthesis Of 1-Hydroxy-Substituted Pyrazolo[3,4-c]- and Pyrazolo[4,3-c] Quinolines and -Isoquinolines From 4- and 5-Aryl-Substituted 1-Benzyloxypyrazoles. J. Org. Chem. 2000, 65, 9001-9006.

Pilling Garry M. et al., The Synthesis Of 1H-Pyrazol-4-OLS From 2-(2-Alkylidenshydrazino) Acetic Acids. Tetrahedron Letters, (1988), vol. 29, No. 12, pp. 1341-1342.

Qing, et al., First Synthesis Of Ortho-Trifluoromethylated Aryl Triflates, J. Chem. Soc Perkin Trans. I, (1997) 3053-3057.

Rodriguez-Franco, et al., A Mild And Efficient Method For The Regioselective Iodination Of Pyrazoles, Tetrahedron Letters, 42 (2001) 863-865.

Sakamoto, et al., Palladium-Catalyzed Cyanation Of Aryl and Heteroaryl Iodides With Copper(I) Cyanide, J. Chem. Soc., Perkin Trans I, (1999), 2323-2326.

Sauer Daryl R. et al., The Synthesis Of 3(5)-[(2-Hydroxyethoxy)methyl]pyrazole-5(3)-carboxamide, An Acrylic Analogue Of 4-Deoxypyrazofurin, J. Org. Chem., (1990), vol. 55, pp. 5535-5538.

Segel, Irwin, Behavior And Analysis Of Rapid Equilibrium And Steady-State Enzyme Systems, Enzyme Kinetics, (1975) John Wiley & Sons, New York, 100-125.

Smith Lee Irvin et al., The Reaction Between Nitrocyclopropyl Ketones And Alkali, J. Am. Chem. Soc.; 1949; 71; pp. 2671-2676.

Storer, et al., The Synthesis And Antiviral Activity Of 4-Fluoro-1-Beta-D-Ribofuranosyl-1H-Pyrazole-3-Carboxamide, Nucleosides & Nucleotides, 16(2), 203-216 (1999).

Su, et al., Methyl Chlorodifluoroacetate A Convenient Trifluoromethylating Agent, Tetrahedron Letters, (1991), 32(52). 7689-7690.

Sucrow Von Wolfgang et al., Stabile Pyrazolium-Betaine durch Addition von 1,1-Dialkylhydrazinen an Acetylenecarbonsaureester, Angew Intl. Ed. 1975; vol. 14:8 pp. 560-561.

Tokmakov, et al., Rearrangement of 1-Arylinodoles To 5H-Dibenz[b,f]Azepines, Tetrahedron (1995) 51(7), 2091-2098.

Turnbull Kenneth et al., A Lithiaton Approach To 5-Substituted-1-Benzenesulfonylpyrazoles, OPPI Briefs, (2000), vol. 32, No. 6, pp. 593-603.

Umemoto, et al., Power And Structure-Variable Fluorinating Agents, The N-Fluoropyridinium Salt System, J. Am. Chem. Soc. (1990), 112, 8563-8575.

Unangst, et al., Synthesis Of Novel 1-Phenyl-1H-Indole-2-Carboxylic Acids. I. Utilization of Ullmann And Dieckmann Reactions For the Preparation Of 3-Hydroxy, 3-Alkoxy, And 3-Alkyl Derivatives, J. Heterocycl. Chem. (1987) 24, 811-815.

Urata, et al., A Novel And Convenient Method For The Trifluoromethylation Of Organic Halides Using CR3SiR3/KF/Cu(l) System, Tetrahedron Letters, (1991), 32(1), 91-94.

Wang, et al., Practical Synthesis Of 1,3-Diaryl-5-Alkylpyrazoles By A Highly Regioselective N-arylation Of 3,5-disubstituted Pyrazoles With 4-Fluoronitrobenzenes, Tetrahedron Letters (2000), 41, 5321-5324.

Washizuka, et al., Novel Generation Of Azomethine Imines From Alpha-Silylnitrosamines by 1,4-Silatropic Shift And Their Cycloaddition, Tetrahedron Letters 40 (1999) 8849-8853.

Wolfe, et al., Simple, Efficient Catalyst System For The Palladium-Catalyzed Aminations Of Aryl Chlorides, Bromides And Triflates, J. Org. Chem. (2000), 65, 1158-1174.

Yang, et al., Palladium-Catalyzed Amination Of Aryl Halides And Sulfonates, Journal Of Organometallic Chemistry (1999) 576, 125-146.

Zhang Jidong et al., Potent Nonpeptide Endothelin Antagonists: Synthesis And Structure-Activity Relationships Of Pyrazole-5-Carboxylic Acids, Bioorganic & Medicinal Chemistry Letters, (2000), vol. 10, pp. 2575-2578.

U.S. Appl. No. 11/469,513, filed Sep. 1, 2006, Urmann, et al.

PYRAZOLE-DERIVATIVES AS FACTOR XA INHIBITORS

RELATED APPLICATIONS

This application is a continuation of application Ser. No. 12/185,388, filed Aug. 4, 2008, which is a continuation of application Ser. No. 10/744,744, filed Dec. 23, 2003, now U.S. Pat. No. 7,429,581, which claims the benefit of U.S. Provisional Application No. 60/468,905, filed May 8, 2003, and U.S. Provisional Application No. 60/507,142, filed Sep. 30, 2003.

FIELD OF THE INVENTION

The present invention is directed to a compound of formula I,

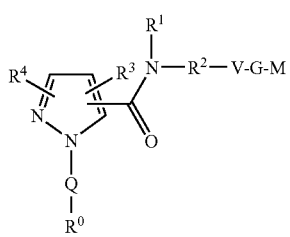

in which $R^0$; $R^1$; $R^2$; $R^3$; $R^4$; Q; V, G and M have the meanings indicated below. The compound of formula I is a pharmacologically active compound. It exhibits a strong anti-thrombotic effect and is suitable, for example, for the therapy and prophylaxis of a cardiovascular disorder like a thromboembolic disease or restenosis. It is a reversible inhibitor of the blood clotting enzymes factor Xa (FXa) and/or factor VIIa (FVIIa), and can in general be applied in conditions in which an undesired activity of factor Xa and/or factor VIIa is present or for the cure or prevention of which an inhibition of factor Xa and/or factor VIIa is intended. The invention furthermore is directed to a process for the preparation of the compound of formula I, and pharmaceutical preparation comprising it.

BACKGROUND OF THE INVENTION

Normal haemeostasis is the result of a complex balance between the processes of clot initiation, formation and clot dissolution. The complex interactions between blood cells, specific plasma proteins and the vascular surface, maintain the fluidity of blood unless injury and blood loss occurs (EP-A-987274). Many significant disease states are related to abnormal haemeostasis. For example, local thrombus formation due to rupture of atheroslerotic plaque is a major cause of acute myocardial infarction and unstable angina. Treatment of an occlusive coronary thrombus by either thrombolytic therapy or percutaneous angioplasty may be accompanied by acute thrombolytic reclosure of the affected vessel.

There continues to be a need for safe and effective therapeutic anticoagulants to limit or prevent thrombus formation. It is most desirable to develop agents that inhibit coagulation without directly inhibiting thrombin but by inhibiting other steps in the coagulation cascade like factor Xa and/or factor VIIa activity. It is now believed that inhibitors of factor Xa carry a lower bleeding risk than thrombin inhibitors (A. E. P. Adang & J. B. M. Rewinkel, Drugs of the Future 2000, 25, 369-383).

Low molecular weight, factor Xa-specific blood clotting inhibitors that are effective but do not cause unwanted side effects have been described, for example, in WO-A-95/29189. However, besides being an effective factor Xa-specific blood clotting inhibitor, it is desirable that such inhibitors also have further advantageous properties, for instance stability in plasma and liver and selectivity versus other serine proteases whose inhibition is not intended, such as thrombin. There is an ongoing need for further low molecular weight factor Xa specific blood clotting inhibitors, which are effective and have the above advantages as well.

Specific inhibition of the factor VIIa/tissue factor catalytic complex using monoclonal antibodies (WO-A-92/06711) or a protein such as chloromethyl ketone inactivated factor VIIa (WO-A-96/12800, WO-A-97/47651) is an extremely effective means of controlling thrombus formation caused by acute arterial injury or the thrombotic complications related to bacterial septicemia. There is also experimental evidence suggesting that inhibition of factor VIIa/tissue factor activity inhibits restenosis following balloon angioplasty. Bleeding studies have been conducted in baboons and indicate that inhibition of the factor VIIa/tissue factor complex has the widest safety window with respect to therapeutic effectiveness and bleeding risk of any anticoagulant approach tested including thrombin, platelet and factor Xa inhibition. Certain inhibitors of factor VIIa have already been described. EP-A-987274, for example discloses compounds containing a tripeptide unit, which inhibit factor VIIa. However, the property profile of these compounds is still not ideal, and there is an ongoing need for further low molecular weight factor VIIa inhibitory blood clotting inhibitors In view of the current situation, it is clear that there is a need for a compound that exhibits better factor Xa and/or factor VIIa inhibitory activity and has high bioavailability.

SUMMARY OF THE INVENTION

The present invention is directed to a compound of formula I,

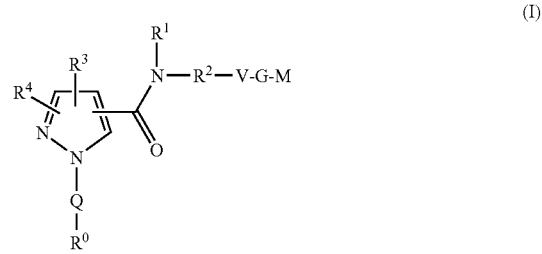

wherein
$R^0$ is 1) a monocyclic or bicyclic 6- to 14-membered aryl, wherein, the aryl is mono-, di- or trisubstituted independently of one another by $R^8$,
2) a monocyclic or bicyclic 4- to 15-membered heterocyclyl, selected from the group consisting of acridinyl, azaindole, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, 1,3-benzodioxolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, indazolyl, indolinyl, indolizinyl, indolyl, isobenzofuranyl, isochromanyl, isoindazolyl, isoindolinyl, isoindolyl, isoquinolyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2-oxathiepanyl, 1,2-oxathiolanyl, 1,4-oxazepanyl, 1,4-oxazepinyl, oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phenylpyridyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyridopyridinyl, pyridopyrimidinyl, pyrimidinyl, pyrrolidinyl, pyrrolidinonyl, pyrrolinyl, pyrrolyl, quinazolinyl, quinolyl, 4H-quinolizinyl, quinoxalinyl, 1,4,5,6-tetrahydropyridazinyl, quinuclidinyl, tetrahydrofuranyl, tetrahydroisoquinolinyl, tetrahydroquinolinyl, tetrahydropyranyl, tetrahydropyridinyl, tetrahydrothiophenyl, tetrazinyl, tetrazolyl, 6H-1,2,5-thiadiazinyl, thiadiazolyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl,

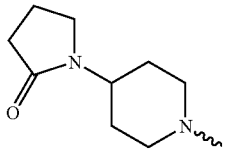

thiomorpholinyl, thiophenolyl, thiophenyl, thiopyranyl, 1,2,3-triazinyl, 1,2,4-triazinyl, 1,3,5-triazinyl, 1,2,3-triazinyl, 1,2,3-triazolyl, 1,2,4-triazolyl, 1,2,5-triazolyl, 1,3,4-triazolyl, xanthenyl, or 3) a monocyclic or bicyclic 4- to 15-membered heterocyclyl, containing one, two, three or four heteroatoms chosen from the group consisting of nitrogen, sulfur or oxygen, wherein, said heterocyclyl is unsubstituted or mono-, di- or trisubstituted independently of one another by $R^8$, and which is additionally substituted by a monocyclic or bicyclic 4- to 15-membered heterocyclyl, containing one, two, three or four heteroatoms chosen from nitrogen, sulfur or oxygen, wherein heterocyclyl is unsubstituted or mono-, di- or trisubstituted independently of one another by $R^8$, $R^8$ is 1) halogen,
2) —$NO_2$,
3) —CN,
4) —C(O)—$NH_2$,
5) —OH,
6) —$NH_2$,
7) —O—$CF_3$
8) a monocyclic or bicyclic 6- to 14-membered aryl, wherein aryl is mono-, di- or trisubstituted independently of one another by halogen or —O—($C_1$-$C_8$)-alkyl,
9) —($C_1$-$C_8$)-alkyl, wherein alkyl is unsubstituted or mono-, di- or trisubstituted independently of one another by halogen, $NH_2$, —OH or methoxy,
10) —O—($C_1$-$C_8$)-alkyl, wherein alkyl is unsubstituted or mono-, di- or trisubstituted independently of one another by halogen, $NH_2$, —OH or methoxy,
11) —$SO_2$—$CH_3$ or
12) —$SO_2$—$CF_3$,
provided that where $R^0$ is a monocyclic or bicyclic 6- to 14-membered aryl, then $R^8$ is at least one halogen, —C(O)—$NH_2$ or —O—($C_1$-$C_8$)-alkyl;

Q is direct bond, —($C_0$-$C_2$)-alkylene-C(O)—$NR^{10}$—, —$NR^{10}$—C(O)—$NR^{10}$—, —$NR^{10}$—C(O)—, —$SO_2$—, —($C_1$-$C_6$)-alkylene, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—S—$(CH_2)_n$—, —$(CH_2)_m$—C(O)—$(CH_2)_n$—, —$(CH_2)_m$—$SO_2$—$NR^{10}$—$(CH_2)_n$—, —$(CH_2)_m$—$NR^{11}$—$SO_2$—$(CH_2)_n$—, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—O—C(O)—$NR^{10}$—$(CH_2)_n$—, —($C_2$-$C_3$)-alkylene-O—($C_0$-$C_3$)-alkylene-, —($C_2$-$C_3$)-alkylene-S(O)—, —($C_2$-$C_3$)-alkylene-S(O)$_2$—, —$(CH_2)_m$—$NR^{10}$—C(O)—O—$(CH_2)_n$—, —($C_2$-$C_3$)-alkylene-S(O)$_2$—NH—($R^{10}$)—, —($C_2$-$C_3$)-alkylene-N($R^{10}$)— or —($C_0$-$C_3$)-alkylene -C(O)—O—,
wherein $R^{10}$ is as defined below, and wherein n and m are independently of one another identical or different and are zero, 1, 2, 3, 4, 5 or 6, wherein the alkylene residues which are formed by —$(CH_2)_m$— or —$(CH_2)_n$— are unsubstituted or mono-, di- or trisubstituted independently of one another by halogen, —$NH_2$ or —OH; or —($C_3$-$C_6$)-cycloalkylene, wherein cycloalkylene is unsubstituted or mono-, di- or trisubstituted independently of one another by halogen, —$NH_2$ or —OH;

$R^1$ is hydrogen, —($C_1$-$C_4$)-alkyl, wherein alkyl is unsubstituted or substituted one to three times by $R^{13}$; —($C_1$-$C_3$)-alkylene-C(O)—NH—$R^0$, —($C_1$-$C_3$)-alkylene-C(O)—O—$R^{10}$, a monocyclic or bicyclic 6- to 14-membered aryl, wherein aryl is mono-, di- or trisubstituted independently of one another by $R^8$, a monocyclic or bicyclic 4- to 15-membered heterocyclyl, containing one, two, three or four heteroatoms chosen from nitrogen, sulfur or oxygen; —($C_1$-$C_3$)-perfluoroalkyl, —($C_1$-$C_3$)-alkylene-S(O)—($C_1$-$C_4$)-alkyl, —($C_1$-$C_3$)-alkylene-S(O)$_2$—($C_1$-$C_3$)-alkyl, —($C_1$-$C_3$)-alkylene-S(O)$_2$—N($R^{4'}$)—$R^{5'}$, —($C_1$-$C_3$)-alkylene-O—($C_1$-$C_4$)-alkyl, —($C_0$-$C_3$)-alkylene-($C_3$-$C_8$)-cycloalkyl, or —($C_0$-$C_3$)-alkylene-het, wherein het is unsubstituted or mono-, di- or trisubstituted independently of one another by $R^{14}$, and;

$R^{4'}$ and $R^{5'}$ are independent of one another are identical or different and are hydrogen or —($C_1$-$C_4$)-alkyl;

$R^2$ is direct bond or —($C_1$-$C_4$)-alkylene,

V is 1) 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by $R^{14}$.
2) 6- to 14-membered aryl, wherein aryl is unsubstituted or mono-, di- or trisubstituted independently of one another by $R^{14}$, or
3) monocyclic or bicyclic 4- to 15-membered heterocyclyl, wherein said heterocyclyl is unsubstituted or mono-, di- or trisubstituted independently of one another by $R^{14}$; or $R^1$ and $R^3$ together with the atoms through which they are bonded form a 6- to 8-membered cyclic group, containing 1, 2, 3 or 4 heteroatoms chosen from nitrogen, sulfur or oxygen, and wherein, said cyclic group is unsubstituted or mono-, di- or trisubstituted independently of one another by $R^{14}$; or $R^1$—N—$R^2$—V forms a 4- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by $R^{14}$.

$R^{14}$ is halogen, —OH, =O, —$(C_1-C_8)$-alkyl, —$(C_1-C_4)$-alkoxy, —$NO_2$, —$(C_0-C_4)$-alkyl-C(O)—O—$R^{18}$, —CN, —$(C_0-C_4)$-alkyl-N$(R^{18})$—$R^{21}$, —$(C_0-C_4)$-alkyl-O—$R^{18}$, —$(C_1-C_4)$-alkyl-het, —$(C_0-C_8)$-alkyl-$SO_2$H, —$SO_2$—$(C_1-C_4)$-alkyl, —$SO_2$—N$(R^{18})$—$R^{21}$, —C(O)—NH—$(C_1-C_8)$-alkyl, —C(O)—N—[$(C_1-C_8)$-alkyl]$_2$, —$NR^{18}$—C(O)—NH—$(C_1-C_8)$-alkyl, —C(O)—$NH_2$, —S—$R^{18}$, or —$NR^{18}$—C(O)—NH—[$(C_1-C_8)$-alkyl]$_2$, wherein $R^{18}$ and $R^{21}$ are independently from each other hydrogen atom, —$(C_1-C_3)$-perfluoroalkyl or —$(C_1-C_6)$-alkyl;

G is direct bond, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—, —$(CH_2)_m$—O—$(CH_2)_n$—, —$(CH_2)_m$—C(O)—$NR^{10}$—$(CH_2)_n$—, —$(CH_2)$—$SO_2$—$(CH_2)_n$—, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—C(O)—$(CH_2)_n$—, —$(CH_2)$—S—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—, —$(CH_2)_m$—O—C(O)—$NR^{10}$—$(CH_2)_n$— or —$(CH_2)_m$—$NR^{10}$—C(O)—O—$(CH_2)_n$—;

n and m are independently of one another identical or different and are zero, 1, 2, 3, 4, 5 or 6;

M is 1) hydrogen,
2) —$(C_1-C_8)$-alkyl, wherein alkyl is unsubstituted or mono-, di- or trisubstituted independently of one another by $R^{14}$,
3) —C(O)—N$(R^{11})$—$R^{12}$,
4) —$(CH_2)_m$—$NR^{10}$,
5) a 6- to 14-membered aryl, wherein aryl is unsubstituted or mono-, di- or trisubstituted independently of one another by $R^{14}$,
6) a monocyclic or bicyclic 4- to 15-membered heterocyclyl, wherein heterocyclyl is unsubstituted or mono-, di- or trisubstituted independently of one another by $R^{14}$,
7) —$(C_3-C_8)$-cycloalkyl, wherein said cycloalkyl is unsubstituted or mono-, di- or trisubstituted independently of one another by $R^{14}$, or
8) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by $R^{14}$;

$R^3$ and $R^4$ are independent of one another are identical or different and are
1) hydrogen,
2) halogen,
3) —$(C_1-C_4)$-alkyl, wherein alkyl is unsubstituted or mono-, di- or trisubstituted independently of one another by $R^{13}$,
4) —$(C_1-C_3)$-perfluoroalkyl,
5) phenyl, wherein phenyl is unsubstituted or mono-, di- or trisubstituted independently of one another by $R^{13}$,
6) —$(C_0-C_4)$-alkylene-O—$R^{19}$, wherein $R^{19}$ is
   a) hydrogen,
   b) —$(C_1-C_4)$-alkyl, wherein alkyl is unsubstituted or mono-, di- or trisubstituted independently of one another by $R^{13}$, or
   c) phenyl, wherein phenyl is unsubstituted or mono-, di- or trisubstituted independently of one another by $R^{13}$,
   d) —$CF_3$, or
   e) —$CHF_2$,
7) —$NO_2$,
8) —CN,
9) —$SO_s$—$R^{11}$, wherein s is 1 or 2,
10) —$SO_t$—N$(R^{11})$—$R^{12}$, wherein t is 1 or 2,
11) —$(C_0-C_4)$-alkylene-C(O)—$R^{11}$,
12) —$(C_0-C_4)$-alkylene-C(O)—O—$R^{11}$,
13) —$(C_0-C_4)$-alkylene-C(O)—N$(R^{11})$—$R^{12}$,
14) —$(C_0-C_4)$-alkylene-N$(R^{11})$—$R^{12}$,
15) —$NR^{10}$—$SO_2$—$R^{10}$,
16) —S—$R^{10}$,
17) —$(C_0-C_2)$alkylene-C(O)—O—$(C_2-C_4)$-alkylene-O—C(O)—$(C_1-C_4)$-alkyl,
18) —C(O)—O—C$(R^{15},R^{16})$—O—C(O)—$R^{17}$,
19) —$(C_0-C_2)$alkylene-C(O)—O—$(C_2-C_4)$-alkylene-O—C(O)—O—$(C_1-C_6)$-alkyl,
20) —C(O)—O—C$(R^{15}, R^{16})$—O—C(O)—O—$R^{17}$,
21) —$(C_0-C_4)$-alkylene-$(C_6-C_{14})$-aryl, wherein aryl is mono-, di- or trisubstituted independently of one another by $R^{13}$,
22) —$(C_0-C_4)$-alkylene-$(C_4-C_{15})$-heterocyclyl, wherein heterocyclyl is unsubstituted or mono-, di- or trisubstituted independently of one another by $R^{13}$
23) —$(C_0-C_4)$-alkylene-$(C_3-C_8)$-cycloalkyl, wherein cycloalkyl is unsubstituted or mono-, di- or trisubstituted independently of one another by $R^{13}$,
24) —$(C_0-C_4)$-alkylene-het, wherein het is unsubstituted or mono-, di- or trisubstituted independently of one another by $R^{13}$,
25) —$(C_0-C_4)$-alkylene-O—$CH_2$—$(C_1-C_3)$-perfluoroalkylene-$CH_2$—O—$(C_0-C_4)$-alkyl, or
26) a residue selected from the group consisting of

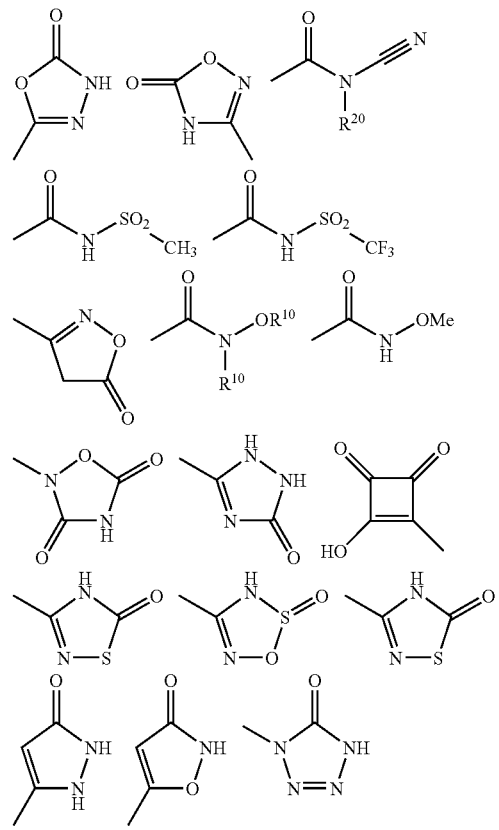

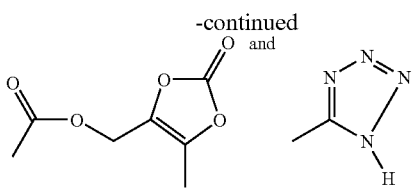

wherein Me is methyl, or two —OR$^{19}$ residues and adjacent atoms through which they are attached form together a 5- or 6-membered ring, that is unsubstituted or substituted one, two, three or four times by R$^{13}$;

R$^{11}$ and R$^{12}$ are independently of one another identical or different and are 1) hydrogen,
2) —(C$_1$-C$_6$)-alkyl, wherein alkyl is unsubstituted or mono-, di- or trisubstituted independently of one another by R$^{13}$,
3) —(C$_0$-C$_6$)-alkyl-(C$_3$-C$_8$)-cycloalkyl,
4) —SO$_t$—R$^{10}$, wherein t is 1 or 2,
5) —(C$_0$-C$_6$)-alkyl-(C$_6$-C$_{14}$)-aryl, wherein alkyl and aryl independently from one another are unsubstituted or mono-, di- or trisubstituted by R$^{13}$,
6) —(C$_1$-C$_3$)-perfluoroalkyl,
7) —O—R$^{17}$, or
8) —(C$_0$-C$_6$)-alkyl-(C$_4$-C$_{15}$)-heterocyclyl, wherein alkyl and heterocyclyl independently from one another are unsubstituted or mono-, di- or trisubstituted by R$^{13}$, or R$^{11}$ and R$^{12}$ together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen; wherein said heterocyclic ring is unsubstituted or mono-, di- or trisubstituted independently of one another by R$^{13}$;

R$^{13}$ is halogen, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_3$-C$_8$)-cycloalkyl, —(C$_0$-C$_3$)-alkylene-O—R$^{10}$, —Si—(CH$_3$)$_3$, —N(R$^{10}$)—S(O)$_u$—R$^{10}$, wherein u is 1 or 2, —S—R$^{10}$, —SO$_r$—R$^{10}$, wherein r is 1 or 2, —S(O)$_v$—N(R$^{10}$)—R$^{20}$ wherein v is 1 or 2, —C(O)—R$^{10}$, —(C$_1$-C$_8$)-alkyl, —(C$_1$-C$_8$)-alkoxy, phenyl, phenyloxy-, —O—CF$_3$, —(C$_0$-C$_4$)-alkyl-C(O)—O—C(R$^{15}$, R$^{16}$)—C(O)—R$^{17}$, —(C$_1$-C$_4$)-alkoxy-phenyl, —(C$_0$-C$_4$)-alkyl-C(O)—O—C(R$^{15}$, R$^{16}$)—O—C(O)—O—R$^{17}$, —(C$_1$-C$_3$)-perfluoroalkyl, —O—R$^{15}$, —NH—C(O)—NH—R$^{10}$, —NH—C(O)—O—R$^{10}$, or residue selected from the group consisting of

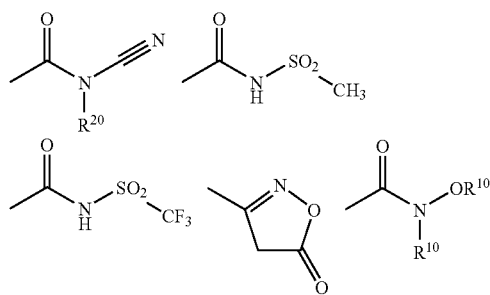

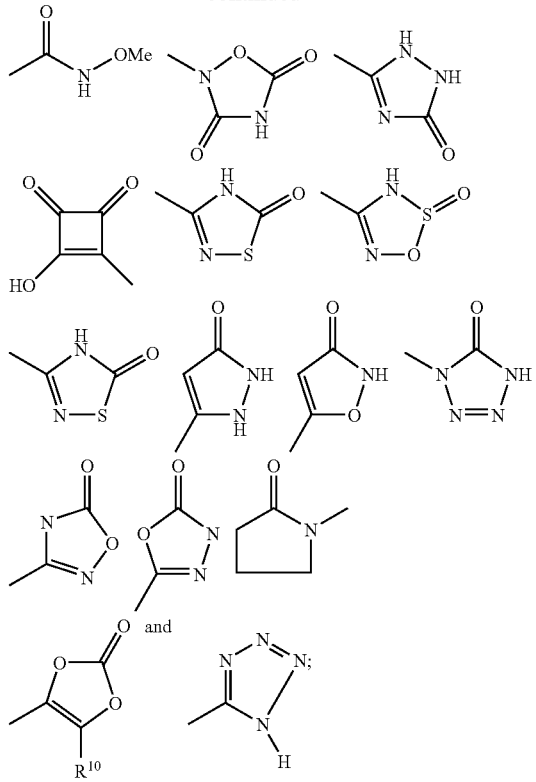

R$^{10}$ and R$^{20}$ are independently of one another hydrogen, —(C$_1$-C$_6$)-alkyl, —(C$_0$-C$_4$)-alkyl-OH, —(C$_0$-C$_4$)-alkyl-O—(C$_1$-C$_4$)-alkyl or —(C$_1$-C$_3$)-perfluoroalkyl;

R$^{15}$ and R$^{16}$ are independently of one another hydrogen, —(C$_1$-C$_6$)-alkyl, or together with the carbon atom to which they are bonded they can form a 3- to 6 membered carbocyclic ring which is unsubstituted or substituted one to three times by R$^{10}$; and R$^{17}$ is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$; or a stereoisomer thereof, mixture of stereoisomers thereof in any ratio, or a physiological tolerable salt thereof.

The invention also is directed to a method for preparing the compound according to the invention, a pharmaceutical preparation thereof, and its use for inhibiting factor Xa and/or factor VIIa or influencing blood coagulation or fibrinolysis.

DETAILED DESCRIPTION OF THE INVENTION

Definitions

The following are abbreviations used herein:
tert-Butyl t-Bu
2,2'-bis(diphenylphoshino-1,1'-binaphthyl Binap
Bis-(oxo-3-oxazolidinyl)-phosphoryl chloride BOP-Cl
dibenzylidenacetone dba
Dichloromethane DCM
Dicyclohexyl-carbodiimide DCC
Diethylphosphoryl cyanide DEPC
Diisopropylethyl amine DIPEA
4-Dimethyaminopyridine DMAP N,N-Dimethylformamide DMF
Dimethylsulfoxide DMSO
1,1'-Bis(diphenylphosphino)ferrocene DPPF
O-(7-Azabenzotriazol-1-yl)-N,N,N',N'-tetramethyluronium-hexafluorophosphate HATU
N-Bromosuccinimide NBS
N-Chlorosuccinimide NCS
N-Iodosuccinimide NIS
N-Ethylmorpholine NEM
Methanol MeOH
Room temperature 20° C. to 25° C. RT
Saturated sat.
Tetrahydrofuran THF
Trifluoroacetic acid TFA
O-((Ethoxycarbonyl)cyanomethyleneamino)-N,N,N',N'-tetramethyluronium tetrafluoroborate TOTU In general, the meaning of any group, residue, heteroatom, number etc., which can occur more than once in the compound of formulae I, Ib and Ic, is independent of the meaning of this group, residue, heteroatom, number etc. in any other occurrence. All groups, residues, heteroatoms, numbers etc., which can occur more than once in the compound of formulae I, Ib and Ic can be identical or different.

As used herein, the term alkyl is to be understood in the broadest sense to mean hydrocarbon residues which can be linear, i.e. straight-chain, or branched and which can be acyclic or cyclic residues or comprise any combination of acyclic and cyclic subunits. Further, the term alkyl as used herein expressly includes saturated groups as well as unsaturated groups which latter groups contain one or more, for example one, two or three, double bonds and/or triple bonds, provided that the double bonds are not located within a cyclic alkyl group in such a manner that an aromatic system results. All these statements also apply if an alkyl group occurs as a substituent on another residue, for example in an alkyloxy residue, an alkyloxycarbonyl residue or an arylalkyl residue. Examples of "—($C_1$-$C_8$) -alkyl" or "—($C_1$-$C_8$)-alkylene" are alkyl residues containing 1, 2, 3, 4, 5, 6, 7 or 8 carbon atoms are methyl, methylene, ethyl, ethylene, propyl, propylene, butyl, butylene, pentyl, pentylene, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, t-Bu, tert-pentyl, sec-butyl, tert-butyl or tert-pentyl. The term "—($C_0$-$C_6$) -alkyl" or "—($C_0$-$C_8$)-alkylene" is a hydrocarbon residue containing 1, 2, 3, 4, 5, 6, 7 or 8 carbon atoms. The term "—$C_0$-alkyl" or "—$C_0$-alkylene" is a covalent bond.

Unsaturated alkyl residues are, for example, alkenyl residues such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl, or alkynyl residues such as ethynyl, 1-propynyl, 2-propynyl (=propargyl) or 2-butynyl. Unsaturated alkyl residues can also be substituted.

Examples of —($C_3$-$C_8$)-cycloalkyl cyclic alkyl residues are cycloalkyl residues containing 3, 4, 5, 6, 7 or 8 ring carbon atoms like cyclopropyl, cyclobutyl, cyclopentyl, cyclohexyl, cyloheptyl or cyclooctyl, which can also be substituted and/or unsaturated. Unsaturated cyclic alkyl groups and unsaturated cycloalkyl groups like, for example, cyclopentenyl or cyclohexenyl can be bonded via any carbon atom.

Of course, a cyclic alkyl group has to contain at least three carbon atoms, and an unsaturated alkyl group has to contain at least two carbon atoms. Thus, a group like ($C_1$-$C_8$) -alkyl is to be understood as comprising, among others, saturated acyclic ($C_1$-$C_8$)-alkyl, ($C_3$-$C_6$)-cycloalkyl, and unsaturated ($C_2$-$C_8$)-alkyl like ($C_2$-$C_8$)-alkenyl or ($C_2$-$C_8$)-alkynyl. Similarly, a group like ($C_1$-$C_4$)-alkyl is to be understood as comprising, among others, saturated acyclic ($C_1$-$C_4$)-alkyl, and unsaturated ($C_2$-$C_4$)-alkyl like ($C_2$-$C_4$)-alkenyl or ($C_2$-$C_4$)-alkynyl.

Unless stated otherwise, the term alkyl preferably comprises acyclic saturated hydrocarbon residues which have from one to six carbon atoms and which can be linear or branched. A particular group of saturated acyclic alkyl residues is formed by ($C_1$-$C_4$)-alkyl residues like methyl, ethyl, n-propyl, isopropyl, n-butyl, isobutyl, sec-butyl and t-Bu.

Unless stated otherwise, and irrespective of any specific substituents bonded to alkyl groups which are indicated in the definition of the compound of formulae I, Ib and Ic, alkyl groups can in general be unsubstituted or substituted by one or more, for example one, two or three, identical or different substituents. Any kind of substituents present in substituted alkyl residues can be present in any desired position provided that the substitution does not lead to an unstable molecule. Examples of substituted alkyl residues are alkyl residues in which one or more, for example 1, 2 or 3, hydrogen atoms are replaced with halogen atoms, in particular fluorine atoms.

The terms "a monocyclic or bicyclic 6- to 14-membered aryl" or "—($C_6$-$C_{14}$)-aryl" are understood as meaning aromatic hydrocarbon radicals containing from 6 to 14 carbon atoms in the ring. Examples of —($C_6$-$C_{14}$)-aryl radicals are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals.

The terms "mono- or bicyclic 4- to 15-membered heterocyclyl" or "—($C_4$-$C_{15}$)-heterocyclyl" refer to heterocycles in which one or more of the 4 to 15 ring carbon atoms are replaced by heteroatoms such as nitrogen, oxygen or sulfur. Examples are acridinyl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

Preferred are heterocyclyls, include benzimidazolyl, 1,3-benzodioxolyl, benzofuranyl, benzothiazolyl, benzothiophenyl, benzoxazolyl, chromanyl, cinnolinyl, 2-furyl, 3-furyl; imidazolyl, indolyl, indazolyl, isochromanyl, isoindolyl, isoquinolinyl, isothiazolyl, isoxazolyl, oxazolyl, phthalazinyl, pteridinyl, purinyl, pyrazinyl, pyrazolyl, pyridazinyl, pyridoimidazolyl, pyridopyridinyl, pyridopyrimidinyl, 2-pyridyl, 3-pyridyl, 4-pyridyl, pyrimidinyl, pyrrolyl; 2-pyrrolyl, 3-pyrrolyl, quinolinyl, quinazolinyl, quinoxalinyl, tetrazolyl, thiazolyl, 2-thienyl and 3-thienyl.

Also preferred are:

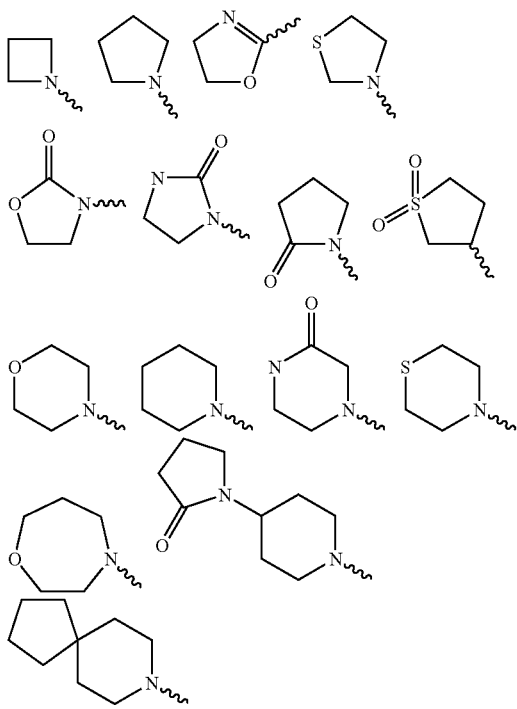

The terms "het" or "a 3- to 7-membered cyclic residue, containing up to 1, 2, 3 or 4 heteroatoms" refer to structures of heterocycles which can be derived from compounds such as azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The term "$R^1$—N—$R^2$—V can form a 4- to 8-membered cyclic group" or "$R^{11}$ and $R^{12}$ together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen" refer to structures of heterocycles which can be derived from compounds such as azepane, azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole.

The term "$R^{15}$ and $R^{16}$ together with the carbon atom to which they are bonded can form a 3-to 6 membered carbocyclic ring" refer to structures, which can be derived from compounds such as cyclopropyl, cyclobutyl, cyclopentyl or cyclohexyl.

The term "$R^1$ and $R^3$ together with the atoms to which they are bonded can form a 6- to 8-membered cyclic group, containing up to 1, 2, 3 or 4 heteroatoms chosen from nitrogen, sulfur or oxygen" refers to structures of heterocycles which can be derived from compounds such as azocane, azocane-2-one, cyloheptyl cyclohexyl, cyclooctane, cyclooctene, 1,4-diazepane, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,4-oxazepane, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,2-oxathiepane, 1,2-oxazine, 1,3-oxazine, 1,4-oxazine, [1,4]oxazocane, [1,3]oxazocan-2-one, oxocane, oxocan-2-one, phenyl, piperazine, piperidine, pyran, pyrazine, pyridazine, pyrimidine, 5,6,7,8-tetrahydro-1H-azocin-2-one or thiomorpholine.

The fact that many of the before-listed names of heterocycles are the chemical names of unsaturated or aromatic ring systems does not imply that the, 4-15 membered mono- or polycyclic group could only be derived from the respective unsaturated ring system. The names here only serve to describe the ring system with respect to ring size and the number of the heteroatoms and their relative positions. As explained above, the 4-15 membered mono- or polycyclic group can be saturated or partially unsaturated or aromatic, and can thus be derived not only from the before-listed heterocycles themselves but also from all their partially or completely hydrogenated analogues and also from their more highly unsaturated analogues if applicable. As examples of completely or partially hydrogenated analogues of the before-listed heterocycles from which this group may be derived the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazole, 1,3-oxazolidine, 4,5-dihydro-1,3-thiazole, 1,3-thiazolidine, perhydro-1,4-dioxane, piperazine, perhydro-1,4-oxazine (=morpholine), perhydro-1,4-thiazine (=thiomorpholine), perhydroazepine, indoline, isoindoline, 1,2,3,4-tetrahydroquinoline, 1,2,3,4-tetrahydroisoquinoline, etc.

The 4-15 membered mono- or polycyclic group may be bonded via any ring carbon atom, and in the case of nitrogen heterocycles via any suitable ring nitrogen atom. Thus, for example, a pyrrolyl residue can be 1-pyrrolyl, 2-pyrrolyl or 3-pyrrolyl, a pyrrolidinyl residue can be pyrrolidin-1-yl (=pyrrolidino), pyrrolidin-2-yl or pyrrolidin-3-yl, a pyridinyl residue can be pyridin-2-yl, pyridin-3-yl or pyridin-4-yl, a piperidinyl residue can be piperidin-1-yl (=piperidino), piperidin-2-yl, piperidin-3-yl or piperidin-4-yl. Furyl can be 2-furyl or 3-furyl, thienyl can be 2-thienyl or 3-thienyl, imidazolyl can be imidazol-1-yl, imidazol-2-yl, imidazol-4-yl or imidazol-5-yl, 1,3-oxazolyl can be 1,3-oxazol-2-yl, 1,3-oxazol-4-yl or 1,3-oxazol-5-yl, 1,3-thiazolyl can be 1,3-thiazol-2-yl, 1,3-thiazol-4-yl or 1,3-thiazol-5-yl, pyrimidinyl can be pyrimidin-2-yl, pyrimidin-4-yl (=6-pyrimidinyl) or 5-pyrimidinyl, piperazinyl can be piperazin-1-yl (=piperazin-4-yl=piperazino) or piperazin-2-yl. Indolyl can be indol-1-yl, indol-2-yl, indol-3-yl, indol-4-yl, indol-5-yl, indol-6-yl or indol-7-yl. Similarly benzimidazolyl, benzoxazolyl and benzothiazol residues can be bonded via the 2-position and via any of the positions 4, 5, 6, and 7. Quinolinyl can be quinolin-2-yl, quinolin-3-yl, quinolin-4-yl, quinolin-5-yl, quinolin-6-yl, quinolin-7-yl or quinolin-8-yl, isoqinolinyl can be isoquinol-1-yl, isoquinolin-3-yl, isoquinolin-4-yl, isoquinolin-5-yl, isoquinolin-6-yl, isoquinolin-7-yl or isoquinolin-8-yl. In addition to being bonded via any of the positions indicated for quinolinyl and isoquinolinyl, 1,2,3,4-tetrahydroquinolinyl and 1,2,3,4-tetrahydroisoquinolinyl can also be bonded via the nitrogen atoms in 1-position and 2-position, respectively.

Unless stated otherwise, and irrespective of any specific substituents bonded to the 4-15 membered mono- or polycyclic group or any other heterocyclic groups which are indicated in the definition of the compound of formulae I, Ib and Ic, the 4-15 membered mono- or polycyclic group can be unsubstituted or substituted on ring carbon atoms with one or more, for example one, two, three, four or five, identical or different substituents like $(C_1-C_8)$-alkyl, in particular $(C_1-C_4)$-alkyl, $(C_1-C_8)$-alkyloxy, in particular $(C_1-C_4)$-alkyloxy, $(C_1-C_4)$-alkylthio, halogen, nitro, amino, $((C_1-C_4)$-alkyl)carbonylamino like acetylamino, trifluoromethyl, trifluoromethoxy, hydroxy, oxo, hydroxy-$(C_1-C_4)$-alkyl such as, for example, hydroxymethyl or 1-hydroxyethyl or 2-hydroxyethyl, methylenedioxy, ethylenedioxy, formyl, acetyl, cyano, aminosulfonyl, methylsulfonyl, hydroxycarbonyl, aminocarbonyl, $(C_1-C_4)$-alkyloxycarbonyl, optionally substituted phenyl, optionally substituted phenoxy, benzyl optionally substituted in the phenyl group, benzyloxy optionally substituted in the phenyl group, etc. The substituents can be present in any desired position provided that a stable molecule results. Of course an oxo group cannot be present in an aromatic ring. Each suitable ring nitrogen atom in the 4-15 membered mono- or polycyclic group can independently of each other be unsubstituted, i.e. carry a hydrogen atom, or can be substituted, i.e. carry a substituent like $(C_1-C_8)$-alkyl, for example $(C_1-C_4)$-alkyl such as methyl or ethyl, optionally substituted phenyl, phenyl-$(C_1-C_4)$-alkyl, for example benzyl, optionally substituted in the phenyl group, hydroxy-$(C_2-C_4)$-alkyl such as, for example 2-hydroxyethyl, acetyl or another acyl group, methylsulfonyl or another sulfonyl group, aminocarbonyl, $(C_1-C_4)$-alkyloxycarbonyl, etc. In general, in the compound of formulae I, Ib and Ic a nitrogen heterocycle can also be present as N-oxides or as quaternary salts. Ring sulfur atoms can be oxidized to the sulfoxide or to the sulfone. Thus, for example a tetrahydrothienyl residue may be present as S,S-dioxotetrahydro-thienyl residue or a thiomorpholinyl residue like thiomorpholin-4-yl may be present as 1-oxo -thiomorpholin-4-yl or 1,1-dioxo-thiomorpholin-4-yl. A substituted 4 to 15 membered mono- or polycyclic group that can be present in a specific position of the compounds of formulae I, Ib and Ic can independently of other groups be substituted by substituents selected from any desired subgroup of the substituents listed before and/or in the definition of that group.

The 3-7 membered monocyclic group may be bonded via any ring carbon atom, and in the case of nitrogen heterocycles via any suitable ring nitrogen atom. Thus, for example, a pyrrolyl residue can be 1-pyrrolyl, 2-pyrrolyl or 3-pyrrolyl, a pyrrolidinyl residue can be pyrrolidin-1-yl (=pyrrolidino), pyrrolidin-2-yl or pyrrolidin-3-yl, a pyridinyl residue can be pyridin-2-yl, pyridin-3-yl or pyridin-4-yl, a piperidinyl residue can be piperidin-1-yl (=piperidino), piperidin-2-yl, piperidin-3-yl or piperidin-4-yl. Furyl can be 2-furyl or 3-furyl, thienyl can be 2-thienyl or 3-thienyl, imidazolyl can be imidazol-1-yl, imidazol-2-yl, imidazol-4-yl or imidazol-5-yl, 1,3-oxazolyl can be 1,3-oxazol-2-yl, 1,3-oxazol-4-yl or 1,3-oxazol-5-yl, 1,3-thiazolyl can be 1,3-thiazol-2-yl, 1,3-thiazol-4-yl or 1,3-thiazol-5-yl, pyrimidinyl can be pyrimidin-2-yl, pyrimidin-4-yl (=6-pyrimidinyl) or 5-pyrimidinyl, piperazinyl can be piperazin-1-yl (=piperazin-4-yl=piperazino) or piperazin-2-yl. Unless stated otherwise, and irrespective of any specific substituents bonded to the 3-7 membered monocyclic group or any other heterocyclic groups which are indicated in the definition of the compound of formulae I, Ib and Ic, can be unsubstituted or substituted on ring carbon atoms with one or more, for example one, two, three, four or five, identical or different substituents like $(C_1-C_8)$-alkyl, in particular $(C_1-C_4)$-alkyl, $(C_1-C_8)$-alkyloxy, in particular $(C_1-C_4)$-alkyloxy, $(C_1-C_4)$-alkylthio, halogen, nitro, amino, $((C_1-C_4)$-alkyl)carbonylamino like acetylamino, trifluoromethyl, trifluoromethoxy, hydroxy, oxo, hydroxy-$(C_1-C_4)$-alkyl such as, for example, hydroxymethyl or 1-hydroxyethyl or 2-hydroxyethyl, methylenedioxy, ethylenedioxy, formyl, acetyl, cyano, aminosulfonyl, methylsulfonyl, hydroxycarbonyl, aminocarbonyl, $(C_1-C_4)$-alkyloxycarbonyl, optionally substituted phenyl, optionally substituted phenoxy, benzyl optionally substituted in the phenyl group, benzyloxy optionally substituted in the phenyl group, etc. The substituents can be present in any desired position provided that a stable molecule results. Of course an oxo group cannot be present in an aromatic ring. Each suitable ring nitrogen atom in the 3-7 membered monocyclic group can independently of each other be unsubstituted, i.e. carry a hydrogen atom, or can be substituted, i.e. carry a substituent like $(C_1-C_8)$-alkyl, for example $(C_1-C_4)$-alkyl such as methyl or ethyl, optionally substituted phenyl, phenyl-$(C_1-C_4)$-alkyl, for example benzyl, optionally substituted in the phenyl group, hydroxy-$(C_2-C_4)$-alkyl such as, for example 2-hydroxyethyl, acetyl or another acyl group, methylsulfonyl or another sulfonyl group, aminocarbonyl, $(C_1-C_4)$-alkyloxycarbonyl, etc. In general, in the compound of formulae I nitrogen heterocycles can also be present as N-oxides or as quaternary salts. Ring sulfur atoms can be oxidized to the sulfoxide or to the sulfone. Thus, for example a tetrahydrothienyl residue may be present as S,S-dioxotetrahydrothienyl residue or a thiomorpholinyl residue like thiomorpholin-4-yl may be present as 1-oxo-thiomorpholin-4-yl or 1,1-dioxo-thiomorpholin-4-yl. A substituted 3-7 membered monocyclic group that can be present in a specific position of the compounds of formulae I can independently of other groups be substituted by substituents selected from any desired subgroup of the substituents listed before and/or in the definition of that group.

The term "—$(C_1-C_3)$-perfluoroalkyl" is a partial or totally fluorinated alkyl-residue, which can be derived from residues such as —$CF_3$, —$CHF_2$, —$CH_2F$, —$CHF$—$CF_3$, —$CHF$—$CHF_2$, —$CHF$—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—$CHF$—$CF_3$, —$CH_2$—$CHF$—$CHF_2$, —$CH_2$—$CHF$—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —$CHF$—$CHF$—$CF_3$, —$CHF$—$CHF$—$CHF_2$, —$CHF$—$CHF$—$CH_2F$, —$CHF$—$CH_2$—$CF_3$, —$CHF$—$CH_2$—$CHF_2$, —$CHF$—$CH_2$—$CH_2F$, —$CHF$—$CF_2$—$CF_3$, —$CHF$—$CF_2$—$CHF_2$, —$CHF$—$CF_2$—$CH_2F$, —$CF_2$—$CHF$—$CF_3$, —$CF_2$—$CHF$—$CHF_2$, —$CF_2$—$CHF$—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

The term "—$(C_1$-$C_3)$-perfluoroalkylene" is a partial or totally fluorinated alkylene-residue, which can be derived from residues such as —$CF_2$—, —$CHF$—, —$CHF$—$CHF_2$—, —$CHF$—$CHF$—, —$CH_2$—$CF_2$—, —$CH_2$—$CHF$—, —$CF_2$—$CF_2$—, —$CF_2$—$CHF$—, —$CH_2$—$CHF$—$CF_2$—, —$CH_2$—$CHF$—$CHF$—, —$CH_2$—$CH_2$—$CF_2$—, —$CH_2$—$CH_2$—$CHF$, —$CH_2$—$CF_2$—$CF_2$—, —$CH_2$—$CF_2$—$CHF$—, —$CHF$—$CHF$—$CF_2$—, —$CHF$—$CHF$—$CHF$—, —$CHF$—$CH_2$—$CF_2$—, —$CHF$—$CH_2$—$CHF$—, —$CHF$—$CF_2$—$CF_2$—, —$CHF$—$CF_2$—$CHF$—, —$CF_2$—$CHF$—$CF_2$—, —$CF_2$—$CHF$—$CHF$—, —$CF_2$—$CH_2$—$CF_2$—, —$CF_2$—$CH_2$—$CHF$—, —$CF_2$—$CF_2$—$CF_2$—, or —$CF_2$—$CF_2$—$CHF$.

Halogen is fluorine, chlorine, bromine or iodine, preferably fluorine, chlorine or iodune, particularly preferably chlorine or iodine.

Optically active carbon atoms present in the compound of formulae I, Ib and Ic can independently of each other have R configuration or S configuration. the compound of formulae I, Ib and Ic can be present in the form of pure enantiomers or pure diastereomers or in the form of mixtures of enantiomers and/or diastereomers, for example in the form of racemates. The present invention is directed to pure enantiomers and mixtures of enantiomers as well as to pure diastereomers and mixtures of diastereomers. The invention comprises mixtures of two or of more than two stereoisomers of the formulae I, Ib and Ic, and it comprises all ratios of the stereoisomers in the mixtures. In case the compound of formulae I, Ib and Ic can be present as E isomers or Z isomers (or cis isomers or trans isomers) the invention relates both to pure E isomers and pure Z isomers and to E/Z mixtures in all ratios. The invention also comprises all tautomeric forms of the compound of formulae I, Ib and Ic.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform a compound of formulae I, Ib and Ic can also be obtained by employing stereochemically uniform starting materials or by using stereoselective reactions. Physiologically tolerable salts of the compounds of formulae I, Ib and Ic are nontoxic salts that are physiologically acceptable, in particular pharmaceutically utilizable salts. Such salts of a compound of formulae I, Ib and Ic containing acidic groups, for example a carboxyl group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl) amine. Basic groups contained in the compound of formulae I, Ib and Ic, for example amino groups or guanidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. A compound of formulae I, Ib and Ic, which simultaneously contain a basic group and an acidic group, for example a guanidino group and a carboxyl group, can also be present as zwitterions (betaines) which are likewise included in the present invention.

Salts of a compound of formulae I, Ib and Ic can be obtained by customary methods known to those skilled in the art, for example by combining a compound of the formulae I, Ib and Ic with an inorganic or organic acid or base in a solvent or dispersant, or from other salts by cation exchange or anion exchange. The present invention also includes all salts of the compound of formulae I, Ib and Ic which, because of low physiologically tolerability, are not directly suitable for use in pharmaceuticals but are suitable, for example, as intermediates for carrying out further chemical modifications of the compound of formulae I, Ib and Ic or as starting materials for the preparation of physiologically tolerable salts.

The present invention furthermore includes all solvates of a compound of formulae I, Ib and Ic, for example hydrates or adducts with alcohols.

The invention also includes derivatives and modifications of the compound of formulae I, Ib and Ic, for example prodrugs, protected forms and other physiologically tolerable derivatives, as well as active metabolites of the compound of formulae I, Ib and Ic. The invention relates in particular to prodrugs and protected forms of the compound of formulae I, Ib and Ic, which can be converted into a compound of formulae I, Ib and Ic under physiological conditions. Suitable prodrugs for the compound of formulae I, Ib and Ic, i.e. chemically modified derivatives of the compound of formulae I, Ib and Ic having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985; Fleisher et al., Advanced Drug Delivery Reviews 19 (1996) 115-130; or H. Bundgaard, Drugs of the Future 16 (1991) 443 which are all incorporated herein by reference. Suitable prodrugs for the compound of formulae I, Ib and Ic are especially acyl prodrugs and carbamate prodrugs of acylatable nitrogen-containing groups such as amino groups and the guanidino group and also ester prodrugs and amide prodrugs of carboxylic acid groups which may be present in a compound of formulae I, Ib and Ic. In the acyl prodrugs and carbamate prodrugs one or more, for example one or two, hydrogen atoms on nitrogen atoms in such groups are replaced with an acyl group or a carbamate, preferably a —$(C_1$-$C_6)$-alkyloxycarbonyl group. Suitable acyl groups and carbamate groups for acyl prodrugs and carbamate prodrugs are, for example, the groups $R^{p1}$—CO— and $R^{p2}$O—CO—, in which $R^{p1}$ is hydrogen, $(C_1$-$C_{18})$-alkyl, $(C_3$-$C_8)$-cycloalkyl, $(C_3$-$C_8)$-cycloalkyl-$(C_1$-$C_4)$-alkyl-, $(C_6$-$C_{14})$-aryl, Het-, $(C_6$-$C_{14})$-aryl-$(C_1$-$C_4)$-alkyl- or Het-$(C_1$-$C_4)$-alkyl- and in which $R^{p2}$ has the meanings indicated for $R^{p1}$ with the exception of hydrogen.

Especially preferred a compound of formulae I, Ib and Ic are those wherein two or more residues are defined as indicated before for preferred a compound of formulae I, Ib and Ic, or residues can have one or some of the specific denotations of the residues given in their general definitions or in the definitions of preferred compounds before. All possible combinations of definitions given for preferred definitions and of specific denotations of residues explicitly are a subject of the present invention.

Particular Embodiments

A particular embodiment of the compound of formula I according to the invention is wherein
$R^0$ as 2) is benzothiophenyl, indazolyl, indolyl, isoindolyl, isoquinolinyl, phenylpyridyl, phthalazinyl, pyridyl, pyrimidinyl, quinazolinyl or quinolyl, that is unsubstituted or mono-, di- or trisubstituted independently of one another by $R^8$;
$R^3$ and $R^4$ as 25) is —$(C_0-C_3)$-alkylene-O—$CH_2$—$(C_1-C_3)$-perfluoroalkylene-$CH_2$—O—$(C_0-C_3)$-alkyl; and
$R^{10}$ and $R^{20}$ are independently of one another hydrogen, —$(C_1-C_6)$-alkyl or —$(C_1-C_3)$-perfluoroalkyl.

Another particular embodiment of the compound of formula I according to the invention is wherein
$R^0$ as 1) is phenyl, naphthyl, biphenylyl, anthryl or fluorenyl, that is mono-, di- or trisubstituted independently of one another by $R^8$,
  2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, that is unsubstituted or mono-, di- or trisubstituted independently of one another by $R^8$, or
  3) is acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 6H-1,5,2-dithiazinyl, furanyl, furazanyl, imidazolidinyl, dihydrofuro[2,3-b]tetrahydrofuranyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 1,4,5,6-tetrahydropyridazinyl, tetrahydropyridinyl, tetrahydrothiophenyl, tetrazinyl, tetrazolyl, 1,2,3-thiadiazolyl, 6H-1,2,5-thiadiazinyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl,
  that is unsubstituted or mono-, di- or trisubstituted independently of one another by $R^8$, and which is additionally substituted by acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 1,4,5,6-tetrahydropyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, that is unsubstituted or mono-, di- or trisubstituted independently of one another by $R^8$;
$R^1$ as —$(C_6-C_{14})$-aryl is phenyl, naphthyl, biphenylyl, anthryl or fluorenyl, that is mono-, di- or trisubstituted independently of one another by $R^8$, or
—$(C_0-C_3)$-alkylene-het, wherein the het is azepine, azetidine, aziridine, azirine, 1,4-diazapane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxazepane, 1,2-oxa-thiepane, 1,2-oxathiolane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, that is unsubstituted or mono-, di- or trisubstituted independently of one another by $R^{14}$, or V is 2) wherein the aryl is phenyl, naphthyl, biphenylyl, anthryl or fluorenyl, that is mono-, di- or trisubstituted independently of one another by $R^{14}$, or 4) wherein the heterocyclyl is acridinyl, azaindole, 1H-pyrrolopyridine, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 1,4-diazepane, 4,5-dihydrooxazolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisochinolinyl, tetrahydrochinolinyl, tetrahydropyridinyl, 1,4,5,6-tetrahydropyridazinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl or xanthenyl, that is unsubstituted or mono-, di- or trisubstituted independently of one another by $R^{14}$, $R^1$ and R3 together with the atoms to which they are bonded form azocane, azocane-2-one, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,2-oxazine, 1,3-oxazine, 1,4-oxazine, [1,4]oxazocane, [1,3]oxazocan-2-one, oxocane, oxocan-2-one, piperazine, piperidine, pyran, pyrazine, pyridazine, pyrimidine or 5,6,7,8-tetrahydro-1H-azocin-2-one, that is unsubstituted or mono-, di- or trisubstituted independently of one another by $R^{14}$, or $R^{14}$ as —($C_0$-$C_4$)-alkyl-het, then het is azetidine, azetidinone, piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,4-diazepane, 1,2-diazepine, 1,3-diazepine, 1,4-diazepine, azepine, ketopiperazine, 1,4-oxazepane, oxazole, isoxazole, isoxazolidine, 2-isoxazoline, morpholine, thiazole, isothiazole, thiadiazole or thiomorpholine;

M is 1) hydrogen,
2) —($C_1$-$C_8$)-alkyl, wherein alkyl is unsubstituted or mono-, di- or trisubstituted independently of one another by $R^{14}$,
3) —C(O)—N($R^{11}$)—$R^{12}$,
4) —($CH_2$)$_m$—$NR^{10}$,
5) —($C_6$-$C_{14}$)-aryl, wherein aryl is unsubstituted or mono-, di- or trisubstituted independently of one another by $R^{14}$,
6) —($C_4$-$C_{15}$)-heterocyclyl, wherein heterocyclyl is unsubstituted or mono-, di- or trisubstituted independently of one another by $R^{14}$, or
7) —($C_3$-$C_8$)-cycloalkyl, wherein said cycloalkyl is unsubstituted or mono-, di- or trisubstituted independently of one another by $R^{14}$, $R^3$ and $R^4$ as 5) —($C_0$-$C_4$)-alkylene-O—$R^{19}$, or
two —$OR^{19}$ residues and adjacent atoms through which they are attached form together a 5- or 6-membered ring, that is unsubstituted or substituted one, two, three or four times by $R^{13}$;

$R^{11}$ and $R^{12}$ together with the nitrogen atom to which they are bonded form azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, 1,4-oxazepine, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, that is unsubstituted or mono-, di- or trisubstituted independently of one another by $R^{13}$; and $R^{15}$ and $R^{16}$ are independently of one another hydrogen, or together with the carbon atom to which they are bonded form —($C_1$-$C_6$)-alkyl, cyclopropyl, cyclobutyl, cyclopentyl or cyclohexyl, wherein each ring is unsubstituted or substituted one to three times by $R^{10}$.

Another particular embodiment of the compound of formula I according to the invention is wherein $R^0$ as 1) is phenyl, naphthyl, biphenyl, anthryl or fluorenyl, that is mono-, di- or trisubstituted independently of one another by $R^8$,
2) is benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, that is unsubstituted or mono-, di- or trisubstituted independently of one another by $R^8$, or
3) is azabenzimidazolyl, benzimidazolyl, 1,3-benzodioxolyl, benzofuranyl, benzothiazolyl, benzothiophenyl, benzoxazolyl, chromanyl, cinnolinyl, 2-furyl, 3-furyl; imidazolyl, indolyl, indazolyl, isochromanyl, isoindolyl, isoquinolinyl, isothiazolyl, isoxazolyl, oxazolyl, phthalazinyl, pteridinyl, purinyl, pyrazinyl, pyrazolyl, pyridazinyl, pyridoimidazolyl, pyridopyridinyl, pyridopyrimidinyl, 2-pyridyl, 3-pyridyl, 4-pyridyl, pyrimidinyl, pyrrolyl; 2-pyrrolyl, 3-pyrrolyl, quinolinyl, quinazolinyl, quinoxalinyl, tetrazolyl, thiazolyl, 2-thienyl or 3-thienyl, which is additionally substituted by a heterocyclyl selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro furanyl, tetrahydroisochinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl and xanthenyl, that is unsubstituted or mono-, di- or trisubstituted independently of one another by $R^8$;

$R^8$ as 1. is fluorine, chlorine or bromine,
provided that $R^8$ is at least one halogen, —C(O)—NH$_2$ or —O—(C$_1$-C$_8$)-alkyl;

Q is direct bond, —(C$_0$-C$_2$)-alkylene-C(O)—NR$^{10}$—, —NR$^{10}$—C(O)—NR$^{10}$—, —NR$^{10}$, —C(O)—, —SO$_2$— or —(C$_1$-C$_6$)-alkylene;

$R^1$ is hydrogen, —(C$_1$-C$_4$)-alkyl, wherein alkyl is unsubstituted or substituted one to three times by $R^{13}$; —(C$_1$-C$_3$)-alkylene-C(O)—NH—R$^0$, —(C$_1$-C$_3$)-alkylene-C(O)—O—R$^{10}$, —(C$_1$-C$_3$)-perfluoroalkyl, —(C$_1$-C$_3$)-alkylene-S(O)—(C$_1$-C$_4$)-alkyl, —(C$_1$-C$_3$)-alkylene-S(O)$_2$—(C$_1$-C$_3$)-alkyl, —(C$_1$-C$_3$)-alkylene-S(O)$_2$—N(R$^{4'}$)—R$^{5'}$, —(C$_1$-C$_3$)-alkylene-O—(C$_1$-C$_4$)-alkyl, —(C$_0$-C$_3$)-alkylene-(C$_3$-C$_8$)-cycloalkyl, or —(C$_0$-C$_3$)-alkylene-het, wherein het is azepine, azetidine, aziridine, azirine, 1,4-diazepane, 1,2-diazepine, 1,3-diazepine, 1,4-diazepine, diaziridine, diazirine, dioxazole, dioxazine, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,4-oxazepine, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, that is unsubstituted or mono-, di- or trisubstituted independently of one another by $R^{14}$, or V is 3) wherein the 4- to 15-membered heterocyclyl is azaindole, 1H-pyrrolopyridine, azepine, azetidine, aziridine, azirine, 1,4-diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine, thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, that is unsubstituted or mono-, di- or trisubstituted independently of one another by $R^{14}$, or 2) phenyl, that is unsubstituted or mono-, di- or trisubstituted independently of one another by $R^{14}$; or $R^1$—N—$R^2$—V form azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2-triazine, 1,2,4-triazine, 1,3,5-triazine, 1,2,3-triazole or 1,2,4-triazole, that is unsubstituted or mono-, di- or trisubstituted independently of one another by $R^{14}$;

$R^{14}$ is fluorine, chlorine, bromine, iodine, —OH, =O, —(C$_1$-C$_8$)-alkyl, —(C$_1$-C$_4$)-alkoxy, —NO$_2$, —C(O)—OH, —CN, —NH$_2$, —C(O)—O—(C$_1$-C$_4$)-alkyl, —(C$_1$-C$_8$)-alkylsulfonyl, —SO$_2$—N—(R$^{18}$)—R$^{21}$, —C(O)—NH—(C$_1$-C$_8$)-alkyl, —C(O)—N—[(C$_1$-C$_8$)-alkyl]$_2$, —NR$^{18}$—C(O)—NH—(C$_1$-C$_8$)-alkyl, —C(O)—NH$_2$, —S—R$^{18}$, or —NR$^{18}$—C(O)—NH—[(C$_1$-C$_8$)-alkyl]$_2$,
wherein $R^{18}$ and $R^{21}$ are independently from each other hydrogen atom, —(C$_1$-C$_3$)-perfluoroalkyl or —(C$_1$-C$_6$)-alkyl;

M is 1) hydrogen,
2) —(C$_1$-C$_8$)-alkyl, wherein alkyl is unsubstituted or mono-, di- or trisubstituted independently of one another by $R^{14}$,
3) —C(O)—N(R$^{11}$)—R$^{12}$,
4) —(CH$_2$)$_m$—NR$^{10}$,
5) phenyl or naphthyl, wherein phenyl or naphthyl are unsubstituted or mono-, di- or trisubstituted independently of one another by $R^{14}$, 6) heterocyclyl, which is azepane, azepine, 1,4-diazepane, 1,2-diazepine, 1,3-diazepine, 1,4-diazepine, imidazole, isothiazole, isoxazole, isoxazolidine, 2-isoxazoline, ketomorpholine, ketopiperazine, morpholine, oxazole, [1,4]-oxazepane, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydro-pyridazinyl, tetrazine, tetrazole, thiadiazole, thiazole, thiophene, thiomorpholine, 1,2,3-triazine, 1,2,4-triazine, 1,3,5-triazine, 1,2,3-triazole or 1,2,4-triazole, wherein said heterocyclyl is unsubstituted or mono-, di- or trisubstituted independently of one another by $R^{14}$, or 7) —($C_8$-$C_9$)-cycloalkyl, wherein said cycloalkyl is unsubstituted or mono-, di- or trisubstituted independently of one another by $R^{14}$, $R^3$ and $R^4$ are independent of one another are identical or different and are 1) hydrogen,
2) halogen,
3) —($C_1$-$C_4$)-alkyl, wherein alkyl is unsubstituted or mono-, di- or trisubstituted independently of one another by $R^{13}$,
4) —($C_1$-$C_3$)-perfluoroalkyl,
5) phenyl, wherein phenyl is unsubstituted or mono-, di- or trisubstituted independently of one another by $R^{13}$,
6) —($C_0$-$C_4$)-alkylene-O—$R^{19}$, wherein $R^{19}$ is
   a) hydrogen,
   b) —($C_1$-$C_4$)-alkyl, wherein alkyl is unsubstituted or mono-, di- or trisubstituted independently of one another by $R^{13}$, or
   c) phenyl, wherein phenyl is unsubstituted or mono-, di- or trisubstituted independently of one another by $R^{13}$,
   d) —$CF_3$, or
   e) —$CHF_2$,
8) —CN,
9) —$SO_s$—$R^{11}$, wherein s is 1 or 2,
10) —$SO_t$—N($R^{11}$)—$R^{12}$, wherein t is 1 or 2,
11) —($C_0$-$C_4$)-alkylene-C(O)—$R^{11}$,
12) —($C_0$-$C_4$)-alkylene-C(O)—O—$R^{11}$,
13) —($C_0$-$C_4$)-alkylene-C(O)—N($R^{11}$)—$R^{12}$,
14) —($C_0$-$C_4$)-alkylene-N($R^1$)—$R^{12}$,
15) —$NR^{10}$—$SO_2$—$R^{10}$,
17) —($C_0$-$C_2$)alkylene-C(O)—O—($C_2$-$C_4$)-alkylene-O—C(O)—($C_1$-$C_4$)-alkyl,
18) —C(O)—O—C($R^{15}$,$R^{16}$)—O—C(O)—$R^{17}$,
19) —($C_0$-$C_2$)alkylene-C(O)—O—($C_2$-$C_4$)-alkylene-O—C(O)—O—($C_1$-$C_6$)-alkyl,
20) —C(O)—O—C($R^{15}$,$R^{16}$)—O—C(O)—O—$R^{17}$,
21) —($C_0$-$C_4$)-alkylene-($C_6$-$C_{14}$)-aryl, wherein aryl is mono-, di- or trisubstituted independently of one another by $R^{13}$,
23) —($C_0$-$C_4$)-alkylene-($C_3$-$C_8$)-cycloalkyl, wherein cycloalkyl is unsubstituted or mono-, di- or trisubstituted independently of one another by $R^{13}$,
25) —($C_0$-$C_3$)-alkylene-O—$CH_2$—$CF_2$—$CH_2$—O—($C_0$-$C_3$)-alkyl, —($C_0$-$C_3$)-alkylene-O—$CH_2$—$CF_2$—$CF_2$—$CH_2$—O—($C_0$-$C_3$)-alkyl, or —($C_0$-$C_3$)-alkylene-O—$CH_2$—($C_1$-$C_3$)-perfluoroalkylene-$CH_2$—OH, or 26) residue selected from the group consisting of

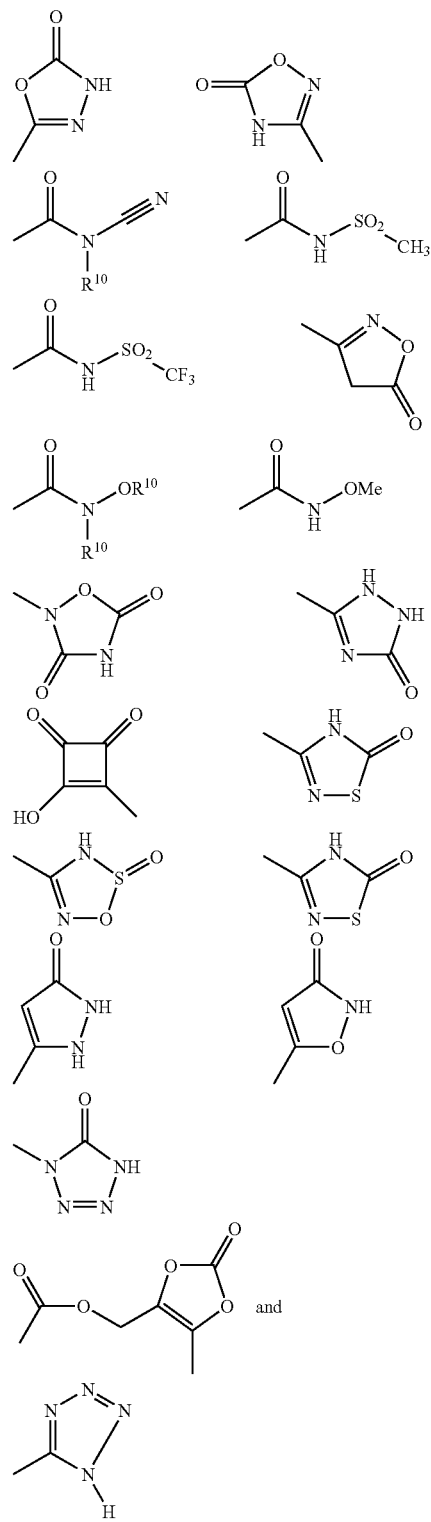

wherein Me is methyl, or two —$OR^{19}$ residues and adjacent atoms through which they are attached form together a 5- or 6-membered ring, that is unsubstituted or substituted one, two, three or four times by $R^{13}$;

$R^{11}$ and $R^{12}$ are independently of one another identical or different and are
1) hydrogen,
2) —$(C_1-C_6)$-alkyl, wherein alkyl is unsubstituted or mono-, di- or trisubstituted independently of one another by $R^{13}$,
5) —$(C_0-C_6)$-alkyl-$(C_6-C_{14})$-aryl, wherein alkyl and aryl independently from one another are unsubstituted or mono-, di- or trisubstituted by $R^{13}$,
7) —O—$R^{17}$, or
8) —$(C_0-C_6)$-alkyl-$(C_4-C_{15})$-heterocyclyl, wherein alkyl and heterocyclyl independently from one another are unsubstituted or mono-, di- or trisubstituted by $R^{13}$, or $R^{11}$ and $R^{12}$ together with the nitrogen atom to which they are bonded form azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, 1,4-oxazepine, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, that is unsubstituted or mono-, di- or trisubstituted independently of one another by $R^{13}$;

$R^{13}$ is fluorine, chlorine, bromine, iodine, —$NO_2$, —CN, =O, —OH, —$CF_3$, —C(O)—O—$R^{10}$, —C(O)—N($R^{10}$)—$R^{20}$, —N($R^{10}$)—$R^{20}$, —$(C_0-C_3)$-alkylene-O—$R^{10}$, —Si—$(CH_3)_3$, —N($R^{10}$)—S(O)$_2$—$R^{10}$, —S—$R^{10}$, —$SO_2$—$R^{10}$, —S(O)$_2$—N($R^{10}$)—$R^{20}$, —C(O)—$R^{10}$, —$(C_1-C_8)$-alkyl, —$(C_1-C_8)$-alkoxy, phenyl, phenyloxy-, —O—$CF_3$, —$(C_1-C_3)$-perfluoroalkyl, —$(C_0-C_4)$-alkyl-C(O)—O—C($R^{15},R^{16}$)—O—C(O)—$R^{17}$, —$(C_1-C_4)$-alkoxy-phenyl, —$(C_0-C_4)$-alkyl-C(O)—O—C($R^{15}$,$R^{16}$)—O—C(O)—O—$R^{17}$, —O—$R^{15}$, —NH—C(O)—NH—$R^{10}$, —NH—C(O)—O—$R^{10}$, or residue selected from the group consisting of

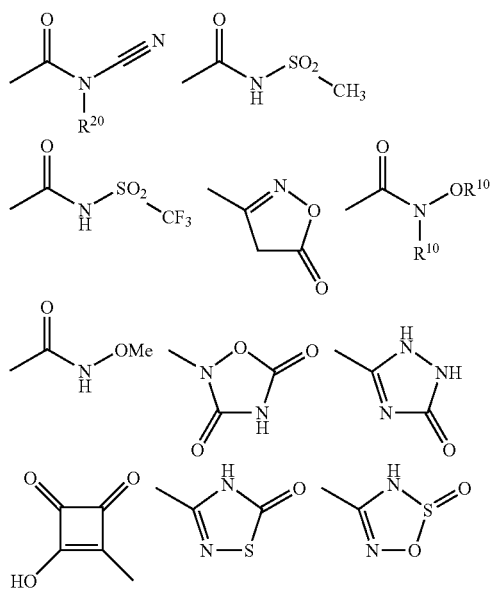

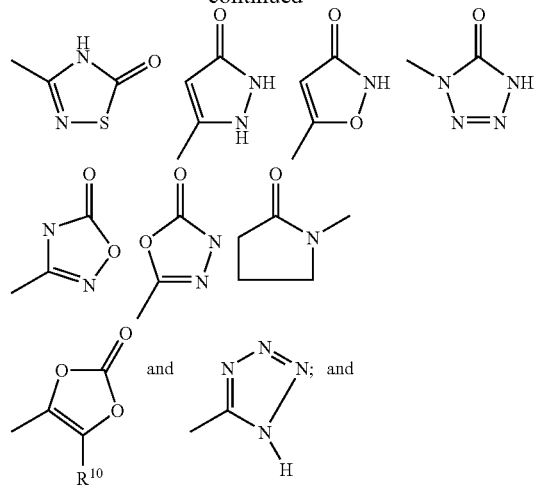

$R^{15}$ and $R^{16}$ are independently of one another hydrogen, or together with the carbon atom to which they are bonded form —$(C_1-C_6)$-alkyl, or together form cyclopropyl, cyclobutyl, cyclopentyl or cyclohexyl, that is unsubstituted or substituted one to three times by $R^{10}$.

Another particular embodiment of the compound of formula I according to the invention is wherein $R^0$ as 1) is phenyl, that is unsubstituted or mono-, di- or trisubstituted independently of one another by $R^8$,
2) is benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridinyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, that is unsubstituted or mono-, di- or trisubstituted independently of one another by $R^8$, or
3) is heterocyclyl, which is pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said heterocyclyl is unsubstituted or mono-, di- or trisubstituted independently of one another by $R^8$,
and in addition is substituted by a residue selected out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl or pyrazinyl, that is unsubstituted or mono-, di- or trisubstituted independently of one another by $R^8$;

$R^8$ is 1. F, Cl, Br or I,
4. —C(O)—$NH_2$,
9. —$(C_1-C_4)$-alkyl, wherein alkyl is unsubstituted or mono-, di- or trisubstituted independently of one another by halogen, —OH or methoxy, or
10. —O—$(C_1-C_4)$-alkyl, wherein alkyl is unsubstituted or mono-, di- or trisubstituted independently of one another by halogen or methoxy, provided that $R^8$ is at least one halogen, —C(O)—$NH_2$ or —O—$(C_1-C_8)$-alkyl;

Q is direct bond, —C(O)—, —$SO_2$—, —$(C_1-C_6)$-alkylene, or —$(C_0-C_2)$-alkylene-C(O)—$NR^{10}$—;

$R^1$ is hydrogen, —$(C_1-C_2)$-alkyl, —$(C_1-C_3)$-alkylene-C(O)—NH—$R^{10}$, —$(C_1-C_3)$-perfluoroalkyl, —$(C_1-C_3)$-alkylene-C(O)—O—$R^{10}$, —$(C_1-C_3)$-alkylene-S(O)$_2$—$(C_1-C_3)$-alkyl or —$(C_1-C_3)$-alkylene-S(O)$_2$—N($R^{4'}$)—$R^{5'}$, wherein $R^{4'}$ and $R^{5'}$ are independent of one another are identical or different and are hydrogen or —$(C_1-C_4)$-alkyl;

V is 1. wherein the 3- to 7-membered cyclic residue is azaindole, 1H-pyrrolopyridine, aziridine, azirine, azetidine, azetidinone, 1,4-diazepane, pyrrole, pyrrolidine, pyridonyl, imidazole, pyrazole, 1,2,3-triazole, 1,2,4-triazole, tetrazole, pyridine, pyrimidine, pyrazine, 1,2,3-triazine, 1,2,4-triazine, 1,3,5-triazine, tetrazine, tetrazole, azepine, diazirine, 1,2-diazepine, 1,3-diazepine, 1,4-diazepine, pyridazine, piperidine, piperazine, pyrrolidinone, ketopiperazine, furan, pyran, dioxole, 1,4-oxazepane, 1,4-oxazepine, oxazole, isoxazole, 2-isoxazoline, isoxazolidine, morpholine, oxirane, oxaziridine, 1,3-dioxolene, 1,3-dioxolane, 1,2-oxazine, 1,3-oxazine, 1,4-oxazine, oxaziridine, thiophene, thiopyran, thietan, thiazole, isothiazole, isothiazoline, isothiazolidine, 1,2-oxathiolan, thiodiazole, thiopyran, 1,2-thiazine, 1,3-thiazole, 1,3-thiazine, 1,4-thiazine, thiadiazine or thiomorpholine,
that is unsubstituted or mono-, di- or trisubstituted independently of one another by $R^{14}$, or
2. wherein, the aryl is phenyl that is unsubstituted or mono-, di- or trisubstituted
independently of one another by $R^{14}$, or $R^1$—N—$R^2$—V forms azetidine, azetidinone, piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,4-diazepane, 1,2-diazepine, 1,3-diazepine, 1,4-diazepine, azepine, ketopiperazine, 1,4-oxazepane, oxazole, isoxazole, isoxazolidine, 2-isoxazoline, morpholine, thiazole, isothiazole, thiadiazole or thiomorpholine, that is unsubstituted or mono-, di- or trisubstituted independently of one another by $R^{14}$, $R^{14}$ is fluorine, chlorine, —OH, =O, —$(C_1-C_8)$-alkyl, —C(O)—OH, —CN, —NH$_2$, —C(O)—O—$(C_1-C_4)$-alkyl, —C(O)—NH—$(C_1-C_8)$-alkyl, —C(O)—N—[$(C_1-C_8)$-alkyl]2, —C(O)—NH$_2$ or —N($R^{18}$)—$R^{21}$, wherein $R^{18}$ and $R^{21}$ are independently from each other hydrogen, —$(C_1-C_3)$-perfluoroalkyl or —$(C_1-C_4)$-alkyl;

G is direct bond, —(CH$_2$)$_m$—, or —(CH$_2$)$_m$—NR$^{10}$—;
m is zero, 1, 2, 3 or 4;
M is 1. hydrogen,
2. —$(C_1-C_6)$-alkyl, wherein alkyl is unsubstituted or mono-, di- or trisubstituted independently of one another by $R^{14}$,
3. —C(O)—N($R^{11}$)—$R^{12}$,
6. heterocyclyl, which is azepane, azepine, 1,4-diazepane, 1,2-diazepine, 1,3-diazepine, 1,4-diazepine, imidazole, isothiazole, isoxazole, isoxazolidine, 2-isoxazoline, ketomorpholine, ketopiperazine, morpholine, oxazole, [1,4]-oxazepane, 1,4-oxazepine, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydro-pyridazinyl, tetrazine, tetrazole, thiadiazole, thiazole, thiomorpholine, thiophene, 1,2,3-triazine, 1,2,4-triazine, 1,3,5-triazine, 1,2,3-triazole or 1,2,4-triazole, wherein said heterocyclyl is unsubstituted or mono-, di- or trisubstituted independently of one another by $R^{14}$, or
7. $(C_3-C_6)$-cycloalkyl;

$R^3$ and $R^4$ are independent of one another are identical or different and are
1) hydrogen,
2) halogen,
3) —$(C_1-C_4)$-alkyl, wherein alkyl is unsubstituted or mono-, di- or trisubstituted independently of one another by $R^{13}$,
4) —$(C_1-C_3)$-perfluoroalkyl,
5) phenyl, wherein phenyl is unsubstituted or mono-, di- or trisubstituted independently of one another by $R^{13}$,
6) —$(C_0-C_4)$-alkylene-O—$R^{19}$, wherein $R^{19}$ is
   a) hydrogen,
   b) —$(C_1-C_4)$-alkyl, wherein alkyl is unsubstituted or mono-, di- or trisubstituted independently of one another by $R^{13}$, or
   c) phenyl, wherein phenyl is unsubstituted or mono-, di- or trisubstituted independently of one another by $R^{13}$,
   d) —CF$_3$, or
   e) —CHF$_2$,
8) —CN,
9) —SO$_s$—$R^{11}$, wherein s is 1 or 2,
10) —SO$_t$—N($R^{11}$)—$R^{12}$, wherein t is 1 or 2,
11) —$(C_0-C_4)$-alkylene-C(O)—$R^{11}$,
12) —$(C_0-C_4)$-alkylene-C(O)—O—$R^{11}$,
13) —$(C_0-C_4)$-alkylene-C(O)—N($R^{11}$)—$R^{12}$,
14) —$(C_0-C_4)$-alkylene-N($R^{11}$)—$R^{12}$,
15) —NR$^{10}$—SO$_2$—$R^{10}$,
17) —$(C_0-C_2)$alkylene-C(O)—O—$(C_2-C_4)$-alkylene-O—C(O)—$(C_1-C_4)$-alkyl,
18) —C(O)—O—C($R^{15}R^{16}$)—O—C(O)—O—$R^{17}$,
19) —$(C_0-C_2)$alkylene-C(O)—O—$(C_2-C_4)$-alkylene-O—C(O)—O—$(C_1-C_6)$-alkyl,
20) —C(O)—O—C($R^{15},R^{16}$)—O—C(O)—$R^{17}$,
23) —$(C_0-C_4)$-alkylene-$(C_3-C_6)$-cycloalkyl, wherein cycloalkyl is unsubstituted or mono-, di- or trisubstituted independently of one another by $R^{13}$,
25) —$(C_0-C_3)$-alkylene-O—CH$_2$—CF$_2$—CH$_2$—O—$(C_0-C_3)$-alkyl, —$(C_0-C_3)$-alkylene-O—CH$_2$—CF$_2$—CF$_2$—CH$_2$—O—$(C_0-C_3)$-alkyl, or —$(C_0-C_3)$-alkylene-O—CH$_2$—$(C_1-C_3)$-perfluoroalkylene-CH$_2$—OH, or
26) residue selected from the group consisting of

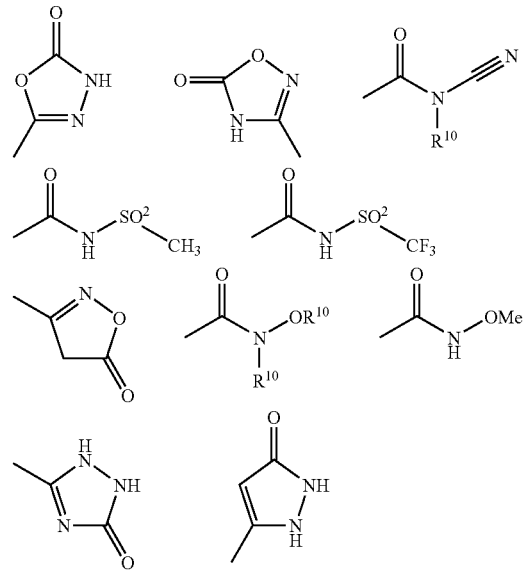

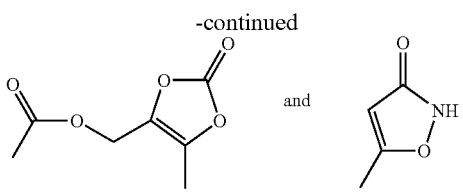

and wherein Me is methyl, or
two —OR$^{19}$ residues and adjacent atoms through which they are attached form together a 5- or 6-membered ring, that is unsubstituted or substituted one, two, three or four times by R$^{13}$;

R$^{11}$ and R$^{12}$ are independently of one another identical or different and are
1) hydrogen,
2) —(C$_1$-C$_6$)-alkyl, wherein alkyl is unsubstituted or mono-, di- or trisubstituted independently of one another by R$^{13}$,
5) —(C$_0$-C$_6$)-alkyl-(C$_6$-C$_{14}$)-aryl, wherein alkyl and aryl independently from one another are unsubstituted or mono-, di- or trisubstituted by R$^{13}$,
7) —O—R$^{17}$, or
8) —(C$_0$-C$_6$)-alkyl-(C$_4$-C$_{15}$)-heterocyclyl, wherein alkyl and heterocyclyl independently from one another are unsubstituted or mono-, di- or trisubstituted by R$^{13}$, or R$^{11}$ and R$^{12}$ together with the nitrogen atom to which they are bonded form azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]-oxazepane, 1,4-oxazepine, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, that is unsubstituted or mono-, di- or trisubstituted independently of one another by R$^{13}$, R$^{13}$ is fluorine, chlorine, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_0$-C$_3$)-alkylene-O—R$^{10}$, —Si—(CH$_3$)$_3$, —N(R$^{10}$)—S(O)$_2$—R$^{10}$, —S—R$^{10}$, —SO$_2$—R$^{10}$, —S(O)$_2$—N(R$^{10}$)—R$^{20}$, —C(O)—R$^{10}$, —(C$_1$-C$_8$)-alkyl, —(C$_1$-C$_8$)-alkoxy, phenyl, phenyloxy-, —O—CF$_3$, —(C$_1$-C$_3$)-perfluoroalkyl, —NH—C(O)—NH—R$^{10}$, —(C$_0$-C$_4$)-alkyl-C(O)—O—C(R$^{15}$, R$^{16}$)—O—C(O)—R$^{17}$, —(C$_1$-C$_4$)-alkoxy-phenyl, —(C$_0$-C$_4$)-alkyl-C(O)—O—C(R$^{15}$,R$^{16}$)—O—C(O)—O—R$^{17}$, —O—R$^{15}$, —NH—C(O)—O—R$^{10}$, or residue selected from the group consisting of

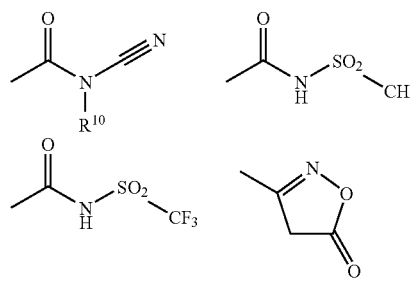

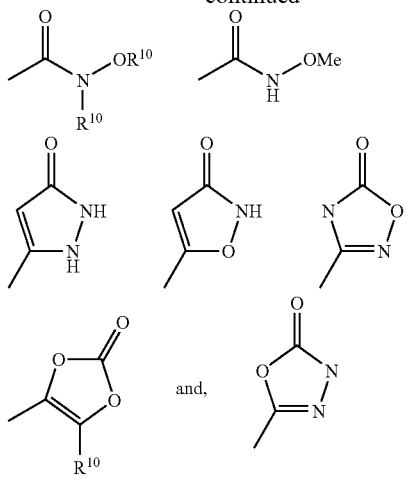

and, wherein Me is methyl.

Another particular embodiment of the compound of formula I according to the invention is wherein R$^0$ is 3) heterocyclyl which is pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said heterocyclyl is unsubstituted or mono-, di- or trisubstituted independently of one another by R$^8$,
and in addition is substituted by a residue selected out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl or pyrazinyl, that is unsubstituted or mono-, di- or trisubstituted independently of one another by R$^8$;

R$^8$ is 1. F, Cl, Br, or I,
4. —C(O)—NH$_2$,
9. —(C$_1$-C$_4$)-alkyl, wherein alkyl is unsubstituted or mono-, di- or trisubstituted independently of one another by halogen, —OH or methoxy, or
10. —O—(C$_1$-C$_4$)-alkyl, wherein alkyl is unsubstituted or mono-, di- or trisubstituted independently of one another by halogen or methoxy, provided that R$^8$ is at least one halogen, —C(O)—NH$_2$ or —O—(C$_1$-C$_8$)-alkyl;

Q is direct bond, —C(O)—, —SO$_2$— or —(C$_1$-C$_6$)-alkylen, —(C$_0$-C$_2$)-alkylen-C(O)—NR$^{16}$—;

R$^1$ is hydrogen or —(C$_1$-C$_2$)-alkyl;

R$^2$ is direct bond or as —(C$_1$-C$_4$)-alkylene is —(C$_1$-C$_2$)-alkylene, or V is 1. wherein the 3- to 7-membered cyclic residue is azaindolyl, azetidine, azepine, aziridine, azirine, 1,4-diazepane, 1,2-diazepine, 1,3-diazepine, 1,4-diazepine, diazirine, 1,3-dioxolane, dioxazole, furan, imidazole, isoquinoline, isothiazole, isothiazolidine, isothiazoline, isoxazole, 2-isoxazoline, isoxazolidine, ketopiperazine, morpholine, 1,2-oxazine, 1,3-oxazine, 1,4-oxazine, oxazole, 1,2-oxathiolan, piperidine, pyran, pyrazine, pyrazole, pyridazine, piperazine, pyridine, pyridone, pyrimidine, pyrrole, pyrrolidine, pyrrolidinone, quinazoline, quinoline, tetrazine, tetrazole, thiadiazine, 1,2-thiazine, 1,3-thiazine, 1,4-thiazine, 1,3-thiazole, thietan, thiomorpholine, thiophene, thiopyran, 1,2,3-triazine, 1,2,4-triazine, 1,3,5-triazine, 1,2,3-triazole or 1,2,4-triazole, that is unsubstituted or mono-, di- or trisubstituted independently of one another by $R^{14}$, or
2. wherein, the aryl is phenyl, that is unsubstituted or mono-, di- or trisubstituted
independently of one another by $R^{14}$;
$R^1$—N—$R^2$—V forms piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, thiadiazole or thiomorpholine, that is unsubstituted or mono-, di- or trisubstituted independently of one another by $R^{14}$;
$R^{14}$ is fluoro, chlorine, —($C_1$-$C_4$)-alkyl or —$NH_2$;
G is direct bond, —$(CH_2)_{m-1}$ or —$(CH_2)_m$—$NR^{10}$—;
m is zero, 1, 2, 3 or 4;
M is 1. hydrogen,
  2. —($C_1$-$C_6$)-alkyl, wherein alkyl is unsubstituted or mono-, di- or trisubstituted independently of one another by $R^{14}$,
  6. heterocyclyl, which is 1,4-diazepane, ketomorpholine, thiophene, pyridazone, piperidine, piperazine, pyridine, pyrimidine, pyrrolidine, pyrrolidinone, pyridonyl, imidazole, pyridazine, pyrazine, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, tetrahydropyran, 1,4,5,6-tetrahydro-pyridazinyl, thiadiazole or thiomorpholine, that is unsubstituted or mono-, di- or trisubstituted independently of one another by $R^{14}$, or
  7. ($C_3$-$C_6$)-cycloalkyl;
$R^3$ and $R^4$ are independent of one another are identical or different and are
  1) hydrogen,
  2) halogen,
  3) —($C_1$-$C_4$)-alkyl, wherein alkyl is unsubstituted or mono-, di- or trisubstituted independently of one another by $R^{13}$,
  4) —($C_1$-$C_3$)-perfluoroalkyl,
  5) phenyl, wherein phenyl is unsubstituted or mono-, di- or trisubstituted independently of one another by $R^{13}$,
  6) —($C_0$-$C_4$)-alkylene-O—$R^{19}$, wherein $R^{19}$ is
     a) hydrogen,
     b) —($C_1$-$C_4$)-alkyl, wherein alkyl is unsubstituted or mono-, di- or trisubstituted independently of one another by $R^{13}$, or
     c) phenyl, wherein phenyl is unsubstituted or mono-, di- or trisubstituted independently of one another by $R^{13}$,
     d) —$CF_3$, or
     e) —$CHF_2$,
  8) —CN,
  9) —$SO_s$—$R^{11}$, wherein s is 1 or 2,
  10) —$SO_t$—N($R^{11}$)—$R^{12}$, wherein t is 1 or 2,
  11) —($C_0$-$C_4$)-alkylene-C(O)—$R^1$,
  12) —($C_0$-$C_4$)-alkylene-C(O)—O—$R^{11}$,
  13) —($C_0$-$C_4$)-alkylene-C(O)—N($R^{11}$)—$R^{12}$,
  14) —($C_0$-$C_4$)-alkylene-N($R^1$)—$R^{12}$,
  15) —$NR^{10}$—$SO_2$—$R^{10}$,
  17) —($C_0$-$C_2$)alkylene-C(O)—O—($C_2$-$C_4$)-alkylene-O—C(O)—($C_1$-$C_4$)-alkyl,
  18) —C(O)—O—C($R^{15}$,$R^{16}$)—O—C(O)—$R^{17}$,
  19) —($C_0$-$C_2$)alkylene-C(O)—O—($C_2$-$C_4$)-alkylene-O—C(O)—O—($C_1$-$C_6$)-alkyl,
  20) —C(O)—O—C($R^{15}R^{16}$)—O—C(O)—O—$R^{17}$,
  23) —($C_0$-$C_3$)-alkylene-($C_3$-$C_6$)-cycloalkyl, or —($C_0$-$C_4$)-alkylene-($C_3$-$C_6$)-cycloalkyl, wherein cycloalkyl is unsubstituted or mono-, di- or trisubstituted independently of one another by $R^{13}$,
  25) —($C_0$-$C_3$)-alkylene-O—$CH_2$—$CF_2$—$CH_2$—O—($C_0$-$C_3$)-alkyl, —($C_0$-$C_3$)-alkylene-O—$CH_2$—$CF_2$—$CF_2$—$CH_2$—O—($C_0$-$C_3$)-alkyl, or —($C_0$-$C_3$)-alkylene-O—$CH_2$—($C_1$-$C_3$)-perfluoroalkylene-$CH_2$—OH, or
  26) residue selected from the group consisting of wherein Me is methyl;
$R^{11}$ and $R^{12}$ are independently of one another identical or different and are
  1) hydrogen,
  2) —($C_1$-$C_4$)-alkyl, wherein alkyl is unsubstituted or mono-, di- or trisubstituted independently of one another by $R^{13}$,
  3) —($C_0$-$C_6$)-alkyl-($C_3$-$C_6$)-cycloalkyl,
  7) —O—$R^{17}$, or
  8) —($C_0$-$C_6$)-alkyl-($C_4$-$C_{15}$)-heterocyclyl, wherein alkyl and heterocyclyl independently from one another are unsubstituted or mono-, di- or trisubstituted by $R^{13}$ and wherein heterocyclyl is selected out of the group azetidine, cyclopropyl, cyclobutyl, 4,5-dihydrooxazole, imidazolidine, morpholine, (1,4)-oxazepane, oxazolidine, piperidine, piperazine, pyrrolidine, tetrahydrothiophene, thiazolidine or thiomorpholine, or
$R^{11}$ and $R^{12}$ together with the nitrogen atom to which they are bonded form azetidine, cyclopropyl, cyclobutyl, 4,5-dihydrooxazole, imidazolidine, morpholine, (1,4)-oxazepane, 1,4-oxazepine, oxazolidine, piperidine, piperazine, pyrrolidine, tetrahydrothiophene, thiazolidine or thiomorpholine;
$R^{13}$ is fluorine, —CN, =O, —OH, —$CF_3$, —C(O)—O—$R^{10}$, —C(O)—N($R^{10}$)—$R^{20}$, —N($R^{10}$)—$R^{20}$, —($C_3$-$C_6$)-cycloalkyl, —($C_0$-$C_3$)-alkylene-O—$R^{10}$, —Si—$(CH_3)_3$, —S—$R^{10}$, —$SO_2$—$R^{10}$, —($C_1$-$C_3$)-perfluoroalkyl, or residue selected from the group consisting of wherein Me is methyl;

$R^{10}$ and $R^{20}$ are independently of one another hydrogen, —($C_1$-$C_4$)-alkyl or —($C_1$-$C_3$)-perfluoroalkyl;

$R^{15}$ and $R^{16}$ are independently of one another hydrogen, —($C_1$-$C_4$)-alkyl, or together with the carbon atom to which they are bonded form cyclopropyl, cyclobutyl, cyclopentyl or cyclohexyl, that is unsubstituted or substituted one to three times by $R^{10}$.

Another particular embodiment of the compound of formula I according to the invention is wherein $R^0$ is phenyl, wherein phenyl is unsubstituted or mono- or disubstituted independently of one another by $R^8$, $R^8$ is 1. F, Cl, Br, or I,
  4. —C(O)—$NH_2$,
  9. —($C_1$-$C_4$)-alkyl, wherein alkyl is unsubstituted or mono-, di- or trisubstituted independently of one another by halogen, —OH or methoxy, or
  10. —O—($C_1$-$C_4$)-alkyl, wherein alkyl is unsubstituted or mono-, di- or trisubstituted independently of one another by halogen or methoxy, provided that $R^8$ is at least one halogen, —C(O)—$NH_2$ or —O—($C_1$-$C_8$)-alkyl;

Q is direct bond, —C(O)—, —$SO_2$— or —($C_1$-$C_6$)-alkylen, —($C_0$-$C_2$)-alkylen-C(O)—$NR^{10}$—;

$R^1$ is hydrogen or —($C_1$-$C_2$)-alkyl;

$R^2$ is direct bond or as —($C_1$-$C_4$)-alkylene is —($C_1$-$C_2$)-alkylene, or V is 1. wherein the 3- to 7-membered cyclic residue is azaindolyl, 1H-pyrrolopyridyl, azetidine, azepine, aziridine, azirine, 1,4-diazepane, 1,2-diazepine, 1,3-diazepine, 1,4-diazepine, diazirine, 1,3-dioxolane, dioxazole, furan, imidazole, isoquinoline, isothiazole, isothiazolidine, isothiazoline, isoxazole, 2-isoxazoline, isoxazolidine, ketopiperazine, morpholine, 1,2-oxazine, 1,3-oxazine, 1,4-oxazine, oxazole, 1,2-oxathiolan, piperidine, pyran, pyrazine, pyrazole, pyridazine, piperazine, pyridine, pyridone, pyrimidine, pyrrole, pyrrolidine, pyrrolidinone, quinazoline, quinoline, tetrazine, tetrazole, thiadiazine, 1,2-thiazine, 1,3-thiazine, 1,4-thiazine, 1,3-thiazole, thietan, thiomorpholine, thiophene, thiopyran, 1,2,3-triazine, 1,2,4-triazine, 1,3,5-triazine, 1,2,3-triazole or 1,2,4-triazole, that is unsubstituted or mono-, di- or trisubstituted independently of one another by $R^{14}$, or
  2. wherein, the aryl is phenyl, that is unsubstituted or mono-, di- or trisubstituted independently of one another by $R^{14}$;

$R^1$—N—$R^2$—V forms piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, thiadiazole or thiomorpholine, that is unsubstituted or mono-, di- or trisubstituted independently of one another by $R^{14}$;

$R^{14}$ is fluoro, chlorine, —($C_1$-$C_4$)-alkyl or —$NH_2$;

G is direct bond, —($CH_2$)$_{m-1}$ or —($CH_2$)$_m$—$NR^{10}$—;

m is zero, 1, 2, 3 or 4;

M is 1. hydrogen,
  2. —($C_1$-$C_6$)-alkyl, wherein alkyl is unsubstituted or mono-, di- or trisubstituted independently of one another by $R^{14}$,
  6. heterocyclyl, which is 1,4-diazepane, ketomorpholine, thiophene, pyridazone, piperidine, piperazine, pyridine, pyrimidine, pyrrolidine, pyrrolidinone, pyridonyl, imidazole, pyridazine, pyrazine, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, tetrahydropyran, 1,4,5,6-tetrahydro-pyridazinyl, thiadiazole or thiomorpholine, that is unsubstituted or mono-, di- or trisubstituted independently of one another by $R^{14}$, or
  7. ($C_3$-$C_6$)-cycloalkyl;

$R^3$ and $R^4$ are independent of one another are identical or different and are
1) hydrogen,
2) halogen,
3) —($C_1$-$C_4$)-alkyl, wherein alkyl is unsubstituted or mono-, di- or trisubstituted independently of one another by $R^{13}$,
4) —($C_1$-$C_3$)-perfluoroalkyl,
5) phenyl, wherein phenyl is unsubstituted or mono-, di- or trisubstituted independently of one another by $R^{13}$,
6) —($C_0$-$C_4$)-alkylene-O—$R^{19}$, wherein $R^{19}$ is
  a) hydrogen,
  b) -($C_1$-$C_4$)-alkyl, wherein alkyl is unsubstituted or mono-, di- or trisubstituted independently of one another by $R^{13}$, or
  c) phenyl, wherein phenyl is unsubstituted or mono-, di- or trisubstituted independently of one another by $R^{13}$,
  d) —$CF_3$, or
  e) —$CHF_2$,
8) —CN,
9) —$SO_s$—$R^{11}$, wherein s is 1 or 2,
10) —$SO_t$—N($R^{11}$)—$R^{12}$, wherein t is 1 or 2,
11) —($C_0$-$C_4$)-alkylene-C(O)—$R^{11}$,
12) —($C_0$-$C_4$)-alkylene-C(O)—O—$R^{11}$,
13) —($C_0$-$C_4$)-alkylene-C(O)—N($R^{11}$)—$R^{12}$, 14) —(C$_0$-C$_4$)-alkylene-N(R$^1$)—R$^{12}$,
15) —NR$^{10}$—SO$_2$—R$^{10}$,
17) —(C$_0$-C$_2$)alkylene-C(O)—O—(C$_2$-C$_4$)-alkylene-O—C(O)—(C$_1$-C$_4$)-alkyl,
18) —C(O)—O—C(R$^{15}$,R$^{16}$)—O—C(O)—R$^{17}$,
19) —(C$_0$-C$_2$)alkylene-C(O)—O—(C$_2$-C$_4$)-alkylene-O—C(O)—O—(C$_1$-C$_6$)-alkyl,
20) —C(O)—O—C(R$^{15}$R$^{16}$)—O—C(O)—O—R$^{17}$,
23) —(C$_0$-C$_3$)-alkylene-(C$_3$-C$_6$)-cycloalkyl, or —(C$_0$-C$_4$)-alkylene-(C$_3$-C$_6$)-cycloalkyl, wherein cycloalkyl is unsubstituted or mono-, di- or trisubstituted independently of one another by R$^{13}$,
25) —(C$_0$-C$_3$)-alkylene-O—CH$_2$—CF$_2$—CH$_2$—O—(C$_0$-C$_3$)-alkyl, —(C$_0$-C$_3$)-alkylene-O—CH$_2$—CF$_2$—CF$_2$—CH$_2$—O—(C$_0$-C$_3$)-alkyl, or —(C$_0$-C$_3$)-alkylene-O—CH$_2$—(C$_1$-C$_3$)-perfluoroalkylene-CH$_2$—OH, or
26) residue selected from the group consisting of

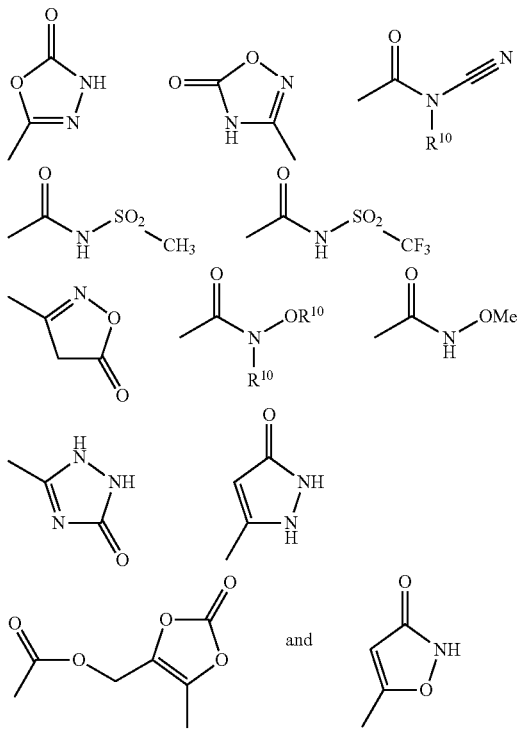

wherein Me is methyl;
R$^{11}$ and R$^{12}$ are independently of one another identical or different and are
1) hydrogen,
2) —(C$_1$-C$_4$)-alkyl, wherein alkyl is unsubstituted or mono-, di- or trisubstituted independently of one another by R$^{13}$,
3) —(C$_0$-C$_6$)-alkyl-(C$_3$-C$_6$)-cycloalkyl,
7) —O—R$^{17}$, or
8) —(C$_0$-C$_6$)-alkyl-(C$_4$-C$_{15}$)-heterocyclyl, wherein alkyl and heterocyclyl independently from one another are unsubstituted or mono-, di- or trisubstituted by R$^{13}$ and wherein heterocyclyl is selected out of the group azetidine, cyclopropyl, cyclobutyl, 4,5-dihydrooxazole, imidazolidine, morpholine, (1,4)-oxazepane, oxazolidine, piperidine, piperazine, pyrrolidine, tetrahydrothiophene, thiazolidine or thiomorpholine, or
R$^{11}$ and R$^{12}$ together with the nitrogen atom to which they are bonded form azetidine, cyclopropyl, cyclobutyl, 4,5-dihydrooxazole, imidazolidine, morpholine, (1,4)-oxazepane, 1,4-oxazepine, oxazolidine, piperidine, piperazine, pyrrolidine, tetrahydrothiophene, thiazolidine or thiomorpholine;
R$^{13}$ is fluorine, —CN, =O, —OH, —CF$_3$, —C(O)—O—R$^{10}$, —C(O)—N(R$^{10}$)—R$^{20}$, —N(R$^{10}$)—R$^{20}$,
—(C$_3$-C$_6$)-cycloalkyl, —(C$_0$-C$_3$)-alkylene-O—R$^{10}$,
—Si—(CH$_3$)$_3$, —S—R$^{10}$, —SO$_2$—R$^{10}$,
—(C$_1$-C$_3$)-perfluoroalkyl, or residue selected from the group consisting of

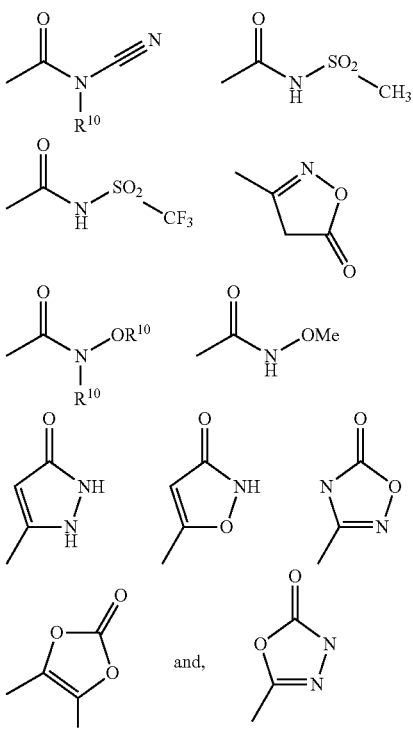

wherein Me is methyl;
R$^{10}$ and R$^{20}$ are independently of one another hydrogen, —(C$_1$-C$_4$)-alkyl or —(C$_1$-C$_3$)-perfluoroalkyl;
R$^{15}$ and R$^{16}$ are independently of one another hydrogen, —(C$_1$-C$_4$)-alkyl, or together with the carbon atom to which they are bonded form cyclopropyl, cyclobutyl, cyclopentyl or cyclohexyl, that is unsubstituted or substituted one to three times by R$^{10}$.

Another particular embodiment of the compound of formula I according to the invention is wherein
R$^0$ is 2) heterocyclyl selected from the group consisting of indolyl, isoindolyl, benzofuranyl, benzothiophenyl, 1,3-benzodioxolyl, indazolyl, benzimidazolyl, benzoxazolyl, benzothiazolyl, quinolinyl, isoquinolinyl, chromanyl, isochromanyl, cinnolinyl, quinazolinyl, quinoxalinyl, phthalazinyl, pyridoimidazolyl, pyridopyridinyl, pyridopyrimidinyl, pyridinyl, purinyl and pteridinyl,
wherein said heterocyclyl is unsubstituted or mono-, di- or trisubstituted independently of one another by R$^8$,
R$^8$ is 1. F, Cl, Br, or I,
4. —C(O)—NH$_2$,
9. —(C$_1$-C$_4$)-alkyl, wherein alkyl is unsubstituted or mono-, di- or trisubstituted independently of one another by halogen, —OH or methoxy, or 10. —O—($C_1$-$C_4$)-alkyl, wherein alkyl is unsubstituted or mono-, di- or trisubstituted independently of one another by halogen or methoxy, provided that $R^8$ is at least one halogen, —C(O)—$NH_2$ or —O—($C_1$-$C_8$)-alkyl;

Q is direct bond, —C(O)—, —$SO_2$— or —($C_1$-$C_6$)-alkylen, —($C_0$-$C_2$)-alkylen-C(O)—$NR^{10}$—;

$R^1$ is hydrogen or —($C_1$-$C_2$)-alkyl;

$R^2$ is direct bond or as —($C_1$-$C_4$)-alkylene is —($C_1$-$C_2$)-alkylene, or V is 1. wherein the 3- to 7-membered cyclic residue is azaindolyl, azetidine, azepine, aziridine, azirine, 1,4-diazepane, 1,2-diazepine, 1,3-diazepine, 1,4-diazepine, diazirine, 1,3-dioxolane, dioxazole, furan, imidazole, isoquinoline, isothiazole, isothiazolidine, isothiazoline, isoxazole, 2-isoxazoline, isoxazolidine, ketopiperazine, morpholine, 1,2-oxazine, 1,3-oxazine, 1,4-oxazine, oxazole, 1,2-oxathiolan, piperidine, pyran, pyrazine, pyrazole, pyridazine, piperazine, pyridine, pyridone, pyrimidine, pyrrole, pyrrolidine, pyrrolidinone, quinazoline, quinoline, tetrazine, tetrazole, thiadiazine, 1,2-thiazine, 1,3-thiazine, 1,4-thiazine, 1,3-thiazole, thietan, thiomorpholine, thiophene, thiopyran, 1,2,3-triazine, 1,2,4-triazine, 1,3,5-triazine, 1,2,3-triazole or 1,2,4-triazole, that is unsubstituted or mono-, di- or trisubstituted independently of one another by $R^{14}$, or 2. aryl is phenyl, that is unsubstituted or mono-, di- or trisubstituted independently of one another by $R^{14}$;

$R^1$—N—$R^2$—V forms piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, thiadiazole or thiomorpholine, that is unsubstituted or mono-, di- or trisubstituted independently of one another by $R^{14}$;

$R^{14}$ is fluoro, chlorine, —($C_1$-$C_4$)-alkyl or —$NH_2$;

G is direct bond, —($CH_2$)$_m$—, or —($CH_2$)$_m$—$NR^{10}$—;

m is zero, 1, 2, 3 or 4;

M is 1. hydrogen,
2. —($C_1$-$C_6$)-alkyl, wherein alkyl is unsubstituted or mono-, di- or trisubstituted independently of one another by $R^{14}$,
6. heterocyclyl, which is 1,4-diazepane, ketomorpholine, thiophene, pyridazone, piperidine, piperazine, pyridine, pyrimidine, pyrrolidine, pyrrolidinone, pyridonyl, imidazole, pyridazine, pyrazine, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, tetrahydropyran, 1,4,5,6-tetrahydro-pyridazinyl, thiadiazole or thiomorpholine, that is unsubstituted or mono-, di- or trisubstituted independently of one another by $R^{14}$, or
7. ($C_3$-$C_6$)-cycloalkyl;

$R^3$ and $R^4$ are independent of one another are identical or different and are
1) hydrogen,
2) halogen,
3) —($C_1$-$C_4$)-alkyl, wherein alkyl is unsubstituted or mono-, di- or trisubstituted independently of one another by $R^{13}$,
4) —($C_1$-$C_3$)-perfluoroalkyl,
5) phenyl, wherein phenyl is unsubstituted or mono-, di- or trisubstituted independently of one another by $R^{13}$, 6) —($C_0$-$C_4$)-alkylene-O—$R^{19}$, wherein $R^{19}$ is
a) hydrogen,
b) -($C_1$-$C_4$)-alkyl, wherein alkyl is unsubstituted or mono-, di- or trisubstituted independently of one another by $R^{13}$, or
c) phenyl, wherein phenyl is unsubstituted or mono-, di- or trisubstituted independently of one another by $R^{13}$,
d) —$CF_3$, or
e) —$CHF_2$,
8) —CN,
9) —$SO_s$—$R^{11}$, wherein s is 1 or 2,
10) —$SO_t$—N($R^{11}$)—$R^{12}$, wherein t is 1 or 2,
11) —($C_0$-$C_4$)-alkylene-C(O)—$R^{12}$,
12) —($C_0$-$C_4$)-alkylene-C(O)—O—$R^{12}$,
13) —($C_0$-$C_4$)-alkylene-C(O)—N($R^{11}$)—$R^{12}$,
14) —($C_0$-$C_4$)-alkylene-N($R^1$)—$R^{12}$,
15) —$NR^{10}$—$SO_2$—$R^{10}$,
17) —($C_0$-$C_2$)alkylene-C(O)—O—($C_2$-$C_4$)-alkylene-O—C(O)—($C_1$-$C_4$)-alkyl,
18) —C(O)—O—C($R^{15}$,$R^{16}$)—O—C(O)—$R^{17}$,
19) —($C_0$-$C_2$)alkylene-C(O)—O—($C_2$-$C_4$)-alkylene-O—C(O)—O—($C_1$-$C_6$)-alkyl,
20) —C(O)—O—C($R^{15}$,$R^{16}$)—O—C(O)—O—$R^{17}$,
23) —($C_0$-$C_3$)-alkylene-($C_3$-$C_6$)-cycloalkyl, or —($C_0$-$C_4$)-alkylene-($C_3$-$C_6$)-cycloalkyl, wherein cycloalkyl is unsubstituted or mono-, di- or trisubstituted independently of one another by $R^{13}$,
25) —($C_0$-$C_3$)-alkylene-O—$CH_2$—$CF_2$—$CH_2$—O—($C_0$-$C_3$)-alkyl, —($C_0$-$C_3$)-alkylene-O—$CH_2$—$CF_2$—$CF_2$—$CH_2$—O—($C_0$-$C_3$)-alkyl, or —($C_0$-$C_3$)-alkylene-O—$CH_2$—($C_1$-$C_3$)-perfluoroalkylene-$CH_2$—OH, or
26) residue selected from the group consisting of

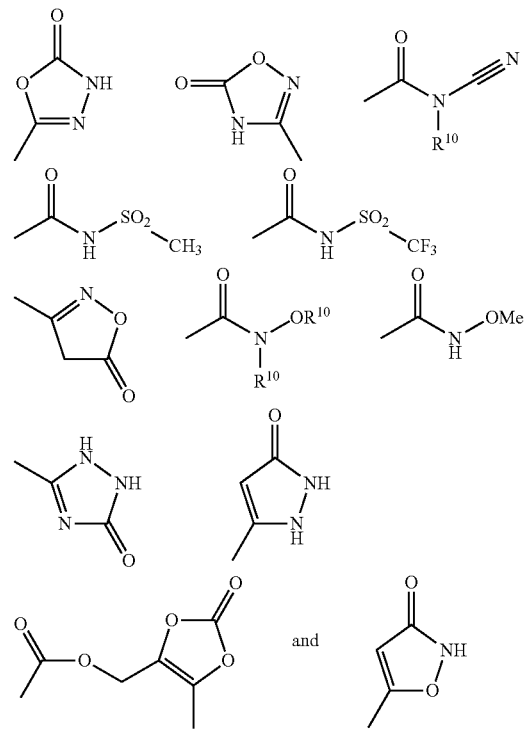

wherein Me is methyl;

$R^{11}$ and $R^{12}$ are independently of one another identical or different and are
1) hydrogen,
2) —$(C_1-C_4)$-alkyl, wherein alkyl is unsubstituted or mono-, di- or trisubstituted independently of one another by $R^{13}$,
3) -$(C_0-C_6)$-alkyl-$(C_3-C_6)$-cycloalkyl,
7) —O—$R^{17}$, or
8) —$(C_0-C_6)$-alkyl-$(C_4-C_{15})$-heterocyclyl, wherein alkyl and heterocyclyl independently from one another are unsubstituted or mono-, di- or trisubstituted by $R^{13}$ and wherein heterocyclyl is selected out of the group azetidine, cyclopropyl, cyclobutyl, 4,5-dihydrooxazole, imidazolidine, morpholine, (1,4)-oxazepane, oxazolidine, piperidine, piperazine, pyrrolidine, tetrahydrothiophene, thiazolidine or thiomorpholine, or
$R^{11}$ and $R^{12}$ together with the nitrogen atom to which they are bonded form azetidine, cyclopropyl, cyclobutyl, 4,5-dihydrooxazole, imidazolidine, morpholine, (1,4)-oxazepane, 1,4-oxazepine, oxazolidine, piperidine, piperazine, pyrrolidine, tetrahydrothiophene, thiazolidine or thiomorpholine;
$R^{13}$ is fluorine, —CN, =O, —OH, —$CF_3$, —C(O)—O—$R^{10}$, —C(O)—N($R^{10}$)—$R^{20}$, —N($R^{10}$)—$R^{20}$, —$(C_3-C_6)$-cycloalkyl, —$(C_0-C_3)$-alkylene-O—$R^{10}$, —Si—$(CH_3)_3$, —S—$R^{10}$, —$SO_2$—$R^{10}$,
—$(C_1-C_3)$-perfluoroalkyl, or residue selected from the group consisting of

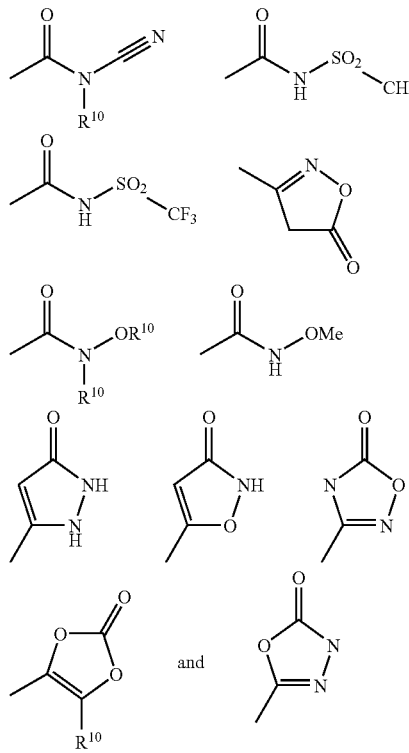

wherein Me is methyl;
$R^{10}$ and $R^{20}$ are independently of one another hydrogen, —$(C_1-C_4)$-alkyl or —$(C_1-C_3)$-perfluoroalkyl;
$R^{15}$ and $R^{16}$ are independently of one another hydrogen, —$(C_1-C_4)$-alkyl, or together form cyclopropyl, cyclobutyl, cyclopentyl or cyclohexyl, that is unsubstituted or substituted one to three times by $R^{10}$.

Another particular embodiment of the compound of formula I according to the invention is wherein
$R^0$ is 3) heterocyclyl selected from the group consisting of thienyl, thiadiazolyl, isoxazolyl and thiazolyl, wherein said heterocyclyl is substituted by a residue selected from the group consisting of thienyl, 2-thienyl and 3-thienyl, wherein said residue is unsubstituted or mono- or disubstituted independently of one another by $R^8$,
$R^8$ is F, Cl, Br, —$OCH_3$, —C(O)—$NH_2$ or —O—$CF_3$,
Q is direct bond, —C(O)—, —$SO_2$—, —$CH_2$—C(O)—NH—, methylene or ethylene,
$R^1$ is hydrogen,
$R^2$ is direct bond or methylene,
V is 1. 3- to 7-membered cyclic residue is azaindolyl, azetidine, 1,4-diazepane, isoxazole, isoquinoline, piperazine, piperidine, pyrazine, pyridazine, pyrimidine, pyrrolidine, quinazoline, quinoline or tetrahydropyran, that is unsubstituted or mono-, di- or trisubstituted independently of one another by $R^{14}$, or
2. aryl is phenyl, that is unsubstituted or mono- or disubstituted independently of one another by $R^{14}$,
$R^1$—N—$R^2$—V forms 4- to 8-membered cyclic group selected from the group consisting of azetidine, pyrrolidine, piperidine and piperazine,
$R^{14}$ is fluorine, chlorine, methyl, ethyl or —$NH_2$,
G is direct bond, —$(CH_2)_{m-1}$ or —$(CH_2)_m$—$NR^{10}$—,
M is zero, 1 or 2,
M is hydrogen, $(C_2-C_4)$-alkyl, azepanyl, cyclopropyl, cyclobutyl, cyclopentyl, cyclohexyl, imidazolyl, ketomorpholinyl, morpholinyl, 1,4-oxazepanyl, piperidinyl, piperidonyl, pyrazinyl, pyrazolyl, pyridazinyl, pyridinyl, pyrimidyl, pyrrolidinyl, 1,4,5,6-tetrahydropyridazinyl, or tetrahydropyranyl, wherein the residues are unsubstituted or mono- or disubstituted independently of one another by $R^{14}$,
$R^3$ and $R^4$ are independent of one another are identical or different and are
1) hydrogen,
2) fluorine or chlorine,
3) —$(C_1-C_4)$-alkyl, wherein alkyl is unsubstituted or mono-, di- or trisubstituted independently of one another by $R^{13}$,
4) —$(C_1-C_3)$-perfluoroalkyl,
5) phenyl that is unsubstituted or mono-, di- or trisubstituted independently of one another by $R^{13}$,
6) —$(C_0-C_2)$-alkylene-O—$R^{19}$, wherein $R^{19}$ is
a) hydrogen,
b) -$(C_1-C_4)$-alkyl, wherein alkyl is unsubstituted or mono-, di- or trisubstituted independently of one another by $R^{13}$, or
c) phenyl, wherein phenyl is unsubstituted or mono-, di- or trisubstituted independently of one another by $R^{13}$,
d) —$CF_3$, or
e) —$CHF_2$,
8) —CN,
9) —$SO_s$—$R^{11}$, wherein s is 1 or 2,
10) —$SO_t$—N($R^{11}$)—$R^{12}$, wherein t is 1 or 2,
11) —$(C_0-C_4)$-alkylene-C(O)—$R^{11}$,
12) —$(C_0-C_4)$-alkylene-C(O)—O—$R^{11}$,
13) —$(C_0-C_4)$-alkylene-C(O)—N($R^{11}$)—$R^{12}$,
14) —$(C_0-C_4)$-alkylene-N($R^{11}$)—$R^{12}$,
15) —$NR^{10}$—$SO_2$—$R^{10}$,
16) —$(C_0-C_2)$alkylene-C(O)—O—$(C_2-C_4)$-alkylene-O—C(O)—$(C_1-C_4)$-alkyl,
18) —C(O)—O—C($R^{15}$,$R^{16}$)—O—C(O)—$R^{17}$,
19) —$(C_0-C_2)$alkylene-C(O)—O—$(C_2-C_4)$-alkylene-O—C(O)—O—$(C_1-C_6)$-alkyl, 20) —C(O)—O—C(R$^{15}$R$^{16}$)—O$^{17}$—C(O)—O—R$^{17}$,
23) —(C$_0$-C$_4$)-alkylene-(C$_3$-C$_8$)-cycloalkyl selected from the group consisting of —(C$_0$-C$_3$)-alkylene-(C$_3$-C$_6$)-cycloalkyl or —(C$_0$-C$_4$)-alkylene-(C$_3$-C$_6$)-cycloalkyl, wherein cycloalkyl is unsubstituted or mono-, di- or trisubstituted independently of one another by R$^{13}$,
24) —(C$_0$-C$_4$)-alkylene-het selected from the group consisting of pyridinyl or thiazolyl that is unsubstituted or mono-, di- or trisubstituted independently of one another by R$^{13}$,
25) —(C$_0$-C$_3$)-alkylene-O—CH$_2$—CF$_2$—CH$_2$—O—(C$_0$-C$_3$)-alkyl, —(C$_0$-C$_3$)-alkylene-O—CH$_2$—CF$_2$—CF$_2$—CH$_2$—O—(C$_0$-C$_3$)-alkyl, or —(C$_0$-C$_3$)-alkylene-O—CH$_2$—(C$_1$-C$_3$)-perfluoroalkylene-CH$_2$—OH, or
26) residue selected from the group consisting of the following

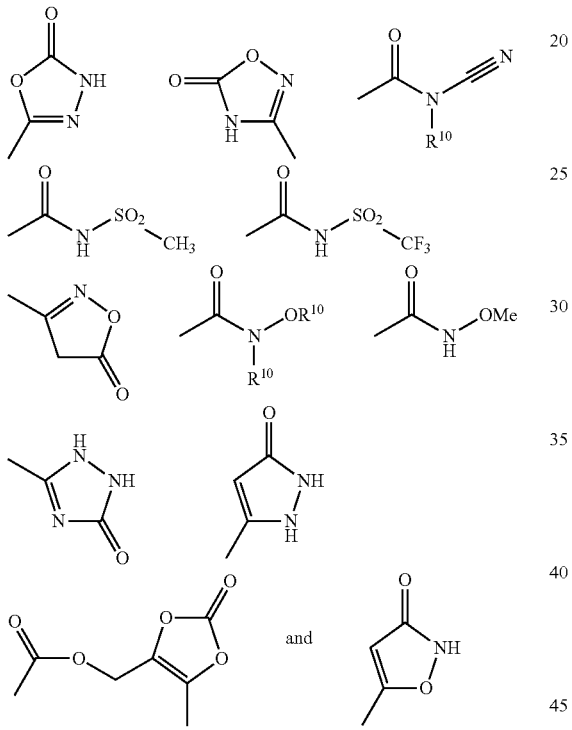

wherein Me is methyl,
R$^{11}$ and R$^{12}$ are independently of one another identical or different and are
1) hydrogen,
2) —(C$_1$-C$_4$)-alkyl, wherein alkyl is unsubstituted or mono-, di- or trisubstituted independently of one another by R$^{13}$,
3) —(C$_0$-C$_6$)-alkyl-(C$_3$-C$_6$)-cycloalkyl,
7) —O—R$^{17}$, or
8) —(C$_0$-C$_6$)-alkyl-heterocyclyl, wherein alkyl and heterocyclyl independently from one another are unsubstituted or mono-, di- or trisubstituted by R$^{13}$ and wherein heterocyclyl is selected out of the group azetidine, imidazolidine, morpholine, 1,4-oxazepane or pyrrolidine or
R$^{11}$ and R$^{12}$ together with the nitrogen atom to which they are bonded can form the 4- to 8-membered monocyclic heterocyclic ring selected from the group consisting of azetidine, imidazolidine, morpholine, 1,4-oxazepane, 1,4-oxazepine, piperazine, piperidine, pyrrolidine and thiomorpholine, R$^{13}$ is fluorine, chlorine, —CN, =O, —OH, —CF$_3$, —C(O)—O—R$^{10}$, —C(O)—N(R$^{10}$)—R$^{20}$, —N(R$^{10}$)—R$^{20}$, —(C$_3$-C$_6$)-cycloalkyl, —(C$_0$-C$_3$)-alkylene-O—R$^{10}$, —Si—(CH$_3$)$_3$, —S—R$^{10}$, —SO$_2$—R$^{10}$, —(C$_1$-C$_4$)-alkyl, —(C$_1$-C$_3$)-perfluoroalkyl, or residue selected from the group consisting of the following

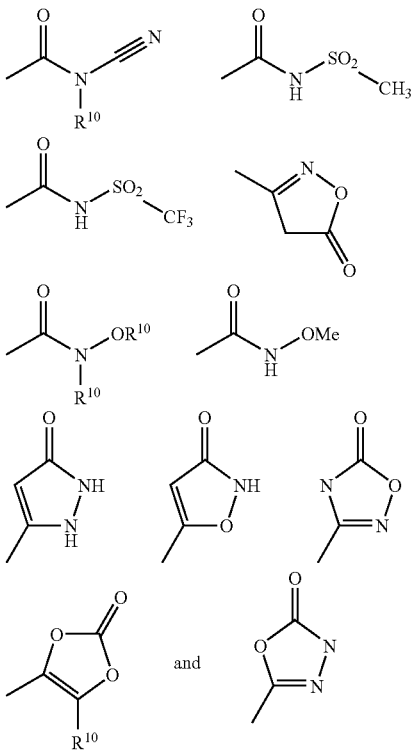

wherein Me is methyl,
R$^{10}$ and R$^{20}$ are independently of one another hydrogen, —(C$_1$-C$_4$)-alkyl or —(C$_1$-C$_3$)-perfluoroalkyl,
R$^{15}$ and R$^{16}$ are independently of one another hydrogen, —(C$_1$-C$_4$)-alkyl, or together with the carbon atom to which they are bonded form a 3- to 6 membered carbocyclic ring selected from the group consisting of cyclopropyl, cyclobutyl, cyclopentyl or cyclohexyl, wherein each ring is unsubstituted or substituted one to three times by R$^{10}$, and
R$^{17}$ is —(C1-C6)-alkyl, —(C1-C6)-alkyl-OH, —(C1-C6)-alkyl-O—(C1-C6)-alkyl, —(C3-C8)-cycloalkyl, —(C1-C6)-alkyl-O—(C1-C8)-alkyl-(C3-C8)-cycloalkyl, —(C1-C6)-alkyl-(C3-C8)-cycloalkyl, wherein said cycloalkyl ring is unsubstituted or substituted one, two or three times by —OH, —O—(C$_1$-C$_4$)-alkyl or R$^{10}$.

Another particular embodiment of the compound of formula I according to the invention is wherein
R$^0$ is pheny that is unsubstituted or mono- or disubstituted independently of one another by R$^8$,
R$^8$ is F, Cl, Br, —OCH$_3$, —C(O)—NH$_2$ or —O—CF$_3$,
Q is direct bond, —C(O)—, —SO$_2$—, —CH$_2$—C(O)—NH—, methylene or ethylene,
R$^1$ is hydrogen,
R$^2$ is direct bond or methylene,
V is 1. 3- to 7-membered cyclic residue is azaindolyl, azetidine, 1,4-diazepane, isoxazole, isoquinoline, piperazine, piperidine, pyrazine, pyridazine, pyrimidine, pyrrolidine, quinazoline, quinoline or tetrahydropyran, that is unsubstituted or mono-, di- or trisubstituted independently of one another by R$^{14}$, or 2. aryl is phenyl, that is unsubstituted or mono- or disubstituted independently of one another by $R^{14}$, $R^1$—N—$R^2$—V forms 4- to 8-membered cyclic group selected from the group consisting of azetidine, pyrrolidine, piperidine and piperazine, $R^{14}$ is fluorine, chlorine, methyl, ethyl or —$NH_2$, G is direct bond, —$(CH_2)_m$—, or —$(CH_2)_m$—$NR^{10}$—, m is zero, 1 or 2, M is hydrogen, or moiety which is $(C_2-C_4)$-alkyl, azepanyl, cyclopropyl, cyclobutyl, cyclopentyl, cyclohexyl, imidazolyl, ketomorpholinyl, morpholinyl, 1,4-oxazepanyl, piperidinyl, piperidonyl, pyrazinyl, pyrazolyl, pyridazinyl, pyridinyl, pyrimidyl, pyrrolidinyl, 1,4,5,6-tetrahydropyridazinyl, or tetrahydropyranyl, wherein the moiety is unsubstituted or mono- or disubstituted independently of one another by $R^{14}$, $R^3$ and $R^4$ are independent of one another are identical or different and are 1) hydrogen,
2) fluorine, chlorine,
3) —$(C_1-C_4)$-alkyl, wherein alkyl is unsubstituted or mono-, di- or trisubstituted independently of one another by $R^{13}$,
4) —$(C_1-C_3)$-perfluoroalkyl,
5) phenyl that is unsubstituted or mono-, di- or trisubstituted independently of one another by $R^{13}$,
6) —$(C_0-C_2)$-alkylene-O—$R^{19}$, wherein $R^{19}$ is
   a) hydrogen,
   b) -$(C_1-C_4)$-alkyl, wherein alkyl is unsubstituted or mono-, di- or trisubstituted independently of one another by $R^{13}$, or
   c) phenyl, wherein phenyl is unsubstituted or mono-, di- or trisubstituted independently of one another by $R^{13}$,
   d) —$CF_3$, or
   e) —$CHF_2$,
8) —CN,
9) —$SO_s$—$R^{11}$, wherein s is 1 or 2,
10) —$SO_t$—$N(R^{11})$—$R^{12}$, wherein t is 1 or 2,
11) —$(C_0-C_4)$-alkylene-C(O)—$R^{11}$,
12) —$(C_0-C_4)$-alkylene-C(O)—O—$R^{11}$,
13) —$(C_0-C_4)$-alkylene-C(O)—$N(R^{11})$—$R^{12}$,
14) —$(C_0-C_4)$-alkylene-$N(R^1)$—$R^{12}$,
15) —$NR^{10}$—$SO_2$—$R^{10}$,
16) —$(C_0-C_2)$alkylene-C(O)—O—$(C_2-C_4)$-alkylene-O—C(O)—$(C_1-C_4)$-alkyl,
18) —C(O)—O—$C(R^{15},R^{16})$—O—C(O)—$R^{17}$,
19) —$(C_0-C_2)$alkylene-C(O)—O—$(C_2-C_4)$-alkylene-O—C(O)—O—$(C_1-C_6)$-alkyl,
20) —C(O)—O—$C(R^{15}R^{16})$—O—C(O)—O—$R^{17}$,
23) —$(C_0-C_4)$-alkylene-$(C_3-C_8)$-cycloalkyl selected from the group consisting of —$(C_0-C_3)$-alkylene-$(C_3-C_6)$-cycloalkyl or —$(C_0-C_4)$-alkylene-$(C_3-C_6)$-cycloalkyl, wherein cycloalkyl is unsubstituted or mono-, di- or trisubstituted independently of one another by $R^{13}$,
24) —$(C_0-C_4)$-alkylene-het selected from the group consisting of pyridinyl or thiazolyl that is unsubstituted or mono-, di- or trisubstituted independently of one another by $R^{13}$,
25) —$(C_0-C_3)$-alkylene-O—$CH_2$—$CF_2$—$CH_2$—O—$(C_0-C_3)$-alkyl, —$(C_0-C_3)$-alkylene-O—$CH_2$—$CF_2$—$CF_2$—$CH_2$—O—$(C_0-C_3)$-alkyl, or —$(C_0-C_3)$-alkylene-O—$CH_2$—$(C_1-C_3)$-perfluoroalkylene -$CH_2$—OH, or 26) residue selected from the group consisting of the following

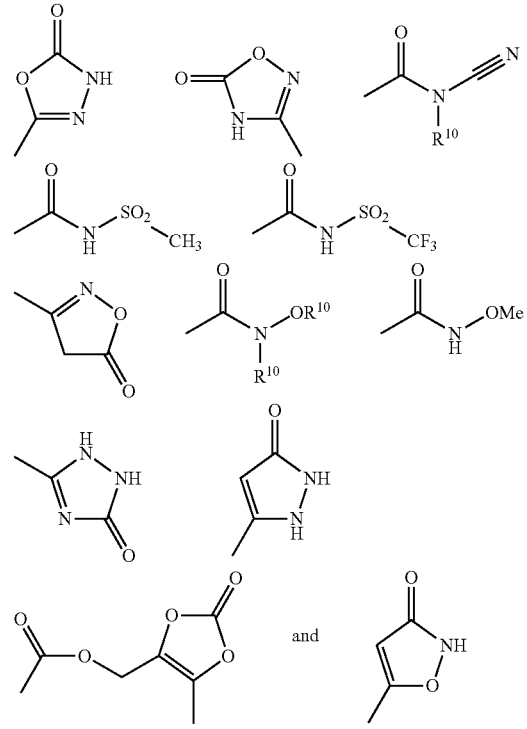

wherein Me is methyl, $R^{11}$ and $R^{12}$ are independently of one another identical or different and are 1) hydrogen,
2) —$(C_1-C_4)$-alkyl, wherein alkyl is unsubstituted or mono-, di- or trisubstituted independently of one another by $R^{13}$,
3) —$(C_0-C_6)$-alkyl-$(C_3-C_6)$-cycloalkyl,
7) —O—$R^{17}$, or
8) —$(C_0-C_6)$-alkyl-heterocyclyl, wherein alkyl and heterocyclyl independently from one another are unsubstituted or mono-, di- or trisubstituted by $R^{13}$ and wherein heterocyclyl is selected out of the group azetidine, imidazolidine, morpholine, 1,4-oxazepane or pyrrolidine or $R^{11}$ and $R^{12}$ together with the nitrogen atom to which they are bonded can form the 4- to 8-membered monocyclic heterocyclic ring selected from the group consisting of azetidine, imidazolidine, morpholine, 1,4-oxazepane, 1,4-oxazepine, piperazine, piperidine, pyrrolidine and thiomorpholine, $R^{13}$ is fluorine, chlorine, —CN, =O, —OH, —$CF_3$, —C(O)—O—$R^{10}$, —C(O)—$N(R^{10})$—$R^{20}$, —$N(R^{10})$—$R^{20}$, —$(C_3-C_6)$-cycloalkyl, —$(C_0-C_3)$-alkylene-O—$R^{10}$, —Si—$(CH_3)_3$, —S—$R^{10}$, —$SO_2$—$R^{10}$, —$(C_1-C_4)$-alkyl, —$(C_1-C_3)$-perfluoroalkyl, or residue selected from the group consisting of the following

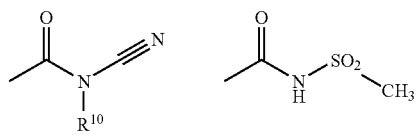

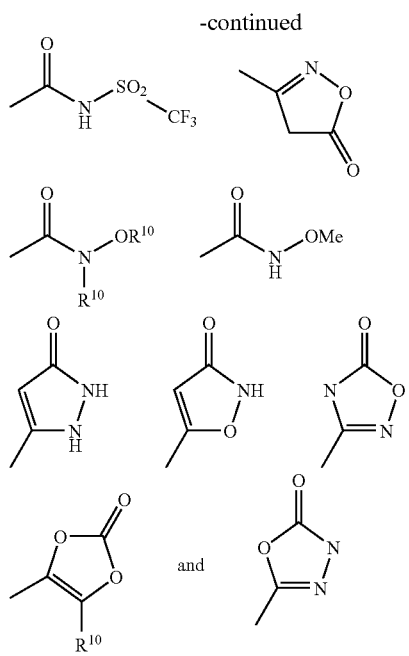

wherein Me is methyl, $R^{10}$ and $R^{20}$ are independently of one another hydrogen, —$(C_1$-$C_4)$-alkyl or —$(C_1$-$C_3)$-perfluoroalkyl, $R^{15}$ and $R^{16}$ are independently of one another hydrogen, —$(C_1$-$C_4)$-alkyl, or together with the carbon atom to which they are bonded form a 3- to 6 membered carbocyclic ring selected from the group consisting of cyclopropyl, cyclobutyl, cyclopentyl or cyclohexyl, wherein each ring is unsubstituted or substituted one to three times by $R^{10}$, and $R^{17}$ is —(C1-C6)-alkyl, —(C1-C6)-alkyl-OH, —(C1-C6)-alkyl-O—(C1-C6)-alkyl, —(C3-C8)-cycloalkyl, —(C1-C6)-alkyl-O—(C1-C8)-alkyl-(C3-C8)-cycloalkyl, —(C1-C6)-alkyl-(C3-C8)-cycloalkyl, wherein said cycloalkyl ring is unsubstituted or substituted one, two or three times by —OH, —O—(C1-C4)-alkyl or $R^{10}$.

Another particular embodiment of the compound of formula I according to the invention is wherein $R^0$ is pyridyl that is unsubstituted or mono- or disubstituted independently of one another by $R^8$, $R^8$ is F, Cl, Br, —$OCH_3$, —C(O)—$NH_2$ or —O—$CF_3$, Q is direct bond, —C(O)—, —$SO_2$—, —$CH_2$—C(O)—NH—, methylene or ethylene, $R^1$ is hydrogen, $R^2$ is direct bond or methylene, V is 1. 3- to 7-membered cyclic residue is azaindolyl, azetidine, 1,4-diazepane, isoxazole, isoquinoline, piperazine, piperidine, pyrazine, pyridazine, pyrimidine, pyrrolidine, quinazoline, quinoline or tetrahydropyran, that is unsubstituted or mono-, di- or trisubstituted independently of one another by $R^{14}$, or 2. aryl is phenyl, that is unsubstituted or mono- or disubstituted independently of one another by $R^{14}$, $R^1$—N—$R^2$—V forms a 4- to 8-membered cyclic group selected from the group consisting of azetidine, pyrrolidine, piperidine and piperazine, $R^{14}$ is fluorine, chlorine, methyl, ethyl or —$NH_2$, G is direct bond, —$(CH_2)_{m-1}$ or —$(CH_2)_m$—$NR^{10}$—, m is zero, 1 or 2, M is hydrogen, or moiety, which is $(C_2$-$C_4)$-alkyl, azepanyl, cyclopropyl, cyclobutyl, cyclopentyl, cyclohexyl, imidazolyl, ketomorpholinyl, morpholinyl, 1,4-oxazepanyl, piperidinyl, piperidonyl, pyrazinyl, pyrazolyl, pyridazinyl, pyridinyl, pyrimidyl, pyrrolidinyl, 1,4,5,6-tetrahydropyridazinyl, or tetrahydropyranyl, wherein the moiety is unsubstituted or mono- or disubstituted independently of one another by $R^{14}$, $R^3$ and $R^4$ are independent of one another are identical or different and are 1) hydrogen,
2) fluorine, chlorine,
3) —$(C_1$-$C_4)$-alkyl, wherein alkyl is unsubstituted or mono-, di- or trisubstituted independently of one another by $R^{13}$,
4) —$(C_1$-$C_3)$-perfluoroalkyl,
5) phenyl that is unsubstituted or mono-, di- or trisubstituted independently of one another by $R^{13}$,
6) —$(C_0$-$C_2)$-alkylene-O—$R^{19}$, wherein $R^{19}$ is
   a) hydrogen,
   b) —$(C_1$-$C_4)$-alkyl, wherein alkyl is unsubstituted or mono-, di- or trisubstituted independently of one another by $R^{13}$, or
   c) phenyl, wherein phenyl is unsubstituted or mono-, di- or trisubstituted independently of one another by $R^{13}$,
   d) —$CF_3$, or
   e) —$CHF_2$,
8) —CN,
9) —$SO_s$—$R^{11}$, wherein s is 1 or 2,
10) —$SO_t$—N($R^{11}$)—$R^{12}$, wherein t is 1 or 2,
11) —$(C_0$-$C_4)$-alkylene-C(O)—$R^{11}$,
12) —$(C_0$-$C_4)$-alkylene-C(O)—O—$R^{11}$,
13) —$(C_0$-$C_4)$-alkylene-C(O)—N($R^{11}$)—$R^{12}$,
14) —$(C_0$-$C_4)$-alkylene-N($R^1$)—$R^{12}$,
15) —$NR^{10}$—$SO_2$—$R^{10}$,
16) —$(C_0$-$C_2)$alkylene-C(O)—O—$(C_2$-$C_4)$-alkylene-O—C(O)—$(C_1$-$C_4)$-alkyl,
18) —C(O)—O—C($R^{15},R^{16}$)—O—C(O)—$R^{17}$,
19) —$(C_0$-$C_2)$alkylene-C(O)—O—$(C_2$-$C_4)$-alkylene-O—C(O)—O—$(C_1$-$C_6)$-alkyl,
20) —C(O)—O—C($R^{15}R^{16}$)—O —C(O)—O—$R^{17}$,
23) —$(C_0$-$C_4)$-alkylene-$(C_3$-$C_8)$-cycloalkyl selected from the group consisting of —$(C_0$-$C_3)$-alkylene-$(C_3$-$C_6)$-cycloalkyl or —$(C_0$-$C_4)$-alkylene-$(C_3$-$C_6)$-cycloalkyl, wherein cycloalkyl is unsubstituted or mono-, di- or trisubstituted independently of one another by $R^{13}$,
24) —$(C_0$-$C_4)$-alkylene-het selected from the group consisting of pyridinyl or thiazolyl that is unsubstituted or mono-, di- or trisubstituted independently of one another by $R^{13}$,
25) —$(C_0$-$C_3)$-alkylene-O—$CH_2$—$CF_2$—$CH_2$—O—$(C_0$-$C_3)$-alkyl, —$(C_0$-$C_3)$-alkylene-O—$CH_2$—$CF_2$—$CF_2$—$CH_2$—O—$(C_0$-$C_3)$-alkyl, or —$(C_0$-$C_3)$-alkylene-O—$CH_2$—$(C_1$-$C_3)$-perfluoroalkylene -$CH_2$—OH, or
26) residue selected from the group consisting of the following

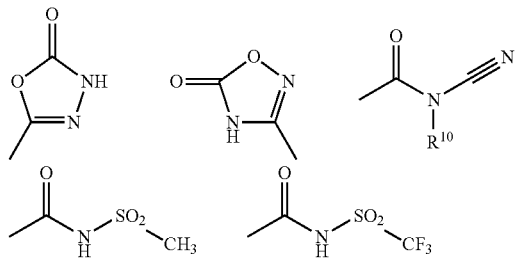

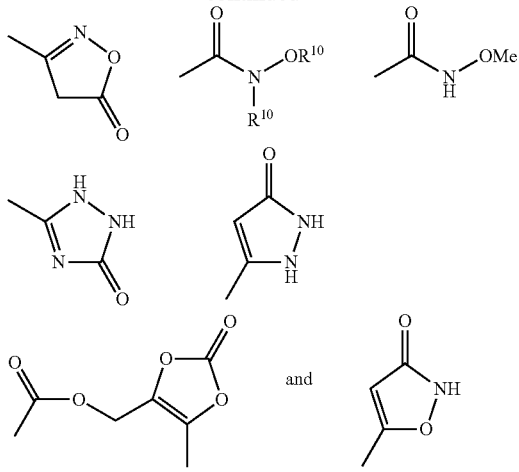
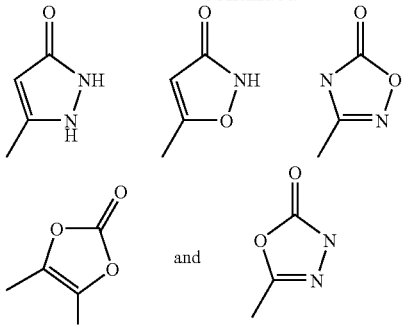

wherein Me is methyl, $R^{11}$ and $R^{12}$ are independently of one another identical or different and are 1) hydrogen,
2) —($C_1$-$C_4$)-alkyl, wherein alkyl is unsubstituted or mono-, di- or trisubstituted independently of one another by $R^{13}$,
3) -($C_0$-$C_6$)-alkyl-($C_3$-$C_6$)-cycloalkyl,
7) —O—$R^{17}$, or
8) —($C_0$-$C_6$)-alkyl-heterocyclyl, wherein alkyl and heterocyclyl independently from one another are unsubstituted or mono-, di- or trisubstituted by $R^{13}$ and wherein heterocyclyl is selected out of the group azetidine, imidazolidine, morpholine, 1,4-oxazepane or pyrrolidine or $R^{11}$ and $R^{12}$ together with the nitrogen atom to which they are bonded can form the 4- to 8-membered monocyclic heterocyclic ring selected from the group consisting of azetidine, imidazolidine, morpholine, 1,4-oxazepane, 1,4-oxazepine, piperazine, piperidine, pyrrolidine and thiomorpholine, $R^{13}$ is fluorine, chlorine, —CN, =O, —OH, —$CF_3$, —C(O)—O—$R^{10}$, —C(O)—N($R^{10}$)—$R^{20}$, —N($R^{10}$)—$R^{20}$, —($C_3$-$C_6$)-cycloalkyl, —($C_0$-$C_3$)-alkylene-O—$R^{10}$, —Si—$(CH_3)_3$, —S—$R^{10}$, —$SO_2$—$R^{10}$, —($C_1$-$C_4$)-alkyl, —($C_1$-$C_3$)-perfluoroalkyl, or residue selected from the group consisting of the following

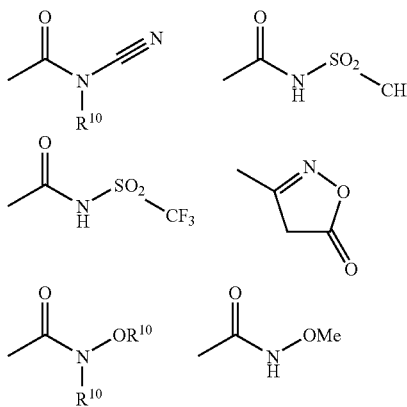

wherein Me is methyl, $R^{10}$ and $R^{20}$ are independently of one another hydrogen, —($C_1$-$C_4$)-alkyl or —($C_1$-$C_3$)-perfluoroalkyl, $R^{15}$ and $R^{16}$ are independently of one another hydrogen, —($C_1$-$C_4$)-alkyl, or together with the carbon atom to which they are bonded form a 3- to 6 membered carbocyclic ring selected from the group consisting of cyclopropyl, cyclobutyl, cyclopentyl or cyclohexyl, wherein each ring is unsubstituted or substituted one to three times by $R^{10}$, and $R^{17}$ is —(C1-C6)-alkyl, —(C1-C6)-alkyl-OH, —(C1-C6)-alkyl-O—(C1-C6)-alkyl, —(C3-C8)-cycloalkyl, —(C1-C6)-alkyl-O—(C1-C8)-alkyl-(C3-C8)-cycloalkyl, —(C1-C6)-alkyl-(C3-C8)-cycloalkyl, wherein said cycloalkyl ring is unsubstituted or substituted one, two or three times by —OH, —O—($C_1$-$C_4$)-alkyl or $R^{10}$.

Another particular embodiment of the invention is wherein the compound of formula I has the following formula

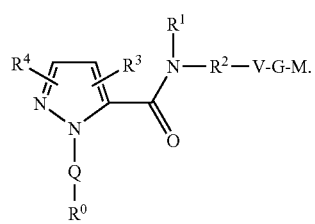

Another particular embodiment of the invention is wherein the compound of formula I has the following formula

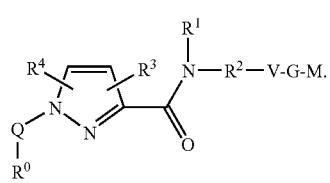

Another particular embodiment of the invention is wherein the compound of formula I is a species selected from the group consisting of 2-[5-(5-Chloro-thiophen-2-yl)-isoxazol-3-ylmethyl]-5-thiophen-2-yl-2H-pyrazole-3-carboxylic acid (1-isopropyl-piperidin-4-yl)-amide, 1-[5-(5-Chloro-thiophen-2-yl)-isoxazol-3-ylmethyl]-5-thiophen-2-yl-1H-pyrazole-3-carboxylic acid (1-isopropyl-piperidin-4-yl)-amide, 2-[5-(5-Chloro-thiophen-2-yl)-isoxazol-3-ylmethyl]-5-methyl-2H-pyrazole-3-carboxylic acid (1-isopropyl-piperidin-4-yl)-amide,
1-[5-(5-Chloro-thiophen-2-yl)-isoxazol-3-ylmethyl]-5-methyl-1H-pyrazole-3-carboxylic acid (1-isopropyl-piperidin-4-yl)-amide,
2-(6-Chloro-benzothiazol-2-yl)-5-methyl-2H-pyrazole-3-carboxylic acid (1-isopropyl-piperidin-4-yl)-amide,
5-(5-Chloro-thiophen-2-yl)-2-[5-(5-chloro-thiophen-2-yl)-isoxazol-3-ylmethyl]-2H-pyrazole-3-carboxylic acid (1-isopropyl-piperidin-4-yl)-amide,
5-(5-Chloro-thiophen-2-yl)-1-[5-(5-chloro-thiophen-2-yl)-isoxazol-3-ylmethyl]-1H-pyrazole-3-carboxylic acid (1-isopropyl-piperidin-4-yl)-amide,
2-[5-(5-Chloro-thiophen-2-yl)-isoxazol-3-ylmethyl]-4-(2,4-dichloro-phenyl)-2H-pyrazole-3-carboxylic acid (1-isopropyl-piperidin-4-yl)-amide,
1-[5-(5-Chloro-thiophen-2-yl)-isoxazol-3-ylmethyl]-4-(2,4-dichloro-phenyl)-1H-pyrazole-3-carboxylic acid (1-isopropyl-piperidin-4-yl)-amide,
2-[5-(5-Chloro-thiophen-2-yl)-isoxazol-3-ylmethyl]-5-propyl-2H-pyrazole-3-carboxylic acid (1-isopropyl-piperidin-4-yl)-amide,
1-[5-(5-Chloro-thiophen-2-yl)-isoxazol-3-ylmethyl]-5-propyl-1H-pyrazole-3-carboxylic acid (1-isopropyl-piperidin-4-yl)-amide,
5-tert-Butyl-2-[5-(5-chloro-thiophen-2-yl)-isoxazol-3-ylmethyl]-2H-pyrazole-3-carboxylic acid (1-isopropyl-piperidin-4-yl)-amide,
5-tert-Butyl-1-[5-(5-chloro-thiophen-2-yl)-isoxazol-3-ylmethyl]-1H-pyrazole-3-carboxylic acid (1-isopropyl-piperidin-4-yl)-amide,
2-[5-(5-Chloro-thiophen-2-yl)-isoxazol-3-ylmethyl]-4-cyano-5-propyl-2H-pyrazole-3-carboxylic acid (1-isopropyl-piperidin-4-yl)-amide,
1-[5-(5-Chloro-thiophen-2-yl)-isoxazol-3-ylmethyl]-4-cyano-5-propyl-1H-pyrazole-3-carboxylic acid (1-isopropyl-piperidin-4-yl)-amide,
2-[5-(5-Chloro-thiophen-2-yl)-isoxazol-3-ylmethyl]-4-cyano-5-thiophen-2-yl-2H-pyrazole-3-carboxylic acid (1-isopropyl-piperidin-4-yl)-amide,
1-[5-(5-Chloro-thiophen-2-yl)-isoxazol-3-ylmethyl]-4-cyano-5-thiophen-2-yl-1H-pyrazole-3-carboxylic acid (1-isopropyl-piperidin-4-yl)-amide,
2-[2-(5-Chloro-thiophen-2-yl)-thiazol-4-ylmethyl]-5-thiophen-2-yl-2H-pyrazole-3-carboxylic acid (1-isopropyl-piperidin-4-yl)-amide,
1-[2-(5-Chloro-thiophen-2-yl)-thiazol-4-ylmethyl]-5-thiophen-2-yl-1H-pyrazole-3-carboxylic acid (1-isopropyl-piperidin-4-yl)-amide,
2-(6-Chloro-benzo[b]thiophen-2-ylmethyl)-5-thiophen-2-yl-2H-pyrazole-3-carboxylic acid (1-isopropyl-piperidin-4-yl)-amide,
1-(6-Chloro-benzo[b]thiophen-2-ylmethyl)-5-thiophen-2-yl-1H-pyrazole-3-carboxylic acid (1-isopropyl-piperidin-4-yl)-amide,
2-[5-(5-Chloro-thiophen-2-yl)-isoxazol-3-ylmethyl]-5-thiophen-2-yl-2H-pyrazole-3-carboxylic acid (3,4,5,6-tetrahydro-2H-[1,4']bipyridinyl-4-ylmethyl)-amide,
1-[5-(5-Chloro-thiophen-2-yl)-isoxazol-3-ylmethyl]-5-thiophen-2-yl-1H-pyrazole-3-carboxylic acid (3,4,5,6-tetrahydro-2H-[1,4']bipyridinyl-4-ylmethyl)-amide,
2-[5-(5-Chloro-thiophen-2-yl)-isoxazol-3-ylmethyl]-5-thiophen-2-yl-2H-pyrazole-3-carboxylic acid (1-isopropyl-piperidin-4-ylmethyl)-amide,
1-[5-(5-Chloro-thiophen-2-yl)-isoxazol-3-ylmethyl]-5-thiophen-2-yl-1H-pyrazole-3-carboxylic acid (1-isopropyl-piperidin-4-ylmethyl)-amide,
2-[5-(5-Chloro-thiophen-2-yl)-isoxazol-3-ylmethyl]-5-thiophen-2-yl-2H-pyrazole-3-carboxylic acid (3,4,5,6-tetrahydro-2H-[1,4']bipyridinyl-4-yl)-amide,
1-[5-(5-Chloro-thiophen-2-yl)-isoxazol-3-ylmethyl]-5-thiophen-2-yl-1H-pyrazole-3-carboxylic acid (3,4,5,6-tetrahydro-2H-[1,4']bipyridinyl-4-yl)-amide,
2-(4-Chloro-benzyl)-4-cyano-5-thiophen-2-yl-2H-pyrazole-3-carboxylic acid (1-isopropyl-piperidin-4-yl)-amide,
1-(4-Chloro-benzyl)-4-cyano-5-thiophen-2-yl-1H-pyrazole-3-carboxylic acid (1-isopropyl-piperidin-4-yl)-amide,
1-[5-(5-Chloro-thiophen-2-yl)-isoxazol-3-ylmethyl]-5-(1-isopropyl-piperidin-4-ylcarbamoyl)-1H-pyrazole-3-carboxylic acid methyl ester,
2-[5-(5-Chloro-thiophen-2-yl)-isoxazol-3-ylmethyl]-5-(1-isopropyl-piperidin-4-ylcarbamoyl)-2H-pyrazole-3-carboxylic acid methyl ester,
1-[5-(5-Chloro-thiophen-2-yl)-isoxazol-3-ylmethyl]-5-(1-isopropyl-piperidin-4-ylcarbamoyl)-1H-pyrazole-3-carboxylic acid,
2-[5-(5-Chloro-thiophen-2-yl)-isoxazol-3-ylmethyl]-5-(1-isopropyl-piperidin-4-ylcarbamoyl)-2H-pyrazole-3-carboxylic acid,
1-[5-(5-Chloro-thiophen-2-yl)-isoxazol-3-ylmethyl]-5-(1-isopropyl-piperidin-4-ylcarbamoyl)-1H-pyrazole-3-carboxylic acid ethyl ester,
2-[5-(5-Chloro-thiophen-2-yl)-isoxazol-3-ylmethyl]-5-(1-isopropyl-piperidin-4-ylcarbamoyl)-2H-pyrazole-3-carboxylic acid ethyl ester,
2-[5-(5-Chloro-thiophen-2-yl)-isoxazol-3-ylmethyl]-5-(morpholine-4-carbonyl)-2H-pyrazole-3-carboxylic acid (1-isopropyl-piperidin-4-yl)-amide,
1-[5-(5-Chloro-thiophen-2-yl)-isoxazol-3-ylmethyl]-5-(morpholine-4-carbonyl)-1H-pyrazole-3-carboxylic acid (1-isopropyl-piperidin-4-yl)-amide,
1-[5-(5-Chloro-thiophen-2-yl)-isoxazol-3-ylmethyl]-1H-pyrazole-3,5-dicarboxylic acid 3-dimethylamide 5-[(1-isopropyl-piperidin-4-yl)-amide],
1-[5-(5-Chloro-thiophen-2-yl)-isoxazol-3-ylmethyl]-1H-pyrazole-3,5-dicarboxylic acid 5-dimethylamide 3-[(1-isopropyl-piperidin-4-yl)-amide],
1-[5-(5-Chloro-thiophen-2-yl)-isoxazol-3-ylmethyl]-1H-pyrazole-3,5-dicarboxylic acid 3-[(2-hydroxy-ethyl)-amide]5-[(1-isopropyl-piperidin-4-yl)-amide],
1-[5-(5-Chloro-thiophen-2-yl)-isoxazol-3-ylmethyl]-1H-pyrazole-3,5-dicarboxylic acid 5-[(2-hydroxy-ethyl)-amide]3-[(1-isopropyl-piperidin-4-yl)-amide],
{1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-acetic acid,
{2-[5-(5-Chloro-thiophen-2-yl)-isoxazol-3-ylmethyl]-5-(1-isopropyl-piperidin-4-ylcarbamoyl)-2H-pyrazole-3-carbonyl]-amino}-acetic acid,
2-[5-(5-Chloro-thiophen-2-yl)-isoxazol-3-ylmethyl]-5-(5-oxo-4,5-dihydro-[1,3,4]oxadiazol-2-yl)-2H-pyrazole-3-carboxylic acid (1-isopropyl-piperidin-4-yl)-amide,
1-[5-(5-Chloro-thiophen-2-yl)-isoxazol-3-ylmethyl]-5-(5-oxo-4,5-dihydro-[1,3,4]oxadiazol-2-yl)-1H-pyrazole-3-carboxylic acid (1-isopropyl-piperidin-4-yl)-amide,
Sulfuric acid mono-(2-{[1-[5-(5-chloro-thiophen-2-yl)-isoxazol-3-ylmethyl]-5-(1-isopropyl-piperidin-4-ylcarbamoyl)-1H-pyrazole-3-carbonyl]-amino}-ethyl) ester, Sulfuric acid mono-(2-{[2-[5-(5-chloro-thiophen-2-yl)-isoxazol-3-ylmethyl]-5-(1-isopropyl-piperidin-4-yl-carbamoyl)-2H-pyrazole-3-carbonyl]-amino}-ethyl) ester, 2-[5-(5-Chloro-thiophen-2-yl)-isoxazol-3-ylmethyl]-5-[4-(2-hydroxy-ethyl)-piperazine-1-carbonyl]-2H-pyrazole-3-carboxylic acid (1-isopropyl-piperidin-4-yl)-amide, 1-[5-(5-Chloro-thiophen-2-yl)-isoxazol-3-ylmethyl]-5-[4-(2-hydroxy-ethyl)-piperazine-1-carbonyl]-1H-pyrazole-3-carboxylic acid (1-isopropyl-piperidin-4-yl)-amide, 2-[5-(5-Chloro-thiophen-2-yl)-isoxazol-3-ylmethyl]-5-(2-oxo-oxazolidine-3-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(2-oxo-oxazolidine-3-carbonyl)-1H-pyrazole-3-carboxylic acid (1-isopropyl-piperidin-4-yl)-amide, 1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-[(2-morpholin-4-yl-ethyl)-amide], 1-[5-(5-Chloro-thiophen-2-yl)-isoxazol-3-ylmethyl]-1H-pyrazole-3,5-dicarboxylic acid 3-[(1-isopropyl-piperidin-4-yl)-amide]5-[(2-morpholin-4-yl-ethyl)-amide], 1-[5-(5-Chloro-thiophen-2-yl)-isoxazol-3-ylmethyl]-1H-pyrazole-3,5-dicarboxylic acid 3-[bis-(2-methoxy-ethyl)-amide]5-[(1-isopropyl-piperidin-4-yl)-amide], 1-[5-(5-Chloro-thiophen-2-yl)-isoxazol-3-ylmethyl]-1H-pyrazole-3,5-dicarboxylic acid 5-[bis-(2-methoxy-ethyl)-amide]3-[(1-isopropyl-piperidin-4-yl)-amide], 1-[5-(5-Chloro-thiophen-2-yl)-isoxazol-3-ylmethyl]-1H-pyrazole-3,5-dicarboxylic acid 3-[(4,5-dihydro-oxazol-2-yl)-amide]5-[(1-isopropyl-piperidin-4-yl)-amide], 1-[5-(5-Chloro-thiophen-2-yl)-isoxazol-3-ylmethyl]-1H-pyrazole-3,5-dicarboxylic acid 5-[(4,5-dihydro-oxazol-2-yl)-amide]3-[(1-isopropyl-piperidin-4-yl)-amide], 2-[5-(5-Chloro-thiophen-2-yl)-isoxazol-3-ylmethyl]-5-[3-(2-hydroxy-ethyl)-2-oxo-imidazolidine-1-carbonyl]-2H-pyrazole-3-carboxylic acid (1-isopropyl-piperidin-4-yl)-amide, 1-[5-(5-Chloro-thiophen-2-yl)-isoxazol-3-ylmethyl]-5-[3-(2-hydroxy-ethyl)-2-oxo-imidazolidine-1-carbonyl]-1H-pyrazole-3-carboxylic acid (1-isopropyl-piperidin-4-yl)-amide, 2-[5-(5-Chloro-thiophen-2-yl)-isoxazol-3-ylmethyl]-5-(2-methoxymethyl-pyrrolidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(2-methoxymethyl-pyrrolidine-1-carbonyl)-1H-pyrazole-3-carboxylic acid (1-isopropyl-piperidin-4-yl)-amide, {[1-[5-(5-Chloro-thiophen-2-yl)-isoxazol-3-ylmethyl]-5-(1-isopropyl-piperidin-4-ylcarbamoyl)-1H-pyrazole-3-carbonyl]-methyl-amino}-acetic acid, {[2-[5-(5-Chloro-thiophen-2-yl)-isoxazol-3-ylmethyl]-5-(1-isopropyl-piperidin-4-ylcarbamoyl)-2H-pyrazole-3-carbonyl]-methyl-amino}-acetic acid, 1-[1-[5-(5-Chloro-thiophen-2-yl)-isoxazol-3-ylmethyl]-5-(1-isopropyl-piperidin-4-ylcarbamoyl)-1H-pyrazole-3-carbonyl]-piperidine-4-carboxylic acid ethyl ester, 1-[2-[5-(5-Chloro-thiophen-2-yl)-isoxazol-3-ylmethyl]-5-(1-isopropyl-piperidin-4-ylcarbamoyl)-2H-pyrazole-3-carbonyl]-piperidine-4-carboxylic acid ethyl ester, 1-[1-[5-(5-Chloro-thiophen-2-yl)-isoxazol-3-ylmethyl]-5-(1-isopropyl-piperidin-4-ylcarbamoyl)-1H-pyrazole-3-carbonyl]-azetidine-2-carboxylic acid, 1-[2-[5-(5-Chloro-thiophen-2-yl)-isoxazol-3-ylmethyl]-5-(1-isopropyl-piperidin-4-ylcarbamoyl)-2H-pyrazole-3-carbonyl]-azetidine-2-carboxylic acid, 2-[5-(5-Chloro-thiophen-2-yl)-isoxazol-3-ylmethyl]-5-(thiomorpholine-4-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(thiomorpholine-4-carbonyl)-1H-pyrazole-3-carboxylic acid (1-isopropyl-piperidin-4-yl)-amide, 1-[1-[5-(5-Chloro-thiophen-2-yl)-isoxazol-3-ylmethyl]-5-(1-isopropyl-piperidin-4-ylcarbamoyl)-1H-pyrazole-3-carbonyl]-pyrrolidine-2-carboxylic acid, 1-[2-[5-(5-Chloro-thiophen-2-yl)-isoxazol-3-ylmethyl]-5-(1-isopropyl-piperidin-4-ylcarbamoyl)-2H-pyrazole-3-carbonyl]-pyrrolidine-2-carboxylic acid, 2-[5-(5-Chloro-thiophen-2-yl)-isoxazol-3-ylmethyl]-5-(4-hydroxy-piperidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(4-hydroxy-piperidine-1-carbonyl)-1H-pyrazole-3-carboxylic acid (1-isopropyl-piperidin-4-yl)-amide, 2-[5-(5-Chloro-thiophen-2-yl)-isoxazol-3-ylmethyl]-5-(2-hydroxymethyl-pyrrolidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(2-hydroxymethyl-pyrrolidine-1-carbonyl)-1H-pyrazole-3-carboxylic acid (1-isopropyl-piperidin-4-yl)-amide, 2-[5-(5-Chloro-thiophen-2-yl)-isoxazol-3-ylmethyl]-5-(3-hydroxy-pyrrolidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(3-hydroxy-pyrrolidine-1-carbonyl)-1H-pyrazole-3-carboxylic acid (1-isopropyl-piperidin-4-yl)-amide, 5-(2,5-Bis-methoxymethyl-pyrrolidine-1-carbonyl)-2-[5-(5-chloro-thiophen-2-yl)-isoxazol-3-ylmethyl]-2H-pyrazole-3-carboxylic acid (1-isopropyl-piperidin-4-yl)-amide, 5-(2,5-Bis-methoxymethyl-pyrrolidine-1-carbonyl)-1-[5-(5-chloro-thiophen-2-yl)-isoxazol-3-ylmethyl]-1H-pyrazole-3-carboxylic acid (1-isopropyl-piperidin-4-yl)-amide, 2-[5-(5-Chloro-thiophen-2-yl)-isoxazol-3-ylmethyl]-5-(4-hydroxymethyl-piperidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(4-hydroxymethyl-piperidine-1-carbonyl)-1H-pyrazole-3-carboxylic acid (1-isopropyl-piperidin-4-yl)-amide, 5-(8-Aza-spiro[4.5]decane-8-carbonyl)-2-[5-(5-chloro-thiophen-2-yl)-isoxazol-3-ylmethyl]-2H-pyrazole-3-carboxylic acid (1-isopropyl-piperidin-4-yl)-amide, 5-(8-Aza-spiro[4.5]decane-8-carbonyl)-1-[5-(5-chloro-thiophen-2-yl)-isoxazol-3-ylmethyl]-1H-pyrazole-3-carboxylic acid (1-isopropyl-piperidin-4-yl)-amide, 2-[5-(5-Chloro-thiophen-2-yl)-isoxazol-3-ylmethyl]-5-(3-methanesulfonyl-pyrrolidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(3-methanesulfonyl-pyrrolidine-1-carbonyl)-1H-pyrazole-3-carboxylic acid (1-isopropyl-piperidin-4-yl)-amide, 1-[5-(5-Chloro-thiophen-2-yl)-isoxazol-3-ylmethyl]-1H-pyrazole-3,5-dicarboxylic acid 3-[(1,1-dioxo-tetrahydro-1-thiophen-3-yl)-methyl-amide]5-[(1-isopropyl-piperidin-4-yl)-amide], 1-[5-(5-Chloro-thiophen-2-yl)-isoxazol-3-ylmethyl]-1H-pyrazole-3,5-dicarboxylic acid 5-[(1,1-dioxo-tetrahydro-1-thiophen-3-yl)-methyl-amide]3-[(1-isopropyl-piperidin-4-yl)-amide], 1-[1-[5-(5-Chloro-thiophen-2-yl)-isoxazol-3-ylmethyl]-5-(1-isopropyl-piperidin-4-ylcarbamoyl)-1H-pyrazole-3-carbonyl]-azetidine-3-carboxylic acid, 1-[2-[5-(5-Chloro-thiophen-2-yl)-isoxazol-3-ylmethyl]-5-(1-isopropyl-piperidin-4-ylcarbamoyl)-2H-pyrazole-3-carbonyl]-azetidine-3-carboxylic acid,
5-(Azetidine-1-carbonyl)-2-[5-(5-chloro-thiophen-2-yl)-isoxazol-3-ylmethyl]-2H-pyrazole-3-carboxylic acid (1-isopropyl-piperidin-4-yl)-amide,
5-(Azetidine-1-carbonyl)-1-[5-(5-chloro-thiophen-2-yl)-isoxazol-3-ylmethyl]-1H-pyrazole-3-carboxylic acid (1-isopropyl-piperidin-4-yl)-amide,
2-[5-(5-Chloro-thiophen-2-yl)-isoxazol-3-ylmethyl]-5-(3-oxo-piperazine-1-carbonyl)-2H-pyrazole-3-carboxylic acid (1-isopropyl-piperidin-4-yl)-amide,
1-[5-(5-Chloro-thiophen-2-yl)-isoxazol-3-ylmethyl]-5-(3-oxo-piperazine-1-carbonyl)-1H-pyrazole-3-carboxylic acid (1-isopropyl-piperidin-4-yl)-amide,
2-[5-(5-Chloro-thiophen-2-yl)-isoxazol-3-ylmethyl]-5-(4,4-difluoro-piperidine-1-carbonyl)-2H-pyrazole-3-carboxylic acid (1-isopropyl-piperidin-4-yl)-amide,
1-[5-(5-Chloro-thiophen-2-yl)-isoxazol-3-ylmethyl]-5-(4,4-difluoro-piperidine-1-carbonyl)-1H-pyrazole-3-carboxylic acid (1-isopropyl-piperidin-4-yl)-amide,
2-[5-(5-Chloro-thiophen-2-yl)-isoxazol-3-ylmethyl]-5-([1,4]oxazepane-4-carbonyl)-2H-pyrazole-3-carboxylic acid (1-isopropyl-piperidin-4-yl)-amide,
1-[5-(5-Chloro-thiophen-2-yl)-isoxazol-3-ylmethyl]-5-([1,4]oxazepane-4-carbonyl)-1H-pyrazole-3-carboxylic acid (1-isopropyl-piperidin-4-yl)-amide,
2-[5-(5-Chloro-thiophen-2-yl)-isoxazol-3-ylmethyl]-5-(3-hydroxy-azetidine-1-carbonyl)-2H-pyrazole-3-carboxylic acid (1-isopropyl-piperidin-4-yl)-amide,
1-[5-(5-Chloro-thiophen-2-yl)-isoxazol-3-ylmethyl]-5-(3-hydroxy-azetidine-1-carbonyl)-1H-pyrazole-3-carboxylic acid (1-isopropyl-piperidin-4-yl)-amide,
2-[5-(5-Chloro-thiophen-2-yl)-isoxazol-3-ylmethyl]-5-(2-trifluoromethyl-pyrrolidine-1-carbonyl)-2H-pyrazole-3-carboxylic acid (1-isopropyl-piperidin-4-yl)-amide,
1-[5-(5-Chloro-thiophen-2-yl)-isoxazol-3-ylmethyl]-5-(2-trifluoromethyl-pyrrolidine-1-carbonyl)-1H-pyrazole-3-carboxylic acid (1-isopropyl-piperidin-4-yl)-amide,
2-[5-(5-Chloro-thiophen-2-yl)-isoxazol-3-ylmethyl]-5-(2,2-dimethyl-pyrrolidine-1-carbonyl)-2H-pyrazole-3-carboxylic acid (1-isopropyl-piperidin-4-yl)-amide,
1-[5-(5-Chloro-thiophen-2-yl)-isoxazol-3-ylmethyl]-5-(2,2-dimethyl-pyrrolidine-1-carbonyl)-1H-pyrazole-3-carboxylic acid (1-isopropyl-piperidin-4-yl)-amide,
1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-[(2-sulfamoyl-ethyl)-amide],
1-[5-(5-Chloro-thiophen-2-yl)-isoxazol-3-ylmethyl]-1H-pyrazole-3,5-dicarboxylic acid 3-[(1-isopropyl-piperidin-4-yl)-amide]5-[(2-sulfamoyl-ethyl)-amide],
1-[5-(5-Chloro-thiophen-2-yl)-isoxazol-3-ylmethyl]-1H-pyrazole-3,5-dicarboxylic acid 3-cyclopropylamide 5-[(1-isopropyl-piperidin-4-yl)-amide],
1-[5-(5-Chloro-thiophen-2-yl)-isoxazol-3-ylmethyl]-1H-pyrazole-3,5-dicarboxylic acid 5-cyclopropylamide 3-[(1-isopropyl-piperidin-4-yl)-amide],
{[1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-methanesulfonic acid,
{[2-[5-(5-Chloro-thiophen-2-yl)-isoxazol-3-ylmethyl]-5-(1-isopropyl-piperidin-4-ylcarbamoyl)-2H-pyrazole-3-carbonyl]-amino}-methanesulfonic acid,
1-[5-(5-Chloro-thiophen-2-yl)-isoxazol-3-ylmethyl]-1H-pyrazole-3,5-dicarboxylic acid 3-cyclobutylamide 5-[(1-isopropyl-piperidin-4-yl)-amide],
1-[5-(5-Chloro-thiophen-2-yl)-isoxazol-3-ylmethyl]-1H-pyrazole-3,5-dicarboxylic acid 5-cyclobutylamide 3-[(1-isopropyl-piperidin-4-yl)-amide],
1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-[(2-methoxy-ethyl)-amide],
1-[5-(5-Chloro-thiophen-2-yl)-isoxazol-3-ylmethyl]-1H-pyrazole-3,5-dicarboxylic acid 3-[(1-isopropyl-piperidin-4-yl)-amide]5-[(2-methoxy-ethyl)-amide],
2-[5-(5-Chloro-thiophen-2-yl)-isoxazol-3-ylmethyl]-5-(pyrrolidine-1-carbonyl)-2H-pyrazole-3-carboxylic acid (1-isopropyl-piperidin-4-yl)-amide,
1-[5-(5-Chloro-thiophen-2-yl)-isoxazol-3-ylmethyl]-5-(pyrrolidine-1-carbonyl)-1H-pyrazole-3-carboxylic acid (1-isopropyl-piperidin-4-yl)-amide,
2-[5-(5-Chloro-thiophen-2-yl)-isoxazol-3-ylmethyl]-5-(cyanamide-1-carbonyl)-2H-pyrazole-3-carboxylic acid (1-isopropyl-piperidin-4-yl)-amide,
1-[5-(5-Chloro-thiophen-2-yl)-isoxazol-3-ylmethyl]-5-(cyanamide-1-carbonyl)-1H-pyrazole-3-carboxylic acid (1-isopropyl-piperidin-4-yl)-amide,
Phosphoric acid mono-(2-{[1-[5-(5-chloro-thiophen-2-yl)-isoxazol-3-ylmethyl]-5-(1-isopropyl-piperidin-4-ylcarbamoyl)-1H-pyrazole-3-carbonyl]-amino}-ethyl) ester,
Phosphoric acid mono-(2-{[2-[5-(5-chloro-thiophen-2-yl)-isoxazol-3-ylmethyl]-5-(1-isopropyl-piperidin-4-ylcarbamoyl)-2H-pyrazole-3-carbonyl]-amino}-ethyl)ester,
1-[(5-Chloro-pyridin-2-ylcarbamoyl)-methyl]-5-(1-isopropyl-piperidin-4-ylcarbamoyl)-1H-pyrazole-3-carboxylic acid methyl ester,
1-[(5-Chloro-pyridin-2-ylcarbamoyl)-methyl]-5-(1-isopropyl-piperidin-4-ylcarbamoyl)-1H-pyrazole-3-carboxylic acid,
1-[(5-Chloro-pyridin-2-ylcarbamoyl)-methyl]-1H-pyrazole-3,5-dicarboxylic acid 3-cyclobutylamide 5-[(1-isopropyl-piperidin-4-yl)-amide],
1-[5-(5-Chloro-thiophen-2-yl)-isoxazol-3-ylmethyl]-3-trifluoromethyl-1H-pyrazole-4-carboxylic acid (1-isopropyl-piperidin-4-yl)-amide,
1-[5-(5-Chloro-thiophen-2-yl)-isoxazol-3-ylmethyl]-1H-pyrazole-3,5-dicarboxylic acid bis-[(1-isopropyl-piperidin-4-yl)-amide],
2-[5-(5-Chloro-thiophen-2-yl)-isoxazol-3-ylmethyl]-4-cyano-2H-pyrazole-3-carboxylic acid (1-isopropyl-piperidin-4-yl)-amide,
1-[5-(5-Chloro-thiophen-2-yl)-isoxazol-3-ylmethyl]-4-cyano-1H-pyrazole-3-carboxylic acid (1-isopropyl-piperidin-4-yl)-amide,
2-[(4-Chloro-phenylcarbamoyl)-methyl]-4-cyano-2H-pyrazole-3-carboxylic acid (1-isopropyl-piperidin-4-yl)-amide,
3-{[1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-propionic acid,
1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-(methoxy-amide),
1-[5-(5-Chloro-thiophen-2-yl)-isoxazol-3-ylmethyl]-1H-pyrazole-3,5-dicarboxylic acid 3-carbamoylmethyl-amide 5-[(1-isopropyl-piperidin-4-yl)-amide],
{[1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-acetic acid ethyl ester,
1-[5-(5-Chloro-thiophen-2-yl)-isoxazol-3-ylmethyl]-1H-pyrazole-3,5-dicarboxylic acid 3-[(3-hydroxy-propyl)-amide]5-[(1-isopropyl-piperidin-4-yl)-amide], 1-[1-[5-(5-Chloro-thiophen-2-yl)-isoxazol-3-ylmethyl]-5-(1-isopropyl-piperidin-4-ylcarbamoyl)-1H-pyrazole-3-carbonyl]-(2S)-azetidine-2-carboxylic acid, 2-[5-(5-Chloro-thiophen-2-yl)-isoxazol-3-ylmethyl]-5-(2S,2-hydroxymethyl-pyrrolidine-1-carbonyl)-2H-pyrazole-3-carboxylic acid (1-isopropyl-piperidin-4-yl)-amide, 1-[1-[5-(5-Chloro-thiophen-2-yl)-isoxazol-3-ylmethyl]-5-(1-isopropyl-piperidin-4-ylcarbamoyl)-1H-pyrazole-3-carbonyl]-2S-pyrrolidine-2-carboxylic acid, 2-[5-(5-Chloro-thiophen-2-yl)-isoxazol-3-ylmethyl]-5-(2S,2-methoxymethyl-pyrrolidine-1-carbonyl)-2H-pyrazole-3-carboxylic acid (1-isopropyl-piperidin-4-yl)-amide, 5-(2R,5R,2,5-Bis-methoxymethyl-pyrrolidine-1-carbonyl)-2-[5-(5-chloro-thiophen-2-yl)-isoxazol-3-ylmethyl]-2H-pyrazole-3-carboxylic acid (1-isopropyl-piperidin-4-yl)-amide, 1-[5-(5-Chloro-thiophen-2-yl)-isoxazol-3-ylmethyl]-1H-pyrazole-3,5-dicarboxylic acid 3-[(4,5-dihydro-oxazol-2-yl)-amide]5-[(1-isopropyl-piperidin-4-yl)-amide], 1-[1-[5-(5-Chloro-thiophen-2-yl)-isoxazol-3-ylmethyl]-5-(1-isopropyl-piperidin-4-ylcarbamoyl)-1H-pyrazole-3-carbonyl]-piperidine-4-carboxylic acid ethyl ester, 1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-[(2-morpholin-4-yl-ethyl)-amide], 2-[5-(5-Chloro-thiophen-2-yl)-isoxazol-3-ylmethyl]-5-(4,4-difluoro-piperidine-1-carbonyl)-2H-pyrazole-3-carboxylic acid (1-isopropyl-piperidin-4-yl)-amide, 2-[5-(5-Chloro-thiophen-2-yl)-isoxazol-3-ylmethyl]-5-(2-oxo-oxazolidine-3-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-{[2-(2-oxo-imidazolidin-1-yl)-ethyl]-amide}, 1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-[(2,2,2-trifluoro-ethyl)-amide], 1-[5-(5-Chloro-thiophen-2-yl)-isoxazol-3-ylmethyl]-1H-pyrazole-3,5-dicarboxylic acid 3-[(1,1-dioxo-tetrahydro-1-thiophen-3-yl)-amide]5-[(1-isopropyl-piperidin-4-yl)-amide], 1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-{[3-(2-oxo-pyrrolidin-1-yl)-propyl]-amide}, 5-(Azetidine-1-carbonyl)-2-[5-(5-chloro-thiophen-2-yl)-isoxazol-3-ylmethyl]-2H-pyrazole-3-carboxylic acid (1-isopropyl-piperidin-4-yl)-amide, 2-[5-(5-Chloro-thiophen-2-yl)-isoxazol-3-ylmethyl]-5-(thiazolidine-3-carbonyl)-2H-pyrazole-3-carboxylic acid (1-isopropyl-piperidin-4-yl)-amide, 2-{[1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-3,3,3-trifluoro-propionic acid, 1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-trimethylsilanylmethyl-amide, 2-[5-(5-Chloro-thiophen-2-yl)-isoxazol-3-ylmethyl]-5-[4-(2-oxo-pyrrolidin-1-yl)-piperidine-1-carbonyl]-2H-pyrazole-3-carboxylic acid (1-isopropyl-piperidin-4-yl)-amide, 2-[5-(5-Chloro-thiophen-2-yl)-isoxazol-3-ylmethyl]-5-methanesulfonylaminocarbonyl-2H-pyrazole-3-carboxylic acid (1-isopropyl-piperidin-4-yl)-amide, 2-[5-(5-Chloro-thiophen-2-yl)-isoxazol-3-ylmethyl]-5-(3-hydroxy-azetidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-furan-2-yl-1H-pyrazole-3-carboxylic acid (1-isopropyl-piperidin-4-yl)-amide, 2-[5-(5-Chloro-thiophen-2-yl)-isoxazol-3-ylmethyl]-5-(1-isopropyl-piperidin-4-ylcarbamoyl)-2H-pyrazole-3-carboxylic acid, 5-(Azetidine-1-carbonyl)-1-[5-(5-chloro-thiophen-2-yl)-isoxazol-3-ylmethyl]-1H-pyrazole-3-carboxylic acid (1-isopropyl-piperidin-4-yl)-amide, 1-[5-(5-Chloro-thiophen-2-yl)-isoxazol-3-ylmethyl]-1H-pyrazole-3,5-dicarboxylic acid 3-[(1-isopropyl-piperidin-4-yl)-amide]5-[(2-sulfamoyl-ethyl)-amide], 1-[5-(5-Chloro-thiophen-2-yl)-isoxazol-3-ylmethyl]-1H-pyrazole-3,5-dicarboxylic acid 3-[bis-(2-hydroxy-ethyl)-amide]5-[(1-isopropyl-piperidin-4-yl)-amide], 1-[5-(5-Chloro-thiophen-2-yl)-isoxazol-3-ylmethyl]-1H-pyrazole-3,5-dicarboxylic acid 3-[(2-hydroxy-1,1-bis-hydroxymethyl-ethyl)-amide]5-[(1-isopropyl-piperidin-4-yl)-amide], {[1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-acetic acid isopropyl ester, 1-[(5-Chloro-pyridin-2-ylcarbamoyl)-methyl]-5-(1-isopropyl-piperidin-4-ylcarbamoyl)-1H-pyrazole-3-carboxylic acid ethyl ester, {[1-[(5-Chloro-pyridin-2-ylcarbamoyl)-methyl]-5-(1-isopropyl-piperidin-4-ylcarbamoyl)-1H-pyrazole-3-carbonyl]-amino}-acetic acid isopropyl ester, {[1-[(5-Chloro-pyridin-2-ylcarbamoyl)-methyl]-5-(1-isopropyl-piperidin-4-ylcarbamoyl)-1H-pyrazole-3-carbonyl]-amino}-acetic acid ethyl ester, {[1-[(5-Chloro-pyridin-2-ylcarbamoyl)-methyl]-5-(1-isopropyl-piperidin-4-ylcarbamoyl)-1H-pyrazole-3-carbonyl]-amino}-acetic acid, 2-[(5-Chloro-pyridin-2-ylcarbamoyl)-methyl]-5-(3-hydroxy-azetidine-1-carbonyl)-2H-pyrazole-3-carboxylic acid (1-isopropyl-piperidin-4-yl)-amide, 1-[(5-Chloro-pyridin-2-ylcarbamoyl)-methyl]-5-(1-isopropyl-piperidin-4-ylcarbamoyl)-1H-pyrazole-3-carboxylic acid cyclopropylmethyl ester, 2-{[1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-3-methyl-butyric acid ethyl ester, 2-{[1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-3-methyl-butyric acid, 1-[5-(5-Chloro-thiophen-2-yl)-isoxazol-3-ylmethyl]-5-furan-2-yl-1H-pyrazole-3-carboxylic acid [4-(3-oxo-morpholin-4-yl)-phenyl]-amide, 1-[5-(5-Chloro-thiophen-2-yl)-isoxazol-3-ylmethyl]-5-hydroxymethyl-1H-pyrazole-3-carboxylic acid [4-(3-oxo-morpholin-4-yl)-phenyl]-amide, 1-[5-(5-Chloro-thiophen-2-yl)-isoxazol-3-ylmethyl]-5-[2-(2-methoxy-ethoxy)-ethoxymethyl]-1H-pyrazole-3-carboxylic acid (1-isopropyl-piperidin-4-yl)-amide, 2-[5-(5-Chloro-thiophen-2-yl)-isoxazol-3-ylmethyl]-5-(2-methoxy-ethoxymethyl)-2H-pyrazole-3-carboxylic acid (1-isopropyl-piperidin-4-yl)-amide, 1-[(5-Chloro-pyridin-2-ylcarbamoyl)-methyl]-5-[2-(2-methoxy-ethoxy)-ethoxymethyl]-1H-pyrazole-3-carboxylic acid (1-isopropyl-piperidin-4-yl)-amide, 2-[(5-Chloro-pyridin-2-ylcarbamoyl)-methyl]-5-[2-(2-methoxy-ethoxy)-ethoxy]-2H-pyrazole-3-carboxylic acid (1-isopropyl-piperidin-4-yl)-amide, 2-[(5-Chloro-pyridin-2-ylcarbamoyl)-methyl]-5-(2,2,2-trif-luoro-ethoxy)-2H-pyrazole-3-carboxylic acid (1-isopropyl-piperidin-4-yl)-amide, 1-[(5-Chloro-pyridin-2-ylcarbamoyl)-methyl]-5-(1-isopropyl-piperidin-4-ylcarbamoyl)-1H-pyrazole-3-carboxylic acid 2-methoxy-ethyl ester, 1-[(5-Chloro-pyridin-2-ylcarbamoyl)-methyl]-5-(1-isopropyl-piperidin-4-ylcarbamoyl)-1H-pyrazole-3-carboxylic acid 2-hydroxy-ethyl ester, 2-[(5-Chloro-pyridin-2-ylcarbamoyl)-methyl]-5-([1,4]oxazepane-4-carbonyl)-2H-pyrazole-3-carboxylic acid (1-isopropyl-piperidin-4-yl)-amide, 5-(1-Isopropyl-piperidin-4-ylcarbamoyl)-1-(3-methoxy-benzyl)-1H-pyrazole-3-carboxylic acid, 1-[5-(5-Chloro-thiophen-2-yl)-isoxazol-3-ylmethyl]-5-(1-isopropyl-piperidin-4-ylcarbamoyl)-1H-pyrazole-3-carboxylic acid 2-hydroxy-ethyl ester, 1-[5-(5-Chloro-thiophen-2-yl)-isoxazol-3-ylmethyl]-5-(1-isopropyl-piperidin-4-ylcarbamoyl)-1H-pyrazole-3-carboxylic acid carboxymethyl ester, 1-[(5-Chloro-pyridin-2-ylcarbamoyl)-methyl]-5-(1-isopropyl-piperidin-4-ylcarbamoyl)-4-(2,2,2-trifluoro-ethoxy)-1H-pyrazole-3-carboxylic acid ethyl ester, and 1-[(5-Chloro-pyridin-2-ylcarbamoyl)-methyl]-5-hydroxymethyl-1H-pyrazole-3-carboxylic acid (1-isopropyl-piperidin-4-yl)-amide.

Another particular embodiment of the invention is a process for the preparation of the compound according to claim 1, comprising condensing a carboxylic acid of the formula 2

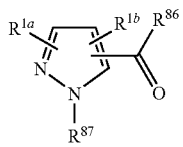

2 with a compound of the formula $HR^{8'}$ or with an amine of the formula $HN(R^{1'})R^{2'}$—V-G-M to give a compound of the formula 3

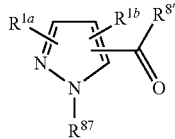

3 and optionally converting the compound of formula 3 into a compound of the formula I, wherein the groups $R^{8'}$ and $R^{87}$ are respectively the groups —$N(R^1)$—$R^2$—V-G-M and $R^0$-Q-, which are as defined in claim 1, and $R^1a$ and $R^1b$ have respectively the meaning of $R^3$ and R4 in claim 1.

Another particular embodiment of the invention is a pharmaceutical preparation comprising a pharmaceutically effective amount of at least one compound according to claim 1 and a pharmaceutically acceptable carrier.

Another particular embodiment of the invention is wherein a method of inhibiting the activity of factor Xa or factor VIIa comprising contacting an inhibitory amount of a compound according to claim 1 with a composition containing factor Xa or factor VIIa to influence blood coagulation.

Another particular embodiment of the invention is wherein the blood coagulation is connected with abnormal thrombus formation, acute myocardial infarction, cardiovascular disorders, unstable angina, thromboembolism, acute vessel closure associated with thrombolytic therapy or percutaneous transluminal coronary angioplasty (PTCA), transient ischemic attacks, stroke, intermittent claudication, bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, viral infections or cancer, or reducing an inflammatory response, fibrinolysis, or treatment of coronary heart disease, myocardial infarction, angina pectoris, vascular restenosis, adult respiratory distress syndrome, multi-organ failure and disseminated intravascular clotting disorder, deep vein or proximal vein thrombosis.

Another particular embodiment of the invention is wherein a method of inhibiting the activity of factor Xa or factor VIIa comprising contacting an inhibitory amount of a compound according to claim 1 with a composition containing factor Xa or factor VIIa to influence fibrinolysis.

Also with respect to all preferred a compound of formulae I, Ib and Ic all their stereoisomeric forms and mixtures thereof in any ratio and their physiologically acceptable salts explicitly are a subject of the present invention, as well as are their prodrugs. Similarly, also in all preferred a compound of formulae I, Ib and Ic, all residues that are present more than one time in the molecule are independent of each other and can be identical or different.

The compound of formulae I, Ib and Ic can be prepared by utilising procedures and techniques, which per se are well known and appreciated by one of ordinary skill in the art. Starting materials or building blocks for use in the general synthetic procedures that can be applied in the preparation of the compounds of formulae I, Ib and Ic are readily available to one of ordinary skill in the art. In many cases they are commercially available or have been described in the literature. Otherwise they can be prepared from readily available precursor compounds analogously to procedures described in the literature, or by procedures or analogously to procedures described in this application.

In general, a compound of formulae I, Ib and Ic can be prepared, for example in the course of a convergent synthesis, by linking two or more fragments which can be derived retrosynthetically from the formulae I, Ib and Ic. More specifically, suitably substituted starting Pyrazole derivatives are employed as building blocks in the preparation of the compounds of formulae I, Ib and Ic. If not commercially available, such Pyrazole derivatives can be prepared according to the well-known standard procedures for the formation of the Pyrazole ring system. By choosing suitable precursor molecules, these pyrazole syntheses allow the introduction of a variety of substituents into the various positions of the pyrazole system, which can be chemically modified in order to finally arrive at the molecule of the formulae I, Ib and Ic having the desired substituent pattern. As one of the comprehensive reviews in which numerous details and literature references on the chemistry of pyrazole and on synthetic procedures for their preparation can be found, J. Eiguero in "Comprehensive Heterocyclic Chemistry II"; Eds. A. Katritzky, Ch. Rees, E. Scriven; Elsevier 1996, Vol. 3; K. Kirschke in Houben-Weyl, "Methoden der Organischen Chemie" (Methods of Organic Chemistry), Georg Thieme Verlag, Stuttgart, Germany 1994, Vol. E8b Hetarene; T. Nagai et al. Org. Prep. Proced. Int. (1993), 25, 403; M. Elnagdi et al.

Heterocycles (1985) 23, 3121; K. Makino et al. J. Heterocycl. Chem. (1998) 35, 489; K. Makino et al. J. Heterocycl. Chem. (1999) 36, 321.

If starting pyrazole derivatives are not commercially available and have to be synthesized this can be done, for example, according to the well-known pyrazole syntheses mentioned above. In the following procedures of particuluar interest for the embodiment of this invention are listed and referenced briefly, however, they are standard procedures comprehensively discussed in the literature, and are well known to one skilled in the art. Although not always shown explicitly, in certain cases positional isomers will occur during the synthesis of the below mentioned reactions. Nevertheless such mixtures of positional isomers, can be separated by modern separation techniques like, for example, preparative HPLC.

1) a) N. Kudo et al. Chem. Pharm. Bull. (1999) 47, 857.
   b) M. Dewar et al. J. Chem. Soc. (1945) 114.
   c) L. J. Smith, J. Am. Chem. Soc. (1949) 71, 2671.
   d) J. Zhang, et al., Bioorg. Med. Chem. Lett. (2000) 10, 2575.

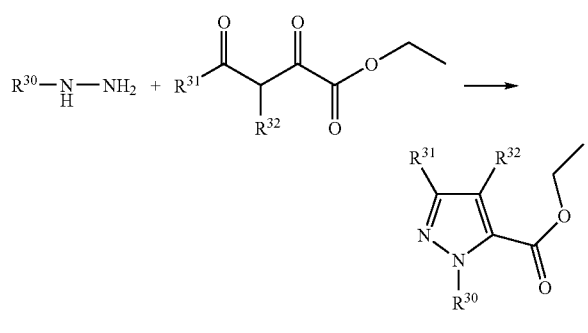

2) a) A. Padwa, J. Heterocycl. Chem. (1987) 24, 1225.
   b) A. W. Erian et al.; Synth Commun. (1999) 29, 1527.

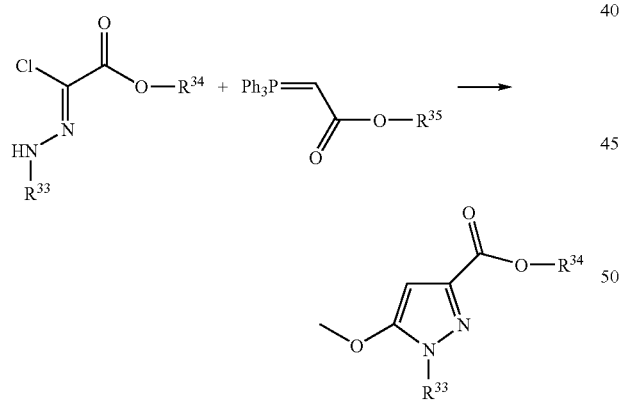

3) N. K. Markova et al., Zh. Org. Khim. (1983) 19, 2281.

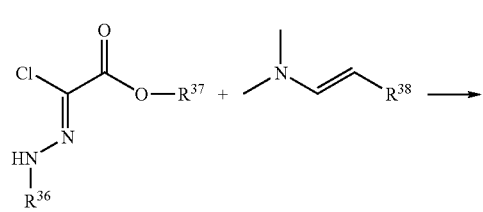

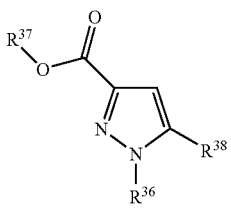

4) P. Bravo et al., Tetrahedron (1994) 50, 8827.

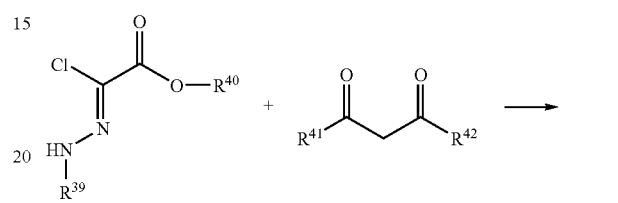

5) a) M. A. Martins et al., Synthesis (1995) 12, 1491.
   b) M. A. Martins et al., J. Heterocycl. Chem. (1999) 36, 217.

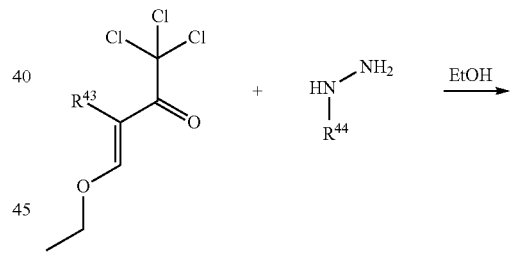

6) R. G. Jones et al., J. Org. Chem. (1955) 20, 1342.

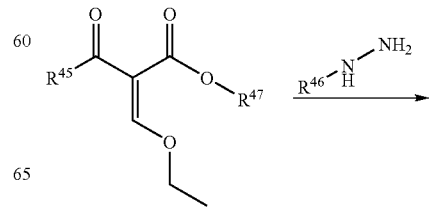

-continued
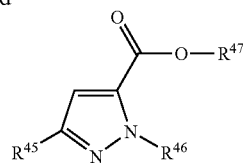
7) W. T. Ashton et al., J. Heterocycl. Chem. (1993) 30, 307.
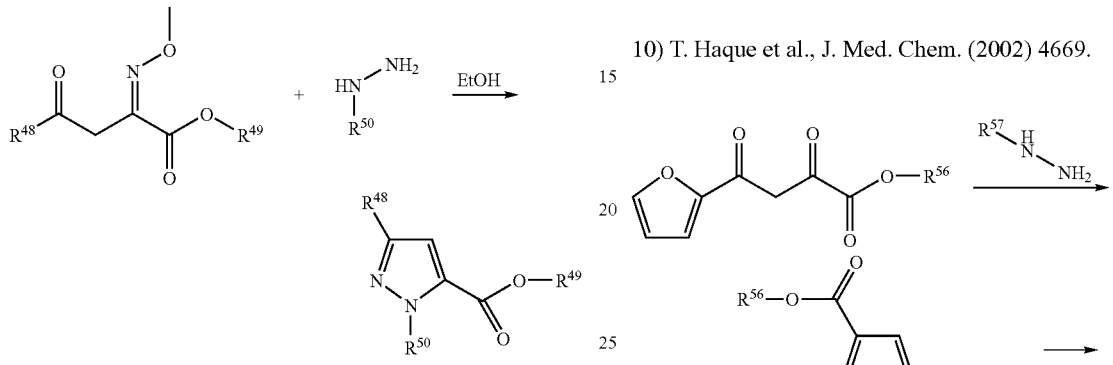
8) a) K. I. Bookermilburn, Synlett, (1992) 327.
   b) G. Heinisch et al., J. Chem. Soc. Perkin. Trans 1 (1990) 1829.
   c) K. Tumbull et al., Org. Prep. Proced. Int. (2000) 32, 593
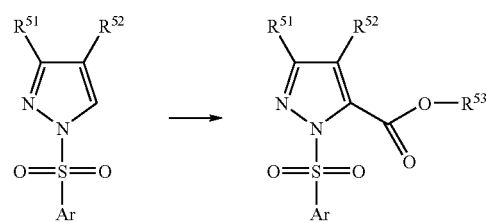
9) F. Farina et al. Heterocycles (1989) 29, 967.
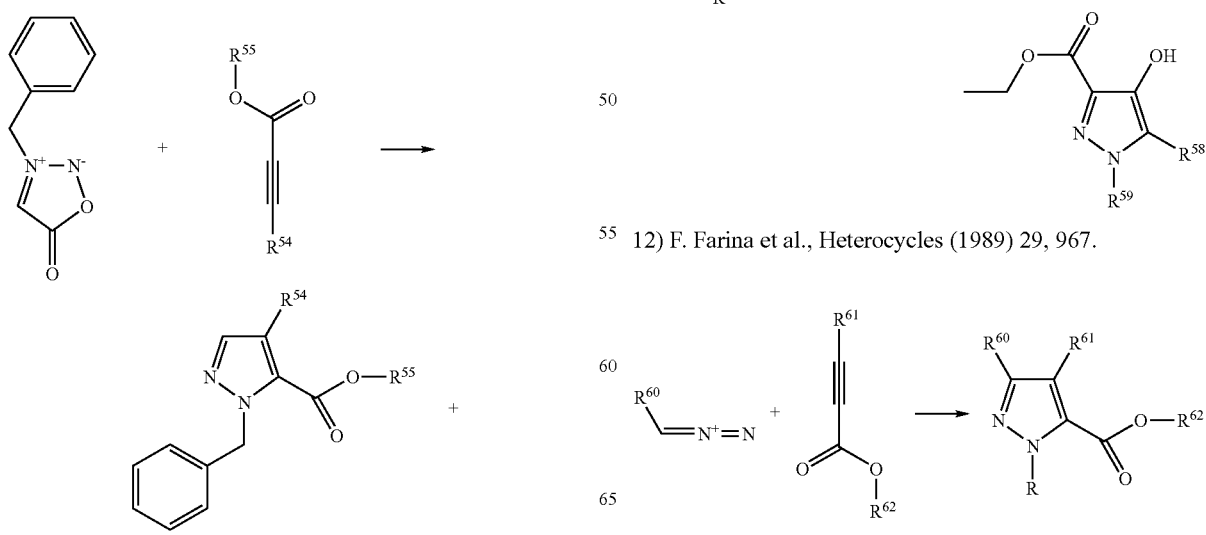
-continued
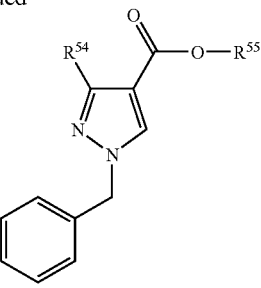
10) T. Haque et al., J. Med. Chem. (2002) 4669.
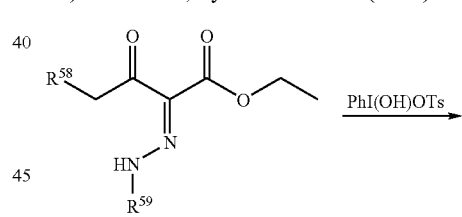
11) H. V. Patel, Synth. Commun. (1991) 21, 1583.
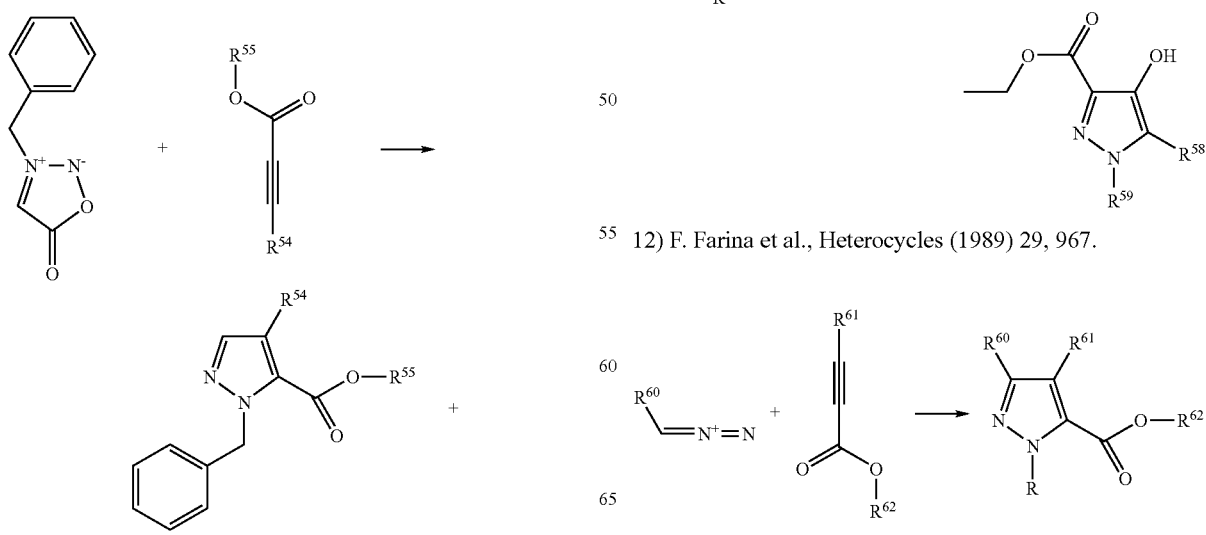
12) F. Farina et al., Heterocycles (1989) 29, 967.

13) R. Huisgen et al., J. Am. Chem. Soc. (1979) 101, 3647.

17) D. Sauer et al., J. Org. Chem. (1990) 55, 5535.

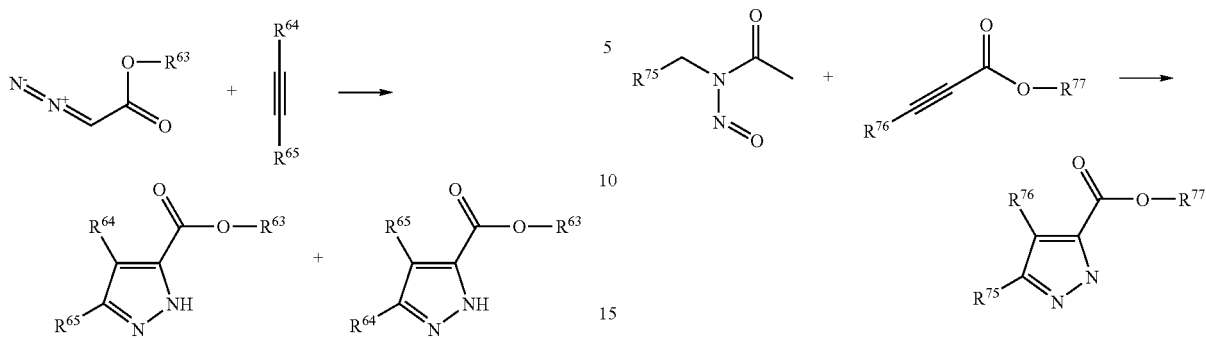

14) W. Sucrow et al., Angew. Chem., Int. Ed. (1975) 14, 560.

18) K. Washizuka et al., Tetrahedron Lett. (1999) 40, 8849.

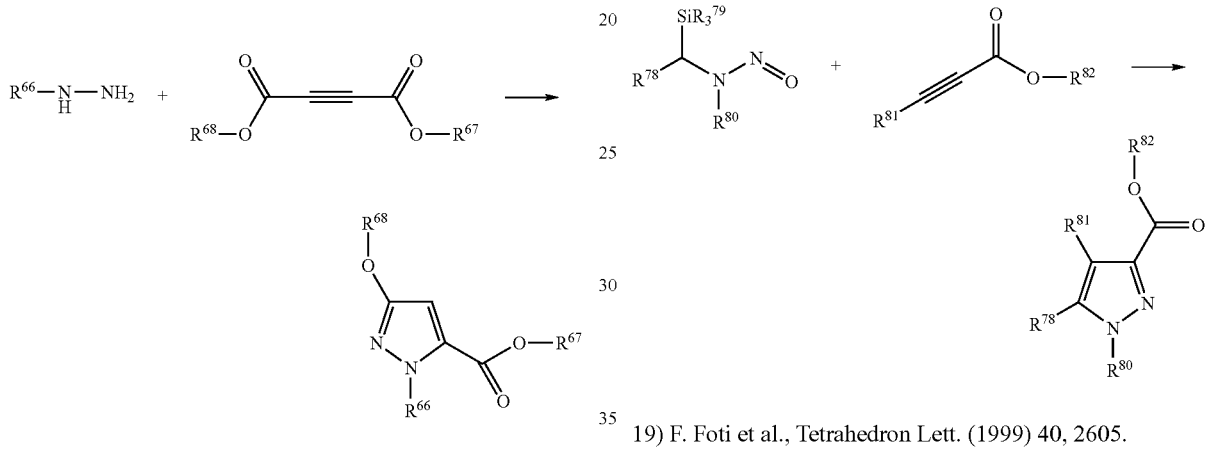

15) C. Baldoli et al., J. Heterocycl. Chem. (1989), 26, 241.

19) F. Foti et al., Tetrahedron Lett. (1999) 40, 2605.

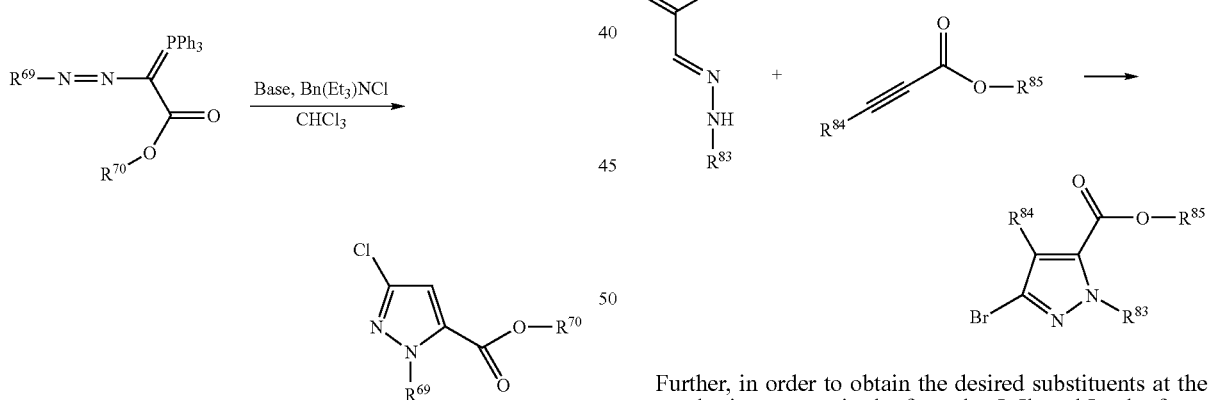

16) G. M. Pilling et al., Tetrahedron Lett. (1988) 29, 1341.

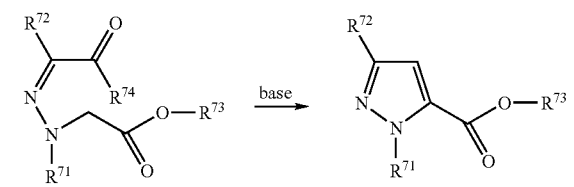

Further, in order to obtain the desired substituents at the pyrazole ring system in the formulae I, Ib and Ic, the functional groups introduced into the ring system during the pyrazole synthesis can be chemically modified. Especially the groups present in the pyrazole ring system can be modified by a variety of reactions and thus the desired residues $R^{1a}$, $R^{1b}$ be obtained. For example, an pyrazole carrying a hydrogen atom in the 3-position can also be obtained by saponification and subsequent decarboxylation of pyrazole carrying an ester group in the respective position. Alkyl- or hydroxymethyl groups as well as formyl groups attached to the pyrazole core can be transformed to a variety of functional groups, for example, to the corresponding carboxylic acid or carboxylic ester by many oxidative reactions well known to those skilled in the art. Moreover a nitrile group attached to the pyrazole ring can, for example, easily be converted into the desired acid under acidic or basic conditions. In addition, carboxylic acid groups and acetic acid groups in the 3-position, the 4-position and the 5-position can be converted into their homologues by usual reactions for chain elongation of carboxylic acids. Halogen atoms can be introduced into the 3-position, the 4-position and the 5-position, for example according to procedures like the following described in the literature. For the fluorination of pyrazoles N-fluoro-2,4,6-trimethylpyridinium triflate is the reagent of choice (T. Umemoto, S. Fukami, G. Tomizawa, K. Harasawa, K. Kawada, K. Tomita, J. Am. Chem. Soc. (1990) 112, 8563 see also K. Manko et al., J. Fluorine Chem. (1988) 39, 435; R. Storer et al. Nucleosides Nucleotides (1999) 18; 203) however, other suitable fluorinating reagents may also be employed where appropriate. The chlorination, bromination, or iodination of pyrazoles can be accomplished by the reaction with elemental halogens or by the use of NCS, NBS or NIS and many other reagents well known to those skilled in the art. In addition, suitable procedures are reported, for example, by M. Rodriguez-Franco et al., Tetrahedron Lett. (2001) 42, 863; J. Pawlas et al., J. Org. Chem. (2000) 65, 9001; Y. Huang et al., Org Lett (2000) 2, 2833; W. Holzer et al., J. Heterocycl. Chem. (1995) 32, 1351; N. Kudo et al., Chem. Pharm. Bull. (1999) 47, 857; G. Auzzi et al., Farmaco, Ed Sci (1979) 34, 743; K. Morimoto et al., J. Heterocycl. Chem. (1997) 34, 537; D. Jeon et al., Synth. Commun. (1998) 28, 2159.

Depending on the reaction conditions, reagent, stochiometry and substitution pattern the halogen is introduced in the 3-position and/or 4-position and/or 5-position. By selective halogen/metal exchange or metalation by selective hydrogen/metal exchange and subsequent reaction with a wide range of electrophiles various substituents can be introduced at the heterocyclic nucleus. (M. R. Grimmett, Heterocycles (1994) 37, 2087; V. D. Gardner et al., J. Heterocycl. Chem. (1984), 21, 121; D. Butler et al., J. Org. Chem. (1971) 36, 2542). Halogens or hydroxy groups (via their triflates or nonaflates)—or primary amines (via their diazonium salts) present in the pyrazole structure—can be converted directly, or after interconversion to the corresponding stannane, or boronic acid, into a variety of other functional groups like for example —CN, —$CF_3$, —$C_2F_5$, ethers, acids, amides, amines, alkyl- or aryl-groups mediated by means of transition metals, namely palladium or nickel catalysts or copper salts and reagents for example referred to below (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. (1998) 110, 2154; B. Yang, S. Buchwald, J. Organomet. Chem. (1999) 576, 125; T. Sakamoto, K. Ohsawa, J. Chem. Soc. Perkin Trans I (1999) 2323; D. Nichols, S. Frescas, D. Marona-Lewicka, X. Huang, B. Roth, G. Gudelsky, J. Nash, J. Med. Chem. (1994) 37, 4347; P. Lam, C. Clark, S. Saubem, J. Adams, M. Winters, D. Chan, A. Combs, Tetrahedron Lett. (1998) 39, 2941; D. Chan, K. Monaco, R. Wang, M. Winters, Tetrahedron Lett. (1998) 39, 2933; V. Farina, V. Krishnamurthy, W. Scott, The Stille Reaction, Wiley, 1994; F. Qing et al. J. Chem. Soc. Perkin Trans. 1 (1997) 3053; S. Buchwald et al. J. Am. Chem. Soc. (2001) 123, 7727; S. Kang et al. Synlett (2002) 3, 427; S. Buchwald et al. Organic Lett. (2002) 4, 581; T. Fuchikami et al. Tetrahedron Lett. (1991) 32, 91; Q. Chen et al. Tetrahedron Lett. (1991) 32, 7689).

Nitro groups can be reduced to amino groups by means of various reducing agents, such as sulfides, dithionites, complex hydrides or by catalytic hydrogenation. A reduction of a nitro group may also be carried out at a later stage of the synthesis of a compound of the formulae I, Ib and Ic, and a reduction of a nitro group to an amino group may also occur simultaneously with a reaction performed on another functional group, for example when reacting a group like a cyano group with hydrogen sulfide or when hydrogenating a group. In order to introduce the residues $R^{1a}$, $R^{1b}$, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivatives such as acid chlorides, anhydrides, activated esters or others or by reaction with carboxylic acids in the presence of an activating agent, or according to standard procedures for sulfonylation, for example by reaction with sulfonyl chlorides.

Ester groups present in the pyrazole nucleus can be hydrolyzed to the corresponding carboxylic acids, which after activation can then be reacted with amines or alcohols under standard conditions to give amides or alcohols, respectively. Ester groups present in the pyrazole nucleus can be converted to other esters by transesterification. Carboxylic acids attached to a suitable pyrazole nucleus can also be alkylated to give esters. Ether groups present at the pyrazole nucleus, for example benzyloxy groups or other easily cleavable ether groups, can be cleaved to give hydroxy groups which then can be reacted with a variety of agents, for example etherification agents or activating agents allowing replacement of the hydroxy group by other groups. Sulfur-containing groups can be reacted analogously.

During the course of the synthesis in order to modify the groups $R^{87}$ or $R^{8'}$ attached to the pyrazole ring system by application of parallel synthesis methodology, a variety of reactions can be extremely useful, including, for example, palladium, nickel or copper catalysis. Such reactions are described for example in F. Diederich, P. Stang, Metal-catalyzed Cross-coupling Reactions, Wiley-VCH (1998); or M. Beller, C. Bolm, Transition Metals for Organic Synthesis, Wiley-VCH (1998); J. Tsuji, Palladium Reagents and Catalysts, Wiley (1996); J. Hartwig, Angew. Chem. (1998), 110, 2154; B. Yang, S. Buchwald, J. Organomet. Chem. (1999), 576, 125; P. Lam, C. Clark, S. Saubern, J. Adams, M. Winters, D. Chan, A. Combs, Tetrahedron Lett. (1998), 39, 2941; D. Chan, K. Monaco, R. Wang, M. Winters, Tetrahedron Lett. (1998), 39, 2933; J. Wolfe, H. Tomori, J. Sadight, J. Yin, S. Buchwald, J. Org. Chem. (2000), 65, 1158; V. Farina, V. Krishnamurthy, W. Scott, The Stille Reaction, Wiley, (1994); S. Buchwald et al., J. Am. Chem. Soc. (2001), 123, 7727; S. Kang et al., Synlett (2002), 3, 427; S. Buchwald et al., Org. Lett. (2002), 4, 581.

The previously-mentioned reactions for the conversion of functional groups are furthermore, in general, extensively described in textbooks of organic chemistry like M. Smith, J. March, March's Advanced Organic Chemistry, Wiley-VCH, 2001 and in treatises like Houben-Weyl, "Methoden der Organischen Chemie" (Methods of Organic Chemistry), Georg Thieme Verlag, Stuttgart, Germany, or "Organic Reactions", John Wiley & Sons, New York, or R. C. Larock, "Comprehensive Organic Transformations", Wiley-VCH, $2^{nd}$ ed (1999), B. Trost, I. Fleming (eds.) Comprehensive Organic Synthesis, Pergamon, 1991; A. Katritzky, C. Rees, E. Scriven Comprehensive Heterocyclic Chemistry II, Elsevier Science, 1996) in which details on the reactions and primary source literature can be found. Due to the fact that in the present case the functional groups are attached to an pyrazole ring it may in certain cases become necessary to specifically adapt reaction conditions or to choose specific reagents from a variety of reagents that can in principle be employed in a conversion reaction, or otherwise to take specific measures for achieving a desired conversion, for example to use protection group techniques. However, finding out suitable reaction variants and reaction conditions in such cases does not cause any problems for one skilled in the art.

The structural elements present in the residues attached at the 1-position of the pyrazole ring in the compound of formulae I, Ib and Ic and in the $COR^{8'}$ group present in the 3-position and/or in the 5-position of the pyrazole ring can be introduced into the starting pyrazole derivative obtainable as outlined above by consecutive reaction steps using synthesis methodologies like those outlined below using procedures which per se are well known to one skilled in the art.

The residues $R^{8'}$ that can be introduced in formula 2, for example, by condensing a corresponding carboxylic acid of the formula 2 with a compound of the formula $HR^{8'}$, i.e. with an amine of the formula $HN(R^{1'})R^{2'}$—V-G-M to give a compound of the formula 3. the compound of the formula 3 thus obtained can already contain the desired final groups, i.e. the groups $R^{8'}$ and $R^{8'}$ can be the groups —$N(R^1)$—$R^2$—V-G-M and $R^0$-Q- as defined in the formulae I, Ib and Ic, or optionally in the compound of the formula 3 thus obtained subsequently the residue or the residues $R^{8'}$ and the residue $R^{8'}$ are converted into the residues —$N(R^1)R^2$—V-G-M and $R^0$-Q-, respectively, to give the desired compound of the formulae I, Ib and Ic.

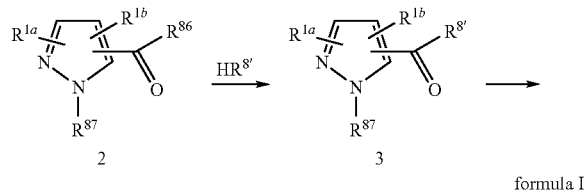

formula I

Thus, the residues $R^{8'}$ and the residues $R^{1'}$ and $R^{2'}$-V-G-M contained therein can have the denotations of $R^1$ and $R^2$—V-G-M, respectively, given above or in addition in the residues $R^{1'}$ and $R^{2'}$—V-G-M functional groups can also be present in the form of groups that can subsequently be transformed into the final groups $R^1$ and $R^2$—V-G-M, i.e. functional groups can be present in the form of precursor groups or of derivatives, for example in protected form. In the course of the preparation of the compound of formulae I, Ib and Ic, it can generally be advantageous or necessary to introduce functional groups which reduce or prevent undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991, or P. Kocienski, Protecting Groups, Thieme 1994). Examples of precursor groups are cyano and nitro. The cyano group can in a later step be transformed into carboxylic acid derivatives or by reduction into aminomethyl groups, or the nitro groups may be transformed by reduction like catalytic hydrogenation into amino groups. Protective groups can also have the meaning of a solid phase, and cleavage from the solid phase stands for the removal of the protective group. The use of such techniques is known to those skilled in the art (Burgess K (Ed.) Solid Phase Organic Synthesis, New York, Wiley, 2000). For example, a phenolic hydroxy group can be attached to a trityl-polystyrene resin, which serves as a protecting group, and the molecule is cleaved from this resin by treatment with TFA at a later stage of the synthesis.

The residue $R^{87}$ in the compound of formulae 2 and 3 can denote the group -Q-$R^0$ as defined above which finally is to be present in the desired target molecule of the formulae I, Ib and Ic, or it can denote a group which can subsequently be transformed into the group -Q-$R^0$, for example a precursor group or a derivative of the group -Q-$R^0$ in which functional groups are present in protected form, or $R^{87}$ can denote a hydrogen atom or a protective group for the nitrogen atom of the pyrazole ring. Similarly, the residues $R^{1a}$ and $R^{1b}$ in the formulae 2 and 3 have the corresponding definitions of $R^4$, and $R^3$ in formulae I, Ib and Ic as defined above, however, for the synthesis of the compound of formulae I, Ib and Ic these residues, too, can in principle be present at the stage of the condensation of a compound of the formula 2 with a compound of the formula $HR^{8'}$ giving a compound of the formula 3 in the form of precursor groups or in protected form.

The residues $R^{86}$ in the compound of formula 2 which can be identical or different, can be, for example, hydroxy or ($C_1$-$C_4$)-alkoxy, i.e., the groups $COR^{86}$ present in the compound of formula 2 can be, for example, the free carboxylic acids or esters thereof like alkyl esters as can be the groups $COR^{8'}$ in the compound of formulae I, Ib and Ic. The groups $COR^{86}$ can also be any other activated derivative of a carboxylic acid which allows amide formation, ester formation or thioester formation with a compound of the formula $HR^{8'}$. The group $COR^{86}$ can be, for example, an acid chloride, an activated ester like a substituted phenyl ester or an N-hydroxysuccinimide or a hydroxybenzotriazole ester, an azolide like an imidazolide, an azide or a mixed anhydride, for example a mixed anhydride with a carbonic acid ester or with a sulfonic acid, which derivatives can all be prepared from the carboxylic acid by standard procedures and can be reacted with an amine, an alcohol or a mercaptan of the formula $HR^{8'}$ under standard conditions. A carboxylic acid group COOH representing $COR^{86}$ in a compound of the formula 2 can be obtained, for example, from an ester group introduced into the pyrazole system during a pyrazole synthesis by standard hydrolysis procedures. It can also be obtained, for example, by hydrolysis of a nitrile group introduced into the pyrazole system during a pyrazole synthesis.

A compound of formulae I, Ib and Ic in which a group $COR^{8'}$ is an ester group can also be prepared from a compound of formula 2 in which $COR^{86}$ is a carboxylic acid group by common esterification reactions like, for example, reacting the acid with an alcohol under acid catalysis, or alkylation of a salt of the carboxylic acid with an electrophile like an alkyl halogenide, or by transesterification from another ester. A compound of formulae I, Ib and Ic in which a group $COR^{8'}$ is an amide group can be prepared from amines and a compound of formula 2 in which $COR^{86}$ is a carboxylic acid group or an ester thereof by common amination reactions. Especially for the preparation of amides the compound of formula 2 in which $COR^{86}$ is a carboxylic acid group can be condensed under standard conditions with a compound of formula $HR^{8'}$ which are amines by means of common coupling reagents used in peptide synthesis. Such coupling reagents are, for example, carbodiimides like dicyclohexylcarbodiimide (DCC) or diisopropylcarbodiimide, carbonyldiazoles like carbonyldiimidazole (CDI) and similar reagents, propylphosphonic anhydride, O-((cyano-(ethoxycarbonyl)-methylene) amino)-N,N,N',N'-tetramethyluronium tetrafluoroborate (TOTU), diethylphosphoryl cyanide (DEPC) or bis-(2-oxo-3-oxazolidinyl)-phosphoryl chloride (BOP-Cl) and many others.

If the residue -Q-R⁰ present in an pyrazole of the formulae I, Ib and Ic or the residue $R^{87}$ present in an pyrazole of the formula 2, or a residue in which functional groups within the residue -Q-R⁰ or $R^{87}$ are present in protected form or in the form of a precursor group, have not already been introduced during a preceding step, for example during a synthesis of the pyrazole nucleus, these residues can, for example, be introduced into the 1-position of the pyrazole system by conventional literature procedures well known to one skilled in the art for N-alkylation, reductive amination, N-arylation, N-acylation or N-sulfonylation of ring nitrogen atoms of heterocycles. The starting pyrazole derivative that is to be employed in such a reaction carries a hydrogen atom in the 1-position. N-Alkylation of a ring nitrogen atom can, for example, be performed under standard conditions, preferably in the presence of a base like $K_2CO_3$, $Cs_2CO_3$, NaH or KO'Bu, using an alkylating compound of the formula LG-Q-R⁰ or of the formula $R^{87}$-LG, wherein the atom in the group Q or in the group $R^{87}$ bonded to the group LG in this case is an aliphatic carbon atom of an alkyl moiety and LG is a leaving group, for example halogen like chlorine, bromine or iodine, or a sulfonyloxy group like tosyloxy, mesyloxy or trifluormethylsulfonyloxy. LG may, for example, also be a hydroxy group which, in order to achieve the alkylation reaction, is activated in a well-known Mitsunobu reaction by a conventional activating agent. The regioselectivity of the N-alkylation can be controlled by the choice of the base, solvent and reaction conditions. Nevertheless mixtures of positional isomers, can be separated by modern separation techniques like, for example, flash chromatography, crystallisation or preparative HPLC.

For the preparation of compounds in which A is a direct linkage and an aromatic group is directly bonded to the 1-position of the pyrazole system, conventional arylation procedures can be used. For example aryl fluorides like alkyl fluorobenzoates or 4-fluorophenyl nitriles can be employed as arylating agents. Such processes are described, for example, by K. Cooper et al., J. Med. Chem. (1992), 35, 3115; M. Artico et al., Eur. J. Med. Chem. Chim. Ther. (1992) 27, 219; X.-J. Wang et al., Tetrahedron Letters (2000) 41, 5321; M. L. Cerrada et al., Synth. Commun. (1993) 23, 1947. Alternatively a wide variety of substituted aryl iodides, aryl bromides or aryl triflates can serve as arylating agents at the 1-position of the heterocyclic nitrogen in a copper salt or palladium mediated reaction according for example to P. Cozzi et al. Farmaco (1987) 42, 205; P. Unangst, D. Connor, R. Stabler, R. Weikert, J. Heterocycl. Chem. (1987) 24, 811; G. Tokmakov, I. Grandberg, Tetrahedron (1995) 51, 2091; D. Old, M. Harris, S. Buchwald, Org. Lett. (2000) 2, 1403, G. Mann, J. Hartwig, M. Driver, C. Fernandez-Rivas, J. Am. Chem. Soc. (1998) 120, 827; J. Hartwig, M. Kawatsura, S. Hauk, K. Shaughnessy, L. J. Org. Chem. (1999) 64, 5575; S. Buchwald et al., J. Am. Chem. Soc. (2001) 123, 7727. Moreover such arylations can also be accomplished by reaction of a wide range of substituted aryl boronic acids as demonstrated for example by P. Lam et al., Tetrahedron Lett. (1998) 39, 2941; V. Collot et al., Tetrahedron Lett. (2000) 41, 9053; P. Lam et al., Tetrahedron Lett. (2001) 42, 3415;

Preferred methods include, but are not limited to those described in the examples.

The compounds of the present invention are serine protease inhibitors, which inhibit the activity of the blood coagulation enzyme factors Xa and/or factor VIIa. In particular, they are highly active inhibitors of factor Xa. They are specific serine protease inhibitors inasmuch as they do not substantially inhibit the activity of other proteases whose inhibition is not desired. The activity of the compound of formulae I, Ib and Ic can be determined, for example, in the assays described below or in other assays known to those skilled in the art. With respect to factor Xa inhibition, a preferred embodiment of the invention comprises compounds which have a Ki<1 mM for factor Xa inhibition as determined in the assay described below, with or without concomitant factor VIIa inhibition, and which preferably do not substantially inhibit the activity of other proteases involved in coagulation and fibrinolysis whose inhibition is not desired (using the same concentration of the inhibitor). the compounds of the invention inhibit factor Xa catalytic activity either directly, within the prothrombinase complex or as a soluble subunit, or indirectly, by inhibiting the assembly of factor Xa into the prothrombinase complex.

As inhibitors of factor Xa and/or factor VIIa the compound of formulae I, Ib and Ic and their physiologically tolerable salts and their prodrugs are generally suitable for the therapy and prophylaxis of conditions in which the activity of factor Xa and/or factor VIIa plays a role or has an undesired extent, or which can favorably be influenced by inhibiting factor Xa and/or factor VIIa or decreasing their activities, or for the prevention, alleviation or cure of which an inhibition of factor Xa and/or factor VIIa or a decrease in their activity is desired by the physician. As inhibition of factor Xa and/or factor VIIa influences blood coagulation and fibrinolysis, the compound of formulae I, Ib and Ic and their physiologically tolerable salts and their prodrugs are generally suitable for reducing blood clotting, or for the therapy and prophylaxis of conditions in which the activity of the blood coagulation system plays a role or has an undesired extent, or which can favorably be influenced by reducing blood clotting, or for the prevention, alleviation or cure of which a decreased activity of the blood coagulation system is desired by the physician. A specific subject of the present invention thus are the reduction or inhibition of unwanted blood clotting, in particular in an individual, by administering an effective amount of a compound I or a physiologically tolerable salt or a prodrug thereof, as well as pharmaceutical preparations therefor.

The present invention also is directed to the compound of formulae I, Ib and Ic and/or their physiologically tolerable salts and/or their prodrugs for use as pharmaceuticals (or medicaments), to the use of the compound of formulae I, Ib and Ic and/or their physiologically tolerable salts and/or their prodrugs for the production of pharmaceuticals for inhibition of factor Xa and/or factor VIIa or for influencing blood coagulation, inflammatory response or fibrinolysis or for the therapy or prophylaxis of the diseases mentioned above or below, for example for the production of pharmaceuticals for the therapy and prophylaxis of cardiovascular disorders, thromboembolic diseases or restenoses. The invention also is directed to the use of the compound of formulae I, Ib and Ic and/or their physiologically tolerable salts and/or their prodrugs for the inhibition of factor Xa and/or factor VIIa or for influencing blood coagulation or fibrinolysis or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis. The present invention also is directed to pharmaceutical preparations (or pharmaceutical compositions) which contain an effective amount of at least one compound of the formulae I, Ib and Ic and/or its physiologically tolerable salts and/or its prodrugs in addition to a customary pharmaceutically acceptable carrier, i.e. one or more pharmaceutically acceptable carrier substances or excipients and/or auxiliary substances or additives.

The invention also is directed to the treatment of disease states such as abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer. The compounds of the present invention can also be used to reduce an inflammatory response. Examples of specific disorders for the treatment or prophylaxis of which the compound of formulae I, Ib and Ic can be used are coronary heart disease, myocardial infarction, angina pectoris, vascular restenosis, for example restenosis following angioplasty like PTCA, adult respiratory distress syndrome, multi-organ failure and disseminated intravascular clotting disorder. Examples of related complications associated with surgery are thromboses like deep vein and proximal vein thrombosis, which can occur following surgery.

The compound of formulae I, Ib and Ic and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations, which permit enteral or parenteral administration.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formulae I, Ib and Ic and/or its (their) physiologically tolerable salts and/or its (their) prodrugs. For the production of pills, tablets, coated tablets and hard gelatin capsules it is possible to use, for example, lactose, cornstarch or derivatives thereof, talc, stearic acid or its salts, etc. Carriers for soft gelatin capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compound of formulae I, Ib and Ic and/or their physiologically tolerable salts and/or their prodrugs. The amount of the active ingredient of the formulae I, Ib and Ic and/or its physiologically tolerable salts and/or its prodrugs in the pharmaceutical preparations normally is from about 0.5 mg to about 1000 mg, preferably from about 1 mg to about 500 mg.

In addition to the active ingredients of the formulae I, Ib and Ic and/or their physiologically acceptable salts and/or prodrugs and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of formulae I, Ib and Ic, and/or their physiologically tolerable salts and/or their prodrugs. In case a pharmaceutical preparation contains two or more a compound of formulae I, Ib and Ic, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compound of formulae I, Ib and Ic allows a great deal of control over the biological and physico-chemical properties of the compounds and thus allows the selection of such desired compounds. Furthermore, in addition to at least one compound of formulae I, Ib and Ic and/or its physiologically tolerable salt and/or its prodrug, the pharmaceutical preparations can also contain one or more other therapeutically or prophylactically active ingredients.

When using the compound of formulae I, Ib and Ic the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 0.1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

A compound of the formulae I, Ib and Ic can also advantageously be used as an anticoagulant outside an individual. For example, an effective amount of a compound of the invention can be contacted with a freshly drawn blood sample to prevent coagulation of the blood sample. Further, a compound of the formulae I, Ib and Ic or its salts can be used for diagnostic purposes, for example in in vitro diagnoses, and as an auxiliary in biochemical investigations. For example, a compound of the formulae I, Ib and Ic can be used in an assay to identify the presence of factor Xa and/or factor VIIa or to isolate factor Xa and/or factor VIIa in a substantially purified form. A compound of the invention can be labeled with, for example, a radioisotope, and the labeled compound bound to factor Xa and/or factor VIIa is then detected using a routine method useful for detecting the particular label. Thus, a compound of the formulae I, Ib and Ic or a salt thereof can be used as a probe to detect the location or amount of factor Xa and/or factor VIIa activity in vivo, in vitro or ex vivo.

Furthermore, the compound of formulae I, Ib and Ic can be used as synthesis intermediates for the preparation of other compounds, in particular of other pharmaceutical active ingredients, which are obtainable from the compound of formulae I, Ib and Ic, for example by introduction of substituents or modification of functional groups.

The general synthetic sequences for preparing the compounds useful according to the present invention are outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention.

It is understood that changes that do not substantially affect the activity of the various embodiments of this invention are included within the invention disclosed herein. Thus, the following examples are intended to illustrate but not limit the present invention.

EXAMPLES

When in the final step of the synthesis of a compound an acid such as trifluoroacetic acid or acetic acid was used, for example when trifluoroacetic acid was employed to remove a t-Bu group or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt or hydrochloric acid salt.

Example 1

2-[5-(5-Chloro-thiophen-2-yl)-isoxazol-3-ylmethyl]-5-thiophen-2-yl-2H-pyrazole-3-carboxylic acid (1-isopropyl-piperidin-4-yl)-amide (i) (1-Isopropyl-piperidin-4-yl)-carbamic acid tert-butyl ester To a solution of 5.0 g Piperidin-4-yl-carbamic acid tert-butyl ester in 15 ml methanol 7.34 ml acetone, 3.14 g Na(CN)BH$_3$ and 0.3 ml acetic acid were added. After stirring for 16 h at RT the solvent was removed under reduced pressure and the residue was partitioned between 30 ml of water and 30 ml of ethyl acetate. The organic layer was washed with saturated Na$_2$CO$_3$ solution, water and then dried over Na$_2$SO$_4$. Following filtration, the solvent was removed under reduced pressure to yields a white solid. Yield: 4.8 g MS (ES$^+$): m/e=243.

(ii) 1-Isopropyl-piperidin-4-ylamine

To 4.8 g (1-Isopropyl-piperidin-4-yl)-carbamic acid tert-butyl ester in 15 ml methanol, 20 ml methanolic hydrochloric acid (8M) were added and the mixture was stirred for 16 h. Removal of the solvent under reduced pressure yielded a white solid, which was coevaporated twice with 20 ml toluene. The product was obtained as its hydrochloride. Yield: 5.42 g MS (ES$^+$): m/e=143.

(iv) 2-[5-(5-Chloro-thiophen-2-yl)-isoxazol-3-ylmethyl]-5-thiophen-2-yl-2H-pyrazole-3-carboxylic acid ethyl ester To a solution of 2.0 g 5-Thiophen-2-yl-2H-pyrazole-3-carboxylic acid ethyl ester in 5 ml DMF, 360 mg NaH (60% in mineral oil) and subsequently 2.8 g 3-Bromomethyl-5-(5-chloro-thiophen-2-yl)-isoxazole [prepared by adopting a procedure described by Ewing, William R.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, Christopher J.; Jiang, John Z.; Li, Aiwen; Myers, Michael R.; Lau, Wan F.; Poli, Gregory B; PCT Int. Appl. (2001) 460 pp. WO 0107436 A2] were added and the mixture was stirred at 80° C. for 1 h. After the addition of 5 ml water the mixture was filtered through a Chem Elut® cartridge by elution with ethyl acetate and then concentrated under reduced pressure. The residue was directly subjected to the subsequent saponification reaction without further purification. Yield: 4 g.

(v) 2-[5-(5-Chloro-thiophen-2-yl)-isoxazol-3-ylmethyl]-5-thiophen-2-yl-2H-pyrazole-3-carboxylic acid To a solution of 4 g 2-[5-(5-Chloro-thiophen-2-yl)-isoxazol-3-ylmethyl]-5-thiophen-2-yl-2H-pyrazole-3-carboxylic acid ethyl ester in 20 ml THF, 10 ml water and 500 mg lithium hydroxide monohydrate were added. After stirring for 2 h at 60° C. the reaction was cooled to RT. The mixture was acidified with half concentrated hydrochloric acid to pH 3 and the precipitate collected by filtration and washed with 10 ml water. The product was obtained as a white solid which was dried under reduced pressure. Yield: 3.8 g.

(vi) 2-[5-(5-Chloro-thiophen-2-yl)-isoxazol-3-ylmethyl]-5-thiophen-2-yl-2H-pyrazole-3-carboxylic acid (1-isopropyl-piperidin-4-yl)-amide To a solution of 200 mg 2-[5-(5-Chloro-thiophen-2-yl)-isoxazol-3-ylmethyl]-5-thiophen-2-yl-2H-pyrazole-3-carboxylic acid, 0.3 ml N-NEM in 2 ml DCM, 168 mg TOTU were added and the mixture was stirred for 30 min at RT. Then 136 mg 1-Isopropyl-piperidin-4-ylamine hydrochloride were added and the reaction was further stirred for 2 h. After the addition of 2 ml sat. NaHCO$_3$ the mixture was filtered through a Chem Elut® cartridge by elution with ethyl acetate and then concentrated under reduced pressure. The residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt. Yield: 120 mg MS (ES$^+$): m/e=516, chloro pattern.

Example 2

1-[5-(5-Chloro-thiophen-2-yl)-isoxazol-3-ylmethyl]-5-thiophen-2-yl-1H-pyrazole-3-carboxylic acid (1-isopropyl-piperidin-4-yl)-amide This compound was isolated as a by-product in example 1.
MS (ES$^+$): m/e=516, chloro pattern.

Example 3

2-[5-(5-Chloro-thiophen-2-yl)-isoxazol-3-ylmethyl]-5-methyl-2H-pyrazole-3-carboxylic acid (1-isopropyl-piperidin-4-yl)-amide The title compound was prepared analogously to example 1 with the difference that 5-Methyl-2H-pyrazole-3-carboxylic acid methyl ester was used instead of 5-Thiophen-2-yl-2H-pyrazole-3-carboxylic acid ethyl ester. MS (ESI+): m/e=448, chloro pattern.

Example 4

2-(6-Chloro-benzothiazol-2-yl)-5-methyl-2H-pyrazole-3-carboxylic acid (1-isopropyl-piperidin-4-yl)-amide The title compound was prepared analogously to example 1 with the difference that 2-(6-Chloro-benzothiazol-2-yl)-5-methyl-2H-pyrazole-3-carboxylic acid was used instead of of 5-Thiophen-2-yl-2H-pyrazole-3-carboxylic acid ethyl ester. MS (ESI+): m/e=418, chloro pattern.

Example 5

5-(5-Chloro-thiophen-2-yl)-2-[5-(5-chloro-thiophen-2-yl)-isoxazol-3-ylmethyl]-2H-pyrazole-3-carboxylic acid (1-isopropyl-piperidin-4-yl)-amide The title compound was prepared analogously to example 1 with the difference that 5-(5-Chloro-thiophen-2-yl)-2H-pyrazole-3-carboxylic acid methyl ester was used instead of of 5-Thiophen-2-yl-2H-pyrazole-3-carboxylic acid ethyl ester. MS (ESI+): m/e=550, chloro pattern.

Example 6

5-(5-Chloro-thiophen-2-yl)-1-[5-(5-chloro-thiophen-2-yl)-isoxazol-3-ylmethyl]-1H-pyrazole-3-carboxylic acid (1-isopropyl-piperidin-4-yl)-amide This compound was isolated as a by-product in example 5. MS (ES+): m/e=550, chloro pattern.

Example 7

2-[5-(5-Chloro-thiophen-2-yl)-isoxazol-3-ylmethyl]-4-(2,4-dichloro-phenyl)-2H-pyrazole-3-carboxylic acid (1-isopropyl-piperidin-4-yl)-amide The title compound was prepared analogously to example 1 with the difference that 4-(2,4-Dichloro-phenyl)-2H-pyrazole-3-carboxylic acid methyl ester was used instead of 5-Thiophen-2-yl-2H-pyrazole-3-carboxylic acid ethyl ester. MS (ESI+): m/e=578, chloro pattern.

Example 8

2-[5-(5-Chloro-thiophen-2-yl)-isoxazol-3-ylmethyl]-5-propyl-2H-pyrazole-3-carboxylic acid (1-isopropyl-piperidin-4-yl)-amide The title compound was prepared analogously to example 1 with the difference that 5-Propyl-2H-pyrazole-3-carboxylic acid methyl ester was used instead of 5-Thiophen-2-yl-2H-pyrazole-3-carboxylic acid ethyl ester. MS (ESI+): m/e=476, chloro pattern.

Example 9

5-tert-Butyl-2-[5-(5-chloro-thiophen-2-yl)-isoxazol-3-ylmethyl]-2H-pyrazole-3-carboxylic acid (1-isopropyl-piperidin-4-yl)-amide The title compound was prepared analogously to example 1 with the difference that 5-tert-Butyl-2H-pyrazole-3-carboxylic acid methyl ester was used instead of 5-Thiophen-2-yl-2H-pyrazole-3-carboxylic acid ethyl ester. MS (ESI+): m/e=490, chloro pattern.

Example 10

2-[5-(5-Chloro-thiophen-2-yl)-isoxazol-3-ylmethyl]-4-cyano-5-propyl-2H-pyrazole-3-carboxylic acid (1-isopropyl-piperidin-4-yl)-amide (i) 4-Iodo-5-propyl-2H-pyrazole-3-carboxylic acid ethyl ester 1.0 g (5.5 mmol) of 5-propyl-2H-pyrazole-3-carboxylic acid ethyl ester was dissolved in 15 ml of dichloromethane and 1.23 g (5.5 mmol) of N-iodosuccinimide was added. The resulting solution was stirred at room temperature for 16 h. The solution was washed with aqueous sodium thiosulfate solution. The organic phase was dried with sodium sulfate and filtered. The resulting solution was passed through a short silica gel column, washing with dichloromethane. The solvent was removed under reduced pressure.

Yield: 1.5 g MS (LCMS-ES+): m/e=309.

(ii) 4-Cyano-5-propyl-2H-pyrazole-3-carboxylic acid ethyl ester 1.5 g (4.9 mmol) of 4-Iodo-5-propyl-2H-pyrazole-3-carboxylic acid ethyl ester, 0.87 g (9.7 mmol) of copper cyanide and 404 mg (2.4 mmol) of tetraethylammonium cyanide were dissolved in 10 ml of DMF and 20 ml of tetrahydrofuran and the solution was degassed with argon. 223 mg (0.2 mmol) of Tris(dibenzylideneacetone)dipalladium (0) and 404 mg (0.7 mmol) of 1,1'-bis-(diphenylphosphino) ferrocene were added at RT. The reaction was stirred at 120° C. for 5 h. The solvent was removed under reduced pressure. The residue was dissolved in ethyl acetate and this solution was washed with saturated aqueous sodium bicarbonate. The organic phase was dried with sodium sulfate, filtered and the solvent was removed under reduced pressure. The product was purified by silica gel chromatography eluting with n-heptane:ethyl acetate/1:1.

Yield: 110 mg MS (LCMS-ES+): m/e=208.

(iii) 2-[5-(5-Chloro-thiophen-2-yl)-isoxazol-3-ylmethyl]-4-cyano-5-propyl-2H-pyrazole-3-carboxylic acid 112 mg (0.5 mmol) of 4-cyano-5-propyl-2H-pyrazole-3-carboxylic acid ethyl ester was dissolved in 2 ml of DMF and 23.8 mg (0.6 mmol) of sodium hydride (60% in mineral oil) were added at RT. After stirring for 20 min at room temperature the solution was cooled to −70° C. and 166 mg (0.6 mmol) of 3-bromomethyl-5-(5-chloro-thiophen-2-yl)-isoxazole were added. The reaction was stirred at room temperature for 3 h. The reaction solution was treated with 1 ml of 2N aqueous NaOH for 16 h at room temperature. The product was purified by preparative RP-HPLC eluting with a gradient of 0-100% acetonitrile in water (+0.01% trifluoroacetic acid). After lyophilization the product was obtained as a white solid.

Yield 55.3 mg. MS (LCMS-ES$^+$): m/e=377, chloro pattern.

(iv) 2-[5-(5-Chloro-thiophen-2-yl)-isoxazol-3-ylmethyl]-4-cyano-5-propyl-2H-pyrazole-3-carboxylic acid (1-isopropyl-piperidin-4-yl)-amide To a solution of 55 mg 2-[5-(5-Chloro-thiophen-2-yl)-isoxazol-3-ylmethyl]-4-cyano-5-propyl-2H-pyrazole-3-carboxylic acid, 0.1 ml N-NEM in 2 ml DMF, 48 mg TOTU were added and the mixture was stirred for 30 min at RT. Then 31 mg of 1-Isopropyl-piperidin-4-ylamine hydrochloride were added and the reaction was further stirred for 2 h. After addition of 2 ml sat. NaHCO$_3$ the mixture was filtered through a Chem Elut® cartridge by elution with ethyl acetate and then concentrated under reduced pressure. After removal of the solvent under reduced pressure the residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt.

Yield: 18 mg MS (ES$^+$): m/e=501, chloro pattern.

Example 11

1-[5-(5-Chloro-thiophen-2-yl)-isoxazol-3-ylmethyl]-4-cyano-5-propyl-1H-pyrazole-3-carboxylic acid (1-isopropyl-piperidin-4-yl)-amide This compound was isolated as a by-product in example 10.

MS (ES$^+$): m/e=501, chloro pattern.

Example 12

2-[5-(5-Chloro-thiophen-2-yl)-isoxazol-3-ylmethyl]-4-cyano-5-thiophen-2-yl-2H-pyrazole-3-carboxylic acid (1-isopropyl-piperidin-4-yl)-amide

(i) 4-Iodo-5-thiophen-2-yl-2H-pyrazole-3-carboxylic acid ethyl ester 1.0 g (4.5 mmol) of 5-thiophen-2-yl-2H-pyrazole-3-carboxylic acid ethyl ester was dissolved in 15 ml of dichloromethane and 1.01 g (4.5 mmol) of N-iodosuccinimide was added. The resulting solution was stirred at room temperature for 16 h. The solution was washed with aqueous sodium thiosulfate solution. The organic phase was dried with sodium sulfate and filtered. The resulting solution was passed through a short silica gel column, washing with dichloromethane. The solvent was removed under reduced pressure.

Yield: 1.57 g MS (LCMS-ES$^+$): m/e=349.

(ii) 4-Cyano-5-thiophen-2-yl-2H-pyrazole-3-carboxylic acid ethyl ester 1.57 g (4.5 mmol) of 4-Iodo-5-thiophen-2-yl-2H-pyrazole-3-carboxylic acid ethyl ester, 0.81 g (9.0 mmol) of copper cyanide and 352 mg (2.3 mmol) of tetraethylammonium cyanide were dissolved in 10 ml of DMF and 20 ml of tetrahydrofuran and the solution was degassed with argon. 223 mg (0.2 mmol) of Tris(dibenzylideneacetone)dipalladium (0) and 374 mg (0.7 mmol) of 1,1'-bis-(diphenylphosphino) ferrocene were added at RT. The reaction was stirred at 120° C. for 5 h. The solvent was removed under reduced pressure. The residue was dissolved in ethyl acetate and this solution was washed with saturated aqueous sodium bicarbonate. The organic phase was dried with sodium sulfate, filtered and the solvent was removed under reduced pressure. The product was purified by silica gel chromatography eluting with n-heptane:ethyl acetate/1:1.

Yield: 287 mg MS (LCMS-ES$^+$): m/e=248.

(iii) 2-[5-(5-Chloro-thiophen-2-yl)-isoxazol-3-ylmethyl]-4-cyano-5-thiophen-2-yl-2H-pyrazole-3-carboxylic acid 287 mg (1.2 mmol) of 4-Cyano-5-thiophen-2-yl-2H-pyrazole-3-carboxylic acid ethyl ester was dissolved in 2 ml of DMF and 51.1 mg (1.3 mmol) of sodium hydride (60% in mineral oil) were added at RT. After stirring for 20 min at room temperature the solution was cooled to −70° C. and 355 mg (1.3 mmol) of 3-bromomethyl-5-(5-chloro-thiophen-2-yl)-isoxazole were added. The reaction was stirred at room temperature for 3 h. The reaction solution was treated with 1 ml of 2N aqueous NaOH for 16 h at room temperature. The product was purified by preparative RP-HPLC eluting with a gradient of 0-100% acetonitrile in water (+0.01% trifluoroacetic acid). After lyophilization the product was obtained as a white solid.

Yield 122 mg. MS (LCMS-ES$^+$): m/e=417.

(iv) 2-[5-(5-Chloro-thiophen-2-yl)-isoxazol-3-ylmethyl]-4-cyano-5-thiophen-2-yl-2H-pyrazole-3-carboxylic acid (1-isopropyl-piperidin-4-yl)-amide To a solution of 31 mg 2-[5-(5-Chloro-thiophen-2-yl)-isoxazol-3-ylmethyl]-4-cyano-5-thiophen-2-yl-2H-pyrazole-3-carboxylic acid, 0.1 ml N-NEM in 1 ml DMF, 24 mg TOTU were added and the mixture was stirred for 30 min at RT. Then 16 mg 1-Isopropyl-piperidin-4-ylamine hydrochloride were added and the reaction was further stirred for 2 h. After addition of 2 ml sat. NaHCO$_3$ the mixture was filtered through a Chem Elut® cartridge by elution with ethyl acetate and then concentrated under reduced pressure. After removal of the solvent under reduced pressure the residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt.

Yield: 18 mg MS (ES$^+$): m/e=541, chloro pattern.

Example 13

1-[5-(5-Chloro-thiophen-2-yl)-isoxazol-3-ylmethyl]-4-cyano-5-thiophen-2-yl-1H-pyrazole-3-carboxylic acid (1-isopropyl-piperidin-4-yl)-amide This compound was isolated as a by-product in example 12.

MS (ES$^+$): m/e=541, chloro pattern.

Example 14

2-[2-(5-Chloro-thiophen-2-yl)-thiazol-4-ylmethyl]-5-thiophen-2-yl-2H-pyrazole-3-carboxylic acid (1-isopropyl-piperidin-4-yl)-amide The title compound was prepared analogously to example 1 with the difference that 5-Bromomethyl-2-(5-chlorothiophen-2-yl)-thiazole [prepared by adopting a procedure described by Ewing, William R. et al.; PCT Int. Appl. (2001) 460 pp. WO 0107436 A2] was used instead of 3-Bromomethyl-5-(5-chloro-thiophen-2-yl)-isoxazole. MS (ES$^+$): m/e=532, chloro pattern.

Example 15

2-(6-Chloro-benzo[b]thiophen-2-ylmethyl)-5-thiophen-2-yl-2H-pyrazole-3-carboxylic acid (1-isopropyl-piperidin-4-yl)-amide The title compound was prepared analogously to example 1 with the difference that 2-Bromomethyl-6-chloro-benzo[b]thiophene [prepared by adopting a procedure described by Ewing, William R. et al.; PCT Int. Appl. (1999) 300 pp. WO 9937304 A1; and Ewing, William R. et al. PCT Int. Appl. (2001) 460 pp. WO 0107436 A2] was used instead of 3-Bromomethyl-5-(5-chloro-thiophen-2-yl)-isoxazole. MS (ES$^+$): m/e=499, chloro pattern.

Example 16

2-[5-(5-Chloro-thiophen-2-yl)-isoxazol-3-ylmethyl]-5-thiophen-2-yl-2H-pyrazole-3-carboxylic acid (3,4,5,6-tetrahydro-2H-[1,4']bipyridinyl-4-ylmethyl)-amide (i) (3,4,5,6-Tetrahydro-2H-[1,4']bipyridinyl-4-ylmethyl)-carbamic acid tBu ester A suspension of 5 g (23.3 mmol) Piperidin-4-ylmethyl-carbamic acid tBu ester, 3.85 g (25.7 mmol) 4-Chloropyridine hydrochloride in 15 ml n-BuOH/H$_2$O/NEt$_3$ 1:1:1 was boiled under reflux for 3 days. After removal of the solvent under reduced pressure the residue was purified by chromatography on silica with DCM/MeOH 100:1->50:1-> 10:1->5:1 to yield a white solid.
Yield: 4.3 g.

(ii) C-(3,4,5,6-Tetrahydro-2H-[1,4']bipyridinyl-4-yl)-methylamine

To a solution of 4.58 g (3,4,5,6-Tetrahydro-2H-[1,4']bipyridinyl-4-ylmethyl)-carbamic acid tBu ester in 12 ml DCM, 12 ml of TFA were added at RT. After stirring for 30 min the solution was diluted with 20 ml of toluene and then evaporated under reduced pressure. The residue was codestilled twice with toluene and was used in the subsequent reactions without further purification. The product was obtained as its trifluoroacetate salt. Yield: 3.3 g.

(iii) -[5-(5-Chloro-thiophen-2-yl)-isoxazol-3-ylmethyl]-5-thiophen-2-yl-2H-pyrazole-3-carboxylic acid (3,4,5,6-tetrahydro-2H-[1,4']bipyridinyl-4-ylmethyl)-amide To a solution of 50 mg 2-[5-(5-Chloro-thiophen-2-yl)-isoxazol-3-ylmethyl]-5-thiophen-2-yl-2H-pyrazole-3-carboxylic acid, 0.3 ml N-NEM in 1 ml DCM, 59 mg TOTU were added and the mixture was stirred for 30 min at RT. Then 36 mg of C-(3,4,5,6-Tetrahydro-2H-[1,4']bipyridinyl-4-yl)-methylamine trifluoroacetate were added and the reaction was further stirred for 2 h. After the addition of 2 ml sat. NaHCO$_3$ the mixture was filtered through a Chem Elut® cartridge by elution with ethyl acetate and then concentrated under reduced pressure. The residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt.
Yield: 23 mg MS (ES$^+$): m/e=565, chloro pattern.

Example 17

2-[5-(5-Chloro-thiophen-2-yl)-isoxazol-3-ylmethyl]-5-thiophen-2-yl-2H-pyrazole-3-carboxylic acid (1-isopropyl-piperidin-4-ylmethyl)-amide (i) (1-Isopropyl-piperidin-4-ylmethyl)-carbamic acid tert-butyl ester To a solution of 1.0 g Piperidin-4-ylmethyl-carbamic acid tert-butyl ester in 20 ml acetonitrile 2.6 ml acetone and 586 mg Na(CN)BH$_3$ were added. After stirring for 16 h at RT the solvent was removed under reduced pressure and the residue was partitioned between 30 ml of water and 30 ml of ethylacetate. The organic layer was washed with saturated Na$_2$CO$_3$ solution, water and then was dried over Na$_2$SO$_4$. Removal of the solvent under reduced pressure yielded a white solid. Yield: 802 mg.

(ii) C-(1-Isopropyl-piperidin-4-yl)-methylamine

To a solution of 802 mg (1-Isopropyl-piperidin-4-ylmethyl)-carbamic acid tert-butyl ester in 5 ml DCM 4 ml of TFA were added at RT. After stirring for 20 h the solution was diluted with 20 ml of toluene and the solvents were evaporated under reduced pressure. The residue was codestilled twice with toluene and used in the subsequent reaction without further purification. The product was obtained as its trifluoroacetate salt. Yield: 1.7 g (iii) 2-[5-(5-Chloro-thiophen-2-yl)-isoxazol-3-ylmethyl]-5-thiophen-2-yl-2H-pyrazole-3-carboxylic acid (1-isopropyl-piperidin-4-ylmethyl)-amide To a solution of 50 mg 2-[5-(5-Chloro-thiophen-2-yl)-isoxazol-3-ylmethyl]-5-thiophen-2-yl-2H-pyrazole-3-carboxylic acid, 0.3 ml N-NEM in 1 ml DCM, 59 mg TOTU were added and the mixture was stirred for 30 min at RT. Then 30 mg C-(1-Isopropyl-piperidin-4-yl)-methylamine trifluoroacetate were added and the reaction was stirred for a further 2 h. After the addition of 2 ml sat. NaHCO$_3$ the mixture was filtered through a Chem Elut® cartridge by elution with ethyl acetate and then concentrated under reduced pressure. After removal of the solvent under reduced pressure the residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt. Yield: 14 mg MS (ES$^+$): m/e=530, chloro pattern.

Example 18

2-[5-(5-Chloro-thiophen-2-yl)-isoxazol-3-ylmethyl]-5-thiophen-2-yl-2H-pyrazole-3-carboxylic acid (3,4,5,6-tetrahydro-2H-[1,4']bipyridinyl-4-yl)-amide (i) (3,4,5,6-Tetrahydro-2H-[1,4']bipyridinyl-4-yl)-carbamic acid tert-butyl ester A solution of 3 g Piperidin-4-yl-carbamic acid tert-butyl ester and 2.5 g 4-Chloropyridine in 9 ml n-butanol/water/

NEt₃ 1:1:1 was heated at 100° C. for 48 h. Then the solution was cooled to RT diluted with DCM and washed with NaHCO₃ solution and water. The organic layer was dried over Na₂SO₄, filtered, and the solvent was removed under reduced pressure. Chromatographic purification of the residue on silica with DCM as eluent gave after evaporation of the fractions containing the product a white foam. Yield 1.7 g.

(ii) 3,4,5,6-Tetrahydro-2H-[1,4']bipyridinyl-4-ylamine

To a solution of 4 g (3,4,5,6-Tetrahydro-2H-[1,4']bipyridinyl-4-yl)-carbamic acid tert-butyl ester in 4 ml DCM, 12 ml TFA were added at RT. After stirring for 20 h the solution was diluted with 20 ml of toluene and the solvents were evaporated under reduced pressure. The residue was codestilled twice with toluene and then used in the subsequent reaction without further purification. The product was obtained as its trifluoroacetate salt. Yield: 2.7 g.

(iii) 2-[5-(5-Chloro-thiophen-2-yl)-isoxazol-3-ylmethyl]-5-thiophen-2-yl-2H-pyrazole-3-carboxylic acid (3,4,5,6-tetrahydro-2H-[1,4']bipyridinyl-4-yl)-amide To a solution of 50 mg 2-[5-(5-Chloro-thiophen-2-yl)-isoxazol-3-ylmethyl]-5-thiophen-2-yl-2H-pyrazole-3-carboxylic acid, 0.3 ml N-NEM in 1 ml DCM, 59 mg TOTU were added and the mixture was stirred for 30 min at RT. Then 33 mg 3,4,5,6-Tetrahydro-2H-[1,4']bipyridinyl-4-ylamine trifluoroacetate were added and the reaction was further stirred for 2 h. After the addition of 2 ml sat. NaHCO₃ the mixture was filtered through a Chem Elut® cartridge by elution with ethyl acetate and then concentrated under reduced pressure. The residue was purified by preparative HPLC (C18 reverse phase column, elution with a H₂O/MeCN gradient with 0.1% TFA). The fractions containing the product were evaporated and lyophilized to yield a white solid. The product was obtained as its trifluoroacetate salt. Yield: 25 mg MS (ES⁺): m/e=551, chloro pattern.

Example 19

2-(4-Chloro-benzyl)-4-cyano-5-thiophen-2-yl-2H-pyrazole-3-carboxylic acid (1-isopropyl-piperidin-4-yl)-amide The title compound was prepared analogously to example 12 with the difference that 1-Bromomethyl-4-chloro-benzene was used instead of 3-Bromomethyl-5-(5-chloro-thiophen-2-yl)-isoxazole in the alkylation step. MS (ESI+): m/e=468, chloro pattern.

Example 20

1-[5-(5-Chloro-thiophen-2-yl)-isoxazol-3-ylmethyl]-5-(1-isopropyl-piperidin-4-ylcarbamoyl)-1H-pyrazole-3-carboxylic acid methyl ester

(i) 1H-Pyrazole-3,5-dicarboxylic acid dimethyl ester

To 12 g of 1H-Pyrazole-3,5-dicarboxylic acid 100 ml HCl in methanol (8M) were added at RT and stirred for 48 h. Then the solvents were removed under reduced pressure and the residue codestilled with toluene (2×50 ml). Yield: 14 g.

(ii) 1-[5-(5-Chloro-thiophen-2-yl)-isoxaz-3-ylmethyl]-1H-pyrazole-3,5-dicarboxylic acid dimethyl ester To a solution of 1 g 1H-Pyrazole-3,5-dicarboxylic acid diethyl ester in 20 ml of DMF and 188 mg of sodium hydride (60% in mineral oil) were added at RT. After stirring for 20 min at room temperature 1.32 g of 3-bromomethyl-5-(5-chloro-thiophen-2-yl)-isoxazole were added. The reaction was stirred at room temperature for 3 h. Then 100 ml water were added and the precipitating product was collected by filtration. Yield: 1.7 g.

(iii) 1-[5-(5-Chloro-thiophen-2-yl)-isoxazol-3-ylmethyl]-1H-pyrazole-3,5-dicarboxylic acid 3-methyl ester To a solution of 1.7 g 1-[5-(5-Chloro-thiophen-2-yl)-isoxazol-3-ylmethyl]-1H-pyrazole-3,5-dicarboxylic acid dimethyl ester in 10 ml water/THF 1:1, 4 ml of a 1M aqueous NaOH were added at RT and the mixture was stirred for 3 h with LCMS reaction control. Then the reaction mixture was acidified to pH 3 with half concentrated HCl and extracted with DCM (3×50 ml). The organic phase was dried over MgSO₄, filtered and the solvent removed under reduced pressure. The residue was subjected to the next reaction step without further purification.

(iv) 1-[5-(5-Chloro-thiophen-2-yl)-isoxazol-3-ylmethyl]-5-(1-isopropyl-piperidin-4-ylcarbamoyl)-1H-pyrazole-3-carboxylic acid methyl ester To 1 g 1-[5-(5-Chloro-thiophen-2-yl)-isoxazol-3-ylmethyl]-1H-pyrazole-3,5-dicarboxylic acid 3-methyl ester in 10 ml DCM and 1.4 ml NEt₃, 667 mg BOP-Cl were added at RT and the mixture was stirred for 30 min. After addition of 563 mg 1-Isopropyl-piperidin-4-ylamine hydrochloride the mixture was stirred for 16 h. After removal of the solvent under reduced pressure the residue was purified by silica gel chromatography eluting with DCM/MeOH/AcOH/H₂O 20:10:1:1 to yield a white solid. Yield: 800 mg MS (ES⁺): m/e=492, chloro pattern.

Example 21

1-[5-(5-Chloro-thiophen-2-yl)-isoxazol-3-ylmethyl]-5-(1-isopropyl-piperidin-4-ylcarbamoyl)-1H-pyrazole-3-carboxylic acid To a solution of 800 mg 1-[5-(5-Chloro-thiophen-2-yl)-isoxazol-3-ylmethyl]-5-(1-isopropyl-piperidin-4-ylcarbamoyl)-1H-pyrazole-3-carboxylic acid methyl ester in 5 ml water/THF 1:1, 3 ml of a 1M aqueous NaOH were added at RT and the mixture was heated for 10 h at 60° C. Then the reaction mixture was acidified to pH 3 with half concentrated HCl and extracted with DCM (3×50 ml). The organic phase was dried over MgSO₄, filtered and the solvent removed under reduced pressure. The residue was purified by preparative HPLC (C18 reverse phase column, elution with a H₂O/MeCN gradient with 0.1% TFA). The fractions containing the product were evaporated and lyophilized to yield a white solid. The product was obtained as its trifluoroacetate salt.

Yield: 503 mg MS (ES⁺): m/e=478, chloro pattern.

Example 22

2-[5-(5-Chloro-thiophen-2-yl)-isoxazol-3-ylmethyl]-5-(1-isopropyl-piperidin-4-ylcarbamoyl)-2H-pyrazole-3-carboxylic acid This compound was isolated as a by-product in example 21.
MS (ES$^+$): m/e=478, chloro pattern.

Example 23

1-[5-(5-Chloro-thiophen-2-yl)-isoxazol-3-ylmethyl]-5-(1-isopropyl-piperidin-4-ylcarbamoyl)-1H-pyrazole-3-carboxylic acid ethyl ester The title compound was prepared analogously to example 20 with the difference that 1H-Pyrazole-3,5-dicarboxylic acid diethyl ester was used instead of 1H-Pyrazole-3,5-dicarboxylic acid diethyl ester. MS (ES$^+$): m/e=506, chloro pattern.

Example 24

2-[5-(5-Chloro-thiophen-2-yl)-isoxazol-3-ylmethyl]-5-(1-isopropyl-piperidin-4-ylcarbamoyl)-2H-pyrazole-3-carboxylic acid ethyl ester This compound was isolated as a by-product in example 23.
MS (ES$^+$): m/e=506, chloro pattern.

Example 25

2-[5-(5-Chloro-thiophen-2-yl)-isoxazol-3-ylmethyl]-5-(morpholine-4-carbonyl)-2H-pyrazole-3-carboxylic acid (1-isopropyl-piperidin-4-yl)-amide To a solution of 100 mg 2-[5-(5-Chloro-thiophen-2-yl)-isoxazol-3-ylmethyl]-5-thiophen-2-yl-2H-pyrazole-3-carboxylic acid, 0.5 ml N-NEM in 2 ml DCM, 68 mg TOTU were added and the mixture was stirred for 30 min at RT. Then 49 mg morpholine were added and the reaction was further stirred for 16 h. After the addition of 2 ml sat. NaHCO$_3$ the mixture was filtered through a Chem Elut® cartridge by elution with ethyl acetate and then concentrated under reduced pressure. The residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt.
Yield: 73 mg MS (ES$^+$): m/e=547, chloro pattern.

Example 26

1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-methylamide The title compound was prepared analogously to example 25 with the difference that methyl-amine hydrochloride was used instead of morpholine. MS (ES$^+$): m/e=491, chloro pattern.

Example 27

1-[5-(5-Chloro-thiophen-2-yl)-isoxazol-3-ylmethyl]-1H-pyrazole-3,5-dicarboxylic acid 3-[(2-hydroxy-ethyl)-amide]5-[(1-isopropyl-piperidin-4-yl)-amide]

The title compound was prepared analogously to example 25 with the difference that 2-amino-ethanol was used instead of morpholine. MS (ES$^+$): m/e=521, chloro pattern.

Example 28

{[1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-acetic acid The title compound was prepared analogously to example 25 with the difference that amino-acetic acid hydrochloride was used instead of morpholine.
MS (ES$^+$): m/e=535, chloro pattern.

Example 29

2-[5-(5-Chloro-thiophen-2-yl)-isoxazol-3-ylmethyl]-5-(5-oxo-4,5-dihydro-[1,3,4]oxadiazol-2-yl)-2H-pyrazole-3-carboxylic acid (1-isopropyl-piperidin-4-yl)-amide To a solution of 50 mg 1-[5-(5-Chloro-thiophen-2-yl)-isoxazol-3-ylmethyl]-5-(1-isopropyl-piperidin-4-ylcarbamoyl)-1H-pyrazole-3-carboxylic acid, 0.1 ml N-NEM in 1 ml DCM, 34 mg TOTU were added and the mixture was stirred for 10 min at RT. Then 10 µl hydrazine hydrate were added and the reaction was further stirred for 2 h. After removal of the solvent under reduced pressure the residue was codestilled with toluene (2×10 ml) and the dissolved in 1 ml THF. Then 91 mg Carbonic acid ditrichloromethyl ester were added at RT and the reaction mixture was stirred for 48 h. After the addition of 2 ml sat. NaHCO$_3$ the mixture was filtered through a Chem Elut® cartridge by elution with ethyl acetate and then concentrated under reduced pressure. The residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt.
Yield: 7 mg MS (ES$^+$): m/e=518, chloro pattern.

Example 30

2-[5-(5-Chloro-thiophen-2-yl)-isoxazol-3-ylmethyl]-5-[4-(2-hydroxy-ethyl)-piperazine-1-carbonyl]-2H-pyrazole-3-carboxylic acid (1-isopropyl-piperidin-4-yl)-amide The title compound was prepared analogously to example 25 with the difference that 2-piperazin-1-yl-ethanol was used instead of morpholine. MS (ES$^+$): m/e=590, chloro pattern.

Example 31

1-[5-(5-Chloro-thiophen-2-yl)-isoxazol-3-ylmethyl]-
1H-pyrazole-3,5-dicarboxylic acid 3-[bis-(2-methoxy-ethyl)-amide]5-[(1-isopropyl-piperidin-4-yl)-
amide]

The title compound was prepared analogously to example 25 with the difference that bis-(2-methoxy-ethyl)-amine was used instead of morpholine. MS (ES$^+$): m/e=593, chloro pattern.

Example 32

1-[5-(5-Chloro-thiophen-2-yl)-isoxazol-3-ylmethyl]-
5-(1-isopropyl-piperidin-4-ylcarbamoyl)-1H-pyrazole-3-carboxylic acid 2-(2-oxo-imidazolidin-1-yl)-
ethyl ester The title compound was prepared analogously to example 25 with the difference that 1-(2-hydroxy-ethyl)-imidazolidin-2-one was used instead of morpholine.
MS (ES$^+$): m/e=590, chloro pattern.

Example 33

{[1-[5-(5-Chloro-thiophen-2-yl)-isoxazol-3-ylmethyl]-5-(1-isopropyl-piperidin-4-ylcarbamoyl)-1H-
pyrazole-3-carbonyl]-methyl-amino}-acetic acid The title compound was prepared analogously to example 25 with the difference that methylamino-acetic acid was used instead of morpholine. MS (ES$^+$): m/e=549, chloro pattern.

Example 34

2-[5-(5-Chloro-thiophen-2-yl)-isoxazol-3-ylmethyl]-
5-(thiomorpholine-4-carbonyl)-2H-pyrazole-3-carboxylic acid (1-isopropyl-piperidin-4-yl)-amide The title compound was prepared analogously to example 25 with the difference that thiomorpholine was used instead of morpholine. MS (ES$^+$): m/e=563, chloro pattern.

Example 35

2-[5-(5-Chloro-thiophen-2-yl)-isoxazol-3-ylmethyl]-
5-(4-hydroxy-piperidine-1-carbonyl)-2H-pyrazole-3-
carboxylic acid (1-isopropyl-piperidin-4-yl)-amide The title compound was prepared analogously to example 25 with the difference that piperidin-4-ol was used instead of morpholine. MS (ES$^+$): m/e=561, chloro pattern.

Example 36

2-[5-(5-Chloro-thiophen-2-yl)-isoxazol-3-ylmethyl]-
5-(3-hydroxy-pyrrolidine-1-carbonyl)-2H-pyrazole-
3-carboxylic acid (1-isopropyl-piperidin-4-yl)-amide The title compound was prepared analogously to example 25 with the difference that pyrrolidin-3-ol was used instead of morpholine. MS (ES$^+$): m/e=547, chloro pattern.

Example 37

2-[5-(5-Chloro-thiophen-2-yl)-isoxazol-3-ylmethyl]-
5-(4-hydroxymethyl-piperidine-1-carbonyl)-2H-
pyrazole-3-carboxylic acid (1-isopropyl-piperidin-4-
yl)-amide The title compound was prepared analogously to example 25 with the difference that piperidin-4-yl-methanol was used instead of morpholine. MS (ES$^+$): m/e=575, chloro pattern.

Example 38

5-(8-Aza-spiro[4.5]decane-8-carbonyl)-2-[5-(5-
chloro-thiophen-2-yl)-isoxazol-3-ylmethyl]-2H-
pyrazole-3-carboxylic acid (1-isopropyl-piperidin-4-
yl)-amide The title compound was prepared analogously to example 25 with the difference that 8-aza-spiro[4.5]decane hydrochloride was used instead of morpholine.
MS (ES$^+$): m/e=599, chloro pattern.

Example 39

2-[5-(5-Chloro-thiophen-2-yl)-isoxazol-3-ylmethyl]-
5-(3-methanesulfonyl-pyrrolidine-1-carbonyl)-2H-
pyrazole-3-carboxylic acid (1-isopropyl-piperidin-4-
yl)-amide The title compound was prepared analogously to example 25 with the difference that 3-methanesulfonyl-pyrrolidine was used instead of morpholine.
MS (ES$^+$): m/e=609, chloro pattern.

Example 40

1-[5-(5-Chloro-thiophen-2-yl)-isoxazol-3-ylmethyl]-
1H-pyrazole-3,5-dicarboxylic acid 3-[(1,1-dioxo-
tetrahydro-1-thiophen-3-yl)-methyl-amide]5-[(1-
isopropyl-piperidin-4-yl)-amide]

The title compound was prepared analogously to example 25 with the difference that (1,1-Dioxo-tetrahydro-1-thiophen-3-yl)-methyl-amine was used instead of morpholine.
MS (ES$^+$): m/e=609, chloro pattern.

Example 41

2-[5-(5-Chloro-thiophen-2-yl)-isoxazol-3-ylmethyl]-
5-(3-oxo-piperazine-1-carbonyl)-2H-pyrazole-3-
carboxylic acid (1-isopropyl-piperidin-4-yl)-amide The title compound was prepared analogously to example 25 with the difference that piperazin-2-one was used instead of morpholine. MS (ES$^+$): m/e=560, chloro pattern.

Example 42

2-[5-(5-Chloro-thiophen-2-yl)-isoxazol-3-ylmethyl]-
5-([1,4]oxazepane-4-carbonyl)-2H-pyrazole-3-carboxylic acid (1-isopropyl-piperidin-4-yl)-amide The title compound was prepared analogously to example 25 with the difference that [1,4]oxazepane was used instead of morpholine. MS (ES$^+$): m/e=561, chloro pattern.

Example 43

2-[5-(5-Chloro-thiophen-2-yl)-isoxazol-3-ylmethyl]-
5-(2-trifluoromethyl-pyrrolidine-1-carbonyl)-2H-
pyrazole-3-carboxylic acid (1-isopropyl-piperidin-4-
yl)-amide The title compound was prepared analogously to example 25 with the difference that 2-trifluoromethyl-pyrrolidine was used instead of morpholine. MS (ES$^+$): m/e=599, chloro pattern.

Example 44

1-[5-(5-Chloro-thiophen-2-yl)-isoxazol-3-ylmethyl]-
1H-pyrazole-3,5-dicarboxylic acid 5-[(1-isopropyl-
piperidin-4-yl)-amide]3-[(2-sulfamoyl-ethyl)-amide]

The title compound was prepared analogously to example 25 with the difference that 2-amino-ethanesulfonic acid amide was used instead of morpholine. MS (ES$^+$): m/e=584, chloro pattern.

Example 45

1-[5-(5-Chloro-thiophen-2-yl)-isoxazol-3-ylmethyl]-
1H-pyrazole-3,5-dicarboxylic acid 3-cyclopropyla-
mide 5-[(1-isopropyl-piperidin-4-yl)-amide]

The title compound was prepared analogously to example 25 with the difference that cyclopropylamine was used instead of morpholine. MS (ES$^+$): m/e=517, chloro pattern.

Example 46

1-[5-(5-Chloro-thiophen-2-yl)-isoxazol-3-ylmethyl]-
1H-pyrazole-3,5-dicarboxylic acid 3-cyclobutyla-
mide 5-[(1-isopropyl-piperidin-4-yl)-amide]

The title compound was prepared analogously to example 25 with the difference that cyclobutylamine was used instead of morpholine. MS (ES$^+$): m/e=531, chloro pattern.

Example 47

1-[5-(5-Chloro-thiophen-2-yl)-isoxazol-3-ylmethyl]-
1H-pyrazole-3,5-dicarboxylic acid 5-[(1-isopropyl-
piperidin-4-yl)-amide]3-[(2-methoxy-ethyl)-amide]

The title compound was prepared analogously to example 25 with the difference that 2-methoxy-ethylamine was used instead of morpholine. MS (ES$^+$): m/e=535, chloro pattern.

Example 48

2-[5-(5-Chloro-thiophen-2-yl)-isoxazol-3-ylmethyl]-
5-(pyrrolidine-1-carbonyl)-2H-pyrazole-3-carboxylic
acid (1-isopropyl-piperidin-4-yl)-amide The title compound was prepared analogously to example 25 with the difference that pyrrolidine was used instead of morpholine. MS (ES$^+$): m/e=531, chloro pattern.

Example 49

2-[5-(5-Chloro-thiophen-2-yl)-isoxazol-3-ylmethyl]-
5-(cyanamide-1-carbonyl)-2H-pyrazole-3-carboxylic
acid (1-isopropyl-piperidin-4-yl)-amide The title compound was prepared analogously to example 25 with the difference that cyanamide was used instead of morpholine. MS (ES$^+$): m/e=502, chloro pattern.

Example 50

1-[(5-Chloro-pyridin-2-ylcarbamoyl)-methyl]-5-(1-
isopropyl-piperidin-4-ylcarbamoyl)-1H-pyrazole-3-
carboxylic acid methyl ester (i) 2-Bromo-N-(5-chloro-pyridin-2-yl)-acetamide To a solution of 5 g 5-Chloro-pyridin-2-ylamine and 1.5 ml pyridine in 30 ml toluene, 8 g bromo-acetyl bromide dissolved in 10 ml toluene was added dropwise under ice cooling. After 2 h the precipitate was isolated by filtration and recrystallized from toluene to yield a white solid.
Yield: 12 g.

(ii) 1-[(5-Chloro-pyridin-2-ylcarbamoyl)-methyl]-5-
(1-isopropyl-piperidin-4-ylcarbamoyl)-1H-pyrazole-
3-carboxylic acid methyl ester The title compound was prepared analogously to example 20 with the difference that 2-Bromo-N-(5-chloro-pyridin-2-yl)-acetamide was used instead of 3-Bromomethyl-5-(5-chloro-thiophen-2-yl)-isoxazole in the alkylation step. MS (ES$^+$): m/e=463, chloro pattern.

Example 51

1-[(5-Chloro-pyridin-2-ylcarbamoyl)-methyl]-5-(1-
isopropyl-piperidin-4-ylcarbamoyl)-1H-pyrazole-3-
carboxylic acid The title compound was prepared analogously to example 21 with the difference that 2-Bromo-N-(5-chloro-pyridin-2-yl)-acetamide was used instead of 3-Bromomethyl-5-(5-chloro-thiophen-2-yl)-isoxazole in the alkylation step. MS (ES$^+$): m/e=449, chloro pattern.
Alternatively 1-[(5-Chloro-pyridin-2-ylcarbamoyl)-methyl]-5-(1-isopropyl-piperidin-4-ylcarbamoyl)-1H-pyrazole-3-carboxylic acid can be prepared by the following procedure: To a solution of 1.5 g 1-[(5-Chloro-pyridin-2-ylcarbamoyl)-methyl]-5-(1-isopropyl-piperidin-4-ylcarbamoyl)-1H-pyrazole-3-carboxylic acid ethyl ester in 100 ml CH$_2$Cl$_2$, 13.96 ml BBR$^3$ (1M in CH$_2$Cl$_2$) were added and the mixture stirred at RT for 2 days. The solvent was removed in vacuo and the residue was purified by chromatography on silica gel using CH$_2$Cl$_2$/MeOH/HOAC/H$_2$O=9/1/0.1/0.1. The fractions containing the product were evaporated and lyophilized. The product was obtained as its hydrobromide. Yield: 1.33 g
MS (ES$^+$): m/e=449, chloro pattern.

Example 52

1-[(5-Chloro-pyridin-2-ylcarbamoyl)-methyl]-1H-
pyrazole-3,5-dicarboxylic acid 3-cyclobutylamide
5-[(1-isopropyl-piperidin-4-yl)-amide]

The title compound was prepared analogously to example 46 with the difference that 2-Bromo-N-(5-chloro-pyridin-2-

Example 53

1-[5-(5-Chloro-thiophen-2-yl)-isoxazol-3-ylmethyl]-3-trifluoromethyl-1H-pyrazole-4-carboxylic acid (1-isopropyl-piperidin-4-yl)-amide The title compound was prepared analogously to example 1 with the difference that 3-Trifluoromethyl-1H-pyrazole-4-carboxylic acid ethyl ester was used instead of 5-Thiophen-2-yl-2H-pyrazole-3-carboxylic acid ethyl ester. MS (ES$^+$): m/e=502, chloro pattern.

Example 54

1-[5-(5-Chloro-thiophen-2-yl)-isoxazol-3-ylmethyl]-1H-pyrazole-3,5-dicarboxylic acid bis-[(1-isopropyl-piperidin-4-yl)-amide]

The title compound was prepared analogously to example 25 with the difference that 1-Isopropyl-piperidin-4-ylamine dihydrochloride was used instead of morpholine.
MS (ES$^+$): m/e=602, chloro pattern.

Example 55

2-[5-(5-Chloro-thiophen-2-yl)-isoxazol-3-ylmethyl]-4-cyano-2H-pyrazole-3-carboxylic acid (1-isopropyl-piperidin-4-yl)-amide The title compound was prepared analogously to example 1 with the difference that 4-Cyano-2H-pyrazole-3-carboxylic acid ethyl ester was used instead of 5-Thiophen-2-yl-2H-pyrazole-3-carboxylic acid ethyl ester. MS (ES$^+$): m/e=459, chloro pattern.

Example 56

1-[5-(5-Chloro-thiophen-2-yl)-isoxazol-3-ylmethyl]-4-cyano-1H-pyrazole-3-carboxylic acid (1-isopropyl-piperidin-4-yl)-amide This compound was isolated as a by-product in example 55. MS (ES$^+$): m/e=459, chloro pattern.

Example 57

2-[(4-Chloro-phenylcarbamoyl)-methyl]-4-cyano-2H-pyrazole-3-carboxylic acid (1-isopropyl-piperidin-4-yl)-amide The title compound was prepared analogously to example 1 with the difference that 2-Bromo-N-(4-chloro-phenyl)-acetamide and 4-Cyano-2H-pyrazole-3-carboxylic acid ethyl ester were used instead of 2-Bromo-N-(5-chloro-pyridin-2-yl)-acetamide and 5-Thiophen-2-yl-2H-pyrazole-3-carboxylic acid ethyl ester in the alkylation step. MS (ESI$^+$): m/e=429, chloro pattern.

Example 58

3-{[1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-propionic acid The title compound was prepared analogously to example 25 with the difference that 3-Amino-propionic acid was used instead of morpholine. MS (ES$^+$): m/e=549, chloro pattern.

Example 59

1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-(methoxy-amide)

The title compound was prepared analogously to example 25 with the difference that O-Methyl-hydroxylamine hydrochloride was used instead of morpholine.
MS (ES$^+$): m/e=507, chloro pattern.

Example 60

1-[5-(5-Chloro-thiophen-2-yl)-isoxazol-3-ylmethyl]-1H-pyrazole-3,5-dicarboxylic acid 3-carbamoylmethyl-amide 5-[(1-isopropyl-piperidin-4-yl)-amide]

The title compound was prepared analogously to example 25 with the difference that 2-Amino-acetamide hydrochloride was used instead of morpholine. MS (ES$^+$): m/e=534, chloro pattern.

Example 61

{[1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-acetic acid ethyl ester The title compound was prepared analogously to example 25 with the difference that Amino-acetic acid ethyl ester hydrochloride was used instead of morpholine.
MS (ES$^+$): m/e=563, chloro pattern.

Example 62

1-[5-(5-Chloro-thiophen-2-yl)-isoxazol-3-ylmethyl]-1H-pyrazole-3,5-dicarboxylic acid 3-[(3-hydroxy-propyl)-amide]5-[(1-isopropyl-piperidin-4-yl)-amide]

The title compound was prepared analogously to example 25 with the difference that 3-Amino-propan-1-ol was used instead of morpholine. MS (ES$^+$): m/e=535, chloro pattern.

Example 63

1-[1-[5-(5-Chloro-thiophen-2-yl)-isoxazol-3-ylmethyl]-5-(1-isopropyl-piperidin-4-ylcarbamoyl)-1H-pyrazole-3-carbonyl]-(2S)-azetidine-2-carboxylic acid The title compound was prepared analogously to example 25 with the difference that 2S-Azetidine-2-carboxylic acid was used instead of morpholine.
MS (ES$^+$): m/e=561, chloro pattern.

(Top of page, continuation:) yl)-acetamide was used instead of 3-Bromomethyl-5-(5-chloro-thiophen-2-yl)-isoxazole in the alkylation step. MS (ES$^+$): m/e=502, chloro pattern.

Example 64

2-[5-(5-Chloro-thiophen-2-yl)-isoxazol-3-ylmethyl]-5-(2S,2-hydroxymethyl-pyrrolidine-1-carbonyl)-2H-pyrazole-3-carboxylic acid (1-isopropyl-piperidin-4-yl)-amide The title compound was prepared analogously to example 25 with the difference that 2S-Pyrrolidin-2-yl-methanol was used instead of morpholine.
MS (ES$^+$): m/e=561, chloro pattern.

Example 65

1-[1-[5-(5-Chloro-thiophen-2-yl)-isoxazol-3-ylmethyl]-5-(1-isopropyl-piperidin-4-ylcarbamoyl)-1H-pyrazole-3-carbonyl]-2S-pyrrolidine-2-carboxylic acid The title compound was prepared analogously to example 25 with the difference that 2S-Pyrrolidine-2-carboxylic acid was used instead of morpholine.
MS (ES$^+$): m/e=575, chloro pattern.

Example 66

2-[5-(5-Chloro-thiophen-2-yl)-isoxazol-3-ylmethyl]-5-(2S,2-methoxymethyl-pyrrolidine-1-carbonyl)-2H-pyrazole-3-carboxylic acid (1-isopropyl-piperidin-4-yl)-amide The title compound was prepared analogously to example 25 with the difference that 2S,2-Methoxymethyl-pyrrolidine was used instead of morpholine.
MS (ES$^+$): m/e=575, chloro pattern.

Example 67

5-(2R,5R,2,5-Bis-methoxymethyl-pyrrolidine-1-carbonyl)-2-[5-(5-chloro-thiophen-2-yl)-isoxazol-3-ylmethyl]-2H-pyrazole-3-carboxylic acid (1-isopropyl-piperidin-4-yl)-amide The title compound was prepared analogously to example 25 with the difference that 2R,5R,2,5-Bis-methoxymethyl-pyrrolidine was used instead of morpholine.
MS (ES$^+$): m/e=619, chloro pattern.

Example 68

1-[5-(5-Chloro-thiophen-2-yl)-isoxazol-3-ylmethyl]-1H-pyrazole-3,5-dicarboxylic acid 3-[(4,5-dihydro-oxazol-2-yl)-amide]5-[(1-isopropyl-piperidin-4-yl)-amide]

The title compound was prepared analogously to example 25 with the difference that 4,5-Dihydro-oxazol-2-ylamine hydrochloride was used instead of morpholine.
MS (ES$^+$): m/e=546, chloro pattern.

Example 69

1-[1-[5-(5-Chloro-thiophen-2-yl)-isoxazol-3-ylmethyl]-5-(1-isopropyl-piperidin-4-ylcarbamoyl)-1H-pyrazole-3-carbonyl]-piperidine-4-carboxylic acid ethyl ester The title compound was prepared analogously to example 25 with the difference that Piperidine-4-carboxylic acid ethyl ester was used instead of morpholine.
MS (ES$^+$): m/e=617, chloro pattern.

Example 70

1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-[(2-morpholin-4-yl-ethyl)-amide]

The title compound was prepared analogously to example 25 with the difference that 2-Morpholin-4-yl-ethylamine was used instead of morpholine.
MS (ES$^+$): m/e=590, chloro pattern.

Example 71

2-[5-(5-Chloro-thiophen-2-yl)-isoxazol-3-ylmethyl]-5-(4,4-difluoro-piperidine-1-carbonyl)-2H-pyrazole-3-carboxylic acid (1-isopropyl-piperidin-4-yl)-amide The title compound was prepared analogously to example 25 with the difference that 4,4-Difluoro-piperidine hydrochloride was used instead of morpholine.
MS (ES$^+$): m/e=581, chloro pattern.

Example 72

2-[5-(5-Chloro-thiophen-2-yl)-isoxazol-3-ylmethyl]-5-(2-oxo-oxazolidine-3-carbonyl)-2H-pyrazole-3-carboxylic acid (1-isopropyl-piperidin-4-yl)-amide The title compound was prepared analogously to example 25 with the difference that Oxazolidin-2-one was used instead of morpholine. MS (ES$^+$): m/e=547, chloro pattern.

Example 73

1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-{[2-(2-oxo-imidazolidin-1-yl)-ethyl]-amide}

The title compound was prepared analogously to example 25 with the difference that 1-(2-Amino-ethyl)-imidazolidin-2-one was used instead of morpholine.
MS (ES$^+$): m/e=589, chloro pattern.

Example 74

1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-[(2,2,2-trifluoro-ethyl)-amide]

The title compound was prepared analogously to example 25 with the difference that 2,2,2-Trifluoro-ethylamine was used instead of morpholine. MS (ES$^+$): m/e=559, chloro pattern.

Example 75

1-[5-(5-Chloro-thiophen-2-yl)-isoxazol-3-ylmethyl]-1H-pyrazole-3,5-dicarboxylic acid 3-[(1,1-dioxo-tetrahydro-1-thiophen-3-yl)-amide]5-[(1-isopropyl-piperidin-4-yl)-amide]

The title compound was prepared analogously to example 25 with the difference that 1,1-Dioxo-tetrahydro-1-thiophen-3-ylamine was used instead of morpholine.
MS (ES$^+$): m/e=595, chloro pattern.

Example 76

1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-{[3-(2-oxo-pyrrolidin-1-yl)-propyl]-amide}

The title compound was prepared analogously to example 25 with the difference that 1-(3-Amino-propyl)-pyrrolidin-2-one was used instead of morpholine.
MS (ES$^+$): m/e=602, chloro pattern.

Example 77

5-(Azetidine-1-carbonyl)-2-[5-(5-chloro-thiophen-2-yl)-isoxazol-3-ylmethyl]-2H-pyrazole-3-carboxylic acid (1-isopropyl-piperidin-4-yl)-amide The title compound was prepared analogously to example 25 with the difference that Azetidine was used instead of morpholine. MS (ES$^+$): m/e=517, chloro pattern.

Example 78

2-[5-(5-Chloro-thiophen-2-yl)-isoxazol-3-ylmethyl]-5-(thiazolidine-3-carbonyl)-2H-pyrazole-3-carboxylic acid (1-isopropyl-piperidin-4-yl)-amide The title compound was prepared analogously to example 25 with the difference that Thiazolidine was used instead of morpholine. MS (ES$^+$): m/e=549, chloro pattern.

Example 79

2-{[1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-3,3,3-trifluoro-propionic acid The title compound was prepared analogously to example 25 with the difference that 2-Amino-3,3,3-trifluoro-propionic acid was used instead of morpholine.
MS (ES$^+$): m/e=603, chloro pattern.

Example 80

1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-trimethylsilanylmethyl-amide The title compound was prepared analogously to example 25 with the difference that C-Trimethylsilanyl-methylamine was used instead of morpholine.
MS (ES$^+$): m/e=563, chloro pattern.

Example 81

2-[5-(5-Chloro-thiophen-2-yl)-isoxazol-3-ylmethyl]-5-[4-(2-oxo-pyrrolidin-1-yl)-piperidine-1-carbonyl]-2H-pyrazole-3-carboxylic acid (1-isopropyl-piperidin-4-yl)-amide The title compound was prepared analogously to example 25 with the difference that 1-Piperidin-4-yl-pyrrolidin-2-one hydrochloride was used instead of morpholine.
MS (ES$^+$): m/e=628, chloro pattern.

Example 82

2-[5-(5-Chloro-thiophen-2-yl)-isoxazol-3-ylmethyl]-5-methanesulfonylaminocarbonyl-2H-pyrazole-3-carboxylic acid (1-isopropyl-piperidin-4-yl)-amide The title compound was prepared analogously to example 25 with the difference that Methanesulfonamide was used instead of morpholine. MS (ES$^+$): m/e=555, chloro pattern.

Example 83

2-[5-(5-Chloro-thiophen-2-yl)-isoxazol-3-ylmethyl]-5-(3-hydroxy-azetidine-1-carbonyl)-2H-pyrazole-3-carboxylic acid (1-isopropyl-piperidin-4-yl)-amide The title compound was prepared analogously to example 25 with the difference that Azetidin-3-ol hydrochloride was used instead of morpholine. MS (ES$^+$): m/e=533, chloro pattern.

Example 84

1-[5-(5-Chloro-thiophen-2-yl)-isoxazol-3-ylmethyl]-5-furan-2-yl-1H-pyrazole-3-carboxylic acid (1-isopropyl-piperidin-4-yl)-amide (i) 4-Furan-2-yl-2,4-dioxo-butyric acid ethyl ester To a solution of 16 g oxalic acid diethyl ester in 350 ml THF, 10.1 g KOt-Bu were added at 0° C. Then 10 g 1-furan-2-yl-ethanone in 50 ml THF were added dropwise. After 1 h the reaction mixture was diluted with 300 ml ethyl acetate and 200 ml water. This solution was acidified with diluted hydrochloric acid to pH 5. The organic layer was separated, washed with 150 ml water, dried over MgSO$_4$, filtered and concentrated under reduced pressure to yield a white solid.
Yield: 12 g.

(ii) N,N'-[5-(5-Chloro-thiophen-2-yl)-isoxazol-3-ylmethyl]-hydrazine dicarboxylic acid tert-butyl ester To a solution of 1 g [5-(5-Chloro-thiophen-2-yl)-isoxazol-3-yl]-methanol [prepared by adopting a procedure described by Ewing, William R.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, Christopher J.; Jiang, John Z.; Li, Aiwen; Myers, Michael R.; Lau, Wan F.; Poli, Gregory B; PCT Int. Appl. (2001) 460 pp. WO 0107436 A2] and 3.01 g polymer bound triphenyl phosphine (Fluka, 3 mmol triphenylphosphine/g resin) added at 0° C. Then 2.1 g di-tert-butyl azodicarboxylate were added and the reaction mixture was stirred at RT for 2 h. The solids were filtered off and the filtrate was concentrated under reduced pressure. The residue was purified by silica gel chromatography eluting with a n-heptane/ethyl acetate gradient 100%->50%.
Yield: 1.6 g.

(iii) [5-(5-Chloro-thiophen-2-yl)-isoxazol-3-ylmethyl]-hydrazine

A solution of 1 g N,N'-[5-(5-Chloro-thiophen-2-yl)-isoxazol-3-ylmethyl]-hydrazine dicarboxylic acid tert-butyl ester was stirred in 15 ml methanolic hydrochloric acid (8M) for 16 h at RT. Then 150 ml toluene were added and the solvents were removed under reduced pressure.

Yield: 780 mg.

(iv) 1-[5-(5-Chloro-thiophen-2-yl)-isoxazol-3-ylmethyl]-5-furan-2-yl-1H-pyrazole-3-carboxylic acid ethyl ester A solution of 550 mg 4-Furan-2-yl-2,4-dioxo-butyric acid ethyl ester and 601 mg [5-(5-Chloro-thiophen-2-yl)-isoxazol-3-ylmethyl]-hydrazine in 10 ml acetic acid was heated to 80° C. for 2 h. Then the reaction mixture was diluted with 20 ml water and extracted with ethyl acetate (3×100 ml). The combined organic layers were dried over $MgSO_4$. The solvents were removed under reduced pressure and the residue was purified by silica gel chromatography eluting with a n-heptane:ethyl acetate gradient 100%->50%.

(v) 1-[5-(5-Chloro-thiophen-2-yl)-isoxazol-3-ylmethyl]-5-furan-2-yl-1H-pyrazole-3-carboxylic acid To a solution of 400 mg 1-[5-(5-Chloro-thiophen-2-yl)-isoxazol-3-ylmethyl]-5-furan-2-yl-1H-pyrazole-3-carboxylic acid ethyl ester in 5 ml THF and 1 ml water, 1 ml aqueous NaOH (1M) were added and the mixture was stirred for 16 h at RT. Then the solution was acidified to pH 3 with half concentrated hydrochloric acid to precipitate the pure product, which was collected by filtration. Yield: 360 mg.

(vi) 1-[5-(5-Chloro-thiophen-2-yl)-isoxazol-3-ylmethyl]-5-furan-2-yl-1H-pyrazole-3-carboxylic acid (1-isopropyl-piperidin-4-yl)-amide To 240 mg 1-[5-(5-Chloro-thiophen-2-yl)-isoxazol-3-ylmethyl]-5-furan-2-yl-1H-pyrazole-3-carboxylic acid in 4 ml DCM and 0.4 ml $NEt_3$, 173 mg 1-Isopropyl-piperidin-4-ylamine dihydrochloride and 163 mg BOP-Cl were added at RT and the mixture was stirred for 16 h. After addition of 5 ml of water the mixture was filtered through a Chem Elut® cartridge by elution with ethyl acetate and then concentrated under reduced pressure. The residue was purified by preparative HPLC (C18 reverse phase column, elution with a $H_2O$/MeCN gradient with 0.1% TFA). The fractions containing the product were evaporated and lyophilized to yield a white solid. The product was obtained as its trifluoroacetate salt.

Yield: 260 mg MS ($ES^+$): m/e=500, chloro pattern.

Example 85

2-[5-(5-Chloro-thiophen-2-yl)-isoxazol-3-ylmethyl]-5-(1-isopropyl-piperidin-4-ylcarbamoyl)-2H-pyrazole-3-carboxylic acid To a solution of 260 mg 1-[5-(5-Chloro-thiophen-2-yl)-isoxazol-3-ylmethyl]-5-furan-2-yl-1H-pyrazole-3-carboxylic acid (1-isopropyl-piperidin-4-yl)-amide in 10 ml $CCl_4$/MeCN/water 2:2:3, 500 mg $NaIO_4$ and 2.1 mg Ru(III) $Cl_3$ were added at RT. The reaction mixture was vigorously stirred for 16 h and then filtered through a Chem Elut® cartridge by elution with ethyl acetate and then concentrated under reduced pressure. The residue was purified by preparative HPLC (C18 reverse phase column, elution with a $H_2O$/MeCN gradient with 0.1% TFA). The fractions containing the product were evaporated and lyophilized to yield a brown solid. The product was obtained as its trifluoroacetate salt.

Yield: 130 mgMS ($ES^+$): m/e=478, chloro pattern.

Example 86

5-(Azetidine-1-carbonyl)-1-[5-(5-chloro-thiophen-2-yl)-isoxazol-3-ylmethyl]-1H-pyrazole-3-carboxylic acid (1-isopropyl-piperidin-4-yl)-amide To a solution of 50 mg 2-[5-(5-Chloro-thiophen-2-yl)-isoxazol-3-ylmethyl]-5-(1-isopropyl-piperidin-4-ylcarbamoyl)-2H-pyrazole-3-carboxylic acid, 0.1 ml N-NEM in 2 ml DCM, 34 mg TOTU and 9 mg azetidine were added and the mixture was stirred for 16 h at RT. Then, the reaction mixture was concentrated under reduced pressure and the residue was purified by preparative HPLC (C18 reverse phase column, elution with a $H_2O$/MeCN gradient with 0.1% TFA). The fractions containing the product were evaporated and lyophilized to yield a white solid. The product was obtained as its trifluoroacetate salt.

Yield: 2.7 mg MS ($ES^+$): m/e=517, chloro pattern.

Example 87

1-[5-(5-Chloro-thiophen-2-yl)-isoxazol-3-ylmethyl]-1H-pyrazole-3,5-dicarboxylic acid 3-[(1-isopropyl-piperidin-4-yl)-amide]5-[(2-sulfamoyl-ethyl)-amide]

The title compound was prepared analogously to example 86 with the difference that 2-Amino-ethanesulfonic acid amide hydrochloride was used instead of azetidine.

MS ($ES^+$): m/e=584, chloro pattern.

Example 88

1-[5-(5-Chloro-thiophen-2-yl)-isoxazol-3-ylmethyl]-1H-pyrazole-3,5-dicarboxylic acid 3-[bis-(2-hydroxy-ethyl)-amide]5-[(1-isopropyl-piperidin-4-yl)-amide]

To a solution of 650 mg 1-[5-(5-Chloro-thiophen-2-yl)-isoxazol-3-ylmethyl]-5-(1-isopropyl-piperidin-4-ylcarbamoyl)-1H-pyrazole-3-carboxylic acid hydrochloride and 133 mg dietanolamine in 20 ml absolute DMF, 413 mg TOTU and 441 µl DIPEA were added and the mixture was stirred at RT for 3 h. The solvent was removed in vacuo and the residue purified by chromatography on silica gel using $CH_2Cl_2$/MeOH/HOAC/$H_2O$=8/2/0.2/0.2. The fractions containing the product were evaporated and lyophilized after addition of acetic acid to give a white solid. The product was obtained as its acetate. Yield: 280 mg MS ($ES^+$): m/e=565, chloro pattern.

Example 89

1-[5-(5-Chloro-thiophen-2-yl)-isoxazol-3-ylmethyl]-1H-pyrazole-3,5-dicarboxylic acid 3-[(2-hydroxy-1,1-bis-hydroxymethyl-ethyl)-amide]5-[(1-isopropyl-piperidin-4-yl)-amide]

To a solution of 600 mg 1-[5-(5-Chloro-thiophen-2-yl)-isoxazol-3-ylmethyl]-5-(1-isopropyl-piperidin-4-ylcarbamoyl)-1H-pyrazole-3-carboxylic acid and 141 mg 2-Amino-2-hydroxymethyl-propane-1,3-diol in 20 ml absolute DMF, 381 mg TOTU and 407 µl DIPEA were added and the mixture was stirred at RT for 3 h. The solvent was removed in vacuo and the residue purified by chromatography on silica gel using $CH_2Cl_2$/MeOH/HOAC/$H_2O$=8/2/0.2/0.2. The fractions containing the product were evaporated and lyophilized after addition of acetic acid to give a white solid. The product was obtained as its acetate.

Yield: 210 mg MS (ES$^+$): m/e=581, chloro pattern.

Example 90

{1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-acetic acid isopropyl ester To a solution of 800 mg 1-[5-(5-Chloro-thiophen-2-yl)-isoxazol-3-ylmethyl]-5-(1-isopropyl-piperidin-4-ylcarbamoyl)-1H-pyrazole-3-carboxylic acid hydrochloride and 239 mg L-glycine-isopropylester hydrochloride in 10 ml absolute DMF, 509 mg TOTU and 813 µl DIPEA were added and the mixture was stirred at RT for 3 h. The solvent was removed in vacuo and the residue purified by preparative HPLC (C18 reverse phase column, elution with a H$_2$O/MeCN gradient with 0.1% TFA). The fractions containing the product were evaporated and lyophilized after addition of hydrochloric acid to give a white solid. The product was obtained as its hydrochloride.

Yield: 585 mg MS (ES$^+$): m/e=577, chloro pattern.

Example 91

1-[(5-Chloro-pyridin-2-ylcarbamoyl)-methyl]-5-(1-isopropyl-piperidin-4-ylcarbamoyl)-1H-pyrazole-3-carboxylic acid ethyl ester (i) 1-[(5-Chloro-pyridin-2-ylcarbamoyl)-methyl]-1H-pyrazole-3,5-dicarboxylic acid diethyl ester To a solution of 10 g 1H-Pyrazole-3,5-dicarboxylic acid diethyl ester in 200 ml absolute DMF 1.885 g of a 60% suspension of NaH in mineral oil were added in an argon atmosphere. The mixture was stirred for 15 min at RT. 11.76 g 2-Bromo-N-(5-chloro-pyridin-2-yl)-acetamide were added and the mixture stirred for 2 h at RT. After concentration in vacuo the residue was purified by chromatography on silica gel using CH$_2$Cl$_2$/ethylacetate=8/2. The fractions containing the product were evaporated.

Yield: 16.05 g.

(ii) 1-[(5-Chloro-pyridin-2-ylcarbamoyl)-methyl]-1H-pyrazole-3,5-dicarboxylic acid 3-ethyl ester To a solution of 8 g 1-[(5-Chloro-pyridin-2-ylcarbamoyl)-methyl]-1H-pyrazole-3,5-dicarboxylic acid diethyl ester in 200 ml THF and 50 ml H$_2$O 17.2 ml 1N NaOH is added. After standing for 16 h, the solution was acidified using 1 N HCl. THF was removed in vacuo and water was removed by lyophilization. The residue was purified by chromatography on silica gel using ethyl acetate followed by CH$_2$Cl$_2$/MeOH/HOAC/H$_2$O=9/1/0.1/0.1. The fractions containing the product were evaporated and lyophilized to give a white solid.

Yield: 4.42 g.

(iii) 1-[(5-Chloro-pyridin-2-ylcarbamoyl)-methyl]-5-(1-isopropyl-piperidin-4-ylcarbamoyl)-1H-pyrazole-3-carboxylic acid ethyl ester To a solution of 4.42 g 1-[(5-Chloro-pyridin-2-ylcarbamoyl)-methyl]-1H-pyrazole-3,5-dicarboxylic acid 3-ethyl ester and 2.69 g 1-Isopropyl-piperidin-4-ylamine dihydrochloride in 100 ml absolute DMF, 4.1 g TOTU and 6.54 ml DIPEA were added and the mixture was stirred at RT for 4 h. Then 1.345 g 1-Isopropyl-piperidin-4-ylamine dihydrochloride, 2.05 g TOTU and 3.27 ml DIPEA were added. After standing for 16 h the solvent was removed in vacuo, the residue was dissolved in CH$_2$Cl$_2$ and the CH$_2$Cl$_2$ solution washed two times with a saturated NaHCO$_3$ solution. The organic phase was dried over Na$_2$SO$_4$. After filtration and removal of the solvent in vacuo the residue was purified by chromatography on silica gel using CH$_2$Cl$_2$/MeOH/HOAC/H$_2$O=9/1/0.1/0.1. The fractions containing the product were evaporated and lyophilized to give a white solid. The product was obtained as its acetate. Yield: 2.96 g MS (ES$^+$): m/e=477, chloro pattern.

Example 92

{1-[(5-Chloro-pyridin-2-ylcarbamoyl)-methyl]-5-(1-isopropyl-piperidin-4-ylcarbamoyl)-1H-pyrazole-3-carbonyl]-amino}-acetic acid isopropyl ester (i) 1-[(5-Chloro-pyridin-2-ylcarbamoyl)-methyl]-5-(1-isopropyl-piperidin-4-ylcarbamoyl)-1H-pyrazole-3-carboxylic acid To a solution of 1.5 g 1-[(5-Chloro-pyridin-2-ylcarbamoyl)-methyl]-5-(1-isopropyl-piperidin-4-ylcarbamoyl)-1H-pyrazole-3-carboxylic acid ethyl ester in 100 ml CH$_2$Cl$_2$, 13.96 ml BBR$^3$ (1M in CH$_2$Cl$_2$) were added and the mixture stirred at RT for 2 days. The solvent was removed in vacuo and the residue was purified by chromatography on silica gel using CH$_2$Cl$_2$/MeOH/HOAC/H$_2$O=9/1/0.1/0.1. The fractions containing the product were evaporated and lyophilized. The product was obtained as its hydrobromide.

Yield: 1.33 g.

(ii) {1-[(5-Chloro-pyridin-2-ylcarbamoyl)-methyl]-5-(1-isopropyl-piperidin-4-ylcarbamoyl)-1H-pyrazole-3-carbonyl]-amino}-acetic acid isopropyl ester To a solution of 400 mg 1-[(5-Chloro-pyridin-2-ylcarbamoyl)-methyl]-5-(1-isopropyl-piperidin-4-ylcarbamoyl)-1H-pyrazole-3-carboxylic acid hydrobromide and 116 mg glycine-isopropyl ester-hydrochloride in 15 ml absolute DMF, 247 mg TOTU and 401 µl DIPEA were added and the mixture was stirred at RT for 2 h. The solvent was removed in vacuo, the residue was dissolved in CH$_2$Cl$_2$ and the CH$_2$Cl$_2$ solution washed two times with a saturated NaHCO$_3$ solution. The organic phase was dried over Na$_2$SO$_4$. After filtration and removal of the solvent in vacuo the residue was purified by chromatography on silica gel using CH$_2$Cl$_2$/MeOH/HOAC/H$_2$O=9/1/0.1/0.1. The fractions containing the product were evaporated and lyophilized. The residue was dissolved in CH$_2$Cl$_2$. Water was added and the pH of the mixture was adjusted to pH 13 by adding 1N NaOH. The phases were separated and the organic phase dried over Na$_2$SO$_4$. After filtration, the solvent was evaporated, the residue dissolved in water and lyophilized after addition of hydrochloric acid. The product was obtained as its hydrochloride.

Yield: 352 mg MS (ES$^+$): m/e=548, chloro pattern.

Example 93

{1-[(5-Chloro-pyridin-2-ylcarbamoyl)-methyl]-5-(1-isopropyl-piperidin-4-ylcarbamoyl)-1H-pyrazole-3-carbonyl]-amino}-acetic acid ethyl ester To a solution of 400 mg 1-[(5-Chloro-pyridin-2-ylcarbamoyl)-methyl]-5-(1-isopropyl-piperidin-4-ylcarbamoyl)-1H-pyrazole-3-carboxylic acid hydrobromide and 105 mg glycine-ethyl ester-hydrochloride in 15 ml absolute DMF, 247 mg TOTU and 401 µl DIPEA were added and the mixture was stirred at RT for 2 h. The solvent was removed in vacuo, the residue was dissolved in $CH_2Cl_2$ and the $CH_2Cl_2$ solution washed two times with a saturated $NaHCO_3$ solution. The organic phase was dried over $Na_2SO_4$. After filtration and removal of the solvent in vacuo the residue was purified by chromatography on silica gel using $CH_2Cl_2$/MeOH/HOAC/ $H_2O$=9/1/0.1/0.1. The fractions containing the product were evaporated and lyophilized. The residue was dissolved in $CH_2Cl_2$. Water was added and the pH of the mixture was adjusted to pH 13 by adding 1N NaOH. The phases were separated and the organic phase dried over $Na_2SO_4$. After filtration, the solvent was evaporated, the residue dissolved in water and lyophilized after addition of hydrochloric acid. The product was obtained as its hydrochloride.

Yield: 352 mg MS (ES$^+$): m/e=534, chloro pattern.

Example 94

{1-[(5-Chloro-pyridin-2-ylcarbamoyl)-methyl]-5-(1-isopropyl-piperidin-4-ylcarbamoyl)-1H-pyrazole-3-carbonyl]-amino}-acetic acid To a solution of 250 mg 1-[(5-Chloro-pyridin-2-ylcarbamoyl)-methyl]-5-(1-isopropyl-piperidin-4-ylcarbamoyl)-1H-pyrazole-3-carboxylic acid hydrobromide and 62 mg glycine-tert.butyl ester in 10 ml absolute DMF, 154 mg TOTU and 167 µl DIPEA were added and the mixture was stirred at RT for 2 h. The solvent was removed in vacuo, the residue was dissolved in $CH_2Cl_2$ and the $CH_2Cl_2$ solution washed two times with a saturated $NaHCO_3$ solution. The organic phase was dried over $Na_2SO_4$. After filtration and removal of the solvent in vacuo the residue was purified by chromatography on silica gel using $CH_2Cl_2$/MeOH/HOAC/$H_2O$=9/1/0.1/0.1. The fractions containing the product were evaporated and lyophilized. The residue was dissolved in $CH_2Cl_2$. Water was added and the pH of the mixture was adjusted to pH 13 by adding 1N NaOH. The phases were separated and the organic phase dried over $Na_2SO_4$. After filtration, the solvent was evaporated and the residue dissolved in 10 ml of 90% trifluoro acetic acid. After 1 h at RT trifluoro acetic acid was removed in vacuo, the residue dissolved in water by adding $CH_3CN$ and lyophilized after addition of hydrochloric acid. The product was obtained as its hydrochloride.

Yield: 114 mg MS (ES$^+$): m/e=506, chloro pattern.

Example 95

2-[(5-Chloro-pyridin-2-ylcarbamoyl)-methyl]-5-(3-hydroxy-azetidine-1-carbonyl)-2H-pyrazole-3-carboxylic acid (1-isopropyl-piperidin-4-yl)-amide To a solution of 500 mg 1-[(5-Chloro-pyridin-2-ylcarbamoyl)-methyl]-5-(1-isopropyl-piperidin-4-ylcarbamoyl)-1H-pyrazole-3-carboxylic acid hydrobromide and 103 mg Azetidin-3-ol in 20 ml absolute DMF 309 mg TOTU and 501 µl DIPEA were added and the mixture was stirred at RT for 2 h. The solvent was removed in vacuo, the residue was dissolved in $CH_2Cl_2$ and the $CH_2Cl_2$ solution washed two times with a saturated $NaHCO_3$ solution. The organic phase was dried over $Na_2SO_4$. After filtration and removal of the solvent in vacuo the residue was purified by chromatography on silica gel using $CH_2Cl_2$/MeOH/HOAC/$H_2O$=9/1/0.1/0.1. The fractions containing the product were evaporated and lyophilized. The residue was dissolved in $CH_2Cl_2$. Water was added and the pH of the mixture was adjusted to pH 13 by adding 1N NaOH. The phases were separated and the organic phase dried over $Na_2SO_4$. After filtration, the solvent was evaporated, the residue dissolved in water and lyophilized after addition of acetic acid. The product was obtained as its acetate. Yield: 249 mg MS (ES$^+$): m/e=504, chloro pattern.

Example 96

1-[(5-Chloro-pyridin-2-ylcarbamoyl)-methyl]-5-(1-isopropyl-piperidin-4-ylcarbamoyl)-1H-pyrazole-3-carboxylic acid cyclopropylmethyl ester To a solution of 400 mg 1-[(5-Chloro-pyridin-2-ylcarbamoyl)-methyl]-5-(1-isopropyl-piperidin-4-ylcarbamoyl)-1H-pyrazole-3-carboxylic acid hydrobromide and 327 mg Cyclopropyl-methanol in 15 ml absolute DMF 171 mg Dicyclohexylcarbodiimide and 83 mg DMAP were added and the mixture was stirred at RT for 16 h. Then additional 171 mg Dicyclohexylcarbodiimide were added. After 1 day at RT the solvent was removed in vacuo and the residue was purified by chromatography on silica gel using $CH_2Cl_2$/MeOH/HOAc/$H_2O$=9/1/0.1/0.1 and by preparative HPLC (C18 reverse phase column, elution with a $H_2O$/MeCN gradient with 0.1% TFA). The fractions containing the product were evaporated and lyophilized. The residue was dissolved in $CH_2Cl_2$. Water was added and the pH of the mixture was adjusted to pH 13 by adding 1N NaOH. The phases were separated and the organic phase dried over $Na_2SO_4$. After filtration, the solvent was evaporated, the residue dissolved in water and lyophilized after addition of acetic acid. The product was obtained as its acetate. Yield: 92 mg MS (ES$^+$): m/e=503, chloro pattern.

Example 97

2-{[1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-3-methyl-butyric acid ethyl ester To a solution of 1.5 g 1-[5-(5-Chloro-thiophen-2-yl)-isoxazol-3-ylmethyl]-5-(1-isopropyl-piperidin-4-ylcarbamoyl)-1H-pyrazole-3-carboxylic acid hydrochloride and 530 mg L-valine-isopropylester hydrochloride in 20 ml absolute DMF 954 mg TOTU and 1.524 ml DIPEA were added and the mixture was stirred at RT for 3 h. After standing for 16 h at RT, the solvent was removed in vacuo. The residue was dissolved in ethyl acetate and the solution washed with a solution of $KHSO_4/K_2SO_4$ in water (2 times) and a saturated $NaHCO_3$ solution. The phases were separated and the organic phase dried over $Na_2SO_4$. After filtration, the solvent was removed in vacuo and the residue purified by chromatography on silica gel using $CH_2Cl_2$/MeOH=100/0->40/60 and preparative HPLC (C18 reverse phase column, elution with a $H_2O$/MeCN gradient with 0.1% TFA). The fractions containing the product were evaporated and lyophilized after addition of hydrochloric acid to give a white solid. The product was obtained as its hydrochloride.

Yield: 1.36 g MS (ES$^+$): m/e=605, chloro pattern.

Example 98

2-{[1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-3-methyl-butyric acid To a solution of 760 mg 2-{[1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-3-methyl-butyric acid ethyl ester in 12.5 ml THF and 3.1 ml water 1.256 ml of 1N NaOH were added and the mixture stirred for 8 h at RT. The solution was diluted with water, acidified by adding HCl and lyophilized. The residue was purified by preparative HPLC (C18 reverse phase column, elution with a $H_2O$/MeCN gradient with 0.1% TFA). The fractions containing the product were evaporated and lyophilized after addition of hydrochloric acid to give a white solid. The product was obtained as its hydrochloride.

Yield: 608 mg MS (ES$^+$): m/e=577, chloro pattern.

Example 99

1-[5-(5-Chloro-thiophen-2-yl)-isoxazol-3-ylmethyl]-5-furan-2-yl-1H-pyrazole-3-carboxylic acid [4-(3-oxo-morpholin-4-yl)-phenyl]-amide (i) 4-(4-Nitro-phenyl)-morpholine A mixture of 24.5 g morpholine and 13.3 g 1-Fluoro-4-nitro-benzene in 30 ml DMSO was heated to 100° C. for 4 h. This solution was poured on to 300 ml of water and the resulting precipitate was collected by filtration to yield a bright yellow crystalline product, which was dried in vacuo.
Yield: 19.7 g.

(ii) 4-(4-Nitro-phenyl)-morpholin-3-one

To a solution of 10 g 4-(4-Nitro-phenyl)-morpholine in 200 ml DCM, 32 g Benzyl-triethyl-ammonium chloride and 22.7 g potassium permanganate (325 mesh) were cautiously added at RT. After stirring for 1 h at RT the reaction mixture was heated to reflux for 10 h. Then a solution of 95 g $Na_2SO_3$ in 450 ml water were added under ice cooling and vigourous stirring. The mixture was filtered through a pad of celite and the filtrate was concentrated under reduced pressure. The yellow solid was stirred with 250 ml water and the precipitated product was collected by filtration. This crude product was purified by chromatography on silica gel eluting with a gradient of DCM/MeOH 100%->50%. The fractions containing the product were combined and the solvent evaporated under reduced pressure. Yield: 2.6 g.

(iii) 4-(4-Amino-phenyl)-morpholin-3-one

To a solution of 2.6 g 4-(4-Nitro-phenyl)-morpholin-3-one in 350 ml ethyl acetate and 17 ml ethanol, 13.2 g $SnCl_2$ dihydrate were added and the reaction mixture was heated to reflux for 2 h. Then after cooling to RT the mixture was stirred for 16 h. The precipitated product was collected by filtration and was pure enough for the next reaction step. Yield: 2.07 g.

(iv) 1-[5-(5-Chloro-thiophen-2-yl)-isoxazol-3-ylmethyl]-5-furan-2-yl-1H-pyrazole-3-carboxylic acid [4-(3-oxo-morpholin-4-yl)-phenyl]-amide To 100 mg 1-[5-(5-Chloro-thiophen-2-yl)-isoxazol-3-ylmethyl]-5-furan-2-yl-1H-pyrazole-3-carboxylic acid in 2 ml DCM and 0.1 ml NEt$_3$, 62 mg 4-(4-Amino-phenyl)-morpholin-3-one and 67 mg BOP-Cl were added at RT and the mixture was stirred for 16 h. The mixture was was concentrated under reduced pressure and the residue was purified by preparative HPLC (C18 reverse phase column, elution with a $H_2O$/MeCN gradient with 0.1% TFA). The fractions containing the product were evaporated and lyophilized to yield a white solid.
Yield: 63 mg MS (ES$^+$): m/e=550, chloro pattern.

Example 100

1-[5-(5-Chloro-thiophen-2-yl)-isoxazol-3-ylmethyl]-5-hydroxymethyl-1H-pyrazole-3-carboxylic acid [4-(3-oxo-morpholin-4-yl)-phenyl]-amide (i) 1-[5-(5-Chloro-thiophen-2-yl)-isoxazol-3-ylmethyl]-5-hydroxymethyl-1H-pyrazole-3-carboxylic acid ethyl ester To a solution of 4 g 1-[5-(5-Chloro-thiophen-2-yl)-isoxazol-3-ylmethyl]-1H-pyrazole-3,5-dicarboxylic acid 3-ethyl ester in 50 ml THF 26 ml $BH_3$*THF (1M in THF) were added slowly at RT. Then the mixture was warmed to 40° C. for 6 h. After cooling to 0° C. 20 ml MeOH were added cautiously and the mixture was concentrated to dryness. The residue was again codistilled with 20 ml of MeOH and then purified by chromatography on silica gel eluting with n-heptane/ethyl acetate. The fractions containing the product were combined and the solvent evaporated under reduced pressure. Yield: 1.9 g.

(ii) 1-[5-(5-Chloro-thiophen-2-yl)-isoxazol-3-ylmethyl]-5-hydroxymethyl-1H-pyrazole-3-carboxylic acid To a solution of 380 mg 1-[5-(5-Chloro-thiophen-2-yl)-isoxazol-3-ylmethyl]-5-hydroxymethyl-1H-pyrazole-3-carboxylic acid ethyl ester in 5 ml THF and 5 ml of water 3 ml of a 1M NaOH were added and the reaction mixture was stirred for 3 h at RT. Then the mixture was acidified with half concentrated hydrochloric acid to pH 3 and the precipitate collected by filtration and washed with 10 ml water. The product was obtained as a white solid which was dried under reduced pressure. Yield: 320 mg.

(iii) 1-[5-(5-Chloro-thiophen-2-yl)-isoxazol-3-ylmethyl]-5-hydroxymethyl-1H-pyrazole-3-carboxylic acid [4-(3-oxo-morpholin-4-yl)-phenyl]-amide To 100 mg 1-[5-(5-Chloro-thiophen-2-yl)-isoxazol-3-ylmethyl]-5-hydroxymethyl-1H-pyrazole-3-carboxylic acid in 2 ml DCM and 0.1 ml NEt$_3$, 67 mg 4-(4-Amino-phenyl)-morpholin-3-one and 74 mg BOP-Cl were added at RT and the mixture was stirred for 16 h. The mixture was concentrated under reduced pressure and triturated in a mixture of water/DMF. The precipitate was collected by filtration and washed with water containing 0.5% TFA. The product was obtained as a white solid which was dried under reduced pressure.
Yield: 108 mg MS (ES$^+$): m/e=514, chloro pattern.

Example 101

1-[5-(5-Chloro-thiophen-2-yl)-isoxazol-3-ylmethyl]-5-[2-(2-methoxy-ethoxy)-ethoxymethyl]-1H-pyrazole-3-carboxylic acid (1-isopropyl-piperidin-4-yl)-amide (i) 1-[5-(5-Chloro-thiophen-2-yl)-isoxazol-3-ylmethyl]-5-[2-(2-methoxy-ethoxy)-ethoxymethyl]-1H-pyrazole-3-carboxylic acid ethyl ester To a solution of 100 mg 1-[5-(5-Chloro-thiophen-2-yl)-isoxazol-3-ylmethyl]-5-hydroxymethyl-1H-pyrazole-3-carboxylic acid ethyl ester in 2 ml DMF 11 mg NaH (60% in mineral oil) were added at RT and stirred for 10 min. Then 100 mg 1-Bromo-2-(2-methoxy-ethoxy)-ethane were added and the mixture was stirred for 16 h. After addition of 5 ml of water the mixture was filtered through a Chem Elut® cartridge by elution with ethyl acetate and then concentrated under reduced pressure. The crude residue was directly subjected to the next reaction step. Yield: 130 mg.

(ii) 1-[5-(5-Chloro-thiophen-2-yl)-isoxazol-3-ylmethyl]-5-[2-(2-methoxy-ethoxy)-ethoxymethyl]-1H-pyrazole-3-carboxylic acid To a solution of 130 mg 1-[5-(5-Chloro-thiophen-2-yl)-isoxazol-3-ylmethyl]-5-[2-(2-methoxy-ethoxy)-ethoxymethyl]-1H-pyrazole-3-carboxylic acid ethyl ester in 5 ml THF and 5 ml of water 3 ml of a 1M NaOH were added and the reaction mixture was stirred for 3 h at RT. Then the mixture was acidified with half concentrated hydrochloric acid to pH 3 and the precipitate collected by filtration and washed with 10 ml water. The product was obtained as a white solid which was dried under reduced pressure. Yield: 60 mg.

(iii) 1-[5-(5-Chloro-thiophen-2-yl)-isoxazol-3-ylmethyl]-5-[2-(2-methoxy-ethoxy)-ethoxymethyl]-1H-pyrazole-3-carboxylic acid (1-isopropyl-piperidin-4-yl)-amide To 60 mg 1-[5-(5-Chloro-thiophen-2-yl)-isoxazol-3-ylmethyl]-5-[2-(2-methoxy-ethoxy)-ethoxymethyl]-1H-pyrazole-3-carboxylic acid in 2 ml DCM and 0.1 ml NEt$_3$, 30 mg 1-Isopropyl-piperidin-4-ylamine hydrochloride and 34 mg BOP-Cl were added at RT and the mixture was stirred for 16 h. The mixture was concentrated under reduced pressure and the residue was purified by preparative HPLC (C18 reverse phase column, elution with a H$_2$O/MeCN gradient with 0.1% TFA). The fractions containing the product were evaporated and lyophilized to yield a white solid. Yield: 19 mg MS (ES$^+$): m/e=566, chloro pattern.

Example 102

2-[5-(5-Chloro-thiophen-2-yl)-isoxazol-3-ylmethyl]-5-(2-methoxy-ethoxymethyl)-2H-pyrazole-3-carboxylic acid (1-isopropyl-piperidin-4-yl)-amide (i) 2-[5-(5-Chloro-thiophen-2-yl)-isoxazol-3-ylmethyl]-5-hydroxymethyl-2H-pyrazole-3-carboxylic acid To a solution of 1 g 1-[5-(5-Chloro-thiophen-2-yl)-isoxazol-3-ylmethyl]-1H-pyrazole-3,5-dicarboxylic acid 3-ethyl ester in 15 ml THF 314 mg LiBH$_4$ were added cautiously. Then the reaction mixture was stirred for 16 h, quenched with diluted HCl and filtered through a Chem Elut® cartridge by elution with ethyl acetate and DCM. After concentration under reduced pressure the crude residue was directly subjected to the next reaction step.
Yield: 800 mg.

(ii) 2-[5-(5-Chloro-thiophen-2-yl)-isoxazol-3-ylmethyl]-5-(2-methoxy-ethoxymethyl)-2H-pyrazole-3-carboxylic acid To a solution of 500 mg of 2-[5-(5-Chloro-thiophen-2-yl)-isoxazol-3-ylmethyl]-5-hydroxymethyl-2H-pyrazole-3-carboxylic acid in 5 ml DMF 480 mg Cs$_2$CO$_3$ and 204 mg 1-Bromo-2-methoxy-ethane were added and the mixture was heated to 80° C. for 5 h. Then the mixture was acidified to pH 4 with aqueous HCl and filtered through a Chem Elut® cartridge by elution with ethyl acetate. After concentration the crude product was directly subjected to the next reaction step.

(iii) 2-[5-(5-Chloro-thiophen-2-yl)-isoxazol-3-ylmethyl]-5-(2-methoxy-ethoxymethyl)-2H-pyrazole-3-carboxylic acid (1-isopropyl-piperidin-4-yl)-amide To a solution of 200 mg 2-[5-(5-Chloro-thiophen-2-yl)-isoxazol-3-ylmethyl]-5-(2-methoxy-ethoxymethyl)-2H-pyrazole-3-carboxylic acid, 0.25 ml N-NEM in 5 ml DCM, 165 mg TOTU were added and the mixture was stirred for 30 min at RT. Then 165 mg 1-Isopropyl-piperidin-4-ylamine hydrochloride were added and the reaction was further stirred for 16 h. The reaction mixture was concentrated under reduced pressure and then purified by preparative HPLC (C18 reverse phase column, elution with a H$_2$OAMeCN gradient with 0.1% TFA). The fractions containing the product were evaporated and lyophilized to yield a white solid. The product was obtained as its trifluoroacetate salt.
Yield: 200 mg MS (ES$^+$): m/e=523, chloro pattern.

Example 103

1-[(5-Chloro-pyridin-2-ylcarbamoyl)-methyl]-5-[2-(2-methoxy-ethoxy)-ethoxymethyl]-1H-pyrazole-3-carboxylic acid (1-isopropyl-piperidin-4-yl)-amide (i) 3-[2-(2-Methoxy-ethoxy)-ethoxy]-propyne To a solution of 2 g 2-(2-Methoxy-ethoxy)-ethanol in 20 ml THF 1.8 g KOt-Bu were added at 0° C. After stirring for 10 min 8.1 ml 3-Bromo-propyne (75% in toluene) were added and the mixture was warmed to RT and stirred for 4 h. Then 10 ml of water were added and the mixture was filtered through a Chem Elut® cartridge by elution with CHCl$_3$. This solution containing the desired product was subjected to the next reaction step.

(ii) 5-[2-(2-Methoxy-ethoxy)-ethoxymethyl]-2H-pyrazole-3-carboxylic acid tert-butyl ester To a solution containing approx. 2.5 g 3-[2-(2-Methoxy-ethoxy)-ethoxy]-propyne, 2.8 g Diazo-acetic acid tert-butyl ester were added and the mixture was heated to 70° C. for 5 days. Then the solution was concentrated under reduced pressure and directly purified by chromatography on silica eluting with a n-heptane/ethyl acetate gradient. Yield: 1.7 g.

(iii) 1-[(5-Chloro-pyridin-2-ylcarbamoyl)-methyl]-5-[2-(2-methoxy-ethoxy)-ethoxymethyl]-1H-pyrazole-3-carboxylic acid tert-butyl ester To a solution of 350 mg 5-[2-(2-Methoxy-ethoxy)-ethoxymethyl]-2H-pyrazole-3-carboxylic acid tert-butyl ester in 5 ml of DMF and 46 mg of sodium hydride (60% in mineral oil) were added at RT. After stirring for 20 min at room temperature 290 mg of 2-Bromo-N-(5-chloro-pyridin-2-yl)-acetamide were added. The reaction was stirred at room temperature for 3 h. Then 10 ml of water were added and the mixture was filtered through a Chem Elut® cartridge by elution with DCM. After concentration under reduced pressure the crude was subjected to the next reaction without further purification. Yield: 400 mg.

(iv) 1-[(5-Chloro-pyridin-2-ylcarbamoyl)-methyl]-5-[2-(2-methoxy-ethoxy)-ethoxymethyl]-1H-pyrazole-3-carboxylic acid To a solution of 400 mg 1-[(5-Chloro-pyridin-2-ylcarbamoyl)-methyl]-5-[2-(2-methoxy-ethoxy)-ethoxymethyl]-1H-pyrazole-3-carboxylic acid tert-butyl ester in 5 ml DCM, 15 ml TFA were added at RT. After 3 h 30 ml toluene were added and the solvents were removed under reduced pressure. The residue was then three times codistillied with toluene and subjected to the next reaction step without further purification.

(v) 1-[(5-Chloro-pyridin-2-ylcarbamoyl)-methyl]-5-[2-(2-methoxy-ethoxy)-ethoxymethyl]-1H-pyrazole-3-carboxylic acid (1-isopropyl-piperidin-4-yl)-amide To 400 mg 1-[(5-Chloro-pyridin-2-ylcarbamoyl)-methyl]-5-[2-(2-methoxy-ethoxy)-ethoxymethyl]-1H-pyrazole-3-carboxylic acid in 5 ml DCM and 0.3 ml NEt$_3$, 217 mg 1-Isopropyl-piperidin-4-ylamine hydrochloride and 250 mg BOP-Cl were added at RT and the mixture was stirred for 16 h. The mixture was concentrated under reduced pressure and the residue was purified by preparative HPLC (C18 reverse phase column, elution with a H$_2$O/MeCN gradient with 0.1% TFA). The fractions containing the product were evaporated and lyophilized to yield a white solid.
Yield: 87 mg MS (ES$^+$): m/e=537, chloro pattern.

Example 104

2-[(5-Chloro-pyridin-2-ylcarbamoyl)-methyl]-5-[2-(2-methoxy-ethoxy)-ethoxy]-2H-pyrazole-3-carboxylic acid (1-isopropyl-piperidin-4-yl)-amide (i) 5-Hydroxy-2H-pyrazole-3-carboxylic acid ethyl ester To a solution of 5 g Diethyl Oxalacetate sodium salt in 100 ml ethanol, 1.5 g hydrazine monohydrochloride were added and the reaction mixture was heated to 80° C. for 3 h. Then the solution was diluted with 100 ml of water containing 3 ml of half concentrated HCl and extracted with DCM (3×100 ml). The combined organic layers were dried over MgSO$_4$, filtered and concentrated under reduced pressure. The crude product was subjected to the next reaction step without further purification. Yield: 3.4 g (ii) 5-[2-(2-Methoxy-ethoxy)-ethoxy]-2H-pyrazole-3-carboxylic acid ethyl ester To a mixture of 3.4 g 5-Hydroxy-2H-pyrazole-3-carboxylic acid ethyl ester and 3 g K$_2$CO$_3$ in 50 ml acetonitrile, 4 g 1-(2-Bromo-ethoxy)-2-methoxy-ethane were added. After stirring for 1 h at RT the reaction was heated to 50° C. for 4 h. Then 50 ml of water were added and the mixture was extracted with DCM (3×100 ml). The combined organic layers were dried over MgSO$_4$, filtered and concentrated under reduced pressure. The residue was purified by chromatography on silica eluting with a DCM/MeOH gradient. Yield: 1 g.

(iii) 2-[(5-Chloro-pyridin-2-ylcarbamoyl)-methyl]-5-[2-(2-methoxy-ethoxy)-ethoxy]-2H-pyrazole-3-carboxylic acid ethyl ester To a solution of 1 g 5-[2-(2-Methoxy-ethoxy)-ethoxy]-2H-pyrazole-3-carboxylic acid ethyl ester in 10 ml of DMF and 154 mg of sodium hydride (60% in mineral oil) were added at RT. After stirring for 5 min at room temperature, 966 mg of 2-Bromo-N-(5-chloro-pyridin-2-yl)-acetamide were added. The reaction was stirred at room temperature for 2 h. Then 50 ml of water were added and the mixture was extracted with DCM (3×100 ml). The combined organic layers were dried over MgSO$_4$, filtered and concentrated under reduced pressure. The product was used in the next reaction step without further purification. Yield: 1.2 g.

(iv) 2-[(5-Chloro-pyridin-2-ylcarbamoyl)-methyl]-5-[2-(2-methoxy-ethoxy)-ethoxy]-2H-pyrazole-3-carboxylic acid To a solution of 1.2 g 2-[(5-Chloro-pyridin-2-ylcarbamoyl)-methyl]-5-[2-(2-methoxy-ethoxy)-ethoxy]-2H-pyrazole-3-carboxylic acid ethyl ester in 5 ml THF 10 ml of a aqueous KOH solution (10%) were added and the reaction mixture was stirred for 4 h at RT. Then the mixture was acidified with half concentrated hydrochloric acid to pH 3 and the precipitate collected by filtration and washed with 10 ml of water The product was obtained as a white solid which was dried under reduced pressure. Yield: 310 mg.

(v) 2-[(5-Chloro-pyridin-2-ylcarbamoyl)-methyl]-5-[2-(2-methoxy-ethoxy)-ethoxy]-2H-pyrazole-3-carboxylic acid (1-isopropyl-piperidin-4-yl)-amide To 310 mg 2-[(5-Chloro-pyridin-2-ylcarbamoyl)-methyl]-5-[2-(2-methoxy-ethoxy)-ethoxy]-2H-pyrazole-3-carboxylic acid in 5 ml DCM and 0.3 ml NEt$_3$, 110 mg 1-Isopropyl-piperidin-4-ylamine hydrochloride and 197 mg BOP-CL were added at RT and the mixture was stirred for 16 h. The mixture was concentrated under reduced pressure and the residue was purified by preparative HPLC (C18 reverse phase column, elution with a H$_2$O/MeCN gradient with 0.1% TFA). The fractions containing the product were evaporated and lyophilized to yield a white solid.
Yield: 108 mg MS (ES$^+$): m/e=523, chloro pattern.

Example 105

2-[(5-Chloro-pyridin-2-ylcarbamoyl)-methyl]-5-(2,2,2-trifluoro-ethoxy)-2H-pyrazole-3-carboxylic acid (1-isopropyl-piperidin-4-yl)-amide The title compound was prepared analogously to example 104 with the difference that Trifluoro-methanesulfonic acid 2,2,2-trifluoro-ethyl ester was used instead of 1-(2-Bromo-ethoxy)-2-methoxy-ethane in step (ii). MS (ES$^+$): m/e=503, chloro pattern.

Example 106

1-[(5-Chloro-pyridin-2-ylcarbamoyl)-methyl]-5-(1-isopropyl-piperidin-4-ylcarbamoyl)-1H-pyrazole-3-carboxylic acid 2-methoxy-ethyl ester To a solution of 600 mg 1-[(5-Chloro-pyridin-2-ylcarbamoyl)-methyl]-5-(1-isopropyl-piperidin-4-ylcarbamoyl)-1H-pyrazole-3-carboxylic acid in 10 ml DMF, 0.9 ml 2-Methoxyethanol, 934 mg DCC and 552 mg DMAP were added. After stirring for 8 h at 40° C. the reaction mixture was directly purified by chromatography on silica gel using CH$_2$Cl$_2$/MeOH/HOAc/H$_2$O=9/1/0.1/0.1 and by preparative HPLC (C18 reverse phase column, elution with a H$_2$O/MeCN gradient with 0.1% TFA). The fractions containing the product were evaporated and lyophilized. The residue was dissolved in CH$_2$Cl$_2$. Water was added and the pH of the mixture was adjusted to pH 13 by adding 1N NaOH. The phases were separated and the organic phase dried over Na$_2$SO$_4$. After filtration, the solvent was evaporated, the residue was dissolved in water and lyophilized after addition of hydrochloric acid. The product was obtained as its hydrochloride.

Yield: 345 mg MS (ES$^+$): m/e=507, chloro pattern.

Example 107

1-[(5-Chloro-pyridin-2-ylcarbamoyl)-methyl]-5-(1-isopropyl-piperidin-4-ylcarbamoyl)-1H-pyrazole-3-carboxylic acid 2-hydroxy-ethyl ester The title compound was prepared analogously to example 106 with the difference that 10 equivalents of Ethane-1,2-diol were used instead of 2-Methoxyethanol.

MS (ES$^+$): m/e=493, chloro pattern.

Example 108

2-[(5-Chloro-pyridin-2-ylcarbamoyl)-methyl]-5-([1,4]oxazepane-4-carbonyl)-2H-pyrazole-3-carboxylic acid (1-isopropyl-piperidin-4-yl)-amide The title compound was prepared analogously to example 92 with the difference that[1,4]Oxazepane hydrochloride was used instead of glycine-isopropyl ester-hydrochloride.

MS (ES$^+$): m/e=532, chloro pattern.

Example 109

5-(1-Isopropyl-piperidin-4-ylcarbamoyl)-1-(3-methoxy-benzyl)-1H-pyrazole-3-carboxylic acid The title compound was prepared analogously to example 21 with the difference that 1-Bromomethyl-3-methoxy-benzene was used instead of 3-bromomethyl-5-(5-chloro-thiophen-2-yl)-isoxazole. MS (ES$^+$): m/e=401.

Example 110

1-[5-(5-Chloro-thiophen-2-yl)-isoxazol-3-ylmethyl]-5-(1-isopropyl-piperidin-4-ylcarbamoyl)-1H-pyrazole-3-carboxylic acid 2-hydroxy-ethyl ester The title compound was prepared analogously to example 107 with the difference that 1-[5-(5-Chloro-thiophen-2-yl)-isoxazol-3-ylmethyl]-5-(1-isopropyl-piperidin-4-ylcarbamoyl)-1H-pyrazole-3-carboxylic acid was used instead of 1-[(5-Chloro-pyridin-2-ylcarbamoyl)-methyl]-5-(1-isopropyl-piperidin-4-ylcarbamoyl)-1H-pyrazole-3-carboxylic acid. MS (ES$^+$): m/e=522, chloro pattern.

Example 111

1-[5-(5-Chloro-thiophen-2-yl)-isoxazol-3-ylmethyl]-5-(1-isopropyl-piperidin-4-ylcarbamoyl)-1H-pyrazole-3-carboxylic acid carboxymethyl ester (i) 1-[5-(5-Chloro-thiophen-2-yl)-isoxazol-3-ylmethyl]-5-(1-isopropyl-piperidin-4-ylcarbamoyl)-1H-pyrazole-3-carboxylic acid tert-butoxycarbonylmethyl ester The title compound was prepared analogously to example 110 with the difference that Hydroxy-acetic acid tert-butyl ester was used instead of 1 Ethane-1,2-diol.

(ii) 1-[5-(5-Chloro-thiophen-2-yl)-isoxazol-3-ylmethyl]-5-(1-isopropyl-piperidin-4-ylcarbamoyl)-1H-pyrazole-3-carboxylic acid carboxymethyl ester A solution of 180 mg 1-[5-(5-Chloro-thiophen-2-yl)-isoxazol-3-ylmethyl]-5-(1-isopropyl-piperidin-4-ylcarbamoyl)-1H-pyrazole-3-carboxylic acid tert-butoxycarbonylmethyl ester in 20 ml TFA were allowed to stand for 20 min at RT. Then the solvent was removed under reduced pressure and the residue was dissolved in water and lyophilized after addition of hydrochloric acid. The product was obtained as its hydrochloride. Yield: 145 mg MS (ES$^+$): m/e=536, chloro pattern.

Example 112

1-[(5-Chloro-pyridin-2-ylcarbamoyl)-methyl]-5-(1-isopropyl-piperidin-4-ylcarbamoyl)-4-(2,2,2-trifluoro-ethoxy)-1H-pyrazole-3-carboxylic acid ethyl ester (i) 4-Iodo-1H-pyrazole-3,5-dicarboxylic acid diethyl ester To a solution of 10 g 1H-Pyrazole-3,5-dicarboxylic acid diethyl ester in 400 ml acetonitrile 13 g ammonium cerium (iv) nitrate (CAN) and 7.17 g iodine were added and the mixture was heated to reflux for 5 h. Then, after cooling to RT, 30 ml sat. sodium thiosulfate solution were added. The mixture was extracted with ethyl acetate (3×100 ml), the combined organic layers were washed with water and then dried over MgSO$_4$, filtered and the solvents were removed under reduced pressure. The residue was filtered through a pad of silica gel eluting with heptane/ethyl acetate 1:1. Yield: 13 g.

(ii) 4-(2,2,2-Trifluoro-ethoxy)-1H-pyrazole-3,5-dicarboxylic acid diethyl ester

To a solution of 1 g 4-Iodo-1H-pyrazole-3,5-dicarboxylic acid diethyl ester in 5 ml 2,2,2-trifluoro-ethanol 1.4 g Cs$_2$CO$_3$, 56 mg CuI and 106 mg 1,10-Phenanthroline were added. The reaction mixture heated for 4 h to 100° C. under microwave irradiation (100 W, CEM Discover™ apparatus). Then 10 HCl in ethanol (8M) was added and the solution was stirred at RT. After 16 h the solvents were removed under reduced pressure and the residue taken up in DCM and water. The organic phase was separated and the aqueous layer was extracted with DCM (2×50 ml). The combined organic layers were dried over MgSO$_4$, filtered and the solvent was removed under reduced pressure. The residue was purified by preparative HPLC (C18 reverse phase column, elution with a H$_2$O/MeCN gradient with 0.1% TFA). The fractions containing the product were evaporated and lyophilized to yield a white solid. Yield: 359 mg.

(iii) 1-[(5-Chloro-pyridin-2-ylcarbamoyl)-methyl]-4-(2,2,2-trifluoro-ethoxy)-1H-pyrazole-3,5-dicarboxylic acid diethyl ester To a solution of 260 mg 4-(2,2,2-Trifluoro-ethoxy)-1H-pyrazole-3,5-dicarboxylic acid diethyl ester in 4 ml absolute DMF 33.5 mg of a 60% suspension of NaH in mineral oil were added under an argon atmosphere. The mixture was stirred for 15 min at RT. Then 209 mg 2-Bromo-N-(5-chloro-pyridin-2-yl)-acetamide were added and the mixture stirred for 2 h at RT. After concentration in vacuo the residue was directly subjected to the next reaction step without further purification.

Yield: 400 mg.

(iv) 1-[(5-Chloro-pyridin-2-ylcarbamoyl)-methyl]-4-(2,2,2-trifluoro-ethoxy)-1H-pyrazole-3,5-dicarboxylic acid 3-ethyl ester To a solution of 400 mg 1-[(5-Chloro-pyridin-2-ylcarbamoyl)-methyl]-4-(2,2,2-trifluoro-ethoxy)-1H-pyrazole-3,5-dicarboxylic acid diethyl ester in 5 ml THF and 0.9 ml 1N NaOH were added. After standing for 16 h, the solution was acidified using 1 N HCl to pH 1. The precipitating product was collected by filtration and dried under reduced pressure. Yield: 142 mg.

(v) 1-[(5-Chloro-pyridin-2-ylcarbamoyl)-methyl]-5-(1-isopropyl-piperidin-4-ylcarbamoyl)-4-(2,2,2-trifluoro-ethoxy)-1H-pyrazole-3-carboxylic acid ethyl ester To 100 mg 1-[(5-Chloro-pyridin-2-ylcarbamoyl)-methyl]-4-(2,2,2-trifluoro-ethoxy)-1H-pyrazole-3,5-dicarboxylic acid 3-ethyl ester in 2 ml DCM and 0.2 ml $NEt_3$, 128 mg 1-Isopropyl-piperidin-4-ylamine dihydrochloride and 87 mg BOP-Cl were added at RT and the mixture was stirred for 16 h. The mixture was concentrated under reduced pressure and the residue was purified by preparative HPLC (C18 reverse phase column, elution with a $H_2O$/MeCN gradient with 0.1% TFA). The fractions containing the product were evaporated and lyophilized to yield a white solid. The product was obtained as its trifluoroacetate salt.
Yield: 10 mg MS ($ES^+$): m/e=575, chloro pattern.

Example 113

1-[(5-Chloro-pyridin-2-ylcarbamoyl)-methyl]-5-hydroxymethyl-1H-pyrazole-3-carboxylic acid (1-isopropyl-piperidin-4-yl)-amide

(i) 5-Hydroxymethyl-2H-pyrazole-3-carboxylic acid ethyl ester

A solution of 2 g Prop-2-yn-1-ol and 3 g Ethyl diazoacetate in 16 ml trichloromethane was stirred at 70° C. for 24 h. Then the solvent was removed under reduced pressure and the residue was purified on silica gel eluting with a gradient n-heptane/ethyl acetate 1:1->1:2. The fractions containing the product were collected and evaporated under reduced pressure.
Yield: 1.9 g.

(ii) 5-(tert-Butyl-diphenyl-silanyloxymethyl)-2H-pyrazole-3-carboxylic acid ethyl ester To a solution of 768 mg 5-Hydroxymethyl-2H-pyrazole-3-carboxylic acid ethyl ester in 5 ml DMF, 1.9 g Imidazole and 3.2 g tert-Butyl-chloro-diphenyl-silane were added at RT and stirred for 3 h. Then 10 ml of water were added and the mixture was extracted with ethyl acetate (2×30 ml). The combined organic layers were washed with brine, dried over $MgSO_4$ and filtered. The solids were removed under reduced pressure to yield the product as a yellow oil. Yield: 5 g.

(iii) 5-(tert-Butyl-diphenyl-silanyloxymethyl)-1-[(5-chloro-pyridin-2-ylcarbamoyl)-methyl]-1H-pyrazole-3-carboxylic acid ethyl ester To a solution of 5 g 5-(tert-Butyl-diphenyl-silanyloxymethyl)-2H-pyrazole-3-carboxylic acid ethyl ester in 10 ml DMF 4 g $Cs_2CO_3$ and 3 g 2-Bromo-N-(5-chloro-pyridin-2-yl)-acetamide were added and the mixture was stirred for 3 h. Then 10 ml of water were added and the mixture was extracted with ethyl acetate (2×50 ml). The combined organic layers were dried over $MgSO_4$, filtered and concentrated under reduced pressure. Inspection of the TLC and HPLC/MS indicated that a 1:1 mixture of the desired product together with the regioisomeric 5-(tert-Butyl-diphenyl-silanyloxymethyl)-2-[(5-chloro-pyridin-2-ylcarbamoyl)-methyl]-2H-pyrazole-3-carboxylic acid ethyl ester was present. Purification of this mixture on silica gel eluting with a gradient on n-heptane/ethylacetate yielded the desired product as the faster eluting less polar isomer.
Yield: 2 g.

(iv) 5-(tert-Butyl-diphenyl-silanyloxymethyl)-1-[(5-chloro-pyridin-2-ylcarbamoyl)-methyl]-1H-pyrazole-3-carboxylic acid To a solution of 2 g 5-(tert-Butyl-diphenyl-silanyloxymethyl)-1-[(5-chloro-pyridin-2-ylcarbamoyl)-methyl]-1H-pyrazole-3-carboxylic acid ethyl ester in 10 ml THF, 7 ml aqueous KOH solution (10%) were added at RT and the mixture was stirred for 16 h. Then the solution was acidified by addition of 10 ml half concentrated acetic acid and extracted with ethyl acetate (3×50 ml). The combined organic layers were dried over $MgSO_4$, filtered and concentrated under reduced pressure. Yield: 1.8 g.

(v) 1-[(5-Chloro-pyridin-2-ylcarbamoyl)-methyl]-5-hydroxymethyl-1H-pyrazole-3-carboxylic acid (1-isopropyl-piperidin-4-yl)-amide To 500 mg 5-(tert-Butyl-diphenyl-silanyloxymethyl)-1-[(5-chloro-pyridin-2-ylcarbamoyl)-methyl]-1H-pyrazole-3-carboxylic acid in 10 ml DCM and 0.8 ml $NEt_3$, 370 mg 1-Isopropyl-piperidin-4-ylamine dihydrochloride and 208 mg BOP-Cl were added at RT and the mixture was stirred for 16 h. Then 3 ml half concentrated HCl were added and the mixture was stirred for 2 h. After neutralization with of saturated aqueous $NaHCO_3$ the mixture was extracted with ethyl acetate (2×50 ml) and DCM (1×50 ml). The combined organic layers were dried over $MgSO_4$, filtered and concentrated under reduced pressure. The residue was purified by preparative HPLC (C18 reverse phase column, elution with a $H_2O$/MeCN gradient with 0.1% TFA). The fractions containing the product were evaporated and lyophilized to yield a white solid. The product was obtained as its trifluoroacetate salt.
Yield: 16 mg MS ($ES^+$): m/e=435, chloro pattern.

Example 114

1-[(5-Chloro-pyridin-2-ylcarbamoyl)-methyl]-5-(1-isopropyl-piperidin-4-ylcarbamoyl)-4-(2,2,2-trifluoro-ethoxy)-1H-pyrazole-3-carboxylic acid can be prepared from 1-[(5-Chloro-pyridin-2-ylcarbamoyl)-methyl]-5-(1-isopropyl-piperidin-4-ylcarbamoyl)-4-(2,2,2-trifluoro-ethoxy)-1H-pyrazole-3-carboxylic acid ethyl ester by a procedure analogous to example 21 or example 51.

Example 115

1-[(5-Chloro-pyridin-2-ylcarbamoyl)-methyl]-4-(2,2-difluoro-ethoxy)-5-(1-isopropyl-piperidin-4-ylcarbamoyl)-1H-pyrazole-3-carboxylic acid ethyl ester can be prepared from 2,2-Difluoro-ethanol using a procedure analogous to example 112.

Example 116

1-[(5-Chloro-pyridin-2-ylcarbamoyl)-methyl]-4-(2,2-difluoro-ethoxy)-5-(1-isopropyl-piperidin-4-ylcarbamoyl)-1H-pyrazole-3-carboxylic acid can be prepared from 1-[(5-Chloro-pyridin-2-ylcarbamoyl)-methyl]-4-(2,2-difluoro-ethoxy)-5-(1-isopropyl-piperidin-4-ylcarbamoyl)-1H-pyrazole-3-carboxylic acid ethyl ester using a procedure analogous to example 21 or example 51.

Example 117

2-[(5-Chloro-pyridin-2-ylcarbamoyl)-methyl]-5-hydroxymethyl-2H-pyrazole-3-carboxylic acid (1-isopropyl-piperidin-4-yl)-amide can be prepared from 5-(tert-Butyl-diphenyl-silanyloxymethyl)-2-[(5-chloro-pyridin-2-ylcarbamoyl)-methyl]-2H-pyrazole-3-carboxylic acid ethyl ester using a procedure analogous to example 113.

Example 118

2-[(5-Chloro-pyridin-2-ylcarbamoyl)-methyl]-5-difluoromethoxymethyl-2H-pyrazole-3-carboxylic acid (1-isopropyl-piperidin-4-yl)-amide can be prepared from 2-[(5-Chloro-pyridin-2-ylcarbamoyl)-methyl]-5-hydroxymethyl-2H-pyrazole-3-carboxylic acid (1-isopropyl-piperidin-4-yl)-amide using a procedure described by Q. Y. Chen et al. J. Fluorine Chem. (1989) 44, 433.

Example 119

2-[(5-Chloro-pyridin-2-ylcarbamoyl)-methyl]-5-(2,2,2-trifluoro-ethoxymethyl)-2H-pyrazole-3-carboxylic acid (1-isopropyl-piperidin-4-yl)-amide can be prepared from Trifluoro-methanesulfonic acid 2,2,2-trifluoro-ethyl ester using a procedure analogous to example 103.

Example 120

2-[(5-Chloro-pyridin-2-ylcarbamoyl)-methyl]-5-(2,2-difluoro-ethoxymethyl)-2H-pyrazole-3-carboxylic acid (1-isopropyl-piperidin-4-yl)-amide can be prepared from Trifluoro-methanesulfonic acid 2,2-difluoro-ethyl ester using a procedure analogous to example 103.

Example 121

2-[(5-Chloro-pyridin-2-ylcarbamoyl)-methyl]-5-(2,2-difluoro-3-hydroxy-propoxymethyl)-2H-pyrazole-3-carboxylic acid (1-isopropyl-piperidin-4-yl)-amide can be prepared from Trifluoro-methanesulfonic acid 2,2-difluoro-3-hydroxy-propyl ester using a procedure analogous to example 103.

Example 122

2-[(5-Chloro-pyridin-2-ylcarbamoyl)-methyl]-5-(2,2-difluoro-3-methoxy-propoxymethyl)-2H-pyrazole-3-carboxylic acid (1-isopropyl-piperidin-4-yl)-amide can be prepared from Trifluoro-methanesulfonic acid 2,2-difluoro-3-methoxy-propyl ester using a procedure analogous to example 103.

Example 123

2-[(5-Chloro-pyridin-2-ylcarbamoyl)-methyl]-5-(3-difluoromethoxy-2,2-difluoro-propoxymethyl)-2H-pyrazole-3-carboxylic acid (1-isopropyl-piperidin-4-yl)-amide can be prepared from Trifluoro-methanesulfonic acid 3-difluoromethoxy-2,2-difluoro-propyl ester using a procedure analogous to example 103.

Example 124

1-[(5-Chloro-pyridin-2-ylcarbamoyl)-methyl]-1H-pyrazole-3,5-dicarboxylic acid 5-[(1-isopropyl-piperidin-4-yl)-amide]3-(cyanamide)

can be prepared from 1-[(5-Chloro-pyridin-2-ylcarbamoyl)-methyl]-5-(1-isopropyl-piperidin-4-ylcarbamoyl)-1H-pyrazole-3-carboxylic acid using a procedure analogous to example 49.

Example 125

1-[(5-Chloro-pyridin-2-ylcarbamoyl)-methyl]-1H-pyrazole-3,5-dicarboxylic acid 5-[(1-isopropyl-piperidin-4-yl)-amide]3-(N-cyano-methyl-amide)

can be prepared from 1-[(5-Chloro-pyridin-2-ylcarbamoyl)-methyl]-5-(1-isopropyl-piperidin-4-ylcarbamoyl)-1H-pyrazole-3-carboxylic acid and Methyl-cyanamide [can be prepared adapting a procedure described by R. Niwa et al. Chem. Pharm. Bull. (1996) 44, 2314]using a procedure analogous to example 49.

Example 126

1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-(N-cyano-methyl-amide)

can be prepared from 1-[5-(5-Chloro-thiophen-2-yl)-isoxazol-3-ylmethyl]-5-(1-isopropyl-piperidin-4-ylcarbamoyl)-1H-pyrazole-3-carboxylic acid and Methyl-cyanamide [can be prepared adapting a procedure described by R. Niwa et al. Chem. Pharm. Bull. (1996) 44, 2314] using a procedure analogous to example 49.

Example 127

1-[(5-Chloro-pyridin-2-ylcarbamoyl)-methyl]-1H-pyrazole-3,5-dicarboxylic acid 5-[(1-isopropyl-piperidin-4-yl)-amide]3-[N-cyano-(2,2,2-trifluoro-ethyl)-amide]

can be prepared from 1-[(5-Chloro-pyridin-2-ylcarbamoyl)-methyl]-5-(1-isopropyl-piperidin-4-ylcarbamoyl)-1H-pyrazole-3-carboxylic acid and 2,2,2-Trifluoro-ethyl-cyanamide [can be prepared adapting a procedure described by R. Niwa et al. Chem. Pharm. Bull. (1996) 44, 2314] using a procedure analogous to example 49.

Example 128

1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-[N-cyano-(2,2,2-trifluoro-ethyl)-amide]

can be prepared from 1-[5-(5-Chloro-thiophen-2-yl)-isoxazol-3-ylmethyl]-5-(1-isopropyl-piperidin-4-ylcarbamoyl)-1H-pyrazole-3-carboxylic acid and 2,2,2-Trifluoro-ethyl-cyanamide [can be prepared adapting a procedure described by R. Niwa et al. Chem. Pharm. Bull. (1996) 44, 2314] using a procedure analogous to example 49.

Example 129

1-[(5-Chloro-pyridin-2-ylcarbamoyl)-methyl]-1H-pyrazole-3,5-dicarboxylic acid 3-[(2,2-difluoro-ethyl)-N-cyano-amide]5-[(1-isopropyl-piperidin-4-yl)-amide]

can be prepared from 1-[(5-Chloro-pyridin-2-ylcarbamoyl)-methyl]-5-(1-isopropyl-piperidin-4-ylcarbamoyl)-1H-pyrazole-3-carboxylic acid and 2,2-difluoro-ethyl-cyanamide [can be prepared adapting a procedure described by R. Niwa et al. Chem. Pharm. Bull. (1996) 44, 2314] using a procedure analogous to example 49.

Example 130

1-[5-(5-Chloro-thiophen-2-yl)-isoxazol-3-ylmethyl]-1H-pyrazole-3,5-dicarboxylic acid 3-[(2,2-difluoro-ethyl)-N-cyano-amide]5-[(1-isopropyl-piperidin-4-yl)-amide]

can be prepared from 1-[5-(5-Chloro-thiophen-2-yl)-isoxazol-3-ylmethyl]-5-(1-isopropyl-piperidin-4-ylcarbamoyl)-1H-pyrazole-3-carboxylic acid and 2,2-difluoro-ethyl-cyanamide [can be prepared adapting a procedure described by R. Niwa et al. Chem. Pharm. Bull. (1996) 44, 2314] using a procedure analogous to example 49.

Example 131

1-[(5-Chloro-pyridin-2-ylcarbamoyl)-methyl]-1H-pyrazole-3,5-dicarboxylic acid 5-[(1-isopropyl-piperidin-4-yl)-amide]3-(methoxy-amide)

can be prepared from 1-[(5-Chloro-pyridin-2-ylcarbamoyl)-methyl]-5-(1-isopropyl-piperidin-4-ylcarbamoyl)-1H-pyrazole-3-carboxylic acid using a procedure analogous to example 59.

Example 132

1-[(5-Chloro-pyridin-2-ylcarbamoyl)-methyl]-1H-pyrazole-3,5-dicarboxylic acid 5-[(1-isopropyl-piperidin-4-yl)-amide]3-(methoxy-methyl-amide)

can be prepared from 1-[(5-Chloro-pyridin-2-ylcarbamoyl)-methyl]-5-(1-isopropyl-piperidin-4-ylcarbamoyl)-1H-pyrazole-3-carboxylic acid and O,N-dimethyl-hydroxylamine [can be prepared by adapting a procedure described by M. Strasser et al. Helv. Chim. Acta (1988) 71, 1156 or P. Beak et al. J. Org. Chem. (1989) 54, 5574] using a procedure analogous to example 59.

Example 133

1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-(methoxy-methyl-amide)

can be prepared from 1-[5-(5-Chloro-thiophen-2-yl)-isoxazol-3-ylmethyl]-5-(1-isopropyl-piperidin-4-ylcarbamoyl)-1H-pyrazole-3-carboxylic acid and O,N-dimethyl-hydroxylamine [can be prepared by adapting a procedure described by M. Strasser et al. Helv. Chim. Acta (1988) 71, 1156 or P. Beak et al. J. Org. Chem. (1989) 54, 5574] using a procedure analogous to example 59.

Example 134

1-[(5-Chloro-pyridin-2-ylcarbamoyl)-methyl]-1H-pyrazole-3,5-dicarboxylic acid 5-[(1-isopropyl-piperidin-4-yl)-amide]3-[methoxy-(2,2,2-trifluoro-ethyl)-amide]

can be prepared from 1-[(5-Chloro-pyridin-2-ylcarbamoyl)-methyl]-5-(1-isopropyl-piperidin-4-ylcarbamoyl)-1H-pyrazole-3-carboxylic acid and O-methyl-N-(2,2,2-trifluoro-ethyl)-hydroxylamine [can be prepared by adapting a procedure described by M. Strasser et al. Helv. Chim. Acta (1988) 71, 1156 or P. Beak et al. J. Org. Chem. (1989) 54, 5574] using a procedure analogous to example 59.

Example 135

1-[5-(5-Chloro-thiophen-2-yl)-isoxazol-3-ylmethyl]-1H-pyrazole-3,5-dicarboxylic acid 5-[(1-isopropyl-piperidin-4-yl)-amide] 3-[methoxy-(2,2,2-trifluoro-ethyl)-amide]

can be prepared from 1-[5-(5-Chloro-thiophen-2-yl)-isoxazol-3-ylmethyl]-5-(1-isopropyl-piperidin-4-ylcarbamoyl)-1H-pyrazole-3-carboxylic acid and O-methyl-N-(2,2,2-trifluoro-ethyl)-hydroxylamine [can be prepared by adapting a procedure described by M. Strasser et al. Helv. Chim. Acta (1988) 71, 1156 or P. Beak et al. J. Org. Chem. (1989) 54, 5574] using a procedure analogous to example 59.

Example 136

1-[(5-Chloro-pyridin-2-ylcarbamoyl)-methyl]-1H-pyrazole-3,5-dicarboxylic acid 3-[(2,2-difluoro-ethyl)-methoxy-amide]5-[(1-isopropyl-piperidin-4-yl)-amide]

can be prepared from 1-[(5-Chloro-pyridin-2-ylcarbamoyl)-methyl]-5-(1-isopropyl-piperidin-4-ylcarbamoyl)-1H-pyrazole-3-carboxylic acid and N-(2,2-difluoro-ethyl)-O-methyl-hydroxylamine [can be prepared by adapting a procedure

Example 137

1-[5-(5-Chloro-thiophen-2-yl)-isoxazol-3-ylmethyl]-1H-pyrazole-3,5-dicarboxylic acid 3-[(2,2-difluoro-ethyl)-methoxy-amide]5-[(1-isopropyl-piperidin-4-yl)-amide]

can be prepared from 1-[5-(5-Chloro-thiophen-2-yl)-isoxazol-3-ylmethyl]-5-(1-isopropyl-piperidin-4-ylcarbamoyl)-1H-pyrazole-3-carboxylic acid and N-(2,2-difluoro-ethyl)-O-methyl-hydroxylamine [can be prepared by adapting a procedure described by M. Strasser et al. Helv. Chim. Acta (1988) 71, 1156 or P. Beak et al. J. Org. Chem. (1989) 54, 5574] using a procedure analogous to example 59.

Example 138

2-[(5-Chloro-pyridin-2-ylcarbamoyl)-methyl]-5-difluoromethoxy-2H-pyrazole-3-carboxylic acid (1-isopropyl-piperidin-4-yl)-amide can be prepared from 5-Hydroxy-2H-pyrazole-3-carboxylic acid ethyl ester using a procedure described by Q. Y. Chen et al. J. Fluorine Chem. (1989) 44, 433 and example 105.

Example 139

2-[5-(5-Chloro-thiophen-2-yl)-isoxazol-3-ylmethyl]-5-difluoromethoxy-2H-pyrazole-3-carboxylic acid (1-isopropyl-piperidin-4-yl)-amide can be prepared from 5-Hydroxy-2H-pyrazole-3-carboxylic acid ethyl ester and 3-Bromomethyl-5-(5-chloro-thiophen-2-yl)-isoxazole using a procedure described by Q. Y. Chen et al. J. Fluorine Chem. (1989) 44, 433 and example 105.

Example 140

2-[(5-Chloro-pyridin-2-ylcarbamoyl)-methyl]-5-(2,2-difluoro-ethoxy)-2H-pyrazole-3-carboxylic acid (1-isopropyl-piperidin-4-yl)-amide can be prepared from 5-Hydroxy-2H-pyrazole-3-carboxylic acid ethyl ester and Trifluoro-methanesulfonic acid 2,2-difluoro-ethyl ester using a procedure analogous to example 105.

Example 141

2-[5-(5-Chloro-thiophen-2-yl)-isoxazol-3-ylmethyl]-5-(2,2-difluoro-ethoxy)-2H-pyrazole-3-carboxylic acid (1-isopropyl-piperidin-4-yl)-amide can be prepared from 5-Hydroxy-2H-pyrazole-3-carboxylic acid ethyl ester, 3-Bromomethyl-5-(5-chloro-thiophen-2-yl)-isoxazole and Trifluoro-methanesulfonic acid 2,2-difluoro-ethyl ester using a procedure analogous to example 105.

Example 142

2-[(5-Chloro-pyridin-2-ylcarbamoyl)-methyl]-5-(2,2-difluoro-3-hydroxy-propoxy)-2H-pyrazole-3-carboxylic acid (1-isopropyl-piperidin-4-yl)-amide can be prepared from 5-Hydroxy-2H-pyrazole-3-carboxylic acid ethyl ester and Trifluoro-methanesulfonic acid 2,2-difluoro-3-hydroxy-propyl ester using a procedure analogous to example 105.

Example 143

2-[5-(5-Chloro-thiophen-2-yl)-isoxazol-3-ylmethyl]-5-(2,2-difluoro-3-hydroxy-propoxy)-2H-pyrazole-3-carboxylic acid (1-isopropyl-piperidin-4-yl)-amide can be prepared from 5-Hydroxy-2H-pyrazole-3-carboxylic acid ethyl ester, 3-Bromomethyl-5-(5-chloro-thiophen-2-yl)-isoxazole and Trifluoro-methanesulfonic acid 2,2-difluoro-3-hydroxy-propyl ester using a procedure analogous to example 105.

Example 144

2-[(5-Chloro-pyridin-2-ylcarbamoyl)-methyl]-5-(2,2-difluoro-3-methoxy-propoxy)-2H-pyrazole-3-carboxylic acid (1-isopropyl-piperidin-4-yl)-amide can be prepared from 5-Hydroxy-2H-pyrazole-3-carboxylic acid ethyl ester and Trifluoro-methanesulfonic acid 2,2-difluoro-3-methoxy-propyl ester using a procedure analogous to example 105.

Example 145

2-[5-(5-Chloro-thiophen-2-yl)-isoxazol-3-ylmethyl]-5-(2,2-difluoro-3-methoxy-propoxy)-2H-pyrazole-3-carboxylic acid (1-isopropyl-piperidin-4-yl)-amide can be prepared from 5-Hydroxy-2H-pyrazole-3-carboxylic acid ethyl ester, 3-Bromomethyl-5-(5-chloro-thiophen-2-yl)-isoxazole and Trifluoro-methanesulfonic acid 2,2-difluoro-3-methoxy-propyl ester using a procedure analogous to example 105.

Example 146

2-[(5-Chloro-pyridin-2-ylcarbamoyl)-methyl]-5-(3-difluoromethoxy-2,2-difluoro-propoxy)-2H-pyrazole-3-carboxylic acid (1-isopropyl-piperidin-4-yl)-amide can be prepared from 5-Hydroxy-2H-pyrazole-3-carboxylic acid ethyl ester and Trifluoro-methanesulfonic acid 3-difluoromethoxy-2,2-difluoro-propyl ester using a procedure analogous to example 105.

Example 147

2-[5-(5-Chloro-thiophen-2-yl)-isoxazol-3-ylmethyl]-5-(3-difluoromethoxy-2,2-difluoro-propoxy)-2H-pyrazole-3-carboxylic acid (1-isopropyl-piperidin-4-yl)-amide can be prepared from 5-Hydroxy-2H-pyrazole-3-carboxylic acid ethyl ester, 3-Bromomethyl-5-(5-chloro-thiophen-2-yl)- isoxazole and Trifluoro-methanesulfonic acid 3-difluoromethoxy-2,2-difluoro-propyl ester using a procedure analogous to example 105.

Pharmacological Testing

The ability of the compound of formulae I, Ib and Ic to inhibit factor Xa or factor VIIa or other enzymes like thrombin, plasmin, or trypsin can be assessed by determining the concentration of the compound of the formulae I, Ib and Ic that inhibits enzyme activity by 50%, i.e. the IC50 value, which was related to the inhibition constant Ki. Purified enzymes were used in chromogenic assays. The concentration of inhibitor that causes a 50% decrease in the rate of substrate hydrolysis was determined by linear regression after plotting the relative rates of hydrolysis (compared to the uninhibited control) versus the log of the concentration of the compound of formulae I, Ib and Ic. For calculating the inhibition constant Ki, the IC50 value was corrected for competition with substrate using the formula wherein Km is the Michaelis-Menten constant (Chen and Prusoff, Biochem.

$$Ki = IC50/\{1+(\text{substrate concentration}/Km)\}$$

Pharmacol. 22 (1973) 3099-3108; I. H. Segal, Enzyme Kinetics, 1975, John Wiley & Sons, New York, 100-125; which were incorporated herein by reference).

a) Factor Xa Assay

In the assay for determining the inhibition of factor Xa activity TBS-PEG buffer (50 mM Tris-HCl, pH 7.8, 200 mM NaCl, 0.05% (w/v) PEG-8000, 0.02% (w/v) NaN$_3$) was used. The IC$_{50}$ was determined by combining in appropriate wells of a Costar half-area microtiter plate 25 µl human factor Xa (Enzyme Research Laboratories, Inc.; South Bend, Ind.) in TBS-PEG; 40 µl 10% (v/v) DMSO in TBS-PEG (uninhibited control) or various concentrations of the compound to be tested diluted in 10% (v/v) DMSO in TBS-PEG; and substrate S-2765 (N(α)-benzyloxycarbonyl-D-Arg-Gly-L-Arg-p-nitroanilide; Kabi Pharmacia, Inc.; Franklin, Ohio) in TBS-PEG.

The assay was performed by pre-incubating the compound of formulae I, Ib and Ic plus enzyme for 10 min. Then the assay was initiated by adding substrate to obtain a final volume of 100 µl. The initial velocity of chromogenic substrate hydrolysis was measured by the change in absorbance at 405 nm using a Bio-tek Instruments kinetic plate reader (Ceres UV900HDi) at 25° C. during the linear portion of the time course (usually 1.5 min after addition of substrate). The enzyme concentration was 0.5 nM and substrate concentration was 140 µM.

b) Factor VIIa Assay

The inhibitory activity towards factor VIIa/tissue factor activity was determined using a chromogenic assay essentially as described previously (J. A. Ostrem et al., Biochemistry 37 (1998) 1053-1059 which was incorporated herein by reference). Kinetic assays were conducted at 25° C. in half-area microtiter plates (Costar Corp., Cambridge, Mass.) using a kinetic plate reader (Molecular Devices Spectramax 250). A typical assay consisted of 25 µl human factor VIIa and TF (5 nM and 10 nM, respective final concentration) combined with 40 µl of inhibitor dilutions in 10% DMSO/TBS-PEG buffer (50 mM Tris, 15 mM NaCl, 5 mM CaCl$_2$, 0.05% PEG 8000, pH 8.15). Following a 15 minute preincubation period, the assay was initiated by the addition of 35 µl of the chromogenic substrate S-2288 (D-Ile-Pro-Arg-p-nitroanilide, Pharmacia Hepar Inc., 500 µM final concentration). The results (inhibition constants Ki (FXa) for inhibition of factor Xa) are shown in Table 1.

TABLE 1

| Example | Ki (FXa) [µM] |
|---------|---------------|
| 1 | 0.030 |
| 2 | 0.032 |
| 3 | 0.112 |
| 5 | 0.300 |
| 6 | 0.491 |
| 7 | 0.293 |
| 8 | 0.054 |
| 9 | 0.332 |
| 10 | 0.041 |
| 11 | 0.083 |
| 12 | 0.014 |
| 13 | 0.039 |
| 14 | 0.046 |
| 15 | 0.013 |
| 16 | 0.165 |
| 17 | 0.155 |
| 18 | 0.205 |
| 19 | 0.274 |
| 20 | 0.073 |
| 21 | 0.214 |
| 23 | 0.144 |
| 25 | 0.095 |
| 26 | 0.068 |
| 27 | 0.088 |
| 28 | 0.082 |
| 29 | 0.155 |
| 30 | 0.262 |
| 31 | 0.180 |
| 32 | 0.045 |
| 33 | 0.082 |
| 34 | 0.108 |
| 35 | 0.163 |
| 36 | 0.122 |
| 37 | 0.195 |
| 38 | 0.932 |
| 39 | 0.145 |
| 40 | 0.123 |
| 41 | 0.081 |
| 42 | 0.084 |
| 43 | 0.072 |
| 44 | 0.046 |
| 45 | 0.061 |
| 46 | 0.106 |
| 47 | 0.086 |
| 48 | 0.183 |
| 49 | 0.040 |
| 50 | 0.010 |
| 52 | 0.016 |
| 55 | 0.099 |
| 56 | 0.144 |
| 57 | 0.410 |
| 58 | 0.063 |
| 59 | 0.094 |
| 60 | 0.056 |
| 61 | 0.101 |
| 62 | 0.080 |
| 63 | 0.134 |
| 64 | 0.090 |
| 65 | 0.142 |
| 66 | 0.152 |
| 67 | 0.420 |
| 68 | 0.099 |
| 69 | 0.177 |
| 70 | 0.182 |
| 71 | 0.184 |
| 72 | 0.092 |
| 73 | 0.083 |
| 74 | 0.086 |
| 75 | 0.076 |
| 76 | 0.083 |
| 77 | 0.063 |
| 78 | 0.144 |
| 79 | 0.080 |
| 80 | 0.149 |
| 81 | 0.142 |
| 82 | 0.184 |
| 83 | 0.104 |

TABLE 1-continued

| Example | Ki (FXa) [μM] |
|---|---|
| 84 | 0.042 |
| 85 | 0.185 |
| 86 | 0.142 |
| 87 | 0.181 |
| 88 | 0.106 |
| 89 | 0.192 |
| 90 | 0.240 |
| 92 | 0.041 |
| 93 | 0.036 |
| 94 | 0.023 |
| 95 | 0.039 |
| 96 | 0.018 |
| 97 | 0.228 |
| 98 | 0.140 |
| 99 | 0.011 |
| 100 | 0.004 |
| 104 | 0.025 |
| 105 | 0.021 |
| 106 | 0.016 |
| 107 | 0.020 |
| 108 | 0.039 |
| 110 | 0.081 |
| 111 | 0.049 |

What is claimed is:

1. A compound of formula I,

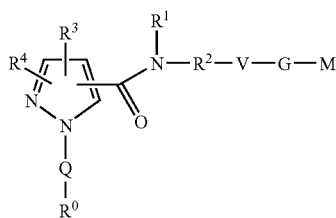

wherein $R^0$ is a monocyclic or bicyclic 6- to 14-membered aryl, wherein, the aryl is mono-, di- or trisubstituted independently of one another by $R^8$, or

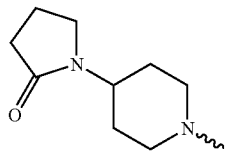

a monocyclic or bicyclic 4- to 15-membered heterocyclyl, containing one, two, three or four heteroatoms selected from the group consisting of nitrogen, sulfur and oxygen, wherein, said heterocyclyl is unsubstituted or mono-, di-, or trisubstituted independently of one another by $R^8$, and which is additionally substituted by a monocyclic or bicyclic 4- to 15-membered heterocyclyl, containing one, two, three or four heteroatoms selected from nitrogen, sulfur and oxygen, wherein heterocyclyl is unsubstituted or mono-, di- or trisubstituted independently of one another by $R^8$, $R^8$ is
1) halogen,
2) $-NO_2$,
3) $-CN$,
4) $-C(O)-NH_2$,
5) $-OH$,
6) $-NH_2$,
7) $-O-CF_3$,
8) a monocyclic or bicyclic 6- to 14-membered aryl, wherein aryl is mono-, di- or trisubstituted independently of one another by halogen or $-O-(C_1-C_8)$-alkyl,
9) $-(C_1-C_8)$-alkyl, wherein alkyl is unsubstituted or mono-, di- or trisubstituted independently of one another by halogen, $NH_2$, $-OH$ or methoxy,
10) $-O-(C_1-C_8)$-alkyl, wherein alkyl is unsubstituted or mono-, di- or trisubstituted independently of one another by halogen, $NH_2$, $-OH$ or methoxy,
11) $-SO_2-CH_3$ or
12) $-SO_2-CF_3$,
provided that where $R^0$ is a monocyclic or bicyclic 6- to 14-membered aryl, then $R^8$ is at least one halogen, $-C(O)-NH_2$ or $-O-(C_1-C_8)$-alkyl;

Q is $-(C_1-C_6)$-alkylene,
$R^1$ is hydrogen or $-(C_1-C_4)$-alkyl, wherein alkyl is unsubstituted or substituted one to three times by $R^{13}$;
$R^2$ is a direct bond,
V is a 3- to 7-membered heterocyclic residue containing 1, 2, 3 or 4 heteroatoms selected from nitrogen, sulfur and oxygen, wherein said heterocyclic residue is unsubstituted or mono-, di- or trisubstituted independently of one another by $R^{14}$,
$R^{14}$ is halogen, $-OH$, $=O$, $-(C_1-C_8)$-alkyl, $-(C_1-C_4)$-alkoxy, $-NO_2$, $-(C_0-C_4)$-alkyl-C(O)$-O-R^{18}$, $-CN$, $-(C_0-C_4)$-alkyl-N(R^{18})-R^{21}$, $-(C_0-C_4)$-alkyl-O$-R^{18}$, $-(C_0-C_4)$-alkyl-het, $-(C_0-C_8)$-alkyl-SO_2H$, $-SO_2-(C_1-C_4)$-alkyl, $-SO_2-N(R^{18})-R^{21}$, $-C(O)-NH-(C_1-C_8)$-alkyl, $-C(O)-N-[(C_1-C_8)$-alkyl]$_2$, $-NR^{18}-C(O)-NH-(C_1-C_8)$-alkyl, $-C(O)-NH_2$, $-S-R^{18}$, or $-NR^{18}-C(O)-NH-[(C_1-C_8)$-alkyl]$_2$,
wherein $R^{18}$ and $R^{21}$ are independently selected from hydrogen atom, $-(C_1-C_3)$-perfluoroalkyl, and $-(C_1-C_6)$-alkyl;
G is a direct bond;
M is
$-(C_1-C_8)$-alkyl, wherein alkyl is unsubstituted or mono-, di- or trisubstituted independently of one another by $R^{14}$;
$R^3$ and $R^4$ are, independent of one another:
1) hydrogen,
2) halogen,
3) $-(C_1-C_4)$-alkyl, wherein alkyl is unsubstituted or mono-, di- or trisubstituted independently of one another by $R^{13}$,
4) $-(C_1-C_3)$-perfluoroalkyl,
5) phenyl, wherein phenyl is unsubstituted or mono-, di- or trisubstituted independently of one another by $R^{13}$,
6) $-(C_0-C_4)$-alkylene-O$-R^{19}$, wherein $R^{19}$ is
a) hydrogen,
b) $-(C_1-C_4)$-alkyl, wherein alkyl is unsubstituted or mono-, di-, or trisubstituted independently of one another by $R^{13}$, or
c) phenyl, wherein phenyl is unsubstituted or mono-, di- or trisubstituted independently of one another by $R^{13}$,
d) $-CF_3$, or
e) $-CHF_2$,
7) $-NO_2$,
8) $-CN$,
9) $-SO_s-R^{11}$, wherein s is 1 or 2,
10) $-SO_t-N(R^{11})-R^{12}$, wherein t is 1 or 2, 11) —(C$_0$-C$_4$)-alkylene-C(O)—R$^{11}$,
12) —(C$_0$-C$_4$)-alkylene-C(O)—O—R$^{11}$,
13) —(C$_0$-C$_4$)-alkylene-C(O)—N(R$^{11}$)—R$^{12}$,
14) —(C$_0$-C$_4$)-alkylene-N(R$^{11}$)—R$^{12}$,
15) —NR$^{10}$—SO$_2$—R$^{10}$,
16) —S—R$^{10}$,
17) —(C$_0$-C$_2$)alkylene-C(O)—O—(C$_2$-C$_4$)-alkylene-O—C(O)—(C$_1$-C$_4$)-alkyl,
18) —C(O)—O—C(R$^{15}$,R$^{16}$)—O—C(O)—R$^{17}$,
19) —(C$_0$-C$_2$)alkylene-C(O)—O—(C$_2$-C$_4$)-alkylene-O—C(O)—O—(C$_1$-C$_6$-alkyl,
20) —C(O)—O—C(R$^{15}$, R$^{16}$)—O—C(O)—O—R$^{17}$,
21) —(C$_0$-C$_4$)-alkylene-(C$_6$-C$_{14}$)-aryl, wherein aryl is mono-, di- or trisubstituted independently of one another by R$^{13}$,
22) —(C$_0$-C$_4$)-alkylene-(C$_4$-C$_{15}$)-heterocyclyl, wherein heterocyclyl is unsubstituted or mono-, di- or trisubstituted independently of one another by R$^{13}$,
23) —(C$_0$-C$_4$)-alkylene-(C$_3$-C$_8$)-cycloalkyl, wherein cycloalkyl is unsubstituted or mono-, di- or trisubstituted independently of one another by R$^{13}$,
24) —(C$_0$-C$_4$)-alkylene-het, wherein het is unsubstituted or mono-, di- or trisubstituted independently of one another by R$^{13}$,
25) —(C$_0$-C$_4$)-alkylene-O—CH$_2$—(C$_1$-C$_3$)-perfluoro-alkylene-CH$_2$—O—(C$_0$-C$_4$)-alkyl, or
26) a residue selected from the group consisting of

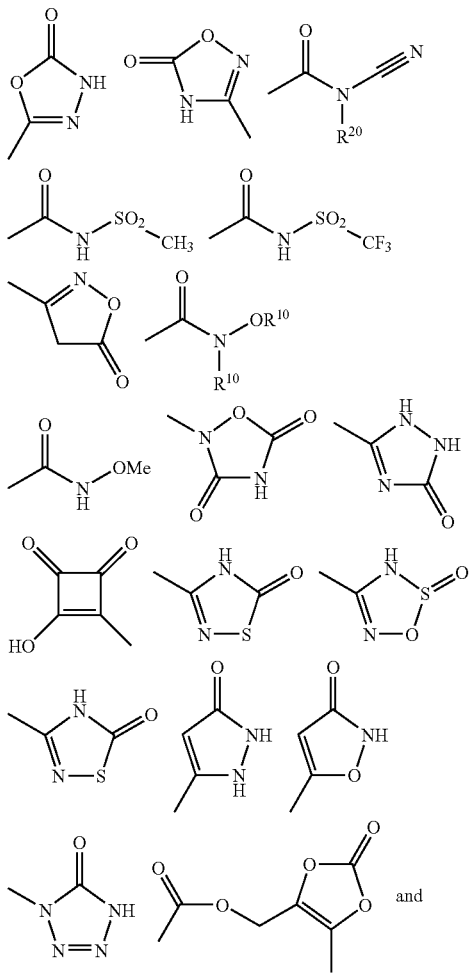

and

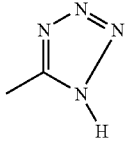

wherein Me is methyl, or two —OR$^{19}$ residues and adjacent atoms through which they are attached form together a 5- or 6-membered ring, that is unsubstituted or substituted one, two, three or four times by R$^{13}$;

R$^{11}$ and R$^{12}$ are, independently of one another:

1) hydrogen,
2) —(C$_1$-C$_6$)-alkyl, wherein alkyl is unsubstituted or mono-, di- or trisubstituted independently of one another by R$^{13}$,
3) —(C$_0$-C$_6$)-alkyl-(C$_3$-C$_8$)-cycloalkyl,
4) —SO$_t$—R$^{10}$, wherein t is 1 or 2,
5) —(C$_0$-C$_6$)-alkyl-(C$_6$-C$_{14}$)-aryl, wherein alkyl and aryl independently from one another are unsubstituted or mono-, di- or trisubstituted by R$^{13}$,
6) —(C$_1$-C$_3$)-perfluoroalkyl,
7) —O—R$^{17}$, or
8) —(C$_0$-C$_6$)-alkyl-(C$_4$-C$_{15}$)-heterocyclyl, wherein alkyl and heterocyclyl independently from one another are unsubstituted or mono-, di- or trisubstituted by R$^{13}$, or R$^{11}$ and R$^{12}$ together with the nitrogen atom to which they are bonded can form a 4- to 8-membered monocyclic heterocyclic ring which in addition to the nitrogen atom can contain one or two identical or different ring heteroatoms selected from oxygen, sulfur and nitrogen;

wherein said heterocyclic ring is unsubstituted or mono-, di- or trisubstituted independently of one another by R$^{13}$;

R$^{13}$ is halogen, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_3$-C$_8$)-cycloalkyl, —(C$_0$-C$_3$)-alkylene-O—R$^{10}$, —Si—(CH$_3$)$_3$, —N(R$^{10}$)—S(O)$_u$—R$^{10}$, wherein u is 1 or 2, —S—R$^{10}$, —SO$_r$—R$^{10}$, wherein r is 1 or 2, —S(O)$_v$—N(R$^{10}$)—R$^{20}$ wherein v is 1 or 2, —C(O)—R$^{10}$, —(C$_1$-C$_8$)-alkyl, —(C$_1$-C$_8$)-alkoxy, phenyl, phenyloxy-, —O—CF$_3$, —(C$_0$-C$_4$)-alkyl-C(O)—O—C(R$^{15}$, R$^{16}$) —C(O)—R$^{17}$, —(C$_1$-C$_4$)-alkoxy-phenyl, —(C$_0$-C$_4$)-alkyl-C(O)—O—C (R$^{15}$, R$^{16}$) —O—C(O)—O—R$^{17}$, —(C$_1$-C$_3$)-perfluoroalkyl, —O—R$^{15}$, —NH—C(O)—NH—R$^{10}$, —NH—C(O)—O—R$^{10}$, or a residue selected from the group consisting of

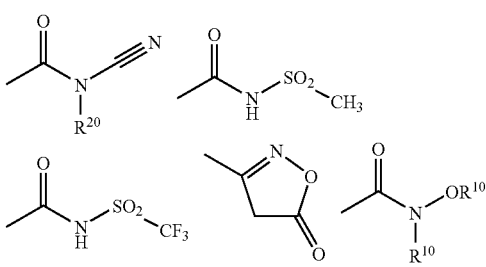

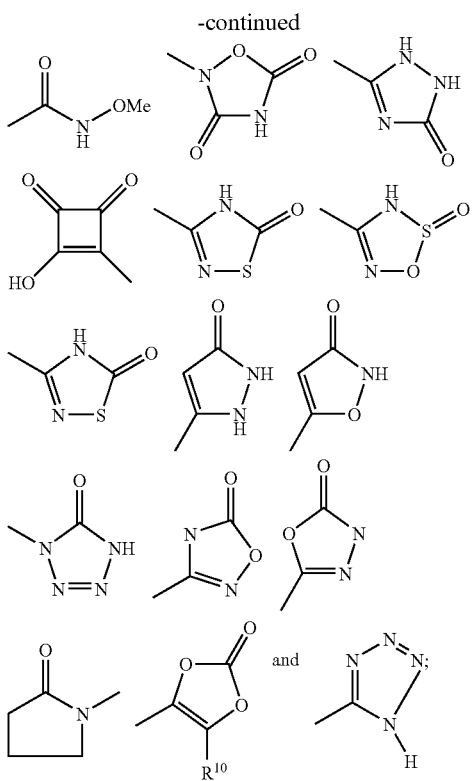

R¹⁰ and R²⁰ are independently selected from hydrogen, —(C₁-C₆)-alkyl, —(C₀-C₄)-alkyl-OH, —(C₀-C₄)-alkyl-O—(C₁-C₄)-alkyl, and —(C₁-C₃)-perfluoroalkyl;

R¹⁵ and R¹⁶ are independently selected from hydrogen, —(C₁-C₆)-alkyl, or, together with the carbon atom to which they are bonded, can form a 3- to 6 membered carbocyclic ring unsubstituted or substituted one to three times by R¹⁰; and R¹⁷ is —(C₁-C₆)-alkyl, —(C₁-C₆)-alkyl-OH, —(C₁-C₆)-alkyl-O—(C₁-C₆)-alkyl, —(C₃-C₈)-cycloalkyl, —(C₁-C₆)-alkyl-O—(C₁-C₈)-alkyl-(C₃-C₈)-cycloalkyl, —(C₁-C₆)-alkyl-(C₃-C₈)-cycloalkyl, wherein said cycloalkyl ring is unsubstituted or substituted one, two or three times by —OH, —O—(C₁-C₄)-alkyl or R¹⁰;

or a stereoisomer thereof, mixture of stereoisomers thereof in any ratio, or a physiological tolerable salt thereof.

2. The compound according to claim 1, wherein,

R⁰ is:

heterocyclyl, selected from pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said heterocyclyl is unsubstituted or mono-, di- or trisubstituted independently of one another by R⁸, and in addition is substituted by a residue selected out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl or pyrazinyl, that is unsubstituted or mono-, di- or trisubstituted independently of one another by R⁸;

R⁸ is selected from:

F, Cl, Br or I;
—C(O)—NH₂;
—(C₁-C₄)-alkyl, wherein alkyl is unsubstituted or mono-, di-, or trisubstituted independently of one another by halogen, —OH, or methoxy; or
—O—(C₁-C₄)-alkyl, wherein alkyl is unsubstituted or mono-, di-, or trisubstituted independently of one another by halogen or methoxy,
provided that R⁸ is at least one halogen, —C(O)—NH₂ or —O—(C₁-C₈)-alkyl;

R¹ is hydrogen or —(C₁-C₂)-alkyl;

V is a 3- to 7-membered heterocyclic residue selected from aziridine, azirine, azetidine, azetidinone, 1,4-diazepane, pyrrole, pyrrolidine, pyridonyl, imidazole, pyrazole, 1,2,3-triazole, 1,2,4-triazole, tetrazole, pyridine, pyrimidine, pyrazine, 1,2,3-triazine, 1,2,4-triazine, 1,3,5-triazine, tetrazine, azepine, diazirine, 1,2-diazepine, 1,3-diazepine, 1,4-diazepine, pyridazine, piperidine, piperazine, pyrrolidinone, ketopiperazine, furan, pyran, dioxole, 1,4-oxazepane, 1,4-oxazepine, oxazole, isoxazole, 2-isoxazoline, isoxazolidine, morpholine, oxirane, oxaziridine, 1,3-dioxolene, 1,3-dioxolane, 1,2-oxazine, 1,3-oxazine, 1,4-oxazine, oxaziridine, thiophene, thiopyran, thietan, thiazole, isothiazole, isothiazoline, isothiazolidine, 1,2-oxathiolan, thiodiazole, thiopyran, 1,2-thiazine, 1,3-thiazole, 1,3-thiazine, 1,4-thiazine, thiadiazine or thiomorpholine, any of which can be unsubstituted or mono-, di- or trisubstituted independently of one another by R¹⁴, R¹⁴ is fluorine, chlorine, —OH, =O, —(C₁-C₈)-alkyl, —CN, —C(O)—NH—(C₁-C₈)-alkyl, —C(O)—N—[(C₁-C₈)-alkyl]₂, or —C(O)—NH₂, M is
—(C₁-C₆)-alkyl, wherein alkyl is unsubstituted or mono-, di- or trisubstituted independently of one another by R¹⁴, R³ and R⁴ are, independent of one another:
1) hydrogen,
2) halogen,
3) —(C₁-C₄)-alkyl, wherein alkyl is unsubstituted or mono-, di- or trisubstituted independently of one another by R¹³,
4) —(C₁-C₃)-perfluoroalkyl,
5) phenyl, wherein phenyl is unsubstituted or mono-, di- or trisubstituted independently of one another by R¹³,
6) —(C₀-C₄)-alkylene-O—R¹⁹, wherein R¹⁹ is
a) hydrogen,
b) —(C₁-C₄)-alkyl, wherein alkyl is unsubstituted or mono-, di- or trisubstituted independently of one another by R¹³, or
c) phenyl, wherein phenyl is unsubstituted or mono-, di- or trisubstituted independently of one another by R¹³,
d) —CF₃, or
e) —CHF₂,
8) —CN,
9) —SO_s—R¹¹, wherein s is 1 or 2,
10) —SO_t—N(R¹¹)—R¹², wherein t is 1 or 2,
11) —(C₀-C₄)-alkylene-C(O)—R¹¹,
12) —(C₀-C₄)-alkylene-C(O)—O—R¹¹
13) —(C₀-C₄)-alkylene-C(O)—N(R¹¹)—R¹²,
14) —(C₀-C₄)-alkylene-N(R¹¹)—R¹²,
15) —NR¹⁰—SO₂—R¹⁰,
17) —(C₀-C₂)alkylene-C(O)—O—(C₂-C₄)-alkylene-O—C(O)—(C₁-C₄)-alkyl,
18) —C(O)—O—C(R¹⁵R¹⁶)—O¹⁷—C(O)—O—R¹⁷,
19) —(C₀-C₂)alkylene-C(O)—O—(C₂-C₄)-alkylene-O—C(O)—O—(C₁-C₆)-alkyl,
20) —C(O)—O—C(R¹⁵,R¹⁶)—O—C(O)—R¹⁷, 23) —($C_0$-$C_4$)-alkylene-($C_3$-$C_6$)-cycloalkyl, wherein cycloalkyl is unsubstituted or mono-, di- or trisubstituted independently of one another by $R^{13}$,
25) —($C_0$-$C_3$)-alkylene-O—$CH_2$—$CF_2$—$CH_2$—O—($C_0$-$C_3$)-alkyl, —($C_0$-$C_3$)-alkylene-O—$CH_2$—$CF_2$—$CF_2$—$CH_2$—O—($C_0$-$C_3$)-alkyl, or —($C_0$-$C_3$)-alkylene-O—$CH_2$—($C_1$-$C_3$)-perfluoroalkylene-$CH_2$—OH, or
26) residue selected from the group consisting of

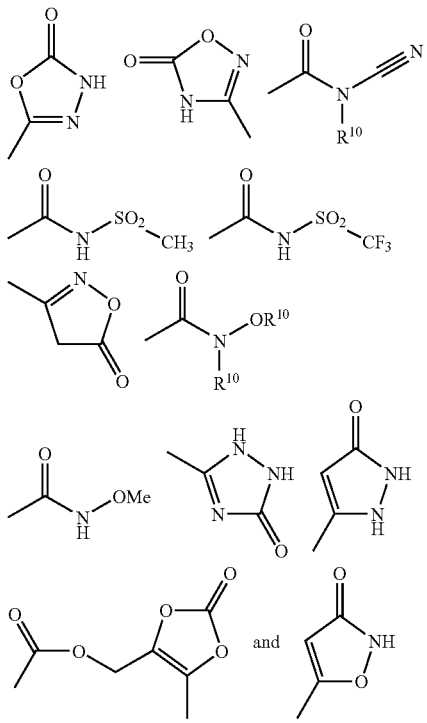

wherein Me is methyl, or two —$OR^{19}$ residues and adjacent atoms through which they are attached form together a 5- or 6-membered ring, that is unsubstituted or substituted one, two, three or four times by $R^{13}$;

$R^{11}$ and $R^{12}$ are, independently of one another:
1) hydrogen,
2) —($C_1$-$C_6$)-alkyl, wherein alkyl is unsubstituted or mono-, di- or trisubstituted independently of one another by $R^{13}$,
5) —($C_0$-$C_6$)-alkyl-($C_6$-$C_{14}$)-aryl, wherein alkyl and aryl independently from one another are unsubstituted or mono-, di- or trisubstituted by $R^{13}$,
7) —O—$R^{17}$, or
8) —($C_0$-$C_6$)-alkyl-($C_4$-$C_{15}$)-heterocyclyl, wherein alkyl and heterocyclyl independently from one another are unsubstituted or mono-, di- or trisubstituted by $R^{13}$, or $R^{11}$ and $R^{12}$ together with the nitrogen atom to which they are bonded form a monocyclic heterocyclic ring selected from azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]-oxazepane, 1,4-oxazepine, oxazole, oxazoline, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole and 1,2,4-triazole, any of which can be unsubstituted or mono-, di- or trisubstituted independently of one another by $R^{13}$;

$R^{13}$ is fluorine, chlorine, —$NO_2$, —CN, =O, —OH, —$CF_3$, —C(O)—O—$R^{10}$, —C(O)—N($R^{10}$)—$R^{20}$, —N($R^{10}$)—$R^{20}$, —($C_0$-$C_3$)-alkylene-O—$R^{10}$, —Si—($CH_3$)$_3$, —N($R^{10}$)—S(O)$_2$—$R^{10}$, —S—$R^{10}$, —$SO_2$—$R^{10}$, —S(O)$_2$—N($R^{10}$)—$R^{20}$, —C(O)—$R^{10}$, —($C_1$-$C_8$)-alkyl, —($C_1$-$C_8$)-alkoxy, phenyl, phenyloxy-, —O—$CF_3$, —($C_1$-$C_3$)-perfluoroalkyl, —NH—C(O)—NH—$R^{10}$, —($C_0$-$C_4$)-alkyl-C(O)—O—C($R^{15}$, $R^{16}$)—O—C(O)—$R^{17}$, —($C_1$-$C_4$)-alkoxy-phenyl, —($C_0$-$C_4$)-alkyl-C(O)—O—C($R^{15}$, $R^{16}$)—O—C(O)—O—$R^{17}$, —O—$R^{15}$, —NH—C(O)—O—$R^{10}$, or residue selected from the group consisting of

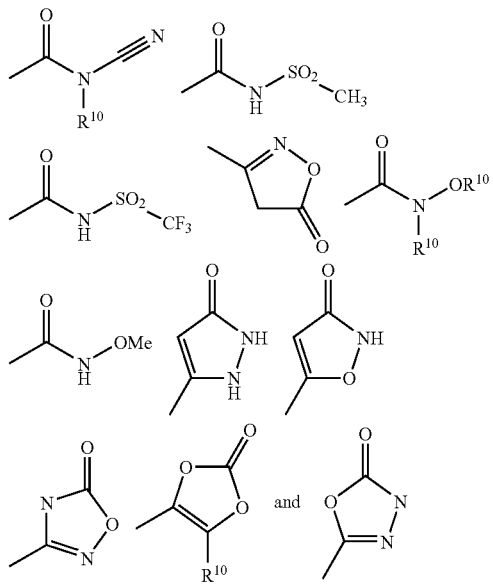

wherein Me is methyl.

3. The compound according to claim 1, wherein,
$R^0$ is heterocyclyl, wherein said heterocyclyl is selected from pyridyl, 2- pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said heterocyclyl is unsubstituted or mono-, di- or trisubstituted independently of one another by $R^8$,
and, in addition, is substituted by a residue selected from pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, which can be unsubstituted or mono-, di- or trisubstituted independently of one another by $R^8$;

$R^8$ is selected from:
F, Cl, Br, or I;
—C(O)—$NH_2$;
—($C_1$-$C_4$)-alkyl, wherein alkyl is unsubstituted or mono-, di- or trisubstituted independently of one another by halogen, —OH or methoxy; and —O—$(C_1$-$C_4)$-alkyl, wherein alkyl is unsubstituted or mono-, di- or trisubstituted independently of one another by halogen or methoxy,
provided that $R^8$ is at least one halogen, —C(O)—$NH_2$ or —O—$(C_1$-$C_8)$-alkyl;
$R^1$ is hydrogen or —$(C_1$-$C_2)$-alkyl;
V is a 3- to 7-membered cyclic residue selected from azetidine, azepine, aziridine, azirine, 1,4-diazepane, 1,2-diazepine, 1,3-diazepine, 1,4-diazepine, diazirine, 1,3-dioxolane, dioxazole, furan, imidazole, isothiazole, isothiazolidine, isothiazoline, isoxazole, 2-isoxazoline, isoxazolidine, ketopiperazine, morpholine, 1,2-oxazine, 1,3-oxazine, 1,4-oxazine, oxazole, 1,2-oxathiolan, piperidine, pyran, pyrazine, pyrazole, pyridazine, piperazine, pyridine, pyridone, pyrimidine, pyrrole, pyrrolidine, pyrrolidinone, tetrazine, tetrazole, thiadiazole, 1,2-thiazine, 1,3-thiazine, 1,4-thiazine, 1,3-thiazole, thietan, thiomorpholine, thiophene, thiopyran, 1,2,3-triazine, 1,2,4-triazine, 1,3,5-triazine, 1,2,3-triazole and 1,2,4-triazole, any of which can be unsubstituted or mono-, di- or trisubstituted independently of one another by $R^{14}$;
$R^{14}$ is fluoro, chloro, or —$(C_1$-$C_4)$-alkyl;
M is
—$(C_1$-$C_6)$-alkyl, wherein alkyl is unsubstituted or mono-, di- or trisubstituted independently of one another by $R^{14}$,
$R^3$ and $R^4$ are, independent of one another:
1) hydrogen,
2) halogen,
3) —$(C_1$-$C_4)$-alkyl, wherein alkyl is unsubstituted or mono-, di- or trisubstituted independently of one another by $R^{13}$,
4) —$(C_1$-$C_3)$-perfluoroalkyl,
5) phenyl, wherein phenyl is unsubstituted or mono-, di- or trisubstituted independently of one another by $R^{13}$,
6) —$(C_0$-$C_4)$-alkylene-O—$R^{19}$, wherein $R^{19}$ is
a) hydrogen,
b) —$(C_1$-$C_4)$-alkyl, wherein alkyl is unsubstituted or mono-, di- or trisubstituted independently of one another by $R^{13}$, or
c) phenyl, wherein phenyl is unsubstituted or mono-, di- or trisubstituted independently of one another by $R^{13}$,
d) —$CF_3$, or
e) —$CHF_2$,
8) —CN,
9) —$SO_s$—$R^{11}$, wherein t is 1 or 2,
10) —$SO_t$—$N(R^{11})$—$R^{12}$, wherein t is 1 or 2,
12) —$(C_0$-$C_4)$-alkylene-C(O)—O—$R^{11}$,
13) —$(C_0$-$C_4)$-alkylene-C(O)—$N(R^{11})$—$R^{12}$,
14) —$(C_0$-$C_4)$-alkylene-$N(R^1)$—$R^{12}$,
15) —$NR^{10}$—$SO_2$—$R^{10}$,
17) —$(C_0$-$C_2)$alkylene-C(O)—O—$(C_2$-$C_4)$-alkylene-O—C(O)—$(C_1$-$C_4)$-alkyl,
18) —C(O)—O—$C(R^{15},R^{16})$—O—C(O)—$R^{17}$
19) —$(C_0$-$C_2)$alkylene-C(O)—O—$(C_2$-$C_4)$-alkylene-O—C(O)—O—$(C_1$-$C_6)$-alkyl,
20) —C(O)—O—$C(R^{15}R^{16})$—$O^{17}$—C(O)—O—$R^{17}$,
23) —$(C_0$-$C_3)$-alkylene-$(C_3$-$C_6)$-cycloalkyl, or —$(C_0$-$C_4)$-alkylene-$(C_3$-$C_6)$-cycloalkyl, wherein cycloalkyl is unsubstituted or mono-, di- or trisubstituted independently of one another by $R^{13}$,
25) —$(C_0$-$C_3)$-alkylene-O—$CH_2$—$CF_2$—$CH_2$—O—$(C_0$-$C_3)$-alkyl, —$(C_0$-$C_3)$-alkylene-O—$CH_2$—$CF_2$—$CF_2$—$CH_2$—O—$(C_0$-$C_3)$-alkyl, or —$(C_0$-$C_3)$-alkylene-O—$CH_2$—$(C_1$-$C_3)$-perfluoroalkylene-$CH_2$—OH, or
26) residue selected from the group consisting of

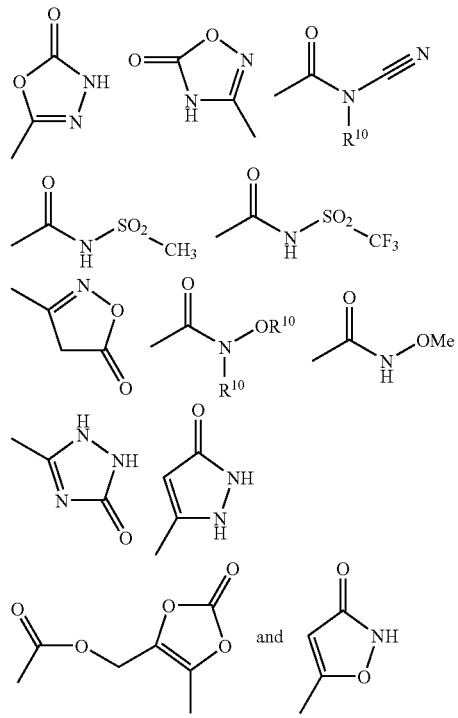

wherein Me is methyl;
$R^{11}$ and $R^{12}$ are, independently of one another:
1) hydrogen,
2) —$(C_1$-$C_4)$-alkyl, wherein alkyl is unsubstituted or mono-, di- or trisubstituted independently of one another by $R^{13}$,
3) —$(C_0$-$C_6)$-alkyl-$(C_3$-$C_6)$-cycloalkyl,
7) —O—$R^{17}$, or
8) —$(C_0$-$C_6)$-alkyl-$(C_4$-$C_{15})$-heterocyclyl, wherein alkyl and heterocyclyl independently from one another are unsubstituted or mono-, di- or trisubstituted by $R^{13}$ and wherein heterocyclyl is selected from azetidine, cyclopropyl, cyclobutyl, 4,5-dihydrooxazole, imidazolidine, morpholine, (1,4)-oxazepane, oxazolidine, piperidine, piperazine, pyrrolidine, tetrahydrothiophene, thiazolidine, and thiomorpholine, or
$R^{11}$ and $R^{12}$ together with the nitrogen atom to which they are bonded form a monocyclic heterocyclic ring selected from azetidine, cyclopropyl, cyclobutyl, 4,5-dihydrooxazole, imidazolidine, morpholine, (1,4)-oxazepane, 1,4-oxazepine, oxazolidine, piperidine, piperazine, pyrrolidine, tetrahydrothiophene, thiazolidine and thiomorpholine;
$R^{13}$ is fluorine, —CN, =O, —OH, —$CF_3$, —C(O)—O—$R^{10}$, —C(O)—$N(R^{10})$—$R^{20}$, —$N(R^{10})$—$R^{20}$, —$(C_3$-$C_6)$-cycloalkyl, —$(C_0$-$C_3)$-alkylene-O—$R^{10}$, —Si—$(CH_3)_3$, —S—$R^{10}$, —$SO_2$—$R^{10}$, —$(C_1$-$C_3)$-perfluoroalkyl, or residue selected from the group consisting of

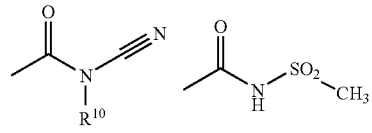

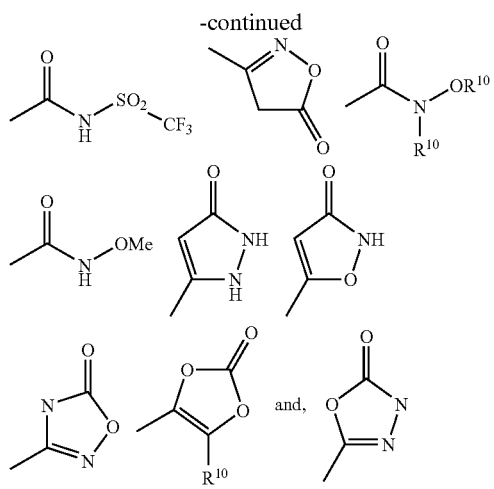

wherein Me is methyl;

$R^{10}$ and $R^{20}$ are independently selected from hydrogen, —$(C_1-C_4)$-alkyl and —$(C_1-C_3)$-perfluoroalkyl;

$R^{15}$ and $R^{16}$ are independently selected from hydrogen and —$(C_1-C_4)$-alkyl, or, together with the carbon atom to which they are bonded, form a cyclopropyl, cyclobutyl, cyclopentyl or cyclohexyl ring, which can be unsubstituted or substituted one to three times by $R^{10}$.

4. The compound according to claim 1, wherein $R^0$ is heterocyclyl selected from the group consisting of thienyl, thiadiazolyl, isoxazolyl and thiazolyl, wherein said heterocyclyl is substituted by a residue selected from the group consisting of thienyl, 2-thienyl and 3-thienyl, wherein said residue is unsubstituted or mono- or disubstituted independently of one another by $R^8$, $R^8$ is F, Cl, Br, —$OCH_3$, —$C(O)$—$NH_2$ or —$O$—$CF_3$, $R^1$ is hydrogen, V is a 3- to 7-membered cyclic residue selected from azetidine, 1,4-diazepane, isoxazole, piperazine, piperidine, pyrazine, pyridazine, pyrimidine, pyrrolidine or tetrahydropyran, any of which can be unsubstituted or mono-, di- or trisubstituted independently of one another by $R^{14}$, $R^{14}$ is fluorine, chlorine, methyl, or ethyl, M is $(C_2-C_4)$-alkyl, wherein alkyl is unsubstituted or mono- or disubstituted independently of one another by $R^{14}$, $R^3$ and $R^4$ are, independent of one another:

1) hydrogen,
2) fluorine or chlorine,
3) —$(C_1-C_4)$-alkyl, wherein alkyl is unsubstituted or mono-, di- or trisubstituted independently of one another by $R^{13}$,
4) —$(C_1-C_3)$-perfluoroalkyl,
5) phenyl that is unsubstituted or mono-, di- or trisubstituted independently of one another by $R^{13}$,
6) —$(C_0-C_2)$-alkylene-O—$R^{19}$, wherein $R^{19}$ is
a) hydrogen,
b) -$(C_1-C_4)$-alkyl, wherein alkyl is unsubstituted or mono-, di- or trisubstituted independently of one another by $R^{13}$, or
c) phenyl, wherein phenyl is unsubstituted or mono-, di- or trisubstituted independently of one another by $R^{13}$,
d) —$CF_3$, or
e) —$CHF_2$,
8) —CN,
9) —$SO_s$—$R^{11}$, wherein s is 1 or 2,
10) —$SO_t$—$N(R^{11})$—$R^{12}$, wherein t is 1 or 2,
11) —$(C_0-C_4)$-alkylene-$C(O)$—$R^{11}$,
12) —$(C_0-C_4)$-alkylene-$C(O)$—$O$—$R^{11}$,
13) —$(C_0-C_4)$-alkylene-$C(O)$—$N(R^{11})$—$R^{12}$,
14) —$(C_0-C_4)$-alkylene-$N(R^{11})$—$R^{12}$,
15) —$NR^{10}$—$SO_2$—$R^{10}$,
16) —$(C_0-C_2)$alkylene-$C(O)$—$O$—$(C_2-C_4)$-alkylene-$O$—$C(O)$—$(C_1-C_4)$-alkyl,
18) —$C(O)$—$O$—$C(R^{15},R^{16})$—$O$—$C(O)$—$R^{17}$,
19) —$(C_0-C_2)$alkylene-$C(O)$—$O$—$(C_2-C_4)$-alkylene-$O$—$C(O)$—$O$—$(C_1-C_6)$-alkyl,
20) —$C(O)$—$O$—$C(R^{15},R^{16})$—$O$—$C(O)$—$O$—$R^{17}$,
23) —$(C_0-C_4)$-alkylene-$(C_3-C_8)$-cycloalkyl selected from the group consisting of —$(C_0-C_3)$-alkylene-$(C_3-C_6)$-cycloalkyl and —$(C_0-C_4)$-alkylene-$(C_3-C_6)$-cycloalkyl, wherein cycloalkyl is unsubstituted or mono-, di- or trisubstituted independently of one another by $R^{13}$,
24) —$(C_0-C_4)$-alkylene-het selected from the group consisting of pyridinyl and thiazolyl, any of which can be unsubstituted or mono-, di- or trisubstituted independently of one another by $R^{13}$,
25) —$(C_0-C_3)$-alkylene-$O$—$CH_2$—$CF_2$—$CH_2$—$O$—$(C_0-C_3)$-alkyl, —$(C_0-C_3)$-alkylene-$O$—$CH_2$—$CF_2$—$CF_2$—$CH_2$—$O$—$(C_0-C_3)$-alkyl, or —$(C_0-C_3)$-alkylene-$O$—$CH_2$—$(C_1-C_3)$-perfluoroalkylene-$CH_2$—OH, or
26) residue selected from the group consisting of the following

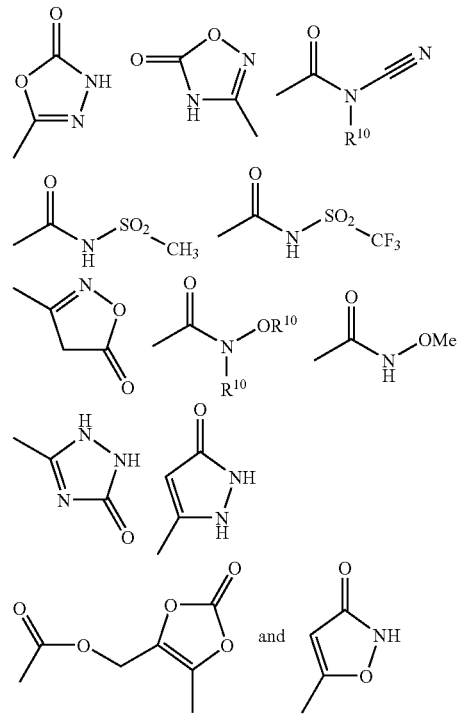

wherein Me is methyl, $R^{11}$ and $R^{12}$ are independently of one another:

1) hydrogen,
2) —$(C_1-C_4)$-alkyl, wherein alkyl is unsubstituted or mono-, di- or trisubstituted independently of one another by $R^{13}$,
3)-$(C_0-C_6)$-alkyl-$(C_3-C_6)$-cycloalkyl,
7) —O—$R^{17}$, or 8) —(C₀-C₆)-alkyl-heterocyclyl, wherein alkyl and heterocyclyl independently from one another are unsubstituted or mono-, di- or trisubstituted by R¹³ and wherein heterocyclyl is selected out of the group azetidine, imidazolidine, morpholine, 1,4-oxazepane or pyrrolidine or R¹¹ and R¹² together with the nitrogen atom to which they are bonded can form a monocyclic heterocyclic ring selected from the group consisting of azetidine, imidazolidine, morpholine, 1,4-oxazepane, 1,4-oxazepine, piperazine, piperidine, pyrrolidine and thiomorpholine, R¹³ is selected from fluorine, chlorine, —CN, =O, —OH, —CF₃, —C(O)—O—R¹⁰, —C(O)—N(R¹⁰) —R²⁰, —N(R¹⁰)—R²⁰, —(C₃-C₆)-cycloalkyl, —(C₀-C₃)-alkylene-O—R¹⁰, —Si—(CH₃)₃, —S—R¹⁰, —SO₂—R¹⁰, —(C₁-C₄)-alkyl, —(C₁-C₃)-perfluoroalkyl, and residues selected from the group consisting of the following

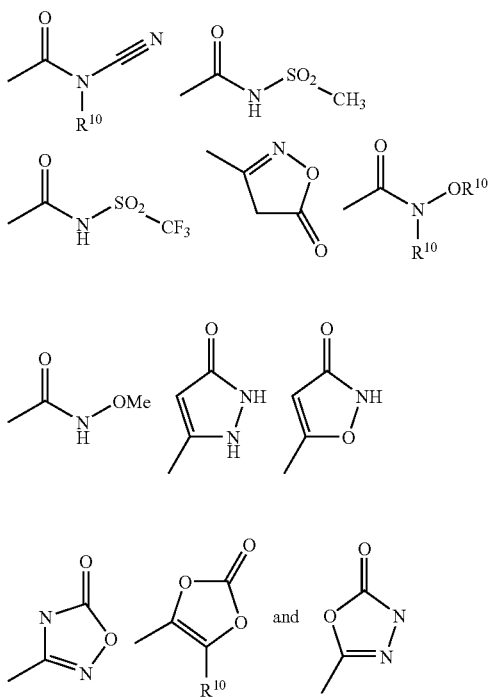

wherein Me is methyl,

R¹⁰ and R²⁰ are independently selected from hydrogen, —(C₁-C₄)-alkyl and —(C₁-C₃)-perfluoroalkyl, R¹⁵ and R¹⁶ are independently selected from hydrogen and —(C₁-C₄)-alkyl, or together with the carbon atom to which they are bonded form a 3- to 6- membered carbocyclic ring selected from the group consisting of cyclopropyl, cyclobutyl, cyclopentyl and cyclohexyl, wherein each ring is unsubstituted or substituted one to three times by R¹⁰, and R¹⁷ is —(C1-C6)-alkyl, —(C1-C6)-alkyl-OH, —(C1-C6)-alkyl-O—(C1-C6)-alkyl, —(C3-C8)-cycloalkyl, —(C1-C6)-alkyl-O—(C1-C8)-alkyl-(C3-C8)-cycloalkyl, —(C1-C6)-alkyl-(C3-C8)-cycloalkyl, wherein said cycloalkyl ring is unsubstituted or substituted one, two or three times by —OH, —O—(C1-C4)-alkyl or R¹⁰.

5. The compound according to claim 1, having the formula Ib,

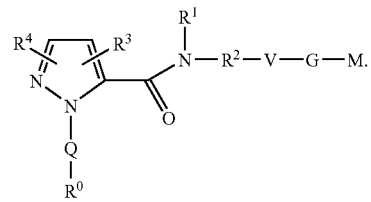

or a stereoisomer thereof, mixture of stereoisomers thereof in any ratio, or a physiological tolerable salt thereof.

6. The compound according to claim 1, having the formula Ic,

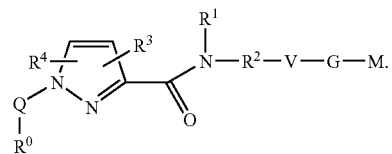

or a stereoisomer thereof, mixture of stereoisomers thereof in any ratio, or a physiological tolerable salt thereof.

7. The compound according to claim 1 selected from the group consisting of
   2-[5-(5-Chloro-thiophen-2-yl)-isoxazol-3-ylmethyl]-5-thiophen-2-yl-2H-pyrazole-3-carboxylic acid (1-isopropyl-piperidin-4-yl)-amide,
   1-[5-(5-Chloro-thiophen-2-yl)-isoxazol-3-ylmethyl]-5-thiophen-2-yl-1H-pyrazole-3-carboxylic acid (1-isopropyl-piperidin-4-yl)-amide,
   2-[5-(5-Chloro-thiophen-2-yl)-isoxazol-3-ylmethyl]-5-methyl-2H-pyrazole-3-carboxylic acid (1-isopropyl-piperidin-4-yl)-amide,
   1-[5-(5-Chloro-thiophen-2-yl)-isoxazol-3-ylmethyl]-5-methyl-1H-pyrazole-3-carboxylic acid (1-isopropyl-piperidin-4-yl)-amide,
   2-(6-Chloro-benzothiazol-2-yl)-5-methyl-2H-pyrazole-3-carboxylic acid (1-isopropyl-piperidin-4-yl)-amide,
   5-(5-Chloro-thiophen-2-yl)-2-[5-(5-chloro-thiophen-2-yl)-isoxazol-3-ylmethyl]-2H-pyrazole-3-carboxylic acid (1-isopropyl-piperidin-4-yl)-amide,
   5-(5-Chloro-thiophen-2-yl)-1-[5-(5-chloro-thiophen-2-yl)-isoxazol-3-ylmethyl]-1H-pyrazole-3-carboxylic acid (1-isopropyl-piperidin-4-yl)-amide,
   2-[5-(5-Chloro-thiophen-2-yl)-isoxazol-3-ylmethyl]-4-(2,4-dichloro-phenyl)-2H-pyrazole-3-carboxylic acid (1-isopropyl-piperidin-4-yl)-amide,
   1-[5-(5-Chloro-thiophen-2-yl)-isoxazol-3-ylmethyl]-4-(2,4-dichloro-phenyl)-1H-pyrazole-3-carboxylic acid (1-isopropyl-piperidin-4-yl)-amide,
   2-[5-(5-Chloro-thiophen-2-yl)-isoxazol-3-ylmethyl]-5-propyl-2H-pyrazole-3-carboxylic acid (1-isopropyl-piperidin-4-yl)-amide,
   1-[5-(5-Chloro-thiophen-2-yl)-isoxazol-3-ylmethyl]-5-propyl-1H-pyrazole-3-carboxylic acid (1-isopropyl-piperidin-4-yl)-amide,
   5-tert-Butyl-2-[5-(5-chloro-thiophen-2-yl)-isoxazol-3-ylmethyl]-2H-pyrazole-3-carboxylic acid (1-isopropyl-piperidin-4-yl)-amide,
   5-tert-Butyl-1-[5-(5-chloro-thiophen-2-yl)-isoxazol-3-ylmethyl]-1H-pyrazole-3-carboxylic acid (1-isopropyl-piperidin-4-yl)-amide,
   2-[5-(5-Chloro-thiophen-2-yl)-isoxazol-3-ylmethyl]-4-cyano-5-propyl-2H-pyrazole-3-carboxylic acid (1-isopropyl-piperidin-4-yl)-amide, 1-[5-(5-Chloro-thiophen-2-yl)-isoxazol-3-ylmethyl]-4-cyano-5-propyl-1H-pyrazole-3-carboxylic acid (1-isopropyl-piperidin-4-yl)-amide,
2-[5-(5-Chloro-thiophen-2-yl)-isoxazol-3-ylmethyl]-4-cyano-5-thiophen-2-yl-2H-pyrazole-3-carboxylicacid (1-isopropyl-piperidin-4-yl)-amide,
1-[5-(5-Chloro-thiophen-2-yl)-isoxazol-3-ylmethyl]-4-cyano-5-thiophen-2-yl-1H-pyrazole-3-carboxylic acid (1-isopropyl-piperidin-4-yl)-amide,
2-[2-(5-Chloro-thiophen-2-yl)-thiazol-4-ylmethyl]-5-thiophen-2-yl-2H-pyrazole-3-carboxylic acid (1-isopropyl-piperidin-4-yl)-amide,
1-[2-(5-Chloro-thiophen-2-yl)-thiazol-4-ylmethyl]-5-thiophen-2-yl-1H-pyrazole-3-carboxylic acid (1-isopropyl-piperidin-4-yl)-amide,
2-(6-Chloro-benzo[b]thiophen-2-ylmethyl)-5-thiophen-2-yl-2H-pyrazole-3-carboxylic acid (1-isopropyl-piperidin-4-yl)-amide,
1-(6-Chloro-benzo[b]thiophen-2-ylmethyl)-5-thiophen-2-yl-1H-pyrazole-3-carboxylic acid (1-isopropyl-piperidin-4-yl)-amide,
2-[5-(5-Chloro-thiophen-2-yl)-isoxazol-3-ylmethyl]-5-thiophen-2-yl-2H-pyrazole-3-carboxylic acid (3,4,5,6-tetrahydro-2H-[1,4']bipyridinyl-4-ylmethyl)-amide,
1-[5-(5-Chloro-thiophen-2-yl)-isoxazol-3-ylmethyl]-5-thiophen-2-yl-1H-pyrazole-3-carboxylic acid (3,4,5,6-tetrahydro-2H-[1,4']bipyridinyl-4-ylmethyl)-amide,
2-[5-(5-Chloro-thiophen-2-yl)-isoxazol-3-ylmethyl]-5-thiophen-2-yl-2H-pyrazole-3-carboxylic acid (1-isopropyl-piperidin-4-ylmethyl)-amide,
1-[5-(5-Chloro-thiophen-2-yl)-isoxazol-3-ylmethyl]-5-thiophen-2-yl-1H-pyrazole-3-carboxylic acid (1-isopropyl-piperidin-4-ylmethyl)-amide,
2-[5-(5-Chloro-thiophen-2-yl)-isoxazol-3-ylmethyl]-5-thiophen-2-yl-2H-pyrazole-3-carboxylic acid (3,4,5,6-tetrahydro-2H-[1,4']bipyridinyl-4-yl)-amide,
1-[5-(5-Chloro-thiophen-2-yl)-isoxazol-3-ylmethyl]-5-thiophen-2-yl-1H-pyrazole-3-carboxylic acid (3,4,5,6-tetrahydro-2H-[1,4']bipyridinyl-4-yl)-amide,
2-(4-Chloro-benzyl)-4-cyano-5-thiophen-2-yl-2H-pyrazole-3-carboxylic acid (1-isopropyl-piperidin-4-yl)-amide,
1-(4-Chloro-benzyl)-4-cyano-5-thiophen-2-yl-1H-pyrazole-3-carboxylic acid (1-isopropyl-piperidin-4-yl)-amide,
1-[5-(5-Chloro-thiophen-2-yl)-isoxazol-3-ylmethyl]-5-(1-isopropyl-piperidin-4-ylcarbamoyl)-1H-pyrazole-3-carboxylic acid methyl ester,
2-[5-(5-Chloro-thiophen-2-yl)-isoxazol-3-ylmethyl]-5-(1-isopropyl-piperidin-4-ylcarbamoyl)-2H-pyrazole-3-carboxylic acid methyl ester,
1-[5-(5-Chloro-thiophen-2-yl)-isoxazol-3-ylmethyl]-5-(1-isopropyl-piperidin-4-ylcarbamoyl)-1H-pyrazole-3-carboxylic acid,
2-[5-(5-Chloro-thiophen-2-yl)-isoxazol-3-ylmethyl]-5-(1-isopropyl-piperidin-4-ylcarbamoyl)-2H-pyrazole-3-carboxylic acid,
1-[5-(5-Chloro-thiophen-2-yl)-isoxazol-3-ylmethyl]-5-(1-isopropyl-piperidin-4-ylcarbamoyl)-1H-pyrazole-3-carboxylic acid ethyl ester,
2-[5-(5-Chloro-thiophen-2-yl)-isoxazol-3-ylmethyl]-5-(1-isopropyl-piperidin-4-ylcarbamoyl)-2H-pyrazole-3-carboxylic acid ethyl ester,
2-[5-(5-Chloro-thiophen-2-yl)-isoxazol-3-ylmethyl]-5-(morpholine-4-carbonyl)-2H-pyrazole-3-carboxylic acid (1-isopropyl-piperidin-4-yl)-amide,
1-[5-(5-Chloro-thiophen-2-yl)-isoxazol-3-ylmethyl]-5-(morpholine-4-carbonyl)-1H-pyrazole-3-carboxylic acid (1-isopropyl-piperidin-4-yl)-amide,
1-[5-(5-Chloro-thiophen-2-yl)-isoxazol-3-ylmethyl]-1H-pyrazole-3,5-dicarboxylic acid 3-dimethylamide 5-[(1-isopropyl-piperidin-4-yl)-amide], 1-[5-(5-Chloro-thiophen-2-yl)-isoxazol-3-ylmethyl]-1H-pyrazole-3,5-dicarboxylic acid 5-dimethylamide 3-[(1-isopropyl-piperidin-4-yl)-amide], 1-[5-(5-Chloro-thiophen-2-yl)-isoxazol-3-ylmethyl]-1H-pyrazole-3,5-dicarboxylic acid 3-[(2-hydroxy-ethyl)-amide]5-[(1-isopropyl-piperidin-4-yl)-amide],
1-[5-(5-Chloro-thiophen-2-yl)-isoxazol-3-ylmethyl]-1H-pyrazole-3,5-dicarboxylic acid 5-[(2-hydroxy-ethyl)-amide]3-[(1-isopropyl-piperidin-4-yl)-amide],
{1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-acetic acid,
{[2-[5-(5-Chloro-thiophen-2-yl)-isoxazol-3-ylmethyl]-5-(1-isopropyl-piperidin-4-ylcarbamoyl)-2H-pyrazole-3-carbonyl]-amino}-acetic acid,
2-[5-(5-Chloro-thiophen-2-yl)-isoxazol-3-ylmethyl]-5-(5-oxo-4,5-dihydro-[1,3,4]oxadiazol-2-yl)-2H-pyrazole-3-carboxylic acid (1-isopropyl-piperidin-4-yl)-amide,
1-[5-(5-Chloro-thiophen-2-yl)-isoxazol-3-ylmethyl]-5-(5-oxo-4,5-dihydro-[1,3,4]oxadiazol-2-yl)-1H-pyrazole-3-carboxylic acid (1-isopropyl-piperidin-4-yl)-amide,
Sulfuric acid mono-(2-{[1-[5-(5-chloro-thiophen-2-yl)-isoxazol-3-ylmethyl]-5-(1-isopropyl-piperidin-4-ylcarbamoyl)-1H-pyrazole-3-carbonyl]-amino}-ethyl) ester,
Sulfuric acid mono-(2-{[2-[5-(5-chloro-thiophen-2-yl)-isoxazol-3-ylmethyl]-5-(1-isopropyl-piperidin-4-ylcarbamoyl)-2H-pyrazole-3-carbonyl]-amino}-ethyl) ester,
2-[5-(5-Chloro-thiophen-2-yl)-isoxazol-3-ylmethyl]-5-[4-(2-hydroxy-ethyl)-piperazine-1-carbonyl]-2H-pyrazole-3-carboxylic acid (1-isopropyl-piperidin-4-yl)-amide,
1-[5-(5-Chloro-thiophen-2-yl)-isoxazol-3-ylmethyl]-5-[4-(2-hydroxy-ethyl)-piperazine-1-carbonyl]-1H-pyrazole-3-carboxylic acid (1-isopropyl-piperidin-4-yl)-amide,
2-[5-(5-Chloro-thiophen-2-yl)-isoxazol-3-ylmethyl]-5-(2-oxo-oxazolidine-3-carbonyl)-2H -pyrazole-3-carboxylic acid (1-isopropyl-piperidin-4-yl)-amide,
1-[5-(5-Chloro-thiophen-2-yl)-isoxazol-3-ylmethyl]-5-(2-oxo-oxazolidine-3-carbonyl)-1H -pyrazole-3-carboxylic acid (1-isopropyl-piperidin-4-yl)-amide,
1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-[(2-morpholin-4-yl-ethyl)-amide],
1-[5-(5-Chloro-thiophen-2-yl)-isoxazol-3-ylmethyl]-1H-pyrazole-3,5-dicarboxylic acid 3-[(1-isopropyl-piperidin-4-yl)-amide]5-[(2-morpholin-4-yl-ethyl)-amide],
1-[5-(5-Chloro-thiophen-2-yl)-isoxazol-3-ylmethyl]-1H-pyrazole-3,5-dicarboxylic acid 3-[bis-(2-methoxy-ethyl)-amide]5-[(1-isopropyl-piperidin-4-yl)-amide],
1-[5-(5-Chloro-thiophen-2-yl)-isoxazol-3-ylmethyl]-1H-pyrazole-3,5-dicarboxylic acid 5-[bis-(2-methoxy-ethyl)-amide]3-[(1-isopropyl-piperidin-4-yl)-amide],
1-[5-(5-Chloro-thiophen-2-yl)-isoxazol-3-ylmethyl]-1H-pyrazole-3,5-dicarboxylic acid 3-[(4,5-dihydro-oxazol-2-yl)-amide]5-[(1-isopropyl-piperidin-4-yl)-amide],
1-[5-(5-Chloro-thiophen-2-yl)-isoxazol-3-ylmethyl]-1H-pyrazole-3,5-dicarboxylic acid 5-[(4,5-dihydro-oxazol-2-yl)-amide]3-[(1-isopropyl-piperidin-4-yl)-amide], 2-[5-(5-Chloro-thiophen-2-yl)-isoxazol-3-ylmethyl]-5-[3-(2-hydroxy-ethyl)-2-oxo-imidazolidine-1-carbonyl]-2H-pyrazole-3-carboxylic acid (1-isopropyl-piperidin-4-yl)-amide, 1-[5-(5-Chloro-thiophen-2-yl)-isoxazol-3-ylmethyl]-5-[3-(2-hydroxy-ethyl)-2-oxo-imidazolidine-1-carbonyl]-1H-pyrazole-3-carboxylic acid (1-isopropyl-piperidin-4-yl)-amide, 2-[5-(5-Chloro-thiophen-2-yl)-isoxazol-3-ylmethyl]-5-(2-methoxymethyl-pyrrolidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(2-methoxymethyl-pyrrolidine-1-carbonyl)-1H-pyrazole-3-carboxylic acid (1-isopropyl-piperidin-4-yl)-amide, {[1-[5-(5-Chloro-thiophen-2-yl)-isoxazol-3-ylmethyl]-5-(1-isopropyl-piperidin-4-ylcarbamoyl)-1H-pyrazole-3-carbonyl]-methyl-amino}-acetic acid, {[2-[5-(5-Chloro-thiophen-2-yl)-isoxazol-3-ylmethyl]-5-(1-isopropyl-piperidin-4-ylcarbamoyl)-2H-pyrazole-3-carbonyl]-methyl-amino}-acetic acid, 1-[1-[5-(5-Chloro-thiophen-2-yl)-isoxazol-3-ylmethyl]-5-(1-isopropyl-piperidin-4-ylcarbamoyl)-1H-pyrazole-3-carbonyl]-piperidine-4-carboxylic acid ethyl ester, 1-[2-[5-(5-Chloro-thiophen-2-yl)-isoxazol-3-ylmethyl]-5-(1-isopropyl-piperidin-4-ylcarbamoyl)-2H-pyrazole-3-carbonyl]-piperidine-4-carboxylic acid ethyl ester, 1-[1-[5-(5-Chloro-thiophen-2-yl)-isoxazol-3-ylmethyl]-5-(1-isopropyl-piperidin-4-ylcarbamoyl)-1H-pyrazole-3-carbonyl]-azetidine-2-carboxylic acid, 1-[2-[5-(5-Chloro-thiophen-2-yl)-isoxazol-3-ylmethyl]-5-(1-isopropyl-piperidin-4-ylcarbamoyl)-2H-pyrazole-3-carbonyl]-azetidine-2-carboxylic acid, 2-[5-(5-Chloro-thiophen-2-yl)-isoxazol-3-ylmethyl]-5-(thiomorpholine-4-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(thiomorpholine-4-carbonyl)-1H-pyrazole-3-carboxylic acid (1-isopropyl-piperidin-4-yl)-amide, 1-[1-[5-(5-Chloro-thiophen-2-yl)-isoxazol-3-ylmethyl]-5-(1-isopropyl-piperidin-4-ylcarbamoyl)-1H-pyrazole-3-carbonyl]-pyrrolidine-2-carboxylic acid, 1-[2-[5-(5-Chloro-thiophen-2-yl)-isoxazol-3-ylmethyl]-5-(1-isopropyl-piperidin-4-ylcarbamoyl)-2H-pyrazole-3-carbonyl]-pyrrolidine-2-carboxylic acid, 2-[5-(5-Chloro-thiophen-2-yl)-isoxazol-3-ylmethyl]-5-(4-hydroxy-piperidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(4-hydroxy-piperidine-1-carbonyl)-1H-pyrazole-3-carboxylic acid (1-isopropyl-piperidin-4-yl)-amide, 2-[5-(5-Chloro-thiophen-2-yl)-isoxazol-3-ylmethyl]-5-(2-hydroxymethyl-pyrrolidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(2-hydroxymethyl-pyrrolidine-1-carbonyl)-1H-pyrazole-3-carboxylic acid (1-isopropyl-piperidin-4-yl)-amide, 2-[5-(5-Chloro-thiophen-2-yl)-isoxazol-3-ylmethyl]-5-(3-hydroxy-pyrrolidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(3-hydroxy-pyrrolidine-1-carbonyl)-1H-pyrazole-3-carboxylic acid (1-isopropyl-piperidin-4-yl)-amide, 5-(2,5-Bis-methoxymethyl-pyrrolidine-1-carbonyl)-2-[5-(5-chloro-thiophen-2-yl)-isoxazol-3-ylmethyl]-2H-pyrazole-3-carboxylic acid (1-isopropyl-piperidin-4-yl)-amide, 5-(2,5-Bis-methoxymethyl-pyrrolidine-1-carbonyl)-1-[5-(5-chloro-thiophen-2-yl)-isoxazol-3-ylmethyl]-1H-pyrazole-3-carboxylic acid (1-isopropyl-piperidin-4-yl)-amide, 2-[5-(5-Chloro-thiophen-2-yl)-isoxazol-3-ylmethyl]-5-(4-hydroxymethyl-piperidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(4-hydroxymethyl-piperidine-1-carbonyl)-1H-pyrazole-3-carboxylic acid (1-isopropyl-piperidin-4-yl)-amide, 5-(8-Aza-spiro[4.5]decane-8-carbonyl)-2-[5-(5-chloro-thiophen-2-yl)-isoxazol-3-ylmethyl]-2H-pyrazole-3-carboxylic acid (1-isopropyl-piperidin-4-yl)-amide, 5-(8-Aza-spiro[4.5]decane-8-carbonyl)-1-[5-(5-chloro-thiophen-2-yl)-isoxazol-3-ylmethyl]-1H-pyrazole-3-carboxylic acid (1-isopropyl-piperidin-4-yl)-amide, 2-[5-(5-Chloro-thiophen-2-yl)-isoxazol-3-ylmethyl]-5-(3-methanesulfonyl-pyrrolidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(3-methanesulfonyl-pyrrolidine-1-carbonyl)-1H-pyrazole-3-carboxylic acid (1-isopropyl-piperidin-4-yl)-amide, 1-[5-(5-Chloro-thiophen-2-yl)-isoxazol-3-ylmethyl]-1H-pyrazole-3,5-dicarboxylic acid 3-[(1,1-dioxo-tetrahydro-1-thiophen-3-yl)-methyl-amide]5-[(1-isopropyl-piperidin-4-yl)-amide], 1-[5-(5-Chloro-thiophen-2-yl)-isoxazol-3-ylmethyl]-1H-pyrazole-3,5-dicarboxylic acid 5-[(1,1-dioxo-tetrahydro-1-thiophen-3-yl)-methyl-amide]3-[(1-isopropyl-piperidin-4-yl)-amide], 1-[1-[5-(5-Chloro-thiophen-2-yl)-isoxazol-3-ylmethyl]-5-(1-isopropyl-piperidin-4-ylcarbamoyl)-1H-pyrazole-3-carbonyl]-azetidine-3-carboxylic acid, 1-[2-[5-(5-Chloro-thiophen-2-yl)-isoxazol-3-ylmethyl]-5-(1-isopropyl-piperidin-4-ylcarbamoyl)-2H-pyrazole-3-carbonyl]-azetidine-3-carboxylic acid, 5-(Azetidine-1-carbonyl)-2-[5-(5-chloro-thiophen-2-yl)-isoxazol-3-ylmethyl]-2H-pyrazole-3-carboxylic acid (1-isopropyl-piperidin-4-yl)-amide, 5-(Azetidine-1-carbonyl)-1-[5-(5-chloro-thiophen-2-yl)-isoxazol-3-ylmethyl]-1H-pyrazole-3-carboxylic acid (1-isopropyl-piperidin-4-yl)-amide, 2-[5-(5-Chloro-thiophen-2-yl)-isoxazol-3-ylmethyl]-5-(3-oxo-piperazine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(3-oxo-piperazine-1-carbonyl)-1H-pyrazole-3-carboxylic acid (1-isopropyl-piperidin-4-yl)-amide, 2-[5-(5-Chloro-thiophen-2-yl)-isoxazol-3-ylmethyl]-5-(4,4-difluoro-piperidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(4,4-difluoro-piperidine-1-carbonyl)-1H-pyrazole-3-carboxylic acid (1-isopropyl-piperidin-4-yl)-amide, 2-[5-(5-Chloro-thiophen-2-yl)-isoxazol-3-ylmethyl]-5-([1,4]oxazepane-4-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-([1,4]oxazepane-4-carbonyl)-1H-pyrazole-3-carboxylic acid (1-isopropyl-piperidin-4-yl)-amide, 2-[5-(5-Chloro-thiophen-2-yl)-isoxazol-3-ylmethyl]-5-(3-hydroxy-azetidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(3-hydroxy-azetidine-1-carbonyl)-1H-pyrazole-3-carboxylic acid (1-isopropyl-piperidin-4-yl)-amide, 2-[5-(5-Chloro-thiophen-2-yl)-isoxazol-3-ylmethyl]-5-(2-trifluoromethyl-pyrrolidine-1-carbonyl) -2H-pyrazole-3-carboxylic acid (1-isopropyl-piperidin-4-yl)-amide, 1-[5-(5-Chloro-thiophen-2-yl)-isoxazol-3-ylmethyl]-5-(2-trifluoromethyl-pyrrolidine-1-carbonyl) -1H-pyrazole-3-carboxylic acid (1-isopropyl-piperidin-4-yl)-amide, 2-[5-(5-Chloro-thiophen-2-yl)-isoxazol-3-ylmethyl]-5-(2,2-dimethyl-pyrrolidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(2,2-dimethyl-pyrrolidine-1-carbonyl)-1H-pyrazole-3-carboxylic acid (1-isopropyl-piperidin-4-yl)-amide, 1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-[(2-sulfamoyl-ethyl)-amide], 1-[5-(5-Chloro-thiophen-2-yl)-isoxazol-3-ylmethyl]-1H-pyrazole-3,5-dicarboxylic acid 3-[(1-isopropyl-piperidin-4-yl)-amide]5-[(2-sulfamoyl-ethyl)-amide], 1-[5-(5-Chloro-thiophen-2-yl)-isoxazol-3-ylmethyl]-1H-pyrazole-3,5-dicarboxylic acid 3-cyclopropylamide 5-[(1-isopropyl-piperidin-4-yl)-amide], 1-[5-(5-Chloro-thiophen-2-yl)-isoxazol-3-ylmethyl]-1H-pyrazole-3,5-dicarboxylic acid 5-cyclopropylamide 3-[(1-isopropyl-piperidin-4-yl)-amide], {1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-methanesulfonic acid, {2-[5-(5-Chloro-thiophen-2-yl)-isoxazol-3-ylmethyl]-5-(1-isopropyl-piperidin-4-ylcarbamoyl)-2H-pyrazole-3-carbonyl]-amino}-methanesulfonic acid, 1-[5-(5-Chloro-thiophen-2-yl)-isoxazol-3-ylmethyl]-1H-pyrazole-3,5-dicarboxylic acid 3-cyclobutylamide 5-[(1-isopropyl-piperidin-4-yl)-amide], 1-[5-(5-Chloro-thiophen-2-yl)-isoxazol-3-ylmethyl]-1H-pyrazole-3,5-dicarboxylic acid 5-cyclobutylamide 3-[(1-isopropyl-piperidin-4-yl)-amide], 1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-[(2-methoxy-ethyl)-amide], 1-[5-(5-Chloro-thiophen-2-yl)-isoxazol-3-ylmethyl]-1H-pyrazole-3,5-dicarboxylic acid 3-[(1-isopropyl-piperidin-4-yl)-amide]5-[(2-methoxy-ethyl)-amide], 2-[5-(5-Chloro-thiophen-2-yl)-isoxazol-3-ylmethyl]-5-(pyrrolidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(pyrrolidine-1-carbonyl)-1H-pyrazole-3-carboxylic acid (1-isopropyl-piperidin-4-yl)-amide, 2-[5-(5-Chloro-thiophen-2-yl)-isoxazol-3-ylmethyl]-5-(cyanamide-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-(cyanamide-1-carbonyl)-1H-pyrazole-3-carboxylic acid (1-isopropyl-piperidin-4-yl)-amide, Phosphoric acid mono-(2-{[1-[5-(5-chloro-thiophen-2-yl)-isoxazol-3-ylmethyl]-5-(1-isopropyl-piperidin-4-ylcarbamoyl)-1H-pyrazole-3-carbonyl]-amino}-ethyl) ester, Phosphoric acid mono-(2-{[2-[5-(5-chloro-thiophen-2-yl)-isoxazol-3-ylmethyl]-5-(1-isopropyl-piperidin-4-ylcarbamoyl)-2H-pyrazole-3-carbonyl]-amino}-ethyl) ester, 1-[(5-Chloro-pyridin-2-ylcarbamoyl)-methyl]-5-(1-isopropyl-piperidin-4-ylcarbamoyl)-1H-pyrazole-3-carboxylic acid methyl ester, 1-[(5-Chloro-pyridin-2-ylcarbamoyl)-methyl]-5-(1-isopropyl-piperidin-4-ylcarbamoyl)-1H-pyrazole-3-carboxylic acid, 1-[(5-Chloro-pyridin-2-ylcarbamoyl)-methyl]-1H-pyrazole-3,5-dicarboxylic acid 3-cyclobutylamide 5-[(1-isopropyl-piperidin-4-yl)-amide], 1-[5-(5-Chloro-thiophen-2-yl)-isoxazol-3-ylmethyl]-3-trifluoromethyl-1H-pyrazole-4-carboxylic acid (1-isopropyl-piperidin-4-yl)-amide, 1-[5-(5-Chloro-thiophen-2-yl)-isoxazol-3-ylmethyl]-1H-pyrazole-3,5-dicarboxylic acid bis-[(1-isopropyl-piperidin-4-yl)-amide], 2-[5-(5-Chloro-thiophen-2-yl)-isoxazol-3-ylmethyl]-4-cyano-2H-pyrazole-3-carboxylic acid (1-isopropyl-piperidin-4-yl)-amide, 1-[5-(5-Chloro-thiophen-2-yl)-isoxazol-3-ylmethyl]-4-cyano-1H-pyrazole-3-carboxylic acid (1-isopropyl-piperidin-4-yl)-amide, 2-[(4-Chloro-phenylcarbamoyl)-methyl]-4-cyano-2H-pyrazole-3-carboxylic acid (1-isopropyl-piperidin-4-yl)-amide, 3-{[1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-propionic acid, 1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-(methoxy-amide), 1-[5-(5-Chloro-thiophen-2-yl)-isoxazol-3-ylmethyl]-1H-pyrazole-3,5-dicarboxylic acid 3-carbamoylmethyl-amide 5-[(1-isopropyl-piperidin-4-yl)-amide], {1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-acetic acid ethyl ester, 1-[5-(5-Chloro-thiophen-2-yl)-isoxazol-3-ylmethyl]-1H-pyrazole-3,5-dicarboxylic acid 3-[(3-hydroxy-propyl)-amide]5-[(1-isopropyl-piperidin-4-yl)-amide], 1-[1-[5-(5-Chloro-thiophen-2-yl)-isoxazol-3-ylmethyl]-5-(1-isopropyl-piperidin-4-ylcarbamoyl)-1H-pyrazole-3-carbonyl]-(2S)-azetidine-2-carboxylic acid, 2-[5-(5-Chloro-thiophen-2-yl)-isoxazol-3-ylmethyl]-5-(2S,2-hydroxymethyl-pyrrolidine-1-carbonyl)-2H-pyrazole-3-carboxylic acid (1-isopropyl-piperidin-4-yl)-amide, 1-[1-[5-(5-Chloro-thiophen-2-yl)-isoxazol-3-ylmethyl]-5-(1-isopropyl-piperidin-4-ylcarbamoyl)-1H-pyrazole-3-carbonyl]-2S-pyrrolidine-2-carboxylic acid, 2-[5-(5-Chloro-thiophen-2-yl)-isoxazol-3-ylmethyl]-5-(2S,2-methoxymethyl-pyrrolidine-1-carbonyl)-2H-pyrazole-3-carboxylic acid (1-isopropyl-piperidin-4-yl)-amide, 5-(2R,5R,2,5-Bis-methoxymethyl-pyrrolidine-1-carbonyl)-2-[5-(5-chloro-thiophen-2-yl)-isoxazol -3-ylmethyl]-2H-pyrazole-3-carboxylic acid (1-isopropyl-piperidin-4-yl)-amide, 1-[5-(5-Chloro-thiophen-2-yl)-isoxazol-3-ylmethyl]-1H-pyrazole-3,5-dicarboxylic acid 3-[(4,5-dihydro-oxazol-2-yl)-amide]5-[(1-isopropyl-piperidin-4-yl)-amide], 1-[1-[5-(5-Chloro-thiophen-2-yl)-isoxazol-3-ylmethyl]-5-(1-isopropyl-piperidin-4-ylcarbamoyl)-1H-pyrazole-3-carbonyl]-piperidine-4-carboxylic acid ethyl ester, 1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-[(2-morpholin-4-yl-ethyl)-amide], 2-[5-(5-Chloro-thiophen-2-yl)-isoxazol-3-ylmethyl]-5-(4,4-difluoro-piperidine-1-carbonyl)-2H-pyrazole-3-carboxylic acid (1-isopropyl-piperidin-4-yl)-amide, 2-[5-(5-Chloro-thiophen-2-yl)-isoxazol-3-ylmethyl]-5-(2-oxo-oxazolidine-3-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-{[2-(2-oxo-imidazolidin-1-yl)-ethyl]-amide}, 1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-[(2,2,2-trifluoro-ethyl)-amide], 1-[5-(5-Chloro-thiophen-2-yl)-isoxazol-3-ylmethyl]-1H-pyrazole-3,5-dicarboxylic acid 3-[(1,1-dioxo-tetrahydro-1-thiophen-3-yl)-amide]5-[(1-isopropyl-piperidin-4-yl)-amide], 1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-{[2-(2-oxo-pyrrolidin-1-yl)-propyl]-amide}, 5-(Azetidine-1-carbonyl)-2-[5-(5-chloro-thiophen-2-yl)-isoxazol-3-ylmethyl]-2H-pyrazole-3-carboxylic acid (1-isopropyl-piperidin-4-yl)-amide, 2-[5-(5-Chloro-thiophen-2-yl)-isoxazol-3-ylmethyl]-5-(thiazolidine-3-carbonyl)-2H-pyrazole-3-carboxylic acid (1-isopropyl-piperidin-4-yl)-amide, 2-{1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-3,3,3-trifluoro-propionic acid, 1-[5-(5-Chloro-thiophen-2-yl)-isoxazol-3-ylmethyl]-1H-pyrazole-3,5-dicarboxylic acid 5-[(1-isopropyl-piperidin-4-yl)-amide]3-trimethylsilanylmethyl-amide, 2-[5-(5-Chloro-thiophen-2-yl)-isoxazol-3-ylmethyl]-5-[4-(2-oxo-pyrrolidin-1-yl)-piperidine-1-carbonyl]-2H-pyrazole-3-carboxylic acid (1-isopropyl-piperidin-4-yl)-amide, 2-[5-(5-Chloro-thiophen-2-yl)-isoxazol-3-ylmethyl]-5-methanesulfonylaminocarbonyl-2H-pyrazole-3-carboxylic acid (1-isopropyl-piperidin-4-yl)-amide, 2-[5-(5-Chloro-thiophen-2-yl)-isoxazol-3-ylmethyl]-5-(3-hydroxy-azetidine-1-carbonyl)-2H-pyrazole-3-carboxylic acid (1-isopropyl-piperidin-4-yl)-amide, 1-[5-(5-Chloro-thiophen-2-yl)-isoxazol-3-ylmethyl]-5-furan-2-yl-1H-pyrazole-3-carboxylic acid (1-isopropyl-piperidin-4-yl)-amide, 2-[5-(5-Chloro-thiophen-2-yl)-isoxazol-3-ylmethyl]-5-(1-isopropyl-piperidin-4-ylcarbamoyl)-2H-pyrazole-3-carboxylic acid, 5-(Azetidine-1-carbonyl)-1-[5-(5-chloro-thiophen-2-yl)-isoxazol-3-ylmethyl]-1H-pyrazole-3-carboxylic acid (1-isopropyl-piperidin-4-yl)-amide, 1-[5-(5-Chloro-thiophen-2-yl)-isoxazol-3-ylmethyl]-1H-pyrazole-3,5-dicarboxylic acid 3-[(1-isopropyl-piperidin-4-yl)-amide]5-[(2-sulfamoyl-ethyl)-amide], 1-[5-(5-Chloro-thiophen-2-yl)-isoxazol-3-ylmethyl]-1H-pyrazole-3,5-dicarboxylic acid 3-[bis-(2-hydroxy-ethyl)-amide]5-[(1-isopropyl-piperidin-4-yl)-amide], 1-[5-(5-Chloro-thiophen-2-yl)-isoxazol-3-ylmethyl]-1H-pyrazole-3,5-dicarboxylic acid 3-[(2-hydroxy-1,1-bis-hydroxymethyl-ethyl)-amide]5-[(1-isopropyl-piperidin-4-yl)-amide], {1-[5-(5-Chloro-thiophen-2-yl)-isoxazol-3-ylmethyl]-5-(1-isopropyl-piperidin-4-ylcarbamoyl)-1H-pyrazole-3-carbonyl]-amino}-acetic acid isopropyl ester, 1-[(5-Chloro-pyridin-2-ylcarbamoyl)-methyl]-5-(1-isopropyl-piperidin-4-ylcarbamoyl)-1H-pyrazole-3-carboxylic acid ethyl ester, {1-[(5-Chloro-pyridin-2-ylcarbamoyl)-methyl]-5-(1-isopropyl-piperidin-4-ylcarbamoyl)-1H-pyrazole-3-carbonyl]-amino}-acetic acid isopropyl ester, {1-[(5-Chloro-pyridin-2-ylcarbamoyl)-methyl]-5-(1-isopropyl-piperidin-4-ylcarbamoyl)-1H-pyrazole-3-carbonyl]-amino}-acetic acid ethyl ester, {1-[(5-Chloro-pyridin-2-ylcarbamoyl)-methyl]-5-(1-isopropyl-piperidin-4-ylcarbamoyl)-1H-pyrazole-3-carbonyl]-amino}-acetic acid, 2-[(5-Chloro-pyridin-2-ylcarbamoyl)-methyl]-5-(3-hydroxy-azetidine-1-carbonyl)-2H-pyrazole-3-carboxylic acid (1-isopropyl-piperidin-4-yl)-amide, 1-[(5-Chloro-pyridin-2-ylcarbamoyl)-methyl]-5-(1-isopropyl-piperidin-4-ylcarbamoyl)-1H-pyrazole-3-carboxylic acid cyclopropylmethyl ester, 2-{1-[5-(5-Chloro-thiophen-2-yl)-isoxazol-3-ylmethyl]-5-(1-isopropyl-piperidin-4-ylcarbamoyl)-1H-pyrazole-3-carbonyl}-amino}-3-methyl-butyric acid ethyl ester, 2-{1-[5-(5-Chloro-thiophen-2-yl)-isoxazol-3-ylmethyl]-5-(1-isopropyl-piperidin-4-ylcarbamoyl)-1H-pyrazole-3-carbonyl}-amino}-3-methyl-butyric acid, 1-[5-(5-Chloro-thiophen-2-yl)-isoxazol-3-ylmethyl]-5-[2-(2-methoxy-ethoxy)-ethoxymethyl]-1H-pyrazole-3-carboxylic acid (1-isopropyl-piperidin-4-yl)-amide, 2-[5-(5-Chloro-thiophen-2-yl)-isoxazol-3-ylmethyl]-5-(2-methoxy-ethoxymethyl)-2H-pyrazole-3-carboxylic acid (1-isopropyl-piperidin-4-yl)-amide, 1-[(5-Chloro-pyridin-2-ylcarbamoyl)-methyl]-5-[2-(2-methoxy-ethoxy)-ethoxymethyl]-1H-pyrazole-3-carboxylic acid (1-isopropyl-piperidin-4-yl)-amide, 2-[(5-Chloro-pyridin-2-ylcarbamoyl)-methyl]-5-[2-(2-methoxy-ethoxy)-ethoxy]-2H-pyrazole-3-carboxylic acid (1-isopropyl-piperidin-4-yl)-amide, 2-[(5-Chloro-pyridin-2-ylcarbamoyl)-methyl]-5-(2,2,2-trifluoro-ethoxy)-2H-pyrazole-3-carboxylic acid (1-isopropyl-piperidin-4-yl)-amide, 1-[(5-Chloro-pyridin-2-ylcarbamoyl)-methyl]-5-(1-isopropyl-piperidin-4-ylcarbamoyl)-1H-pyrazole-3-carboxylic acid 2-methoxy-ethyl ester, 1-[(5-Chloro-pyridin-2-ylcarbamoyl)-methyl]-5-(1-isopropyl-piperidin-4-ylcarbamoyl)-1H-pyrazole-3-carboxylic acid 2-hydroxy-ethyl ester, 2-[(5-Chloro-pyridin-2-ylcarbamoyl)-methyl]-5-([1,4]oxazepane-4-carbonyl)-2H-pyrazole-3-carboxylic acid (1-isopropyl-piperidin-4-yl)-amide, 5-(1-Isopropyl-piperidin-4-ylcarbamoyl)-1-(3-methoxy-benzyl)-1H-pyrazole-3-carboxylic acid, 1-[5-(5-Chloro-thiophen-2-yl)-isoxazol-3-ylmethyl]-5-(1-isopropyl-piperidin-4-ylcarbamoyl)-1H-pyrazole-3-carboxylic acid 2-hydroxy-ethyl ester, 1-[5-(5-Chloro-thiophen-2-yl)-isoxazol-3-ylmethyl]-5-(1-isopropyl-piperidin-4-ylcarbamoyl)-1H-pyrazole-3-carboxylic acid carboxymethyl ester, 1-[(5-Chloro-pyridin-2-ylcarbamoyl)-methyl]-5-(1-isopropyl-piperidin-4-ylcarbamoyl)-4-(2,2,2-trifluoro-ethoxy)-1H-pyrazole-3-carboxylic acid ethyl ester, and 1-[(5-Chloro-pyridin-2-ylcarbamoyl)-methyl]-5-hydroxymethyl-1H-pyrazole-3-carboxylic acid (1-isopropyl-piperidin-4-yl)-amide.

8. A process for the preparation of the compound according to claim 1, comprising condensing a carboxylic acid of the formula 2

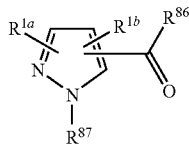

2 with a compound of the formula $HR^{8'}$ or with an amine of the formula $HN(R^{1'})R^{2'}$—V-G-M to give a compound of the formula 3

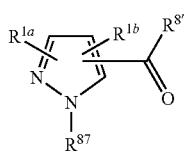

3 and optionally converting the compound of formula 3 into a compound of the formula I,
wherein the groups $R^{8'}$ and $R^{87}$ are respectively the groups $-N(R^1)-R^2-V-G-M$ and $R^0$-Q-, which are as defined in claim 1, $R^{86}$ is hydroxyl, $(C_1-C_4)$-alkoxy, acid chloride, a substituted phenyl ester or an N-hydroxysuccinimide or a hydroxybenzotriazole ester, and $R^1a$ and $R^1b$ have respectively the meaning of $R^3$ and $R^4$ in claim 1.

9. A pharmaceutical preparation comprising a pharmaceutically effective amount of at least one compound according to claim 1, or a stereoisomer thereof, mixture of stereoisomers thereof in any ratio, or a physiological tolerable salt thereof, and a pharmaceutically acceptable carrier.

10. A method of inhibiting the activity of factor Xa or factor VIIa comprising contacting an inhibitory amount of the compound according to claim 1, or a stereoisomer thereof, mixture of stereoisomers thereof in any ratio, or a physiological tolerable salt thereof, with a composition containing factor Xa or factor VIIa to influence blood coagulation, wherein the blood coagulation is connected with abnormal thrombus formation.

11. A method of inhibiting the activity of factor Xa or factor VIIa comprising contacting an inhibitory amount of the compound according to claim 1, or a stereoisomer thereof, mixture of stereoisomers thereof in any ratio, or a physiological tolerable salt thereof, with a composition containing factor Xa or factor VIIa to influence fibrinolysis.

12. The compound according to claim 5, having the formula:

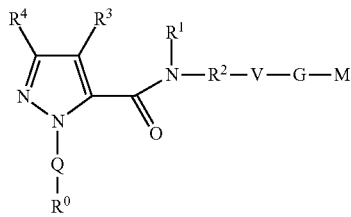

or a stereoisomer thereof, mixture of stereoisomers thereof in any ratio, or a physiological tolerable salt thereof.

13. The compound according to claim 12, wherein:

$R^0$ is isoxazolyl substituted by 2-thienyl or 3-thienyl, wherein said 2-thienyl or 3-thienyl is unsubstituted or mono- or disubstituted independently of one another by $R^8$;

$R^8$ is selected from F, Cl, Br, $-OCH_3$, $-C(O)-NH_2$ and $-O-CF_3$;

Q is $-(C_1-C_6)$-alkylene;

$R^1$ is hydrogen or $-(C_1-C_4)$-alkyl, wherein said alkyl is unsubstituted or substituted one to three times by $R^{13}$;

$R^2$ is a direct bond;

V is a piperidine ring, which can be unsubstituted or mono-, di- or trisubstituted independently of one another by $R^{14}$;

G is a direct bond;

M is $(C_1-C_8)$-alkyl, wherein said alkyl is unsubstituted or independently mono-, di- or trisubstituted by $R^{14}$;

$R^3$ and $R^4$ are selected from hydrogen, halogen, $-(C_1-C_4)$-alkyl, phenyl, $-(C_1-C_3)$-perfluoroalkyl, and $-(C_0-C_2)$-alkylene-O-$R^{19}$ wherein said alkyl and/or phenyl is unsubstituted or independently mono-, di- or trisubstituted independently of one another by $R^{13}$;

$R^{13}$ isselected from $-(C_1-C_4)$-alkyl, fluorine, chlorine, $-OH$, $-(C_3-C_6)$-cycloalkyl, and $-(C_1-C_3)$-perfluoroalkyl;

$R^{14}$ is selected from halogen, $-OH$, and $-(C_1-C_4)$-alkoxy; and $R^{19}$ is selected from hydrogen, $-(C_1-C_4)$-alkyl, or phenyl, wherein alkyl and/or phenyl is unsubstituted or mono-, di- or trisubstituted independently of one another by $R^{13}$.

14. The compound according to claim 13, wherein the compound is 2-[5-(5-Chloro-thiophen-2-yl)-isoxazol-3-ylmethyl]-4-cyano-5-propyl-2H-pyrazole-3- carboxylic acid (1-isopropyl-piperidin-4-yl)-amide in accordance with the following chemical structure:

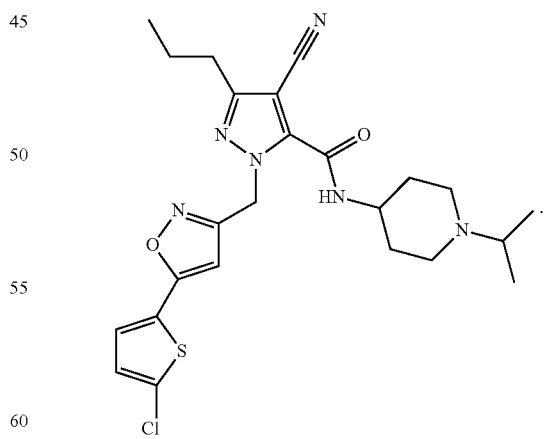

* * * * *